United States Patent
Van Engeland et al.

(10) Patent No.: US 11,149,317 B2
(45) Date of Patent: *Oct. 19, 2021

(54) METHODS FOR DETECTING EPIGENETIC MODIFICATIONS

(71) Applicant: Exact Sciences Development Company, LLC, Madison, WI (US)

(72) Inventors: Manon Van Engeland, Maastricht (NL); Manon Adriaan De Bruine, Maastricht (NL); Arjan Griffioen, Maastricht (NL); Joost Louwagie, Sart-Tilman (BE); Katja Bierau, Sart-Tilman (BE); Gontran Brichard, Sart-Tilman (BE); Gaetan Otto, Sart-Tilman (BE); Maarten Penning, Sart-Tilman (BE)

(73) Assignee: Exact Sciences Development Company, LLC, Madison, WI (US)

( * ) Notice: Subject to any disclaimer, the term of this patent is extended or adjusted under 35 U.S.C. 154(b) by 355 days.

This patent is subject to a terminal disclaimer.

(21) Appl. No.: 16/154,023

(22) Filed: Oct. 8, 2018

(65) Prior Publication Data

US 2019/0032149 A1    Jan. 31, 2019

Related U.S. Application Data

(63) Continuation of application No. 15/971,461, filed on May 4, 2018, now Pat. No. 10,808,286, which is a continuation of application No. 14/613,574, filed on Feb. 4, 2015, now Pat. No. 9,982,308, which is a continuation of application No. 12/522,648, filed as application No. PCT/GB2008/000056 on Jan. 9, 2008, now Pat. No. 8,969,046.

(60) Provisional application No. 60/978,261, filed on Oct. 8, 2007, provisional application No. 60/960,130, filed on Sep. 17, 2007, provisional application No. 60/879,332, filed on Jan. 9, 2007.

(51) Int. Cl.
*C12Q 1/68* (2018.01)
*C12P 19/34* (2006.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/154* (2013.01); *C12Q 2600/158* (2013.01); *C12Q 2600/16* (2013.01)

(58) Field of Classification Search
CPC ............ C12Q 1/6886; C12Q 2600/118; C12Q 2600/154

See application file for complete search history.

(56) References Cited

U.S. PATENT DOCUMENTS

| | | | |
|---|---|---|---|
| 7,794,929 B2 | 9/2010 | Baylin et al. | |
| 8,462,170 B2 | 6/2013 | Diggins et al. | |
| 8,969,046 B2 | 3/2015 | Van Engeland et al. | |
| 9,982,308 B2 | 5/2018 | Van Engeland et al. | |
| 2004/0234960 A1* | 11/2004 | Olek .................... | C12Q 1/6827 435/6.11 |

FOREIGN PATENT DOCUMENTS

| | | |
|---|---|---|
| EP | 1829978 | 9/2007 |
| JP | 2005-110645 | 4/2005 |
| JP | 2005-518822 | 6/2005 |
| JP | 2006-166732 | 6/2006 |
| JP | 2009-545222 | 12/2009 |
| JP | 2010-517582 | 5/2010 |
| WO | WO 03/076593 | 9/2003 |
| WO | WO 2004/083399 | 9/2004 |
| WO | WO 2006/113770 | 10/2006 |

(Continued)

OTHER PUBLICATIONS

Li, L.-C. et al. Bioinformatics, vol. 18, No. 11, pp. 1427-1431. (Year: 2002).*

(Continued)

*Primary Examiner* — Stephen T Kapushoc
(74) *Attorney, Agent, or Firm* — Casimir Jones, S.C.; Mary Ann D. Brow

(57) ABSTRACT

A method of detecting a predisposition to, or the incidence of, cancer in a sample comprises detecting an epigenetic change in at least one gene selected from an NDRG4/NDRG2 subfamily gene, GATA4, OSMR, GATA5, SFRP1, ADAM23, JPH3, SFRP2, APC, MGMT, TFPI2, BNIP3, FOXE1, SYNE1, SOX17, PHACTR3 and JAM3, wherein detection of the epigenetic change is indicative of a predisposition to, or the incidence of, cancer. Also described are pharmacogenetic methods for determining suitable treatment regimens for cancer and methods for treating cancer patients, based around selection of the patients according to the methods of the invention. The present invention is also concerned with improved methods of collecting, processing and analyzing samples, in particular body fluid samples. These methods may be useful in diagnosing, staging or otherwise characterizing various diseases. The invention also relates to methods for identifying, diagnosing, staging or otherwise characterizing cancers, in particular gastrointestinal cancers such as colorectal cancers, gastric cancers and oesophageal cancers. The methods of the invention relate, inter alia, to isolating and analyzing the human DNA component from faecal samples and blood-based samples.

8 Claims, 15 Drawing Sheets
Specification includes a Sequence Listing.

(56) References Cited

FOREIGN PATENT DOCUMENTS

| WO | WO 2007/149269 | 12/2007 |
|---|---|---|
| WO | WO 2008/084219 | 7/2008 |
| WO | WO 2008/100913 | 8/2008 |

OTHER PUBLICATIONS

Seeger, C. et al. BioTechniques, 23:512-517 (Sep. 1997).*
Eads, C.A. et al. Nucleic Acids Research, vol. 28, No. 8; pp. i-viii. (Year: 2000).*
Hu, et al., NDRG2 expression and mutation in human liver and pancreatic cancers, Work Journal of Gastroenterology, WJG Press, vol. 10, No. 4, 2004, pp. 3518-3521.
Liu et al., Promoter methylation, mutation, and genomic deletions are involved in the decreased NDRG2 expression levels in several cancer cell lines, Biochemical and Biophysical Research Communication, 2007, 358:164-169.
Lusis, et al., Integrative genomic analysis identifies NDRG2 as a candidate tumor suppressor gene grequently inactivated in clinically aggressive meningioma, Cancer Research, vol. 65, No. 16, Aug. 15, 2005, pp. 7121-7126.
Matsubayashi, et al., DNA methylation alterations in the pancreatic juice of patients with suspected pancreatic disease, Cancer Research, vol. 66, No. 2, Jan. 15, 2006, pp. 1208-1217.
Muchir, et al., Proteasome-mediated degradation of integral inner nuclear membrane protein emerin in fibroblasts lacking A-type lamins, Biochemical and Biophysical Research Communications, Academic Press Inc., Orlando, FL, US, vol. 351, No. 4, pp. 1011-1017 (Nov. 14, 2006).
Paoni, et al., Transcriptional profiling of the transition from normal intestinal epithelia to adenomas and carcinomas in the APCMin/+ mouse, Physiological genomics, vol. 15, No. 3, Nov. 11, 2003, pp. 228-235.
Qu et al., Characterization and expression of three novel differentiation-related genes belong to the human NDRG gene family, Molecular and Cellular Biochemistry, vol. 229, No. 1-2, Jan. 2002, pp. 35-44.
Subject Matter Eligibility Examples: Life Sciences, May 2016, pp. 1-31.
Takada, et al., ADAM23, a possible tumor suppressor gene, is frequently silenced in gastric cancers by homozygous deletion or aberrant promoter hypermethylation, Oncogene, Nature Publishing Group, GB Basingstoke, Hants, vol. 24, No. 54, Dec. 1, 2005, pp. 8051-8060.
Teodoridis, et al., Epigenetic silencing mediated by CpG island methylation: potential as a therapeutic target and as a biomarker, Drug Resistance Updates, Churchill Livingstone, Edinburgh, GB, vol. 7, No. 4-5, pp. 267-278 (Aug. 1, 2004).
Tepel, et al., N-myc downstream-regulated gene 2 (NDRG2) frequently shows reduced expression and promoter hypermethylation in human glioblastomas, Acta Neuropathol; vol. 110, pp. 342 (2005).
Vannini et al., Crystal structure of a eukaryotic zinc-dependent histone deacetylase, human HDAC8, complexed with a hydroxamic acid inhibitor, PNAS, Oct. 19, 2004, 101(42):15064-15069.
Verma, et al., Epigenetics in cancer: Implications for early detection and prevention, Lancet Oncology, Lancet Publishing Group, London, GB, vol. 3, No. 12, Dec. 1, 2002, pp. 755-763.
Wilson et al., Histone deacetylase 3 (HDAC3) and other class I HDACs regulate colon cell maturation and p21 expression and are deregulated in human colon cancer, Journal of Biological Chemistry, May 12, 2006, 281(19):13548.
Zhang et al., Synergic antiproliferative effect of DNA methyltransferase inhibitor in combination with anticancer drugs in gastric carcinoma, Cancer Sci, Sep. 2006, 97(9):938-944.
Zhou, et al., Characterization of the Human NDRG Gene Family: A Newly Identified Member, NDRG4, Is Specifically Expressed in Brain and Heart, Genomics, Academic Press, San Diego, CA, US, vol. 73, No. 1, pp. 86-97 (Apr. 1, 2001).
International Search Report for PCT/GB2008/000056 dated Sep. 30, 2008.
Search Report for GB0700374.2 dated May 8, 2007.

* cited by examiner

```
gtttaatagagttttgtatggaaaagattggaatttagggaggagtagagtttCGtttaa
ggttatCGgtCGagtttgaatagaattCGgttttttaggagttttgttttagttgtttt
gtttaaataaaattttttaggttattagattttCGtattttttggagtgggatttattt
gggattaaaggagggttggtgaggggagtggtaggagggaggagtgtttCGggtttCGa
gtaggatgagtttgaggaagagaCGgttttttatgttttttttttCGtttagataatgga
ggtgaattgagggagtagagatttttttattttagggtgggatttagggattagga
tattttgttaggggatgtttttttttattttgtataagttttttaaggatattttCGg
gtttCGaaaaCGgggggagggggaCGaCGtttttagaggttttttgagttttttggttttttt
CGatttttaagggtttttttttttCGgttttttaggCGgCGaCGgCGggtagCGCGaagtag
taggCGtagggCGttgggatggggatgtttttgtaggtttaaggtttttttttgggagtt
taaataaagattaCGgtagCGtCGttttttttttCGggaattCGaCGtCGCGCGgttata
gggggtttggaggggCGggtagggtttCGtagCGtatttagtatagttCGCGCGgCGgag
CGggtgagaagtCGgCGggggCGCGgatCGatCGgggtgttttttaggtttCGCGtCGCG
gttttCGttCGttttttCGttCGtttatCGggtatttagtCGCGtagaaggCGgaagtt
aCGCGCGagggatCGCGgttCGttCGggattagttttaggttCGgtatCGtttCGCGggt
CGagCGtttatattCGttaaatttaCGCGggtaCGttttCGCGgCGtatCGttttagtt
CGgttttCGttttttgtagtCGCGggtaCGCGgaggggtttTtggttgttCGtatttgtat
tCGCGCGtCGgCGgCGtCGaagtttCGttttttCGtttgCGCGtttgtttCGttCGtattt
tCGCGgtgagtCGgCGgCGttttCGtttttgagtttagggttagttttttttCGtCGtCGC
GgttgttgCGCGCGttttCGtttagtttagtttagtttCGagtaCGatttttagttttaCG
taCGattttagtttCGCGagtttCGtatCGattCGttttCGttttatttCGttttCGCGg
gggCGgCGtttttttttttttCGCGgttttCGtttttttttttCGttttttCGgtCGCGtt
gggggattttttagtCGtCGttCGCGgattttttatCGCGaCGttCGgaggCGgCGgggttttt
tttgttCGggCGgCGggtaCGggggattattttttaCGgtgttatCGtatttatttCGCG
ttttttttttCGttttttggagtttatCGggattaggtggCGgCGggtgttttttttggggg
tgCGCGgttatgtaattggtggatttttttaaatCGtt gtttgttttgCGttttgCGtaggttttttattaggttttttttgagttatttgattta
gagaCGaatttagatgttggaattttaggttttttttttttttatttaagtaagaCGa
ttttgataaagaaaagtttgtaggtaaaagtttttattCGaggtttttttttttttag
gttttttggtgttgatgagattttttttgtttgCGtattttggttgtgatttttatt
ttagtaggttttttttgtttaggagagtgttaaattggtatttagagggaagaggggat
taggagaggagttagggtgtttagttttgtgttagttttggggaaaagttataaagg
gagtgggagaaaggaatagaagaaagttgggtgttaaattgggggatgtagggggag
tttttagatttggggttgttgaaggttgggttttagttCGattagttttttattgtgg
gttatttttttttttggttttttttttttttagtagattttgttaagtgggatgaa
agggtattgatgtttttggatggagggtatGCGgtggtgagggtggtggtggga
gggtggttttaggtaggaggggtagggaaatttggggttttgggggggtagtCGgtg
ttggtgttgtagttggtagtttaagttttattggtattgttttgattggtttggCGtt
tagttttCGaaatggtaatttaggaattagtttgaagggggttggggtggatatgatttt
gggattggggagttataagggggtaggtggggagaaatttagttaggttttttttgt
ttaaataatttCGaattttttaagttatatttttaattaattaatttatttaggagt
ttttttCGagggtataaggagagtttatttagggtgtgtgtgtgtgtgCGtgtgC
GtgtgtgtaaagtttatagtggtaaatttattCGggtatCGagagggaCGCGgtagat
tttgagattattttCGggtattgCGatttagCGggtttgagttggttttttattggg
tCGgattgggaggggttagCGgCGaagttataggtttttgggttttagtttaggatat
tgCGtttttttaagttttattttatttCGtagggttaatttCGttttgCGtttgtt
tatttaggagttagagttttggggttttCGgttttttttCGCGttttttgaggtatt
gattttagagttttgttggttattttttttattttCGtttgttCGCGatCGttttt
tattatagCGgttttCGtattttCGttttattttCGtttgttgtttaattttt
ttCGgagtagtCGgagagtaggCGtCGggaCGtagtaaagagagagaggtattaggatt
ttgggtaCGagggagtCGgaattttgCGttttCGaCGtttttCGtgttttttCGgC
GttagtatattgtttttgttagtCGgCGagattttCGttttttagCGgCGg

```
ggttggggCGgtCGgggCGggtttgCGggaagttCGagtCGgggCGggttCGagttaa
aggtaagtgaaggtggaagCGgtCGCGgCGgtagtaggtagggggaggggtaggCGaggg
gtCGtagggtttggaaggCGttagtCGggtCGgCGggCGgtgtgattgattCGCGttttt
tggagttggaggttCGggggaaagggttagtaCGgagCGggCGttCGgttgttgCGtata
aaggttgaggttttaagagttgtagggCGtgtttggggtgCGCGCGaggttgtgtgtaag
gttCGgggCGtttggtatCGgttaCGtaagggtgttagttttttaCGCGgaCGggttgCGt
agggattCGtagggaCGggtttCGggtgttgggttCGgtCGgttttttttgttttattta
tttttttCGatggCGtttgtttttCGCGggtCGtCGggggagaaCGggagaagattgtgg
gatCGtttttttttttttttttattCGtgggatttataCGgagattgagtagaggaga
gaagCGaCGgtattaattttttgtgtttgttttaaattgtggagggaaatagttatgttt
tgttatttttttttttattggagagttgttaaaaattttggggattttttatttttCGCG
tttagttttttttgtagatagaaaattgaggttaaatgtagtaattaattgggtaaggtt
atattgggagtggtagagtCGggattCGaattCGgaggttttgatagggttatttttta
ttttatattagtatttttttttttttttCGCGtagtttgaattgatgtttttgtagttt
atattgatttCGgttCGagtttagagaggaCGtgttttttggatttagggggtagatagat
attggggagggttagtgattCGaggaggttgatgatttgggagtttgggttttggttga
ggttttCGttttgaaagattttaggtttgtttttatgttatttatttCGttgttgtg
ttttttttagattttagagttagaaggagtgagaattttgattttaatttttattgtattt
agttaataggagtttagtaagtgattttatttCGtaggttgtaggttttttttgtgtag
gtttgtttaggtgttttgtttttatttattaatgttgaatttgCGgagtttatttagag
ttgggaggaagggtttgggaggaagggaggtattgggttggttggatagatgtttttt
tatgttgttttttttattttttttattggttatgttgttttggttatttttagttttttt
tgagttgtCGatttggggttttaattgaaggttatggttaattgtgaattttatagtt
tCGttttttggtatttttgtttttagaatatttagttattgagttataagtttattttt
tatttgagagtgtggggtggttttaaatatagttCGagaaatttgagttatattttgt
tttattttggtatttttggtttagggtagaggagggagggtttggaggtgtggtgttgag
ggtggtagtggggatggtgagtattaagagaagggttgtttgattttttttttaaagtt
tttatCGattagtttggaaaCGgagttgggggtaggaaaggttttttgtgtgttttagag
tagttttaattttttgggttttttttgttttttgtatttttttgtgttgagagaggaagtt
tggtgtttgaggCGatgtggggatgtagagataattttttagttttattttttttatttg
ttaggttatt<ins>atg</ins>gCGgagttgtaggaggtgtagattatagaggagaagttattgttgtt
aggatagaCGtttgaggCGgttaaggttattagagatCGtttgattttatgtttaaatt
ttagatttttaagtatttttttgtttttaattttttaagCGtattgattttatttttaa
tttatattattgttttattattattttagttttttttttta
```

FIG. 3b
CONT'D

METHODS FOR DETECTING EPIGENETIC MODIFICATIONS

CROSS-REFERENCE TO RELATED APPLICATIONS

The present application is a continuation of U.S. patent application Ser. No. 15/971,461, filed May 4, 2018, which is a continuation of U.S. patent application Ser. No. 14/613,574, filed Feb. 4, 2015, now U.S. Pat. No. 9,982,308, which is a continuation of U.S. patent application Ser. No. 12/522,648, filed Jan. 6, 2010, now U.S. Pat. No. 8,969,046, which is a § 371 U.S. National Entry of PCT/GB2008/000056, filed Jan. 9, 2008, which claims the priority benefit of U.S. Provisional Patent Application Nos. 60/978,261, filed Oct. 8, 2007; 60/960,130, filed Sep. 17, 2007; and 60/879,332, filed Jan. 9, 2007, each of which is incorporated by reference in its entirety.

FIELD OF THE INVENTION

The present invention relates to methods and kits for identifying and diagnosing cancer which include detecting an epigenetic change, such as a change in the methylation status, or the expression levels, or a combination thereof of any one or more of a number of genes. Also described are pharmacogenetic methods for determining suitable treatment regimens for cancer and methods for treating cancer patients, based around selection of the patients according to the methods of the invention. The present invention is also concerned with improved methods of collecting, processing and analyzing samples, in particular body fluid samples. More particularly, the invention relates to methods for identifying epigenetic changes in body fluid samples. These methods may be useful in diagnosing, staging or otherwise characterizing various diseases. The invention also relates to methods for identifying, diagnosing, staging or otherwise characterizing cancers, in particular gastrointestinal cancers such as colorectal cancers, gastric cancers and oesophageal cancers. The methods of the invention relate, inter alia, to isolating and analyzing the human DNA component from faecal samples and blood-based samples.

BACKGROUND OF THE INVENTION

In their earliest stages most cancers are clinically silent. Patient diagnosis typically involves invasive procedures that frequently lack sensitivity and accuracy. Highly reliable, non-invasive screening methods would permit easier patient screening, diagnosis and prognostic evaluation.

Tumour derived markers are biological substances that are usually produced by malignant tumours. Ideally a tumour derived marker should be tumour-specific, provide an indication of tumour burden and should be produced in sufficient amounts to allow the detection of minimal disease. Most tumour derived markers used in clinical practice are tumour antigens, enzymes, hormones, receptors and growth factors that are detected by biochemical assays. The detection of DNA alterations such as mutations, deletions and epigenetic modifications (Baylin et al., 2000) provide another means for identifying cancers.

An epigenetic modification can be described as a stable alteration in gene expression potential that takes place during development and cell proliferation, mediated by mechanisms other than alterations in the primary nucleotide sequence of a gene. It is now general knowledge that both genetic and epigenetic alterations can lead to gene silencing and cellular dysfunction. Synergy between these two processes drives tumor progression and malignancy. Three related mechanisms that cause alteration in gene expression are recognised: DNA methylation, histone code changes and RNA interference.

DNA hypermethylation is an epigenetic modification whereby the gene activity is controlled by adding methyl groups (CH3) to specific cytosines of the DNA. In particular, methylation occurs in the cytosine of the CpG dinucleotides (CpG islands) which are concentrated in the promoter regions and introns in human genes (P. A. Jones et al., 2002; P. W. Laird et al., 2003). Methylation is associated with gene silencing. DNA hypermethylation is found to be involved in a variety of cancers including lung, breast, ovarian, kidney, cervical, prostate and also colorectal cancer. Methylation patterns of DNA from cancer cells are significantly different from those of normal cells. Therefore, detection of methylation patterns in appropriately selected genes of cancer cells can lead to discrimination of cancer cells from normal cells, thereby providing an approach to early detection of cancer.

DNA tumour markers, in particular DNA methylation markers, offer certain advantages when compared to other biochemical markers. An important advantage is that DNA alterations often precede apparent malignant changes and thus may be of use in early diagnosis of cancer. Since DNA is much more stable and, unlike protein, can be amplified by powerful amplification-based techniques for increased sensitivity, it offers applicability for situations where sensitive detection is necessary, such as when tumour DNA is scarce or diluted by an excess of normal DNA (Sidransky et al., 1997). Bodily fluids provide a cost-effective and early non-invasive procedure for cancer detection. In this context, faecal-based cancer testing has been one area of investigation.

Human colorectal cancer has provided a good model for investigating whether DNA cancer markers can be adopted as an optimal faecal-based diagnostic screening test. Central to faecal-based colorectal cancer testing has been the identification of specific and sensitive cancer derived markers.

The N-Myc downstream-regulated gene (NDRG) family comprises four family members: NDRG1 (NDRG-family member 1), NDRG2 (NDRG-family member 2), NDRG3 (NDRG-family member 3) and NDRG4 (NDRG-family member 4). The human NDRG1 and NDRG3 belong to one subfamily, and NDRG2 and NDRG4 to another. At amino acid (aa) level, the four members share 53-65% identity. The four proteins contain an alpha/beta hydrolase fold as in human lysosomal acid lipase but are suggested to display different specific functions in distinct tissues.

NDRG1 codes for a cytoplasmic protein believed to be involved in stress responses, hormone responses, cell growth, and cell differentiation. NDRG1 has been demonstrated to be upregulated during cell differentiation, repressed by N-myc and c-myc in embryonic cells, and suppressed in several tumor cells (Qu X et al., 2002; Guan et al., 2000).

NDRG3 is believed to play a role in spermatogenesis since it is highly expressed in testis, prostate and ovary (Zhao W et al., 2001). Its involvement in brain cancer development has also been suggested (Qu X et al. 2002).

NDRG2 codes for a cytoplasmic protein that seems to be involved in neurite outgrowth and in glioblastoma carcinogenesis (Deng Y et al., 2003). It is upregulated at both the RNA and protein levels in Alzheimer's disease brains (Mitchelmore C et al., 2004), and has also been suggested to play an important role in the development of brain cancer (Qu X et al. 2002), pancreatic cancer and liver cancer (Hu X L et al., 2004).

The NDRG4 cytoplasmic protein is involved in the regulation of mitogenic signalling in vascular smooth muscles cells (Nishimoto S et al). The NDRG4 gene contains 17 exons, and several alternatively spliced transcript variants of this gene have been described. NDRG4 may also be involved in brain cancer development (Qu X et al. 2002).

Suppressed expression of NDRG-family genes has been demonstrated in a number of tumours (Qu X et al. 2002) and the involvement of DNA promoter hypermethylation is limited to the reporting of NDRG2 methylation in brain tumors (Lusis et al., 2005).

Initially, faecal-based DNA assays investigated the usefulness of specific point mutations markers for detecting colorectal cancer. Later, the DNA integrity in faecal samples proved to be a useful marker (Boynton et al., 2003). Finally, faecal testing based on DNA alterations gradually evolved into the development of a multi-target DNA assay using specific point mutation markers, a microsatellite instability marker and a marker for DNA integrity.

Recently, the potential of faecal DNA testing targeting epigenetic alterations has been investigated (Müller et al., 2004, Chen et al., 2005) and has been added to the multi-target DNA assay. Genes having an altered methylation status traceable in faecal DNA from colon cancer patients versus control samples from healthy subjects have been discovered (Belshaw et al., 2004; Petko et al., 2005; Lenhard et al., 2005; Miller et al., 2004; Chen et al., 2005 and Lueng et al., 2004).

Factors that may influence the sensitivity of the selected markers are sampling processing procedures and DNA isolation and extraction protocols. One challenge faced by researchers investigating colorectal cancer is the diversity of DNA present in stool samples. Most of the DNA recovered from faecal samples is bacterial in origin, with the human DNA component representing only a very small minority. Human DNA from cells sloughed from the colonic mucosa represents as little as 0.1 to 0.01% of the total DNA recoverable from stool. Additionally, the human DNA recovered is highly heterogeneous. Normal cells are sloughed into the colonic lumen along with only a small amount of tumour cells (approximately 1% of the cells sloughed). Thus, the DNA of interest represents only a very small percentage of the total DNA isolated from stool. Therefore, along with the exploration of suitable DNA markers, techniques for improved DNA isolation and enrichment of the human DNA component from faecal samples have been developed for more sensitive cancer detection.

The initial DNA isolation techniques typically recovered DNA from 10 g to 4 g stool and more conveniently purified the human DNA component using streptavidin-bound magnetic beads (Dong et al., 2001; Ahlquist et al., 2000). Further improvements in recovery of target human DNA from stool comprised an electrophoresis-driven separation of target DNA sequences, using oligonucleotide capture probes immobilized in an acrylamide gel (Whitney et al., 2004). Later, when DNA integrity proved to be a suitable marker it was also important to prevent degradation during sample handling. Improved results were obtained with stool samples frozen as quickly as possible after collection. Alternatively, stabilization buffer was added to the stool samples before further transport (Olson et al., 2005). A recent improvement involves the use of an MBD column to extract methylated human DNA in a high background of fecal bacterial DNA (Zou et al., 2007). However, despite these advances, current tools for cancer detection in faecal samples are still unsatisfactory.

Cancer at its early stage may release its cells or free DNA into blood through apoptosis, necrosis or local angiogenesis, which establishes a basis for blood-based cancer testing. The usefulness of DNA methylation markers for detecting colorectal cancers in serum and plasma has been demonstrated (Grady et al., 2001, Leung et al., 2005; Nakayama et al., 2007). However, the potential use of serum and plasma for cancer detection is hampered by the limited level of methylated DNA present in the total DNA collected from plasma and serum samples (Zou et al. (2002) Clin Cancer Res 188-91). A further drawback is the partial degradation of the methylated DNA due to bisulfite treatment, a treatment step required by many techniques that monitor DNA methylation.

Methods and compositions for detection of early colorectal cancer or pre-cancer using blood and body fluids have been described.

WO 2006/113770 describes methods in which samples are pooled and concentrated in an attempt to maximize DNA input per reaction. The initial processing of 45 ml of blood allowed a median DNA recovery of 3.86 ng/ml plasma. This was shown to result in a sensitivity of 57% and specificity of 96% for detection of colorectal cancer using a specific real-time assay for detecting whether The Septin 9 gene was methylated. Bisulphite treatment was focused on large volume treatment and achieving maximal conversion.

Lofton-Day et al. (AACR general meeting April 2007, Los Angeles, USA) mention improved detection of colorectal cancer, and obtained a 70% sensitivity and 90% specificity, with the same marker (Septin 9). The proposed method utilised four blood draws (40 ml blood), double centrifugation for plasma recovery and required four PCR reactions to be carried out for each sample tested. Three out of the four reactions used input DNA equivalent to 2 ml of plasma per PCR reaction. The fourth reaction used a $\frac{1}{10}$ dilution of this input DNA. Thus, repeated assays were required (at least 4) and an algorithm utilised to determine the final result. A sample was deemed positive if either two out of the three reactions with input DNA equivalent to 2 ml of plasma, or the diluted measurement, were positive for the Septin 9 assay. The improved sensitivity by using the diluted samples indicates the presence of inhibitors in the methods, a phenomena also described by Nakayama et al. (2007, Anticancer Res. 27(3B):1459-63).

The processing of smaller amounts of blood have been described as well (US 20070141582, Hong-Zhi Zou et al., and Satoru Yamaguchi et al) but all result in low level of methylated modified DNA detection.

Thus, current blood-based screening methods lack sensitivity.

SUMMARY OF THE INVENTION

The invention, as set out in the claims, is based around the finding that NDRG4/2 subfamily genes, undergoe CpG island promoter methylation-associated gene silencing in human cancer cells, in particular colon cancer cells. The hypermethylation of the NDRG family gene, such as NDRG4 and/or NDRG2, in particular in the promoter region leads to its loss of expression. Importantly, the presence of aberrant methylation at the NDRG4/2 subfamily gene promoter has a prognostic value. The epigenetic loss of NDRG4/2 function can be rescued by the use of DNA demethylating agents and thus provides for a method for treatment. These findings underline the significance of the epigenetic silencing of the NDRG4/2 subfamily genes as one key step in cancer development and may have an important clinical impact for the treatment of the patients.

The present invention is also based upon the discovery of specific genes and panels of genes whose methylation status is linked to the incidence of, or predisposition to, gastrointestinal cancers such as colorectal cancer. Use of these genes for detecting gastrointestinal cancers such as colorectal cancer, in particular in the context of appropriate tissue or faecal (stool) samples or of appropriate blood samples (or derivatives thereof) respectively, has been shown to produce highly sensitive and specific results. The invention provides also for a method for isolating increased amount of DNA from faecal samples, which results in improved sensitivity of detection of colorectal cancer in faecal samples.

The invention also provides a method for determining the methylation status of a gene of interest in a blood based sample, which requires only low volumes of blood sample equivalent to generate specific and sensitive results. This is advantageous since it permits smaller blood samples to be obtained from the subject under test.

Accordingly, in a first aspect, the invention provides a method of detecting a predisposition to, or the incidence of, cancer in a sample comprising detecting an epigenetic change in at least one gene selected from an NDRG4/NDRG2 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3, wherein detection of the epigenetic change is indicative of a predisposition to, or the incidence of, cancer.

Subsets of genes for all aspects and embodiments of the invention include an NDRG4/NDRG2 subfamily gene (in particular NDRG4), GATA4, OSMR, GATA5, SFRP1, ADAM23, JPH3, SFRP2, APC and MGMT and TFPI2, BNIP3, FOXE1, SYNE1, SOX17, PHACTR3 and JAM3 respectively. Each subset may be particularly applicable to bodily fluid samples, such as stool and plasma samples as discussed herein.

By "epigenetic change" is meant a modification in the gene caused by an epigenetic mechanism, such as a change in methylation status or histone acetylation for example. Frequently, the epigenetic change will result in an alteration in the levels of expression of the gene which may be detected (at the RNA or protein level as appropriate) as an indication of the epigenetic change. Often the epigenetic change results in silencing or down regulation of the gene, referred to herein as "epigenetic silencing". The most frequently investigated epigenetic change in the methods of the invention involves determining the methylation status of the gene, where an increased level of methylation is typically associated with the relevant cancer (since it may cause down regulation of gene expression).

In a related aspect, the invention provides a method of diagnosing cancer or predisposition to cancer comprising detecting epigenetic silencing of the NDRG4/NDRG2 subfamily gene, wherein epigenetic silencing of the gene is indicative for cancer or predisposition to cancer.

The NDRG family genes have been characterised in the art (see, for example, Qu X et al., 2002 and references cited therein) and their epigenetic silencing can be assessed in terms of DNA methylation status or expression levels as determined by their methylation status.

In one embodiment, the invention provides for a method of diagnosing cancer or predisposition to cancer comprising detecting epigenetic silencing of the NDRG4/NDRG2 sub-family gene, wherein epigenetic silencing of the NDRG2/NDRG4-family gene is detected by determination of the methylation status of the NDRG4/2 family gene and wherein methylation of the gene is indicative for cancer or predisposition to cancer.

Since methylation of the NDRG4/NDRG2 subfamily gene manifests itself in reduced expression of the gene the invention also provides for a method of diagnosing cancer or predisposition to cancer comprising detecting epigenetic silencing of the NDRG4/NDRG2 subfamily gene, wherein epigenetic silencing of the NDRG2/NDRG4-family gene is determined by measurement of expression levels of the gene, wherein reduced expression of the gene is indicative for cancer or predisposition to cancer.

In a related aspect, the invention provides method of prognosis to cancer or predisposition to cancer comprising detecting epigenetic silencing of the NDRG4/NDRG2 subfamily gene, wherein epigenetic silencing of the gene is indicative for cancer development or predisposition to cancer. Preferably, epigenetic silencing is detected by determination of the methylation status and/or measurement of expression levels of the NDRG2/NDRG4-family gene.

The invention also provides a method of detecting a predisposition to, or the incidence of, cancer and in particular a gastrointestinal cancer such as colorectal cancer in a sample comprising detecting an epigenetic change in at least one gene selected from GATA4, OSMR, NDRG4, GATA5, SFRP1, ADAM23, JPH3, SFRP2, APC, and MGMT, and/or TFPI2, BNIP3, FOXE1, SYNE1, SOX17, PHACTR3 and JAM3, wherein detection of the epigenetic change is indicative of a predisposition to, or the incidence of, cancer and in particular a gastrointestinal cancer such as colorectal cancer. These subsets of genes may be particularly useful where faecal test samples are utilised (and plasma in certain embodiments).

In a related aspect, the invention also provides a method of detecting a predisposition to, or the incidence of, cancer and in particular a gastrointestinal cancer such as colorectal cancer in a sample and in particular in a blood sample, or derivative thereof comprising detecting an epigenetic change in at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3 (together with any suitable subset or panel thereof), wherein detection of the epigenetic change is indicative of a predisposition to, or the incidence of, cancer and in particular a gastrointestinal cancer such as colorectal cancer.

By "NDRG2/NDRG4 subfamily gene" is meant any gene which is taken from the subfamily to which NDRG4 and NDRG2 belong and includes according to all aspects of the invention NDRG2 and NDRG4. Note that "NDRG1, NDRG2, NDRG3 and NDRG4" is the standard nomenclature approved by the human genome organisation for the NDRG family genes, to ensure that each symbol is unique. The listed accession number for these genes can be found at www.gene.ucl.ac.uk/nomenclature.

NDRG family genes encompass not only the particular sequences found in the publicly available database entries, but also encompass transcript variants of these sequences. Variant forms of the encoded proteins may comprise post-translational modification, may result from spliced messages, etc. . . . NDRG4 has transcript variants having the accession numbers NM_020465 and NM_022910. NDRG2 has several transcript variants having the accession numbers, NM_201535, NM_201536, NM_201537, NM_201538, NM_201539, NM_201540, NM_2015401 and NM_016250.

Variant sequences may have at least 90%, at least 91%, at least 92%, at least 93%, at least 94%, at least 95%, at least 96%, at least 97%, at least 98%, or at least 99% identity to sequences in the database entries or sequence listing. Computer programs for determining percent identity are available in the art, including Basic Local Alignment Search Tool (BLASTS) available from the National Center for Biotechnology Information.

GATA4 is the gene symbol approved by the HUGO Gene Nomenclature Committee. The gene is located on chromosome 8 (location p23.1-p22) and the gene sequence is listed under the accession numbers AK097060, NM_002052 and ENSG00000136574. The gene encodes GATA binding protein 4.

OSMR is the gene symbol approved by the HUGO Gene Nomenclature Committee. The gene is located on chromosome 5 (location p13.2) and the gene sequence is listed under the accession numbers U60805, NM_003999 and ENSG00000145623. The gene encodes oncostatin M receptor.

NDRG4 is the gene symbol approved by the HUGO Gene Nomenclature Committee. The gene is located on chromosome 16 (location q21-q22.3) and the gene sequence is listed under the accession numbers AB044947 and ENSG00000103034. The gene encodes NDRG family member 4.

GATA5 is the gene symbol approved by the HUGO Gene Nomenclature Committee. The gene is located on chromosome 20 and the gene sequence is listed under the accession number ENSG00000130700. The gene encodes GATA binding protein 5.

SFRP1 is the gene symbol approved by the HUGO Gene Nomenclature Committee. The gene is located on chromosome 8 (location p11.21) and the gene sequence is listed under the accession numbers AF017987, NM_003012 and ENSG00000104332. The gene encodes secreted frizzled-related protein 1.

ADAM23 is the gene symbol approved by the HUGO Gene Nomenclature Committee. The gene is located on chromosome 2 (location q33) and the gene sequence is listed under the accession numbers AB009672 and ENSG00000114948. The gene encodes ADAM metallopeptidase domain 23.

JPH3 is the gene symbol approved by the HUGO Gene Nomenclature Committee. The gene is located on chromosome 16 (location q24.3) and the gene sequence is listed under the accession numbers AB042636 and ENSG00000154118. The gene encodes junctophilin 3.

SFRP2 is the gene symbol approved by the HUGO Gene Nomenclature Committee. The gene is located on chromosome 4 (location q31.3) and the gene sequence is listed under the accession numbers AF017986 and ENSG00000145423. The gene encodes secreted frizzled-related protein 2.

APC is the gene symbol approved by the HUGO Gene Nomenclature Committee. The gene is located on chromosome 5 (location q21-q22) and the gene sequence is listed under the accession numbers M74088 and ENSG00000134982. The gene encodes adenomatosis polyposis coli.

The MGMT gene encodes 06-methylguanine-DNA methyltransferase (MGMT), which is a cellular DNA repair protein that rapidly reverses alkylation (e.g. methylation) at the 06 position of guanine, thereby neutralizing the cytotoxic effects of alkylating agents such as temozolomide (TMZ) and carmustine (1-3). MGMT is the gene symbol approved by the HUGO Gene Nomenclature Committee. The gene is located on chromosome 10 (location 10q26) and the gene sequence is listed under the accession numbers M29971, NM_002412 and ENSG00000170430.

BNIP3 is the gene symbol approved by the HUGO Gene Nomenclature Committee. The gene is located on chromosome 10 (location 10q26.3) and the gene sequence is listed under the accession numbers U15174 and ENSG00000176171. The gene encodes the BCL2/adenovirus E1B 19 kDa interacting protein 3.

FOXE1 is the gene symbol approved by the HUGO Gene Nomenclature Committee. The gene is located on chromosome 9 (location 9q22) and the gene sequence is listed under the accession numbers U89995 and ENSG00000178919. The gene encodes the forkhead box E1 (thyroid transcription factor 2)

JAM3 is the gene symbol approved by the HUGO Gene Nomenclature Committee. The gene is located on chromosome 11 (location 11q25) and the gene sequence is listed under the accession numbers AF356518, NM_032801 and ENSG00000166086. The gene encodes the junctional adhesion molecule 3.

PHACTR3 is the gene symbol approved by the HUGO Gene Nomenclature Committee. The gene is located on chromosome 20 (location 20q13.32) and the gene sequence is listed under the accession numbers AJ311122, NM_080672 and ENSG00000087495. The gene encodes the phosphatase and actin regulator 3.

TFPI2 is the gene symbol approved by the HUGO Gene Nomenclature Committee. The gene is located on chromosome 7 (location 7q22) and the gene sequence is listed under the accession numbers L27624 and ENSG00000105825. The gene encodes the tissue factor pathway inhibitor 2.

SOX17 is the gene symbol approved by the HUGO Gene Nomenclature Committee. The gene is located on chromosome 8 (location 8q11.23) and the gene sequence is listed under the accession numbers AB073988 and ENSG00000164736. The gene encodes the SRY (sex determining region Y)-box 17.

SYNE1 is the gene symbol approved by the HUGO Gene Nomenclature Committee. The gene is located on chromosome 6 (location 6q25) and the gene sequence is listed under the accession numbers AB018339 and ENSG00000131018. The gene encodes the spectrin repeat containing, nuclear envelope 1.

Of course, as appropriate, the skilled person would appreciate that functionally relevant variants of each of the gene sequences may also be detected according to the methods of the invention. For example, the methylation status of a number of splice variants may be determined according to the methods of the invention. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology Information.

The methods of the invention are generally ex vivo or in vitro methods carried out on a test sample, in particular on an isolated test sample. The methods can be used to diagnose any suitable type of cancer. The cancer comprises, consists essentially of or consists of a neoplasia of the gastrointestinal tract such as gastrointestinal cancer in one embodiment. In specific embodiments, the methods of the invention are applied to colorectal cancer, gastric cancer and/or oesophageal cancer. In more specific embodiments, the methods are used to diagnose colorectal cancer, and more particularly to diagnose hereditary nonpolyposis colon cancer and/or sporadic colorectal cancer. Alternatively, the methods are aimed at diagnosis of gastric cancer. Preferably, the methods are used to diagnose colorectal cancer and/or gastric cancer. The methods may be used to detect carcinoma or adenoma, in particular advanced adenoma. The methods may be employed in the diagnosis of both diffuse type and intestinal type carcinomas of the stomach, particularly when the methylation status of NDRG4 is determined. In one embodiment the methods may also include the step of obtaining the sample.

In one specific embodiment, the methods are used to diagnose oesophageal adenocarcinoma. In particular, the methylation status of the NDRG4 gene (promoter) has been shown for the first time herein to be linked with high sensitivity and specificity to the incidence of this particular cancer type. Oesophageal adenocarcinoma may be distinguished from oesophageal squamous cell carcinomas on this basis.

The "test sample" can be any tissue sample or body fluid. Preferably, the test sample is obtained from a human subject. In specific embodiments, the sample is taken from the gastrointestinal tract. The sample may be a colorectal tissue sample or a colon, rectal, oesophageal, stomach or appendix tissue sample or a faecal or blood based sample from a subject. For faecal samples the methods are preferably used with respect to detecting gastrointestinal cancers such as colorectal cancer as discussed herein, but may also be useful in identifying potentially dangerous adenomas. Different markers and panels of markers may be most useful with a specific sample type, such as a tissue, blood based or faecal sample as discussed herein in detail.

Thus, for example, in one embodiment, the methods of the invention involve detecting an epigenetic change, and in particular determining the methylation status, of (at least) the NDRG4 gene in a faecal test sample, wherein detection of the epigenetic change, in particular (hyper)methylation of the NDRG4 gene (promoter) is indicative of gastrointestinal neoplasias/cancer, in particular colorectal cancer, such as adenomas and carcinomas, gastric cancer and other adenocarcinomas of the gastrointestinal tract (such as oesophageal adenocarcinoma) and/or diffuse type and intestinal type carcinomas of the stomach.

The subject may be suspected of being tumorigenic. More specifically the subject may be suspected of suffering from a cancer, such as a gastrointestinal cancer and in particular colorectal cancer, as discussed herein. However, any other suitable test samples in which epigenetic silencing of the appropriate gene or genes of the invention, for example an NDRG4/NDRG2 subfamily gene, can be determined to indicate the presence of cancer are included within the scope of the invention. Preferred panels and subsets of genes are presented herein which provide sensitive and specific diagnosis, including early stage detection, of a gastrointestinal cancer such as colorectal cancer based upon appropriate samples such as tissue, faecal and plasma samples as discussed herein. Thus, in embodiments in which tissue samples are utilised, the methods of the invention may comprise, consist essentially of or consist of detecting an epigenetic change in a panel of genes comprising OSMR, GATA4 and ADAM23 or OSMR, GATA4 and GATA5, wherein detection of the epigenetic change in at least one of the genes in the panel is indicative of a predisposition to, or the incidence of, a gastrointestinal cancer such as colorectal cancer. The tissue sample may comprise, consist essentially of or consist of a colon and/or rectal and/or appendix sample for example.

Other DNA-containing sample which may be used in the methods of the invention include samples for diagnostic, prognostic, or personalised medicinal uses. These samples may be obtained from surgical samples, such as biopsies or fine needle aspirates, from paraffin embedded tissues, from frozen tumour tissue samples, from fresh tumour tissue samples or from a fresh or frozen body fluid, for example. Non-limiting examples include whole blood or parts/fractions thereof, bone marrow, cerebrospinal fluid, peritoneal fluid, pleural fluid, lymph fluid, serum, plasma, urine, chyle, ejaculate, sputum, nipple aspirate, saliva, swabs specimens, colon wash specimens and brush specimens. The tissues and body fluids can be collected using any suitable method, many such methods are well known in the art. Assessment of a paraffin-embedded specimen can be performed directly or on a tissue section. Tissue samples are generally taken from the tissue suspected of being tumourigenic.

In a specific embodiment, the test sample is a blood sample. Any blood sample, or derivative thereof may be utilised. The blood sample, or derivative thereof may comprise, consist essentially or whole blood or any suitable DNA containing parts/fractions thereof. In specific embodiments, the blood sample or derivative thereof comprises, consist essentially of or consists of serum or plasma. The blood sample may be collected using any suitable method, many such methods are well known in the art. In one embodiment, the methods of the invention also incorporate the step of obtaining the blood sample. Any appropriate blood sample may be utilised in the methods of the invention, provided it contains sufficient DNA.

In a specific embodiment, the volume of the blood sample, or derivative thereof that is utilised in the methods is around 5 to 15 ml, such as 10 ml.

Blood samples, or derivatives thereof, may be stored prior to use in the methods of the invention once obtained. They may be frozen for example at a suitable temperature, such as around −80° C.

It is preferred that the blood sample, or derivative thereof comprises, consists essentially of or consists of a plasma or serum sample. Plasma may be derived from whole blood by any suitable means. In one embodiment, the plasma sample is obtained by centrifugation of whole blood. Centrifugation may be carried out at any suitable speed and for any suitable period of time and under any suitable conditions as may be determined by one skilled in the art. For example, centrifugation may be carried out at between around 1000 and 3000 g. Centrifugation may be carried out for between around 1, 2, 3, 4, or 5 and 10, 11, 12, 13, 14 or 15 minutes for example. Centrifugation may be carried out at low temperatures, such as between around 0 and 5° C., for example 4° C., to maintain integrity of the sample. Multiple centrifugation steps may be employed in order to obtain the plasma sample. In a specific embodiment, two centrifugation steps are employed to obtain the plasma sample.

In embodiments where blood and in particular plasma or serum samples are utilised, the at least one gene may be selected from OSMR, SFRP1, NDRG4, GATA5, ADAM23, JPH3, SFRP2 and APC. As shown below, these genes provide sensitive and specific methods for diagnosing colorectal cancer in plasma samples. Suitable panels in this context comprise, consist essentially of or consist of OSMR, NDRG4, GATA5 and ADAM23. Additional genes which may be employed in plasma or serum based methods include TFPI2, BNIP3, FOXE1, SYNE1, SOX17, PHACTR3, and JAM3.

"Diagnosis" is defined herein to include screening for a disease or pre-indication of a disease, identifying a disease or pre-indication of a disease, monitoring the staging and the state and progression of the disease, checking for recurrence of disease following treatment and monitoring the success of a particular treatment. The methods of the invention may also have prognostic value, and this is included within the definition of the term "diagnosis". The prognostic value of the methods of the invention may be used as a marker of potential susceptibility to a number of gastrointestinal cancers such as colorectal cancer or as a marker for progression from adenoma to cancer for example. Thus patients at risk may be identified before the disease has a chance to manifest itself in terms of symptoms identifiable in the patient.

The methods of the invention may be carried out on purified or unpurified DNA-containing samples. However, in specific embodiments, DNA is isolated/extracted/purified from the sample. Any suitable DNA isolation technique may be utilised. Examples of purification techniques may be found in standard texts such as Molecular Cloning—A Laboratory Manual (Third Edition), Sambrook and Russell (see in particular Appendix 8 and Chapter 5 therein). In one embodiment, purification involves alcohol precipitation of DNA. Preferred alcohols include ethanol and isopropanol. Suitable purification techniques also include salt-based precipitation methods. Thus, in one specific embodiment the DNA purification technique comprises use of a high concentration of salt to precipitate contaminants. The salt may comprise, consist essentially of or consist of potassium acetate and/or ammonium acetate for example. The method may further include steps of removal of contaminants which have been precipitated, followed by recovery of DNA through alcohol precipitation.

In an alternative embodiment, the DNA purification technique is based upon use of organic solvents to extract contaminants from cell lysates. Thus, in one embodiment, the method comprises use of phenol, chloroform and isoamyl alcohol to extract the DNA. Suitable conditions are employed to ensure that the contaminants are separated into the organic phase and that DNA remains in the aqueous phase.

In specific embodiments of these purification techniques, extracted DNA is recovered through alcohol precipitation, such as ethanol or isopropanol precipitation.

Amplification of DNA (using PCR) from natural sources is often inhibited by co-purified contaminants and various methods adopted for DNA extraction from environmental samples are available and provide an alternative for isolating DNA from faecal or blood based samples, according to specific embodiments of the invention. For instance, the QIAamp DNA Stool Mini Kit from QIAGEN adsorbs DNA-damaging substances and PCR inhibitors present in the sample by InhibitEX. Other examples for application in particular to faecal samples include the Wizard Genomic DNA Purification Kit (Promega), the NucliSENS® easyMAG™ (Biomerieux) and nucleic acid purification kits manufactured by Macherey Nagel.

In specific embodiments, where the test sample is a blood based sample, the DNA may be isolated by phenol-chloroform extraction since this has been shown to provide particularly high levels of DNA recovery from the sample.

Where blood based test samples are employed, the ChargeSwitch procedure may be utilised for example.

Suitable methods and kits for isolating DNA from blood samples are commercially available. Examples, each of which may be utilised in the methods of the invention are provided in the table below.

TABLE 1

Kits and methods for isolating DNA from blood samples.

| Kit | Company | Method |
| --- | --- | --- |
| UltraClean-htp ™ BloodSpin ™ DNA | Mo Bio Laboratories, Inc. | Silica-membrane |
| PAXgene Blood DNA Kit | Qiagen | isopropanol |
| QIAamp DNA Blood Maxi/Mini Kit | Qiagen | Silica-membrane |
| FlexiGene DNA Kit | Qiagen | isopropanol |
| GeneCatcher gDNA 3-10 ml Blood | Invitrogen | magnetic beads |
| BC-204-10 ml-blood - Blood 10 ml | Baseclear | magnetic beads |
| ZR Genomic DNA I Kit | Zymo research | magnetic beads |
| DNAzol BD | MRC, Inc. | isopropanol |
| Gentra pureGene* DNA Purification Blood | Fischer | isopropanol |
| MasterPure Whole Blood DNA | Epicentre Biotech. | isopropanol |
| Invisorb ® Blood Giga Kit | Westburg | isopropanol |
| 100436-10 (Maxi) | Bioron | Silica-membrane |
| MagNA Pure LC DNA Isolation Kit | Roche | magnetic beads |
| Nuclisens EasyMag | Biomérieux | magnetic beads |
| chemagic blood kit special | chemagen | magnetic beads |

The QIAamp DNA Blood Maxi kit available from Qiagen and the GeneCatcher gDNA kit from Invitrogen both utilise plasma or serum as starting material.

Thus, as can be derived from table 1, DNA isolation may be carried out using silica-membranes, isopropanol or magnetic bead based methods for example.

The methods of the invention may also, as appropriate, incorporate quantification of isolated/extracted/purified DNA in the sample. Quantification of the DNA in the sample may be achieved using any suitable means. Quantitation of nucleic acids may, for example, be based upon use of a spectrophotometer, a fluorometer or a UV transilluminator. Examples of suitable techniques are described in standard texts such as Molecular Cloning—A Laboratory Manual (Third Edition), Sambrook and Russell (see in particular Appendix 8 therein). In one embodiment, kits such as the Picogreen dsDNA quantitation kit available from Molecular Probes, Invitrogen may be employed to quantify the DNA.

"Cancer" is defined herein to include neoplasias. Neoplasia refers to abnormal new growth and thus means the same as tumor, which may be benign or malignant. Particular cancer types which are relevant in accordance with the present invention are discussed above and include those selected from neoplasias of the gastrointestinal tract. Specific examples include colorectal cancer, oesophageal cancer, stomach cancer and gastric cancer.

"Colorectal cancer", also called colon cancer or bowel cancer, is defined to include cancerous growths in the colon, rectum and appendix. Specific markers and panels of markers, as described in greater detail herein, may be particularly applicable to certain cancer types.

Other cancer types which may be relevant in specific (but not all) embodiments of the invention include prostate cancer, breast cancer, ovarian cancer and thyroid cancer.

"Epigenetic silencing" is defined herein to include any alteration in the DNA resulting in diminished gene expression which is mediated by mechanisms other than alterations in the primary nucleotide sequence of a gene. Epigenetic modifications may, in certain circumstances be stable heritable traits. A number of related mechanisms that cause alteration in gene expression are recognised and include DNA methylation, histone changes (for example changes in histone acetylation) which may lead to chromatin remodelling and RNA interference. In many cases, hypermethylation of DNA incorrectly switches off critical genes allowing cancers to develop and progress.

Epigenetic silencing of, or an epigenetic change such as methylation in, the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may manifest itself before abnormal new growth/cancer is observable. A subject may be undergoing routine screening and may not necessarily be suspected of having a disease such as a colon neoplasia. Detecting epigenetic silencing of the gene or genes in an adenoma of such a subject may indicate that the probable course of the adenoma is development to a carcinoma and thus there is a predisposition to neoplasia. In such cases, preventive treatment may be recommended and involve resection of the advanced adenoma.

These methods may advantageously involve detection of methylation of the NDRG4 gene, in particular using primer set 1, as discussed herein.

"Advanced adenoma" refers to an adenoma in which epigenetic silencing of at least one of the gene linked to colorectal cancer is observed, preferably epigenetic silencing such as methylation of the gene or genes of the invention (such as NDRG4 etc.) is detected.

The most preferred epigenetic change in the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) which is detected comprises, consists essentially of or consists of methylation. In particular, aberrant methylation, which may be referred to as hypermethylation, of the gene or genes is detected. Typically, the methylation status is determined in suitable CpG islands which are often found in the promoter region of the gene(s). The term "methylation", "methylation state" or "methylation status" refers to the presence or absence of 5-methylcytosine ("5-mCyt") at one or a plurality of CpG dinucleotides within a DNA sequence. CpG dinucleotides are typically concentrated in the promoter regions and exons of human genes.

Diminished gene expression can be assessed in terms of DNA methylation status or in terms of expression levels as determined by the methylation status of the gene. One method to detect epigenetic silencing is to determine that a gene which is expressed in normal cells is less expressed or not expressed in tumor cells. Accordingly, the invention provides for a method of diagnosing cancer or predisposition to cancer comprising detecting epigenetic silencing of the NDRG4/NDRG2 subfamily gene, wherein epigenetic silencing of the NDRG2/NDRG4-family gene is determined by measurement of expression levels of the gene and wherein reduced expression of the gene is indicative for cancer or predisposition to cancer. The invention also provides a method of detecting a predisposition to, or the incidence of, a cancer in particular a gastrointestinal cancer such as colorectal cancer in a sample comprising detecting an epigenetic change in at least one gene selected from GATA4, OSMR, NDRG4 (or another NDRG4/NDRG2 subfamily member), GATA5, SFRP1, ADAM23, JPH3, SFRP2, APC and, MGMT and/or at least one gene selected from, TFPI2, BNIP3, FOXE1, SYNE1, SOX17, PHACTR3 and JAM3, wherein detection of the epigenetic change is determined by measuring expression levels of the at least one gene and wherein low level, reduced level or a lack of expression of the at least one gene is indicative of a predisposition to, or the incidence of, cancer and in particular a gastrointestinal cancer such as colorectal cancer.

In embodiments where blood and in particular plasma or serum samples are utilised, the at least one gene may be selected from OSMR, SFRP1, NDRG4, GATA5, ADAM23, JPH3, SFRP2 and APC and/or from TFPI2, BNIP3, FOXE1, SYNE1, SOX17, PHACTR3 and JAM3. These genes are also useful where faecal test samples are employed. TFPI2 may be a particularly useful marker. Specific genes such as genes selected from TPF12, BNIP3, FOXE1, SYNE1 and SOX17 may be most useful when plasma samples are employed. For stool samples genes such as GATA4, OSMR, NORG4, GATA5, SFRP1, ADAM23, JPH3, SFRP2, APC and MGMT and also genes selected from TFPI2, FOXE1, SYNE1, SOX17, PHACTR3 and JAM3 may usefully be employed. As shown below, these genes provide sensitive and specific methods for diagnosing colorectal cancer in plasma samples. Suitable panels in this context comprise, consist essentially of or consist of OSMR, NDRG4, GATA5 and ADAM23. Further panels are discussed below. This may be utilised in order to diagnose early stage colorectal cancer, in particular stage 0 to II colorectal cancer.

In embodiments in which tissue samples are utilised, the method preferably comprises, consists essentially of or consists of detecting an epigenetic change in a panel of genes comprising OSMR, GATA4 and ADAM23 or OSMR, GATA4 and GATA5, wherein detection of the epigenetic change in at least one of the genes in the panel is indicative of a predisposition to, or the incidence of, a gastrointestinal cancer such as colorectal cancer. The tissue sample may comprise, consist essentially of or consist of a colon and/or rectal and/or appendix sample for example.

In specific embodiments, total loss of protein expression of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is observed in the sample in order to conclude a diagnosis of cancer and in particular a gastrointestinal cancer such as colorectal cancer or predisposition to cancer and in particular a gastrointestinal cancer such as colorectal cancer, or to make a decision on the best course of treatment in accordance with the other methods of the invention, as described herein (which description applies here mutatis mutandis). However, partial loss of expression of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may also be relevant, due to methylation of the relevant gene or genes.

The decreased level of expression of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may, as necessary, be measured in order to determine if it is statistically significant in the sample. This helps to provide a reliable test for the methods of the invention. Any method for determining whether the expression level of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is significantly reduced may be utilised. Such methods are well known in the art and routinely employed. For example, statistical analyses may be performed. One example involves an analysis of variance test. Typical P values for use in such a method would be P values of <0.05 or 0.01 or 0.001 when determining whether the relative expression or activity is statistically significant. A change in expression may be deemed significant if there is at least a 10% decrease for example. The test may be made more selective by making the change at least 15%, 20%, 25%, 30%, 35%, 40% or 50%, for example, in order to be considered statistically significant.

In a specific embodiment of the methods of the invention, the decreased level of expression or activity of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is determined with reference to a control sample. This control sample is preferably taken from normal (i.e. non-tumorigenic) tissue in the subject, where expression of the corresponding gene or genes is normal. Additionally, or alternatively, control samples may also be utilised in which there is known to be a lack of expression of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein).

Suitable additional controls may also be included to ensure that the test is working properly, such as measuring levels of expression or activity of a suitable reference gene in both test and control samples. Suitable reference genes for the present invention include beta-actin, glyceraldehyde-3-phosphate dehydrogenase (GAPDH), ribosomal RNA genes such as 18S ribosomal RNA and RNA polymerase II gene (Radonic A. et al., Biochem Biophys Res Commun. 2004 January 23; 313(4):856-62). In specific embodiments, the reference gene is beta-actin.

Expression of a nucleic acid can be measured at the RNA level or at the protein level. Cells in test samples can be lysed and the mRNA levels in the lysates, or in the RNA purified or semi-purified from the lysates, determined. Alternatively, methods can be used on unlysed tissues or cell suspensions. Suitable methods for determining expression of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) at the RNA level are well known in the art and described herein.

Methods employing nucleic acid probe hybridization to the relevant transcript(s) of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may be employed for measuring the presence and/or level of the respective mRNA. Such methods are well known in the art and include use of nucleic acid probe arrays (microarray technology) and Northern blots. Advances in genomic technologies now permit the simultaneous analysis of thousands of genes, although many are based on the same concept of specific probe-target hybridization. Sequencing-based methods are an alternative. These methods started with the use of expressed sequence tags (ESTs), and now include methods based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

In certain embodiments, the levels of gene expression of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) are determined using reverse transcriptase polymerase chain reaction (RT-PCR). RT-PCR is a well-known technique in the art which relies upon the enzyme reverse transcriptase to reverse transcribe mRNA to form cDNA, which can then be amplified in a standard PCR reaction. Protocols and kits for carrying out RT-PCR are extremely well known to those of skill in the art and are commercially available.

In one embodiment, primers useful in RT-PCR carried out on the NDRG4 gene are provided. These primers comprise, consist essentially of or consist of the following sequences:

```
                                       SEQ ID NO: 1
  5'-cctgaggagaagccgctg-3' (forward)

SEQ ID NO: 2
  5'-atgtcatgttccttccagtctgt-3' (reverse)

SEQ ID NO: 3
  5'-GGCCTTCTGCATGTAGTGATCCG-3' (forward)

SEQ ID NO: 4
  5'-GGTGATCTCCTGCATGTCCTCG-3' (reverse)
```

Variants of these primers are included within the scope of the invention, as defined herein which definition applies mutatis mutandis.

The RT-PCR can be carried out in a non-quantitative manner. End-point RT-PCR measures changes in expression levels using three different methods: relative, competitive and comparative. These traditional methods are well known in the art. Alternatively, RT-PCR is carried out in a real time and/or in a quantitative manner. Real time quantitative RT-PCR has been thoroughly described in the literature (see Gibson et al for an early example of the technique) and a variety of techniques are possible. Examples include use of hydrolytic probes (Taqman), hairpin probes (Molecular Beacons), FRET probe pairs (LightCycler (Roche)), hairpin probes attached to primers (Scorpion), hairpin primers (Plexor and Amplifluor), DzyNA and oligonucleotide blocker systems. All of these systems are commercially available and well characterised, and may allow multiplexing (that is, the determination of expression of multiple genes in a single sample).

TAQMAN was one of the earliest available real-time PCR techniques and relies upon a probe which binds between the upstream and downstream primer binding sites in a PCR reaction. A TAQMAN probe contains a 5' fluorophore and a 3' quencher moiety. Thus, when bound to its binding site on the DNA the probe does not fluoresce due to the presence of the quencher in close proximity to the fluorophore. During amplification, the 5'-3' exonuclease activity of a suitable polymerase such as Taq digests the probe if it is bound to the strand being amplified. This digestion of the probe causes displacement of the fluorophore. Release of the fluorophore means that it is no longer in close proximity to the quencher moiety and this therefore allows the fluorophore to fluoresce. The resulting fluorescence may be measured and is in direct proportion to the amount of target sequence that is being amplified. These probes are sometimes generically referred to as hydrolytic probes.

In the Molecular Beacons system, the probe is again designed to bind between the primer binding sites. However, here the probe is a hairpin shaped probe. The hairpin in the probe when not bound to its target sequence means that a fluorophore attached to one end of the probe and a quencher attached to the other end of the probe are brought into close proximity and therefore internal quenching occurs. Only when the target sequence for the probe is formed during the PCR amplification does the probe unfold and bind to this sequence. The loop portion of the probe acts as the probe itself, while the stem is formed by complimentary arm sequences (to respective ends of which are attached the fluorophore and quencher moiety). When the beacon probe detects its target, it undergoes a conformational change forcing the stem apart and this separates the fluorophore and quencher. This causes the energy transfer to the quencher to be disrupted and therefore restores fluorescence.

During the denaturation step, the Molecular Beacons assume a random-coil configuration and fluoresce. As the temperature is lowered to allow annealing of the primers, stem hybrids form rapidly, preventing fluorescence. However, at the annealing temperature, Molecular Beacons also bind to the amplicons, undergo conformational reorganisation, leading to fluorescence. When the temperature is raised to allow primer extension, the Molecular Beacons dissociate from their targets and do not interfere with polymerisation. A new hybridisation takes place in the annealing step of every cycle, and the intensity of the resulting fluorescence indicates the amount of accumulated amplicon.

Scorpions primers are based upon the same principles as Molecular Beacons. However, here, the probe is bound to, and forms an integral part of, an amplification primer. The probe has a blocking group at its 5' end to prevent amplification through the probe sequence. After one round of amplification has been directed by this primer, the target sequence for the probe is produced and to this the probe binds. Thus, the name "scorpion" arises from the fact that the probe as part of an amplification product internally hybridises to its target sequence thus forming a tail type structure. Probe-target binding is kinetically favoured over intrastrand secondary structures. Scorpions primers were first described in the paper "Detection of PCR products using self-probing amplicons and fluorescence" (Nature Biotechnology. 17, p804-807 (1999)) and numerous variants on the basic theme have subsequently been produced.

In similar fashion to Scorpions primers, Amplifluor primers rely upon incorporation of a Molecular Beacon type probe into a primer. Again, the hairpin structure of the probe forms part of an amplification primer itself. However, in contrast to Scorpions type primers, there is no block at the 5' end of the probe in order to prevent it being amplified and forming part of an amplification product. Accordingly, the primer binds to a template strand and directs synthesis of the complementary strand. The primer therefore becomes part of the amplification product in the first round of amplification. When the complimentary strand is synthesised amplification occurs through the hairpin structure. This separates the fluorophore and quencher molecules, thus leading to generation of florescence as amplification proceeds.

DzyNA primers incorporate the complementary/antisense sequence of a 10-23 nucleotide DNAzyme. During amplification, amplicons are produced that contain active (sense) copies of DNAzymes that cleave a reporter substrate included in the reaction mixture. The accumulation of amplicons during PCR/amplification can be monitored in real time by changes in fluorescence produced by separation of fluorophore and quencher dye molecules incorporated into opposite sides of a DNAzyme cleavage site within the reporter substrate. The DNAzyme and reporter substrate sequences can be generic and hence can be adapted for use with primer sets targeting various genes or transcripts (Todd et al., Clinical Chemistry 46:5, 625-630 (2000)).

The Plexor™ qPCR and qRT-PCR Systems take advantage of the specific interaction between two modified nucleotides to achieve quantitative PCR analysis. One of the PCR primers contains a fluorescent label adjacent to an iso-dC residue at the 5' terminus. The second PCR primer is unlabeled. The reaction mix includes deoxynucleotides and iso-dGTP modified with the quencher dabcyl. Dabcyl-iso-dGTP is preferentially incorporated at the position complementary to the iso-dC residue. The incorporation of the dabcyl-iso-dGTP at this position results in quenching of the fluorescent dye on the complementary strand and a reduction in fluorescence, which allows quantitation during amplification. For these multiplex reactions, a primer pair with a different fluorophore is used for each target sequence.

Real time quantitative techniques for use in the invention generally produce a fluorescent read-out that can be continuously monitored. Fluorescence signals are generated by dyes that are specific to double stranded DNA, like SYBR Green, or by sequence-specific fluorescently-labeled oligonucleotide primers or probes. Each of the primers or probes can be labelled with a different fluorophore to allow specific detection. These real time quantitative techniques are advantageous because they keep the reaction in a "single tube". This means there is no need for downstream analysis in order to obtain results, leading to more rapidly obtained results. Furthermore, keeping the reaction in a "single tube" environment reduces the risk of cross contamination and allows a quantitative output from the methods of the invention. This may be particularly important in a clinical setting for the present invention.

It should be noted that whilst PCR is a preferred amplification method, to include variants on the basic technique such as nested PCR, equivalents may also be included within the scope of the invention. Examples include without limitation isothermal amplification techniques such as NASBA, 3 SR, TMA and triamplification, all of which are well known in the art and commercially available. Other suitable amplification methods without limitation include the ligase chain reaction (LCR) (Barringer et al, 1990), MLPA, selective amplification of target polynucleotide sequences (U.S. Pat. No. 6,410,276), consensus sequence primed polymerase chain reaction (U.S. Pat. No. 4,437,975), invader technology (Third Wave Technologies, Madison, Wis.), strand displacement technology, arbitrarily primed polymerase chain reaction (WO90/06995) and nick displacement amplification (WO2004/067726).

Suitable methods for determining expression of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) at the protein level are also well known to one of skill in the art. Examples include western blots, immunohistochemical staining and immunolocalization, immunofluorescence, enzyme-linked immunosorbent assay (ELISA), immunoprecipitation assays, complement fixation assay, agglutination reactions, radioimmunoassay, flow cytometry, mass spectrophotometry, and equilibrium dialysis. These methods generally depend upon a reagent specific for identification of the appropriate gene product. Any suitable reagent may be utilised such as lectins, receptors, nucleic acids, antibodies etc. The reagent is preferably an antibody and may comprise monoclonal or polyclonal antibodies. Fragments and derivatized antibodies may also be utilised, to include without limitation Fab fragments, ScFv, single domain antibodies, nano-antibodies, heavy chain antibodies, aptamers etc. which retain gene product binding function. Any detection method may be employed in accordance with the invention. Proteins may be identified on the basis of charge, polarity, amino acid sequence etc. by a range of methods, including SDS-PAGE and amino acid sequencing for example. The nature of the reagent is not limited except that it must be capable of specifically identifying the appropriate gene product.

Of course, in the case of a positive diagnosis of cancer and in particular gastrointestinal cancer such as colorectal cancer, there will be reduced levels of the relevant protein, and perhaps no protein at all. In one embodiment this will present a negative result, if the protein specific reagent is one which binds to the wild type or full length protein. In this case, use of suitable controls ensures that false diagnoses will not be made, for example caused by degraded or non-specific reagents. Thus, the same reagent can be tested on samples in which it is known that the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is expressed at the protein level. A positive result in this control sample, combined with a negative result in the test sample provides a confident diagnosis of cancer and removes any doubt over the quality of the reagent.

Measurement of expression of a gene on its own may not necessarily conclusively indicate that the silencing is epigenetic, as the mechanism of silencing could be genetic, for example, by somatic mutation. Accordingly, in one embodiment, the methods of the invention incorporate an appropriate re-expression assay which is designed to reverse epigenetic silencing. Appropriate treatment of the sample using a demethylating agent, such as a DNA-methyltransferase (DMT) inhibitor may reverse epigenetic silencing of the relevant gene. Suitable reagents include, but are not limited to, DAC (5'-deazacytidine), TSA or any other treatment affecting epigenetic mechanisms present in cell lines. Suitable reagents are discussed herein with respect to the pharmacogenetic and treatment aspects of invention, which discussion applies mutatis mutandis. Typically, expression is reactivated or reversed upon treatment with such reagents, indicating that the silencing is epigenetic.

As discussed in the experimental section, epigenetic silencing resulting in diminished expression of the NDRG4/NDRG2 subfamily gene has been shown in a range of gastrointestinal cancers such as colorectal cancer and gastric cancer. Thus, in one embodiment, the invention provides for a method of diagnosing colorectal cancer and/or gastric cancer or another gastrointestinal cancer as defined herein, predisposition to colorectal cancer and/or gastric cancer or another gastrointestinal cancer as defined herein, comprising detecting epigenetic silencing of the NDRG4/NDRG2 subfamily gene, wherein epigenetic silencing of the NDRG2/NDRG4-family gene is determined by measurement of expression levels of the gene and wherein reduced expression of the gene is indicative for colorectal cancer and/or gastric cancer or another gastrointestinal cancer as defined herein, predisposition to colorectal cancer and/or gastric cancer or another gastrointestinal cancer as defined herein, or progression of adenoma to carcinoma. Preferably, the gene is NDRG2, or NDRG4, or a combination of NDRG2 and NDRG4.

As exemplified in the experimental section, epigenetic silencing resulting in diminished expression of the at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3 has been shown to be sensitively and specifically linked with the incidence of gastrointestinal cancer and in particular colorectal cancer. Thus, in a further embodiment, the invention provides for a method of diagnosing gastrointestinal cancer and in particular colorectal cancer or predisposition to gastrointestinal cancer and in particular colorectal cancer comprising detecting epigenetic silencing of at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3, wherein epigenetic silencing of the at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3 is determined by measurement of expression levels of the gene and wherein reduced expression of the gene is indicative for gastrointestinal cancer and in particular colorectal cancer, predisposition to gastrointestinal cancer and in particular colorectal cancer, or progression of adenoma to carcinoma. These markers may usefully be employed when faecal test samples are utilised.

As is also discussed in the experimental section, epigenetic silencing resulting in diminished expression of the at least one gene selected from GATA4, OSMR, NDRG4, GATA5, SFRP1, ADAM23, JPH3, SFRP2, APC and MGMT has been shown to be sensitively and specifically linked with the incidence of colorectal cancer in specific tissue and bodily fluid, such as faecal and blood-based samples. Thus, in one specific embodiment, the invention provides for a method of diagnosing gastrointestinal cancer and in particular colorectal cancer or predisposition to gastrointestinal cancer and in particular colorectal cancer comprising detecting epigenetic silencing of at least one gene selected from GATA4, OSMR, NDRG4, GATA5, SFRP1, ADAM23, JPH3, SFRP2, APC and MGMT in a tissue, faecal or a blood (plasma or serum) sample, or derivative thereof, wherein epigenetic silencing of the at least one gene selected from GATA4, OSMR, NDRG4, GATA5, SFRP1, ADAM23, JPH3, SFRP2, APC and MGMT is determined by measurement of expression levels of the gene and wherein reduced expression of the gene is indicative for gastrointestinal cancer and in particular colorectal cancer, predisposition to gastrointestinal cancer and in particular colorectal cancer, or progression of adenoma to carcinoma. As discussed above, where plasma or serum samples are utilised, the at least one gene may be selected from OSMR, SFRP1, NDRG4, GATA5, ADAM23, JPH3, SFRP2 and APC.

In alternative and complementary embodiments, in particular where bodily fluid such as faecal and plasma samples are utilised the at least one gene may be selected from TFPI2, BNIP3, FOXE1, SYNE1, SOX17, PHACTR3 and JAM3. Panels may be selected from these genes and the other genes of the invention as desired and as discussed herein. Methylation of these genes in stool and plasma samples has been shown for the first time herein to be linked to colorectal cancer. Particularly useful markers, which give good levels of sensitivity and specificity in both plasma and faecal samples include TFPI2, FOXE1, SYNE1, SOX17, PHACTR3 and JAM3. TFPI2 may be particularly useful. Certain genes such as those selected from TFPI2, BNIP3, FOXE1, SYNE1 and SOX17 may prove most useful when testing plasma samples. This discussion applies to all aspects of the invention as appropriate.

It is noted that the expression of additional genes may also be determined in order to supplement the methods of the invention. In fact, any gene involved in the establishment of cancer, as defined herein and in particular gastrointestinal cancers such as colorectal cancer, gastric cancer and/or oesophageal cancer, may be utilized in combination with the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in the methods of present invention. In certain embodiments, the expression level of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is analysed in combination with at least one other gene involved in the establishment of cancer. In one embodiment, at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is combined with at least two other genes involved in the establishment of cancer. In a further embodiment at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) and at least three, four, five or six other genes involved in the establishment of cancer are combined. Other genes involved in the establishment of (colorectal) cancer may be selected from the group consisting of CHFR, p16, Vimentin, p14, RASSF1a, RAB32, SEPTIN-9, RASSF2A, TMEFF2, NGFR and SMARCA3.

Since epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) manifests itself in methylation of the gene, the methods of the invention preferably involve detecting gene methylation. Accordingly, the invention provides a method of diagnosing cancer or predisposition to cancer, in particular gastrointestinal cancers such as colorectal cancer comprising detecting epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein epigenetic silencing of the at least one gene is detected by determination of the methylation status of the at least one gene and wherein methylation of the at least one gene is indicative for cancer or predisposition to cancer, as defined above and in particular gastrointestinal cancers such as colorectal cancer.

In embodiments where blood and in particular plasma or serum samples are utilised, the at least one gene may be selected from OSMR, SFRP1, NDRG4, GATA5, ADAM23, JPH3, SFRP2 and APC. As shown below, these genes provide sensitive and specific methods for diagnosing colorectal cancer in plasma samples. Suitable panels in this context comprise, consist essentially of or consist of OSMR, NDRG4, GATA5 and ADAM23. This may be utilised in order to diagnose early stage colorectal cancer, in particular stage 0 to II colorectal cancer. Additionally, or alternatively, the at least one gene may be selected from TFPI2, BNIP3, FOXE1, SYNE1, SOX17, PHACTR3 and JAM3, such as from TFPI2, BNIP3, FOXE1, SYNE1 and SOX17, in particular TFPI2.

In embodiments in which tissue samples are utilised, the methods may comprise, consist essentially of or consist of detecting an epigenetic change in a panel of genes comprising OSMR, GATA4 and ADAM23 or OSMR, GATA4 and GATA5, wherein detection of the epigenetic change in at least one of the genes in the panel is indicative of a predisposition to, or the incidence of, colorectal cancer. The tissue sample may comprise, consist essentially of or consist of a colon and/or rectal and/or appendix sample.

In embodiments where faecal samples are employed, the at least one gene may be selected from GATA4, OSMR, NDRG4, GATA5, SERP1, ADAM23, JPH3, SFRP2, APC and MGMT. In addition, or alternatively, the at least one gene may be selected from TFPI2, BNIP3, FOXE1, SYNE1, SOX17, PHACTR3, and JAM3, such as from TFPI2, FOXE1, SYNE1, SOZ17, PHACTR3 and JAM3, in particular TFPI2. Two, three, four, five or six etc. gene panels selected from these genes are also envisaged in the present invention.

CpG dinucleotides susceptible to methylation are typically concentrated in the promoter region, exons and introns of human genes. Promoter, exon and intron regions can be assessed for methylation. In one embodiment, the methylation status of the promoter region of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is determined. A "promoter" is a region extending typically between approximately 1 Kb, 500 bp or 150 to 300 bp upstream from the transcription start site. Frequently, the CpG island surrounding or positioned around the transcription start site of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is analysed to determine its methylation status. Alternatively, the methylation status of the exon and/or intron regions of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may be determined as appropriate.

In one embodiment of the methods of the invention, the methylation status of the promoter region of the NDRG4 gene is analysed. In another embodiment, the methylation status of the promoter region of the NDRG2 gene is analysed. Alternatively, the promoter region of NDRG2 and NDRG4 are analysed simultaneously.

In one embodiment, the region of the NDRG4/NDRG2 subfamily gene comprising, consisting essentially of, or consisting of the nucleotide sequence of NDRG4 as set forth as SEQ ID NO: 524 (FIG. 3a) and/or the nucleotide sequence of NDRG2 as set forth as SEQ ID NO: 525 (FIG. 3b) is analysed in order to determine its methylation status.

Various methylation assay procedures are known in the art, and can be used in conjunction with the present invention. These assays rely onto two distinct approaches: bisulphite conversion based approaches and non-bisulphite based approaches. Non-bisulphite based methods for analysis of DNA methylation rely on the inability of methylation-sensitive enzymes to cleave methylation cytosines in their restriction. The bisulphite conversion relies on treatment of DNA samples with sodium bisulphite which converts unmethylated cytosine to uracil, while methylated cytosines are maintained (Furuichi et al., 1970). This conversion results in a change in the sequence of the original DNA.

DNA methylation analysis has been performed successfully with a number of techniques including: sequencing, methylation-specific PCR (MS-PCR), melting curve methylation-specific PCR (McMS-PCR), MLPA with or without bisulfite treatment, QAMA (Zeschnigk et al, 2004), MSRE-PCR (Melnikov et al, 2005), MethyLight (Eads et al., 2000), ConLight-MSP (Rand et al., 2002), bisulfite conversion-specific methylation-specific PCR (BS-MSP)(Sasaki et al., 2003), COBRA (which relies upon use of restriction enzymes to reveal methylation dependent sequence differences in PCR products of sodium bisulfite-treated DNA), methylation-sensitive single-nucleotide primer extension conformation (MS-SNuPE), methylation-sensitive single-strand conformation analysis (MS-SSCA), Melting curve combined bisulfite restriction analysis (McCOBRA)(Akey et al., 2002), PyroMethA, HeavyMethyl (Cottrell et al. 2004), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR. A review of some useful techniques is provided in Nucleic acids research, 1998, Vol. 26, No. 10, 2255-2264, Nature Reviews, 2003, Vol. 3, 253 266; Oral Oncology, 2006, Vol. 42, 5-13, which references are incorporated herein in their entirety. Any of these techniques may be utilised in accordance with the present invention, as appropriate.

Additional methods for the identification of methylated CpG dinucleotides utilize the ability of the methyl binding domain (MBD) of the MeCP2 protein to selectively bind to methylated DNA sequences (Cross et al, 1994; Shiraishi et al, 1999). Alternatively, the MBD may be obtained from MBP, MBP2, MBP4 or poly-MBD (Jorgensen et al., 2006). In one method, restriction exonuclease digested genomic DNA is loaded onto expressed His-tagged methyl-CpG binding domain that is immobilized to a solid matrix and used for preparative column chromatography to isolate highly methylated DNA sequences. Such methylated DNA enrichment-step may supplement the methods of the invention. Several other methods for detecting methylated CpG islands are well known in the art and include amongst others methylated-CpG island recovery assay (MIRA). Any of these methods may be employed in the present invention where desired.

In specific embodiments, the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) (or portion thereof, especially the CpG islands, as discussed herein) is determined using methylation specific PCR (MSP), or an equivalent amplification technique. The MSP technique will be familiar to one of skill in the art. In the MSP approach, DNA may be amplified using primer pairs designed to distinguish methylated from unmethylated DNA by taking advantage of sequence differences as a result of sodium-bisulphite treatment (Herman et al., 1996; and WO 97/46705).

A specific example of the MSP technique is designated real-time quantitative MSP (QMSP), which permits reliable quantification of methylated DNA in real time. These methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labelled primers and/or labelled probes can be used. They represent a specific application of the well known and commercially available real-time amplification techniques such as hydrolytic probes (TAQMAN®), hairpin probes (MOLECULAR BEACONS®), hairpin primers (AMPLIFLUOR®), hairpin probes integrated into primers (SCORPION®), oligonucleotide blockers (such as the HeavyMethyl technique) and primers incorporating complementary sequences of DNAzymes (DzyNA®), specific interatction between two modified nucleotides (Plexor™) etc as described in more detail herein. Often, these real-time methods are used with the polymerase chain reaction (PCR). In Heavymethyl, described for example in WO02/072880 the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. Heavymethyl can be used in combination with real-time or end point detection in the methods of the invention.

Thus, in specific embodiments, the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is determined by methylation specific PCR/amplification, preferably real-time methylation specific PCR/amplification. In specific embodiments, the real time PCR/amplification involves use of hairpin primers (Amplifluor)/hairpin probes (Molecular Beacons)/hydrolytic probes (Taqman)/FRET probe pairs (Lightcycler)/primers incorporating a hairpin probe (Scorpion)/primers incorporating complementary sequences of DNAzymes that cleave a reporter substrate included in the reaction mixture (DzyNA®)/fluorescent dyes (SYBR Green etc.)/oligonucleotide blockers/the specific interaction between two modified nucleotides (Plexor). Primers and/or probes can be used to investigate the methylation status of the at least one gene.

Real-Time PCR detects the accumulation of amplicon during the reaction. Real-time methods do not need to be utilised, however. Many applications do not require quantification and Real-Time PCR is used principally as a tool to obtain convenient results presentation and storage, and at the same time to avoid post-PCR handling. Analyses can be performed only to know if the target DNA is present in the sample or not. End point verification is carried out after the amplification reaction has finished. This knowledge can be used in a medical diagnostic laboratory to detect a predisposition to, or the incidence of, cancer in a patient. In the majority of such cases, the quantification of DNA template is not very important. Amplification products may simply be run on a suitable gel, such as an agarose gel, to determine if the expected sized products are present. This may involve use of ethidium bromide staining and visualisation of the DNA bands under a UV illuminator for example. Alternatively, fluorescence or energy transfer can be measured to determine the presence of the methylated DNA. The endpoint PCR fluorescence detection technique can use the same approaches as widely used for Real Time PCR: TaqMan assay, Molecular Beacons, Scorpion, Amplifluor etc. For example, «Gene» detector allows the measurement of fluorescence directly in PCR tubes.

In real-time embodiments, quantitation may be on an absolute basis, or may be relative to a constitutively methylated DNA standard, or may be relative to an unmethylated DNA standard. Methylation status may be determined by using the ratio between the signal of the marker under investigation and the signal of a reference gene where methylation status is known (such as β-actin for example), or by using the ratio between the methylated marker and the sum of the methylated and the non-methylated marker. Alternatively, absolute copy number of the methylated marker gene can be determined. Suitable reference genes for the present invention include beta-actin, glyceraldehyde-3-phosphate dehydrogenase (GAPDH), ribosomal RNA genes such as 18S ribosomal RNA and RNA polymerase II gene (Radonic A. et al., Biochem Biophys Res Commun. 2004 January 23; 313(4):856-62). In a particularly preferred embodiment, the reference gene is beta-actin.

In one embodiment, each clinical sample is measured in duplicate and for both Ct values (cycles at which the amplification curves crossed the threshold value, set automatically by the relevant software) copy numbers are calculated. The average of both copy numbers (for each gene) is used for the result classification. To quantify the final results for each sample two standard curves are used, one for either the reference gene (β-actin or the non-methylated marker for example) and one for the methylated version of the marker. The results of all clinical samples (when m-Gene was detectable) are expressed as 1000 times the ratio of "copies m-Gene"/"copies reference gene" or "copies m-Gene"/"copies u-Gene+m-Gene" and then classified accordingly (methylated, non-methylated or invalid) (u=unmethylated; m=methylated).

In one embodiment, primers useful in MSP carried out on the promoter region of the NDRG4 gene are provided. These primers comprise, consist essentially of or consist of the following sequences:

TABLE 2

| SEQ ID NO. | NDRG4 | Primer | Sense primer | SEQ ID NO. | Antisense primer | Annealing temp | Number of PCR cycles |
| --- | --- | --- | --- | --- | --- | --- | --- |
| 5 | Primer set 1 | Flank | GGTTYGTTYGGGA TTAGTTTTAGG | 6 | CRAACAACCAAA AACCCCTC | 56 | 35 |
| 7 | Primer set 1 | U | GATTAGTTTTAGG TTTGGTATTGTTTT GT | 8 | AAAACCAAACTA AAAACAATACAC CA | 66 | 25 |
| 9 | Primer set 1 | M | TTTAGGTTCGGTA TCGTTTCGC | 10 | CGAACTAAAAAC GATACGCCG | 66 | 25 |
| 11 | Primer set 2 | Flank | ATYGGGGTGTTTT TTAGGTTT | 12 | ATACCRAACCTA AAACTAATCCC | 56 | 35 |
| 13 | Primer set 2 | U | GGGTGTTTTTTAG GTTTCGCGTCGC | 14 | CCTAAAACTAATC CCAAACAAACCA | 66 | 30 |
| 15 | Primer set 2 | M | TTTTTTAGGTTTC GCGTCGC | 16 | AAACTAATCCCG AACGAACCG | 66 | 30 |

Where "Flank" = Flanking primers
"U" = Unmethylated NDRG4 specific primers
"M" = Methylated NDRG4 specific primers Primer set 1 is useful in particular applications for predicting the progression of adenomas.

Primer set 2 may provide slightly more sensitive results although both primer sets are clearly useful.

In a further embodiment, primers and probes useful in quantitative MSP carried out on the (promoter region of the) NDRG4 gene are provided. These primers and probes comprise, consist essentially of or consist of the following sequences:

```
                                          SEQ ID NO: 17
5'-GTATTTTAGTCGCGTAGAAGGC-3' (forward primer)

SEQ ID NO: 18
5'-AATTTAACGAATATAAACGCTCGAC-3' (reverse primer)
and
                                          SEQ ID NO: 19
5'-FAM-CGACATGCCCGAACGAACCGCGATCCCTGCATGTCG-3'-
DABCYL (molecular beacon probe)
```

Further characteristics of these primers and probes are summarized in the experimental part.

In a further embodiment, primers useful in MSP carried out on the promoter region of the NDRG2 gene are provided. These primers comprise, consist essentially of or consist of the following sequences:

```
Flanking primers:
                                          SEQ ID NO: 20
5'-YGTTTTTATTTATAGYGGTTTTT-3' (flank up)

SEQ ID NO: 21
5'-TCCTAATACCTCTCCTCTCTTTACTAC-3' (flank down)

Unmethylated NDRG2 specific primers:
                                          SEQ ID NO: 22
5'-TTTTATTTATAGTGGTTTTTTGTATTTTTT-3' (sense)

SEQ ID NO: 23
5'-TCTCCTCTCTTTACTACATCCCAACA-3' (antisense)

Methylated NDRG2 specific primers:
                                          SEQ ID NO: 24
5'-TTTATAGCGGTTTTTCGTATTTTTC-3' (sense)

SEQ ID NO: 25
5'-CCTCTCTTTACTACGTCCCGACG-3' (antisense).
```

In one embodiment, primers and/or probes useful in determining the methylation status of the at least one gene selected from GATA4, OSMR, NDRG4, GATA5, SFRP1, ADAM23, JPH3, SFRP2, APC and MGMT (carried out on the promoter region of at least one gene selected from GATA4, OSMR, NDRG4, GATA5, SFRP1, ADAM23, JPH3, SFRP2, APC and MGMT) are provided. These primers and/or probes comprise, consist essentially of or consist of the following sequences:

TABLE 3

Primer sequences and beacon (probe) sequences

| SEQ ID NO. | | | |
|---|---|---|---|
| 26 | β-Actin | forward primer | 5'-TAGGGAGTATATAGGTTGGGGAAGTT-3' |
| 27 | | reverse primer | 5'-AACACACAATAACAAACACAAATTCAC-3' |
| 28 | | beacon | 5'-FAM-CGACTGCGTGTGGGGTGGTGATGGAGGAGGTTTAGGCAGTCG-3'-DABCYL |
| 29 | GATA4 | forward primer | 5'-AGGTTAGTTAGCGTTTTAGGGTC-3' |
| 30 | | reverse primer | 5'-ACGACGACGAAACCTCTCG-3' |
| 31 | | beacon | 5'-FAM-CGACATGCCTCGCGACTCGAATCCCCGACCCAGCATGTCG-3'-DABCYL |
| 32 | GATA5 | forward primer | 5'-AGTTCGTTTTTAGGTTAGTTTTCGGC-3' |
| 33 | | reverse primer | 5'-CCAATACAACTAAACGAACGAACCG-3 |
| 34 | | beacon | 5'-FAM-CGACATGCGTAGGGAGGTAGAGGGTTCGGGATTCGTAGCATGTCG-3'-DABCYL |
| 35 | SFRP1 | forward primer | 5'-TGTAGTTTTCGGAGTTAGTGTCGCGC-3' |
| 36 | | reverse primer | 5'-CCTACGATCGAAAACGACGCGAACG-3' |
| 37 | | beacon | 5'-FAM-CGACATGCTCGGGAGTCGGGGCGTATTTAGTTCGTAGCGGCATGTCG-3'-DABCYL |
| 38 | SFRP2 | forward primer | 5'-GGGTCGGAGTTTTTCGGAGTTGCGC-3' |
| 39 | | reverse primer | 5'-CCGCTCTCTTCGCTAAATACGACTCG-3' |
| 40 | | beacon | 5'-FAM-CGACATGCGGTGTTTCGTTTTTTCGCGTTTTAGTCGTCGGGCATGTCG-3'-DABCYL |

TABLE 3-continued

Primer sequences and beacon (probe) sequences

| SEQ ID NO. | | | |
|---|---|---|---|
| 17 | NDRG4 | forward primer | 5'-GTATTTTAGTCGCGTAGAAGGC-3' |
| 18 | | reverse primer | 5'-AATTTAACGAATATAAACGCTCGAC-3' |
| 19 | | beacon | 5'-FAM-CGACATGCCCGAACGAACCGCGATCCCTGCATGTCG-3'-DABCYL |
| 41 | APC | forward primer | 5'-GAACCAAAACGCTCCCCAT-3' |
| 42 | | reverse primer | 5'-TTATATGTCGGTTACGTGCGTTTATAT-3' |
| 43 | | beacon | 5'-FAM-CGTCTGCCCCGTCGAAAACCCGCCGATTAACGCAGACG-3'-DABCYL |
| 44 | ADAM23 | forward primer | 5'-GAAGGACGAGAAGTAGGCG-3' |
| 45 | | reverse primer | 5'-CTAACGAACTACAACCTTACCGA-3' |
| 46 | | beacon | 5'-FAM-CGACATGCCCCCGACCCGCACGCCGCCCTGCATGTCG-3'-DABCYL |
| 47 | OSMR (3) | forward primer | 5'-TTTGGTCGGGGTAGGAGTAGC-3' |
| 48 | | reverse primer | 5'-CGAACTTTACGAACGAACGAAC-3' |
| 49 | | beacon | 5'-FAM-CGACATGCCCGTACCCCGCGCGCAGCATGTCG-3'-DABCYL |
| 47 | OSMR (4) | forward primer | 5'-TTTGGTCGGGGTAGGAGTAGC-3' |
| 50 | | reverse primer | 5'-AAAAACTTAAAAACCGAAAACTCG-3' |
| 49 | | beacon | 5'-FAM-CGACATGCCCGTACCCCGCGCGCAGCATGTCG-3'-DABCYL |
| 51 | JPH3 | forward primer | 5'-TTAGATTTCGTAAACGGTGAAAAC-3' |

In specific embodiments, the methods of the invention employ or rely upon or utilise primers and/or probes selected from the primers and probes comprising the nucleotide sequences set forth in Table 4 below to determine the methylation status of the at least one gene. The table presents specific primer and probe combinations for certain preferred genes whose methylation status may be determined according to the methods of the invention.

TABLE 4

Primer sequences and beacon (probe) sequences

| SEQ ID NO. | | | |
|---|---|---|---|
| 26 | β-Actin | forward primer | 5'-TAGGGAGTATATAGGTTGGGGAAGTT-3' |
| 27 | | reverse primer | 5'-AACACACAATAACAAACACAAATTCAC-3' |
| 28 | | beacon | 5'-FAM-CGACTGCGTGTGGGGTGGTGATGGAGGAGGTTTAGGCAGTCG-3'-DABCYL |
| 29 | GATA4 | forward primer | 5'-AGGTTAGTTAGCGTTTTAGGGTC-3' |
| 30 | | reverse primer | 5'-ACGACGACGAAACCTCTCG-3' |
| 31 | | beacon | 5'-FAM-CGACATGCCTCGCGACTCGAATCCCCGACCCAGCATGTCG-3'-DABCYL |

TABLE 4-continued

Primer sequences and beacon (probe) sequences

| SEQ ID NO. | | | |
|---|---|---|---|
| 32 | GATA5 | forward primer | 5'-AGTTCGTTTTTAGGTTAGTTTTCGGC-3' |
| 33 | | reverse primer | 5'-CCAATACAACTAAACGAACGAACCG-3 |
| 34 | | beacon | 5'-FAM-CGACATGCGTAGGGAGGTAGAGGGTTCGGGATTCGTAGCATGTCG-3'-DABCYL |
| 35 | SFRP1 | forward primer | 5'-TGTAGTTTTCGGAGTTAGTGTCGCGC-3' |
| 36 | | reverse primer | 5'-CCTACGATCGAAAACGACGCGAACG-3' |
| 37 | | beacon | 5'-FAM-CGACATGCTCGGGAGTCGGGGCGTATTTAGTTCGTAGCGGCATGTCG-3'-DABCYL |
| 38 | SFRP2 | forward primer | 5'-GGGTCGGAGTTTTTCGGAGTTGCGC-3' |
| 39 | | reverse primer | 5'-CCGCTCTCTTCGCTAAATACGACTCG-3' |
| 40 | | beacon | 5'-FAM-CGACATGCGGTGTTTCGTTTTTTCGCGTTTTAGTCGTCGGGCATGTCG-3'-DABCYL |
| 17 | NDRG4 | forward primer | 5'-GTATTTTAGTCGCGTAGAAGGC-3' |
| 18 | | reverse primer | 5'-AATTTAACGAATATAAACGCTCGAC-3' |
| 19 | | beacon | 5'-FAM-CGACATGCCCGAACGAACCGCGATCCCTGCATGTCG-3'-DABCYL |
| 41 | APC | forward primer | 5'-GAACCAAAACGCTCCCCAT-3' |
| 42 | | reverse primer | 5'-TTATATGTCGGTTACGTGCGTTTATAT-3' |
| 43 | | beacon | 5'-FAM-CGTCTGCCCCGTCGAAAACCCGCCGATTAACGCAGACG-3'-DABCYL |
| 44 | ADAM23 | forward primer | 5'-GAAGGACGAGAAGTAGGCG-3' |
| 45 | | reverse primer | 5'-CTAACGAACTACAACCTTACCGA-3' |
| 46 | | beacon | 5'-FAM-CGACATGCCCCCGACCCGCACGCCGCCCTGCATGTCG-3'-DABCYL |
| 47 | OSMR (3) | forward primer | 5'-TTTGGTCGGGGTAGGAGTAGC-3' |
| 48 | | reverse primer | 5'-CGAACTTTACGAACGAACGAAC-3' |
| 49 | | beacon | 5'-FAM-CGACATGCCCGTACCCCGCGCGCAGCATGTCG-3'-DABCYL |
| 47 | OSMR (4) | forward primer | 5'-TTTGGTCGGGGTAGGAGTAGC-3' |
| 50 | | reverse primer | 5'-AAAAACTTAAAAACCGAAAACTCG-3' |
| 49 | | beacon | 5'-FAM-CGACATGCCCGTACCCCGCGCGCAGCATGTCG-3'-DABCYL |
| 51 | JPH3 | forward primer | 5'-TTAGATTTCGTAAACGGTGAAAAC-3 |

In a further specific embodiment, the methods of the invention employ or rely upon or utilise primers and/or probes selected from the primers comprising the nucleotide sequences set forth in Table 5 below to determine the methylation status of NDRG4. The table presents specific primer and probe combinations for determining the methylation status of this gene and the primer pairs and corresponding probe may be selected according to the table.

TABLE 5

Primer pairs and probes for determining the methylation status of NDRG4, with predicted amplification product lengths shown.

| Assay name | Amplicon length | SEQ ID NO | Oligo nucleotides & probes | 5' to 3' Sequences (all the beacons are 5'-FAM and 3'-DABCYL) |
|---|---|---|---|---|
| NDRG4_1b | 112 | 17 | Forward primer | GTATTTTAGTCGCGTAGAAGGC |
| | | 18 | Reverse primer | AATTTAACGAATATAAACGCTCGAC |
| | | 57 | Beacon | CGACATGCAGGGATCGCGGTTCGTTCGGGCATGTCG |
| NDRG4_13830 | 105 | 58 | Forward primer | GGTATTTTAGTCGCGTAGAAGGC |
| | | 59 | Reverse primer | GAATATAAACGCTCGACCCGC |
| | | 60 | Beacon | CGACATGCGCGGTTCGTTCGGGATTAGTTTTAGGTTCGGCATGTCG |
| NDRG4_2(MvE) | 88 | 9 | Forward primer | TTTAGGTTCGGTATCGTTTCGC |
| | | 10 | Reverse primer | CGAACTAAAAACGATACGCCG |
| | | 61 | Beacon | CGTACCCGCGTTTATATTCGTTAAATTTACGCGGGTACG |
| NDRG4_66292 | 163 | 62 | Forward primer | TAGTCGCGTAGAAGGCGGA |
| | | 63 | Reverse primer | GACTACAAAAACGAAAACCGAAC |
| | | 64 | Beacon | CGACATCGGGTACGTTTTCGCGGCGATGTCG |
| NDRG4_66293 | 168 | 58 | Forward primer | GGTATTTTAGTCGCGTAGAAGGC |
| | | 65 | Reverse primer | CTACAAAAACGAAAACCGAAC |
| | | 66 | Beacon | CGTTTCGCGGGTCGAGCGAAACG |
| NDRG4_66294 | 152 | 62 | Forward primer | TAGTCGCGTAGAAGGCGGA |
| | | 67 | Reverse primer | CGAAAACCGAACTAAAAACGA |
| | | 68 | Beacon | CGACATGCCGCGGTTCGTTCGGGATTAGTTTTAGGGCATGTCG |
| NDRG4_66295 | 90 | 69 | Forward primer | TTTCGTTCGTTTATCGGGT |
| | | 70 | Reverse primer | CGAACCTAAAACTAATCCCGAAC |
| | | 71 | Beacon | CGACACGCGTAGAAGGCGGAAGTTACGCGCGTGTCG |
| NDRG4_66296 | 160 | 72 | Forward primer | GGTTTCGTAGCGTATTTAGTATAGTTC |
| | | 73 | Reverse primer | GTAACTTCCGCCTTCTACGC |
| | | 74 | Beacon | CGACATGCGCGGATCGATCGGGGTGTTTTTAGGGCATGTCG |
| NDRG4_66297 | 143 | 75 | Forward primer | GAGTTGTTTTGTCGTTTCGTTT |
| | | 76 | Reverse primer | AACACCTTCATCTCGACGC |
| | | 77 | Beacon | CGACATGCGGTTCGGTCGAGCGCGCATGTCG |
| NDRG4_66298 | 148 | 78 | Forward primer | GTTGTGAGTTGTTTTTGTCGTTTC |
| | | 76 | Reverse primer | AACACCTTCATCTCGACGC |
| | | 79 | Beacon | CGACATGCCGTTGTTTCGACGTCGTTATTTAGAGTCGGCATGTCG |

TABLE 5-continued

Primer pairs and probes for determining the methylation status of NDRG4, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| NDRG4_66299 | 144 | 80 | Forward primer | TTTTAGTATTTTTATTTCGGCGTTC |
| | | 81 | Reverse primer | CTACTCCTACCGCTTCGCTC |
| | | 82 | Beacon | CGACATCGCGCTCCTCTCCCCGATGTCG |
| NDRG4_66300 | 151 | 83 | Forward primer | CGGTGTTTTAGTATTTTTATTTCGG |
| | | 84 | Reverse primer | AACTACTCCTACCGCTTCGCT |
| | | 85 | Beacon | CGACATCGGTTTTGGGTGGCGGCGATGTCG |
| NDRG4_66301 | 120 | 80 | Forward primer | TTTTAGTATTTTTATTTCGGCGTTC |
| | | 86 | Reverse primer | CTCTCCTACCGCTCCGCTC |
| | | 87 | Beacon | CGACATCGCTCCTCTCCCCGACTCGATGTCG |
| NDRG4_66302 | 125 | 83 | Forward primer | CGGTGTTTTAGTATTTTTATTTCGG |
| | | 86 | Reverse primer | CTCTCCTACCGCTCCGCTC |
| | | 88 | Beacon | CGACATGCCGAACGCGCTACCCCGCATGTCG |
| NDRG4_66303 | 95 | 89 | Forward primer | CGAGTCGTTTTAGTTTTCGGT |
| | | 90 | Reverse primer | TACTCACAAATACCGCCCG |
| | | 91 | Beacon | CGACATCGGAAAGTGGCGGTCGGTTGCGATGTCG |
| NDRG4_66304 | 85 | 92 | Forward primer | TTCGGTGAATTTTAGGAGGC |
| | | 93 | Reverse primer | TCGAACGACGAACACGAAA |
| | | 94 | Beacon | CGACATGCGCGGGTGGGTGCGGCATGTCG |

In a further specific embodiment, the methods of the invention employ or rely upon or utilise primers selected from the primers comprising the nucleotide sequences set forth in Table 6 and 7 below to determine the methylation status of GATA5. The table presents specific primer combinations for determining the methylation status of this gene and the primer pairs may be selected according to the table.

Table 6 also sets forth specific probes which may be utilised to facilitate (quantitative) detection of the methylation status of GATA5 and Table 7 incorporates Amplifluour sequences which allow the primers to act as hairpin primers, thus facilitating quantitative detection (as discussed in detail herein).

TABLE 6

Primer pairs and probes for determining the methylation status of GATA5, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| GATA5_12656 | 94 | 95 | Forward primer | TTCGGGTTGGAGTATTTATTAGC |
| | | 96 | Reverse primer | CGAACTTCCAATCTTCGACC |
| | | 97 | Beacon | CGACATGCGGCGGTGGCGGTGGGTCGGCATGTCG |
| GATA512659 | 102 | 98 | Forward primer | GATTTTTCGGGGTTTACGAAG |
| | | 99 | Reverse primer | GAAACTTAACGACAAAAACGCA |
| | | 100 | Beacon | CGACATGCGTTTAGTTGTATTGGTTCGGGTTTCGCATGTCG |

TABLE 6-continued

Primer pairs and probes for determining the methylation status of GATA5, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| GATA5_12666 | 107 | 101 | Forward primer | GGTTTGTATTCGGATTCGGTC |
| | | 102 | Reverse primer | TCGATAACAACGTCCTACACG |
| | | 103 | Beacon | CGACATGCGAAGGTGGGTTTGCGGTTTGGGAGGTCGCATGTCG |
| GATA5_12669 | 111 | 104 | Forward primer | TAGGGTGCGGGTTTGTATTC |
| | | 105 | Reverse primer | AACAACGTCCTACACGACC |
| | | 106 | Beacon | CGACATGCGTATTTATCGAAGGTGGGTTTGCGGTTTGCATGTCG |
| GATA5_66212 | 118 | 107 | Forward primer | TAGTTGGTGTAGTAGAGGTCGGC |
| | | 108 | Reverse primer | GACCTAAATCTCGCTTCCGT |
| | | 109 | Beacon | CGACATGCCGAGGGAGATTGGAGTGAGTTTCGCATGTCG |
| GATA5_66213 | 139 | 110 | Forward primer | TATAGCGTGGTGTTGGTCGT |
| | | 111 | Reverse primer | CTAAATCTCGCTTCCGTCC |
| | | 112 | Beacon | CGACATGCGCGAGGGAGATTGGAGTGAGTTTCGCATGTCG |
| GATA5_66215 | 80 | 113 | Forward primer | GGTGTCGAGGTTTTTAAGGTTTC |
| | | 114 | Reverse primer | TCACTTTCTAACGAAAACGACT |
| | | 115 | Beacon | CGACATGCGGGACGGGATGGGTTTTTGCGGGCATGTCG |
| GATA5_66216 | 124 | 116 | Forward primer | GTAGTTTCGGAGTTGGGTGTC |
| | | 117 | Reverse primer | AAAAACGACTCTTCCCGATT |
| | | 118 | Beacon | CGACATGCGAGGGACGGGATGGGTTTTTGCATGTCG |
| GATA5_66217 | 118 | 116 | Forward primer | GTAGTTTCGGAGTTGGGTGTC |
| | | 119 | Reverse primer | GACTCTTCCCGATTACAACG |
| | | 120 | Beacon | CGACATGCGAGGGACGGGATGGGTTTTGGCATGTCG |
| GATA5_66218 | 71 | 121 | Forward primer | TTTTGCGTTAAAGGGTCGG |
| | | 122 | Reverse primer | CGAAACCTTAAAAACCTCGACA |
| | | 123 | Beacon | CGACATGCCGGGGTTTTAAAGGTAGTTTCGGAGTTGGCATGTCG |
| GATA5_66219 | 90 | 124 | Forward primer | GATGTCGTTGCGTTCGTTT |
| | | 125 | Reverse primer | CCGAAACCTTAAAAACCTCG |
| | | 126 | Beacon | CGACATGCCGGCGGGGTTTTAAAGGTAGTTTCGGCATGTCG |
| GATA5_66220 | 98 | 127 | Forward primer | GTTTTGCGGATGTCGTTGC |
| | | 125 | Reverse primer | CCGAAACCTTAAAAACCTCG |
| | | 126 | Beacon | CGACATGCCGGCGGGGTTTTAAAGGTAGTTTCGGCATGTCG |

TABLE 6-continued

Primer pairs and probes for determining the methylation status of GATA5, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| GATA5_66221 | 158 | 128 | Forward primer | TAGGGGTTTTGCGGATGTC |
| | | 114 | Reverse primer | TCACTTTCTAACGAAAACGACT |
| | | 126 | Beacon | CGACATGCCGGCGGGGTTTTAAAGGTAGTTTCGGCATGTCG |
| GATA5_66222 | 150 | 129 | Forward primer | TCGAGATTGTGGAGTTTTCGT |
| | | 130 | Reverse primer | TAAAAACCTCGTACTCCGCC |
| | | 131 | Beacon | CGACATCGGTTTGGGAGGTCGTGTAGGACGATGTCG |
| GATA5_66223 | 103 | 129 | Forward primer | TCGAGATTGTGGAGTTTTCGT |
| | | 132 | Reverse primer | GTAACCCAATCCTAAACTACCGA |
| | | 131 | Beacon | CGACATCGGTTTGGGAGGTCGTGTAGGACGATGTCG |
| GATA5_66224 | 112 | 133 | Forward primer | GGTTTGTATTCGGATTCGGT |
| | | 134 | Reverse primer | ACCCTTCGATAACAACGTCC |
| | | 135 | Beacon | CGACATGCCGTATTTATCGAAGGTGGGTTTGCGGGCATGTCG |
| GATA5_66225 | 76 | 136 | Forward primer | GTTTCGAGATTGTGGAGTTTTC |
| | | 137 | Reverse primer | GATAACAACGTCCTACACGACC |
| | | 138 | Beacon | CGACATGCCGAAGGTGGGTTTGCGGTTTGGGGCATGTCG |
| GATA5_66226 | 163 | 139 | Forward primer | TTATTCGTTTCGTTTCGGG |
| | | 140 | Reverse primer | AAACCCACCTTCGATAAATACG |
| | | 141 | Beacon | CGACATCGTTTTTGGTAGGGAGGTTCGGATCGATGTCG |
| GATA5_66227 | 164 | 142 | Forward primer | CGGGGTGTTATTTAGGTTTATTC |
| | | 143 | Reverse primer | AATACGAAAACTCCACAATCTCG |
| | | 144 | Beacon | CGACATGCGTTTTTGGTAGGGAGGTTCGGATCGCATGTCG |
| GATA5_66228 | 76 | 145 | Forward primer | CGTTTTTGGTAGGGAGGTTC |
| | | 146 | Reverse primer | ATCCGAATACAAACCCGCA |
| | | 147 | Beacon | CGACATGCCGTGGGGAGGATGAGGGGAGCGTTTCGGCATGTCG |
| GATA5_66229 | 113 | 142 | Forward primer | CGGGGTGTTATTTAGGTTTATTC |
| | | 148 | Reverse primer | AAACCCGCACCCTACGAAA |
| | | 144 | Beacon | CGACATGCGTTTTTGGTAGGGAGGTTCGGATCGCATGTCG |
| GATA5_66230 | 161 | 149 | Forward primer | ATTAGTGTAGTTAGACGGGCGG |
| | | 150 | Reverse primer | GACTCAACCACCAAACACGA |
| | | 151 | Beacon | CGACATGCGTGGGTTTCGGGGAGTCGCATGTCG |

TABLE 6-continued

Primer pairs and probes for determining the methylation status of GATA5, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| GATA5_66231 | 116 | 95 | Forward primer | TTCGGGTTGGAGTATTTATTAGC |
| | | 152 | Reverse primer | AAACTACGAAACCTCAACGACC |
| | | 153 | Beacon | CGACATGCGGTGGCGGTGGGTCGCATGTCG |
| GATA5_66233 | 134 | 154 | Forward primer | GTTACGGGAGTTTTGCGTTT |
| | | 155 | Reverse primer | CGATTCCTCTCCCTCGAAT |
| | | 156 | Beacon | CGACATGCGAGTTTATGTCGGGTAGGTGTCGCATGTCG |
| GATA5_66234 | 105 | 157 | Forward primer | AATCGTGTTTCGTTCGTATTTTC |
| | | 158 | Reverse primer | GATATACTCCGAACCCGCC |
| | | 159 | Beacon | CGACATGCGCGGAGTAGTTTCGTAGGTTGCGGGCATGTCG |
| GATA5_66235 | 121 | 160 | Forward primer | GCGATTTAGGTTAGGGAATCGT |
| | | 158 | Reverse primer | GATATACTCCGAACCCGCC |
| | | 161 | Beacon | CGACATGCCGGTGAGGGTTGTATGGAGGCGTCGGCATGTCG |
| GATA5_66237 | 99 | 162 | Forward primer | TTTCGGTGGGGTTTTTAGTC |
| | | 163 | Reverse primer | GATTCCCTAACCTAAATCGCCT |
| | | 164 | Beacon | CGACATGCGCGTTAGAAATGCGTGTGGGTAGGAGGCGCATGTCG |
| GATA5_66238 | 72 | 165 | Forward primer | ATTTCGGTGGGGTTTTTAGTC |
| | | 166 | Reverse primer | CACACGCATTTCTAACGCC |
| | | 167 | Beacon | CGACATGCCTCTTCCCGAATCCCCGAAAACCGCATGTCG |
| GATA5_66243 | 91 | 168 | Forward primer | GGGTTTTATCGTCGCGTGT |
| | | 169 | Reverse primer | CCGAAAACTAACCTAAAAACGAA |
| | | 170 | Beacon | CGACATGCCCCGACCCCGCTCACCGGCATGTCG |
| GATA5_66244 | 100 | 171 | Forward primer | GGGGTTTACGGGGTTTTATC |
| | | 172 | Reverse primer | CGAAAACTAACCTAAAAACGAAC |
| | | 173 | Beacon | CGACATGCGATAATCCCGACCCCGCTCACCGCATGTCG |
| GATA5_66245 | 152 | 174 | Forward primer | TTGTTTAGAAATCGAGGAAATCG |
| | | 175 | Reverse primer | CGACGATAAAACCCCGTAA |
| | | 176 | Beacon | CGACATGCGAGTTTCGGGTGCGGTTACGCATGTCG |
| GATA5_66247 | 163 | 177 | Forward primer | TGTGGTTTCGTTTGTTTAGAAATC |
| | | 175 | Reverse primer | CGACGATAAAACCCCGTAA |
| | | 178 | Beacon | CGACATGCGAGTTTCGGGTGCGGTTACGTAACGCATGTCG |
| GATA5_66250 | 151 | 177 | Forward primer | TGTGGTTTCGTTTGTTTAGAAATC |
| | | 179 | Reverse primer | CCCGTAAACCCCCTCGTTA |
| | | 180 | Beacon | CGACATGCCGCGGGGTTTTCGTTAGTGTATTTCGGCATGTCG |

TABLE 6-continued

Primer pairs and probes for determining the methylation status of GATA5, with predicted amplification product lengths shown.

| Assay name | Amplicon length | SEQ ID NO | Oligo nucleotides & probes | 5' to 3' Sequences (all the beacons are 5'-FAM and 3'-DABCYL) |
|---|---|---|---|---|
| GATA5_66251 | 85 | 181 | Forward primer | CGTTTGTTTAGAAATCGAGGAAATC |
| | | 182 | Reverse primer | CATAAAAACGACCGACTCGAA |
| | | 183 | Beacon | CGACATGCGGGGTTTTCGTTAGTGTATTTCGTTTTAGCATGTCG |
| GATA5_66252 | 141 | 184 | Forward primer | TTCGTATTTCGTTATTTATTCGGTT |
| | | 185 | Reverse primer | GAAACTATAAAACCCCCGCA |
| | | 186 | Beacon | CGACATGCCGGGTTTTCGATGGTAGCGTTTTGTACGGCATGTCG |
| GATA5_66254 | 131 | 187 | Forward primer | CGAGTTTTCGTTAGGTCGTTT |
| | | 188 | Reverse primer | ACTCGACTCACACCCGAAC |
| | | 189 | Beacon | CGACATGCGTACGTTTCGGGCGTCGGTTTTCGGCATGTCG |
| GATA5_66255 | 119 | 190 | Forward primer | CGCGAGTTTTCGTTAGGTC |
| | | 191 | Reverse primer | CGAACAAATAAAACAACATCGAA |
| | | 189 | Beacon | CGACATGCGTACGTTTCGGGCGTCGGTTTTCGGCATGTCG |
| GATA5_66256 | 95 | 192 | Forward primer | TCGGGATTTTGGAGGTTTC |
| | | 193 | Reverse primer | CTACGAATACCGCTACGCC |
| | | 194 | Beacon | CGACATGCGGGATTTCGTCGGTTTTTTGGCGTAGGGCATGTCG |

TABLE 7

Additional assay designs: Primer and amplifluor sequences for determining the methylation status of GATA5, with predicted amplification product lengths shown.

| Assay name | Amplicon length | SEQ ID NO | Oligo nucleotides | 5' to 3' Sequences |
|---|---|---|---|---|
| GATA5_12671_S_AMP | 90 | 195 | Forward primer | AGCGATGCGTTCGAGCATCGCUTTTTTCGATGTTGTTTTATTTGTTC |
| | | 196 | Reverse primer | ATAACTATCTACGCCCAACCGA |
| GATA5_12671_AS_AMP | 90 | 197 | Forward primer | TTTTTCGATGTTGTTTTATTTGTTC |
| | | 198 | Reverse primer | AGCGATGCGTTCGAGCATCGCUATAACTATCTACGCCCAACCGA |
| GATA5_66214_S_AMP | 70 | 199 | Forward primer | AGCGATGCGTTCGAGCATCGCUTTCGTGTAGTTTTATGTAGAGGTCG |
| | | 200 | Reverse primer | GCTATAACGACGAAACTCGAA |
| GATA5_66214_AS_AMP | 70 | 201 | Forward primer | TTCGTGTAGTTTTATGTAGAGGTCG |
| | | 202 | Reverse primer | AGCGATGCGTTCGAGCATCGCUGCTATAACGACGAAACTCGAA |
| GATA5_66236_S_AMP | 73 | 203 | Forward primer | AGCGATGCGTTCGAGCATCGCUTAGGCGTTAGAAATGCGTG |
| | | 204 | Reverse primer | CACCGAAAATACGAACGAAA |

TABLE 7-continued

Additional assay designs: Primer and amplifluor sequences for determining the methylation status of GATA5, with predicted amplification product lengths shown.

| Assay name | Amplicon length | SEQ ID NO | Oligo nucleotides | 5' to 3' Sequences |
|---|---|---|---|---|
| GATA5_66236_AS_AMP | 73 | 205 | Forward primer | TTAGGCGTTAGAAATGCGTG |
| | | 206 | Reverse primer | AGCGATGCGTTCGAGCATCGCUCACCGAAAATACGAACGAAA |
| GATA5_66239_S_AMP | 101 | 207 | Forward primer | AGCGATGCGTTCGAGCATCGCUGGTCGTTAAGTTTGGGTTTATTC |
| | | 208 | Reverse primer | AAAACTACATAAAAACGCCGCTA |
| GATA5_66239_AS_AMP | 101 | 209 | Forward primer | GGTCGTTAAGTTTGGGTTTATTC |
| | | 210 | Reverse primer | AGCGATGCGTTCGAGCATCGCUAAAACTACATAAAAACGCCGCTA |
| GATA5_66240_S_AMP | 93 | 207 | Forward primer | AGCGATGCGTTCGAGCATCGCUGGTCGTTAAGTTTGGGTTTATTC |
| | | 211 | Reverse primer | ATAAAAACGCCGCTACCGC |
| GATA5_66240_AS_AMP | 93 | 209 | Forward primer | GGTCGTTAAGTTTGGGTTTATTC |
| | | 212 | Reverse primer | AGCGATGCGTTCGAGCATCGCUATAAAAACGCCGCTACCGC |
| GATA5_66241_S_AMP | 78 | 213 | Forward primer | AGCGATGCGTTCGAGCATCGCUCGTTAAGTTTGGGTTTATTCGGT |
| | | 214 | Reverse primer | CTACCGCGAAACAACTCCG |
| GATA5_66241_AS_AMP | 78 | 215 | Forward primer | CGTTAAGTTTGGGTTTATTCGGT |
| | | 216 | Reverse primer | AGCGATGCGTTCGAGCATCGCUCTACCGCGAAACAACTCCG |
| GATA5_66248_S_AMP | 86 | 217 | Forward primer | AGCGATGCGTTCGAGCATCGCUGTTTAGAAATCGAGGAAATCGC |
| | | 218 | Reverse primer | GACTTCCATAAAAACGACCGA |
| GATA5_66248_AS_AMP | 86 | 219 | Forward primer | GTTTAGAAATCGAGGAAATCGC |
| | | 220 | Reverse primer | AGCGATGCGTTCGAGCATCGCUGACTTCCATAAAAACGACCGA |
| GATA5_66249_S_AMP | 80 | 217 | Forward primer | AGCGATGCGTTCGAGCATCGCUGTTTAGAAATCGAGGAAATCGC |
| | | 182 | Reverse primer | CATAAAAACGACCGACTCGAA |
| GATA5_66249_AS_AMP | 80 | 219 | Forward primer | GTTTAGAAATCGAGGAAATCGC |
| | | 221 | Reverse primer | AGCGATGCGTTCGAGCATCGCUCATAAAAACGACCGACTCGAA |
| GATA5_66257_S_AMP | 78 | 222 | Forward primer | AGCGATGCGTTCGAGCATCGCUTTGCGTGGTCGTAAGGTC |
| | | 223 | Reverse primer | AAATAAACCCCGAACCGAA |
| GATA5_66257_AS_AMP | 78 | 224 | Forward primer | TTTGCGTGGTCGTAAGGTC |
| | | 225 | Reverse primer | AGCGATGCGTTCGAGCATCGCUAAATAAACCCCGAACCGAA |
| GATA5_66246_S_AMP | 70 | 226 | Forward primer | AGCGATGCGTTCGAGCATCGCUCGGGGTTTTCGTTAGTGTATTTC |
| | | 227 | Reverse primer | AAACCGACTTCCATAAAAACGA |

TABLE 7-continued

Additional assay designs: Primer and amplifluor sequences for determining the methylation status of GATA5, with predicted amplification product lengths shown.

| Assay name | Ampli-con length | SEQ ID NO | Oligo nucleotides | 5' to 3' Sequences |
|---|---|---|---|---|
| GATA5_66246_AS_AMP | 70 | 228 | Forward primer | CGGGGTTTTCGTTAGTGTATTTC |
| | | 229 | Reverse primer | AGCGATGCGTTCGAGCATCGCUAAACCGAC TTCCATAAAAACGA |

In a further specific embodiment, the methods of the invention employ or rely upon or utilise primers selected from the primers comprising the nucleotide sequences set forth in Tables 8 and 9 below to determine the methylation status of OSMR. The tables present specific primer combinations for determining the methylation status of this gene and the primer pairs may be selected according to the table.

Table 8 also sets forth specific probes which may be utilised to facilitate (quantitative) detection of the methylation status of OSMR and Table 9 incorporates Amplifluor sequences which allow the primers to act as hairpin primers, thus facilitating quantitative detection (as discussed in detail herein).

TABLE 8

Primer pairs and probes (molecular beacons) for determining the methylation status of OSMR, with predicted amplification product lengths shown.

| Assay name | Ampli-con length | SEQ ID NO | Oligo nucleotides & probes | 5' to 3' Sequences (all the beacons are 5'-FAM and 3'-DABCYL) |
|---|---|---|---|---|
| OSMR_1 | 148 | 230 | Forward primer | GTGTTAAGAGTGCGTAGTAAGACG |
| | | 231 | Reverse primer | GAAACGAACGTACAAAAACGA |
| | | 232 | Beacon | CGACATGCCGAAACTATAAATCAACTAC GAAACAAACGCGCATGTCG |
| OSMR_2 | 142 | 233 | Forward Primer | TTAAGTAAACGTTGGGTAGAGGC |
| | | 234 | Reverse primer | CTCGATAACTTTTCCGACGA |
| | | 235 | Beacon | CGACATGCCGAGGAGGGGAACGGGTTGT TGGCATGTCG |
| OSMR_25259 | 138 | 236 | Forward primer | TGTTCGTTCGTTCGTAAAGTTC |
| | | 237 | Reverse primer | TACAATTTCCCGTCTTACTACGC |
| | | 238 | Beacon | CGACATGCGCGGTCGTTTTTTTTCGGGA TTGAAGGCATGTCG |
| OSMR_25260 | 139 | 47 | Forward primer | TTTGGTCGGGGTAGGAGTAGC |
| | | 239 | Reverse primer | CACAACCCGAACTTTACGAAC |
| | | 240 | Beacon | CGACATGCGCGGGGTACGGAGTTTCGGT CGCATGTCG |
| OSMR_5 | 130 | 241 | Forward primer | ACGTTGGGTAGAGGCGGTATC |
| | | 242 | Reverse primer | ATAACTTTTCCGACGAACGAAC |
| | | 243 | Beacon | CGACATGCACCCATCCCGACTAAACGCG ACGCATGTCG |
| OSMR_66307 | 120 | 244 | Forward primer | GTATAGTACGGGGTTCGTTCGT |
| | | 245 | Reverse primer | ACTCGTAAACCCTTCGCC |
| | | 246 | Beacon | CGACATGCGGTAGGGCGCGAGTAGAGCG CATGTCG |

TABLE 8-continued

Primer pairs and probes (molecular beacons) for determining the methylation status of OSMR, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| OSMR_66308 | 124 | 247 | Forward primer | GGTAGAGGCGGTATCGAGG |
| | | 242 | Reverse primer | ATAACTTTTCCGACGAACGAAC |
| | | 248 | Beacon | CGACATGCGGGATGGGTTGCGAAGTTGTCGCATGTCG |
| OSMR_66309 | 130 | 249 | Forward primer | ACGTTGGGTAGAGGCGGTA |
| | | 242 | Reverse primer | ATAACTTTTCCGACGAACGAAC |
| | | 250 | Beacon | CGACACGCGTTTAGTCGGGATGGGTTGCGTGTCG |
| OSMR_66310 | 76 | 251 | Forward primer | CGGTATCGAGGAGGGGAAC |
| | | 252 | Reverse primer | AAATCCGACAACTTCGCAA |
| | | 253 | Beacon | CGACATGCGTTGTTGTATTTTCGGTCGCGTTTAGTCGCATGTCG |
| OSMR_66311 | 84 | 247 | Forward primer | GGTAGAGGCGGTATCGAGG |
| | | 252 | Reverse primer | AAATCCGACAACTTCGCAA |
| | | 254 | Beacon | CGACATGCCGGGTTGTTGTATTTTCGGTCGCGGCATGTCG |
| OSMR_66312 | 120 | 255 | Forward primer | TAGGTAGGTAGGTCGGGGGC |
| | | 256 | Reverse primer | CGAAAATACAACAACCCGTTC |
| | | 257 | Beacon | CGACATGCGTTGGGTAGAGGCGGTATCGCATGTCG |
| OSMR_Sid | 142 | 258 | Forward primer | TTCGTGCGTTTTTGGTCG |
| | | 259 | Reverse primer | CGAACTTTACGAACGAACG |
| | | 240 | Beacon | CGACATGCGCGGGGTACGGAGTTTCGGTCGCATGTCG |

TABLE 9

Additional assay designs: Primer and amplifluor sequences for determining the methylation status of OSMR, with predicted amplification product lengths shown.

| Assay name | Amplicon length | SEQ ID NO | Oligonucleotides | 5' to 3' Sequences |
|---|---|---|---|---|
| OSMR_25258_S_AMP | 135 | 260 | Forward primer | AGCGATGCGTTCGAGCATCGCUAGAGTGCGTAGTAAGACGGGA |
| | | 261 | Reverse primer | ACGTACAAAAACGACCCGAAC |
| OSMR_25258_AS_AMP | 135 | 262 | Forward primer | AGAGTGCGTAGTAAGACGGGA |
| | | 263 | Reverse primer | AGCGATGCGTTCGAGCATCGCUACGTACAAAAACGACCCGAAC |
| OSMR_25264_S_AMP | 65 | 264 | Forward primer | AGCGATGCGTTCGAGCATCGCUGCGTAGCGTTGTTTTGTTTC |
| | | 265 | Reverse primer | CGACTTACCTCTAATTCCGCC |
| OSMR_25264_AS_AMP | 65 | 266 | Forward primer | GCGTAGCGTTGTTTTGTTTC |
| | | 267 | Reverse primer | AGCGATGCGTTCGAGCATCGCUCGACTTACCTCTAATTCCGCC |

TABLE 9-continued

Additional assay designs: Primer and amplifluor sequences for determining the methylation status of OSMR, with predicted amplification product lengths shown.

| Assay name | Amplicon length | SEQ ID NO | Oligo nucleotides | 5' to 3' Sequences |
|---|---|---|---|---|
| OSMR_66305_S_AMP | 142 | 260 | Forward primer | AGCGATGCGTTCGAGCATCGCUAGAG TGCGTAGTAAGACGGGA |
| | | 231 | Reverse primer | GAAACGAACGTACAAAAACGA |
| OSMR_66305_AS_AMP | 142 | 262 | Forward primer | AGAGTGCGTAGTAAGACGGGA |
| | | 268 | Reverse primer | AGCGATGCGTTCGAGCATCGCUGAAA CGAACGTACAAAAACGA |
| OSMR_66306_S_AMP | 98 | 260 | Forward primer | AGCGATGCGTTCGAGCATCGCUAGAG TGCGTAGTAAGACGGGA |
| | | 269 | Reverse primer | CTACGAAACAAACGCGAAA |
| OSMR_66306_AS_AMP | 98 | 262 | Forward primer | AGAGTGCGTAGTAAGACGGGA |
| | | 270 | Reverse primer | AGCGATGCGTTCGAGCATCGCUCTAC GAAACAAACGCGAAA |
| OSMR_66313_S_AMP | 71 | 271 | Forward primer | AGCGATGCGTTCGAGCATCGCUCGAG GATTTTTCGAGCGTC |
| | | 272 | Reverse primer | ATACCGCCTCTACCCAACG |
| OSMR_66313_AS_AMP | 71 | 273 | Forward primer | CGAGGATTTTTCGAGCGTC |
| | | 274 | Reverse primer | AGCGATGCGTTCGAGCATCGCUATAC CGCCTCTACCCAACG |

In a further specific embodiment, the methods of the invention employ or rely upon or utilise primers selected from the primers comprising the nucleotide sequences set forth in Table 10 below to determine the methylation status of ADAM23. The table presents specific primer combinations for determining the methylation status of this gene and the primer pairs may be selected according to the table. Table 6 also sets forth specific probes which may be utilised to facilitate (quantitative) detection of the methylation status of ADAM23.

TABLE 10

Primer pairs and probes (molecular beacons) for determining the methylation status of ADAM23, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| ADAM23_5 | 99 | 275 | Forward primer | TAACGTAAAGGGTACGGGG |
| | | 276 | Reverse primer | GTCCTTCTCCTACTACCTCCGCT |
| | | 277 | Beacon | CGACATGCCCCGACTCGCCTAACCTC GCAAGCATGTCG |
| ADAM23_66258 | 98 | 278 | Forward primer | GTAGTAGTTCGCGGTAGTCGTTT |
| | | 279 | Reverse primer | AACGCTAACAAACACCGAA |
| | | 280 | Beacon | CGACATGCGCGGGTTGTAGTTTTGTC GGCGGCATGTCG |
| ADAM23_66259 | 169 | 281 | Forward primer | TTCGTAGTCGTTGAAGCGG |
| | | 282 | Reverse primer | GCGAAACTCGAAACTAAACGA |
| | | 283 | Beacon | CGACATCGGGAGTGGTTGCGAGGTTA GGCGATGTCG |

TABLE 10-continued

Primer pairs and probes (molecular beacons) for determining the methylation status of ADAM23, with predicted amplification product lengths shown.

| Assay name | Amplicon length | SEQ ID NO | Oligonucleotides | 5' to 3' Sequences (all the beacons are 5'-FAM and 3'-DABCYL) |
|---|---|---|---|---|
| ADAM23_66260 | 81 | 284 | Forward primer | GCGTCGTTTTAGTATTTTTAGGTTC |
| | | 285 | Reverse primer | GACTACTCCCTCCCCCGAC |
| | | 286 | Beacon | CGACATGCGTTTTCGTAGTCGTTGAAGCGGTCGGCATGTCG |
| ADAM23_66261 | 104 | 287 | Forward primer | GTTTTCGCGTCGTTCGTTT |
| | | 285 | Reverse primer | GACTACTCCCTCCCCCGAC |
| | | 288 | Beacon | CGACATGCGGTTCGGCGGTAGTTTTCGTAGTCGGCATGTCG |
| ADAM23_66263 | 106 | 289 | Forward primer | GGGTACGGGGTTATATTTATCGT |
| | | 290 | Reverse Primer | CTACCGCCTACTTCTCGTCC |
| | | 291 | Beacon | CGACATCGGGACGAGGCGGCGATGTCG |
| ADAM23_66264 | 90 | 289 | Forward primer | GGGTACGGGGTTATATTTATCGT |
| | | 276 | Reverse primer | GTCCTTCTCCTACTACCTCCGCT |
| | | 292 | Beacon | CGACATGCCCCCGCGCCTAAAAAACTACTACGGCATGTCG |
| ADAM23_66265 | 84 | 293 | Forward primer | GGTACGGGGTTATATTTATCGTTG |
| | | 294 | Reverse primer | TCTCCTACTACCTCCGCTCG |
| | | 295 | Beacon | CGACATGCCTCGTCCCGACCCCGCGCATGTCG |
| ADAM23_66266 | 125 | 296 | Forward primer | GTCGAGTCGGGGATAAGTTC |
| | | 297 | Reverse primer | AAAAACTACTACGCCCAACGA |
| | | 298 | Beacon | CGACATGCGCGGGAAAGTTAACGTAAAGGGTACGCATGTCG |
| ADAM23_66267 | 97 | 296 | Forward primer | GTCGAGTCGGGGATAAGTTC |
| | | 299 | Reverse primer | AACCCCGTACCCTTTACGTT |
| | | 300 | Beacon | CGACGCGCGTTTTCGTTTTTTTTGTAGGGTTTCGCGTCG |
| ADAM23_66268 | 133 | 301 | Forward primer | AAGGAAAGGTCGAGTCGGG |
| | | 297 | Reverse primer | AAAAACTACTACGCCCAACGA |
| | | 302 | Beacon | CGACATGCGTAGGGTTTCGCGGGAAAGTTAACGGCATGTCG |
| ADAM23_66269 | 108 | 301 | Forward primer | AAGGAAAGGTCGAGTCGGG |
| | | 303 | Reverse primer | TATAACCCCGTACCCTTTACGTT |
| | | 304 | Beacon | CGACATGCAGTTCGGAGTATACGGATTCGCGCGCATGTCG |
| ADAM23_66271 | 97 | 305 | Forward primer | TTCGTCGGTTATACGGAGC |
| | | 306 | Reverse primer | GACAAAACTACAACCCGCCA |
| | | 307 | Beacon | CGACATGCGGGAGTTATGAGTTATGAAGTCGTTCGCATGTCG |

TABLE 10-continued

Primer pairs and probes (molecular beacons) for determining the methylation status of ADAM23, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| ADAM23_A | 112 | 308 | Forward primer | GAGGTTTTAAGTTGGCGGAGC |
| | | 309 | Reverse primer | ACTCGAAACTAAACGACGCCC |
| | | 277 | Beacon | CGACATGCCCCGACTCGCCTAACCTC GCAAGCATGTCG |

In a further specific embodiment, the methods of the invention employ or rely upon or utilise primers selected from the primers comprising the nucleotide sequences set forth in Table 11 below to determine the methylation status of JPH3. The table presents specific primer combinations for determining the methylation status of this gene and the primer pairs may be selected according to the table. Table 11 also sets forth specific probes which may be utilised to facilitate (quantitative) detection of the methylation status of JPH3.

TABLE 11

Primer pairs and probes (molecular beacons) for determining the methylation status of JPH3, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| JPH3_1(MVE) | 103 | 310 | Forward primer | TTTAATATGGTGTAGTCGTTAGCGTC |
| | | 311 | Reverse primer | CCCACCTACGACTACCGCG |
| | | 312 | Beacon | CGACATGCACGAAACCCGCGAACGAC GACGCATGTCG |
| JPH3_12608 | 90 | 313 | Forward primer | GGGGTAGGTTTAATTTTGACGAC |
| | | 314 | Reverse primer | TAAAACCGATACAAACGCCA |
| | | 315 | Beacon | CGACATGCGGTTGGGAGGACGGTAAG GCGGCATGTCG |
| JPH3_2 | 123 | 316 | Forward primer | TGTAGTCGTTAGCGTCGTCGT |
| | | 317 | Reverse primer | GAAAAACAACTCAAACCCGAA |
| | | 318 | Beacon | CGACATGCACCCGCGAACGACGACGA CGCATGTCG |
| JPH3_3 | 88 | 319 | Forward primer | GTAGGTTTAATTTTGACGACGGA |
| | | 320 | Reverse primer | TTAAAACCGATACAAACGCCA |
| | | 321 | Beacon | CGACATGCCCGTACGCCTTACCGTCC TCGCATGTCG |
| JPH3_4 | 134 | 322 | Forward primer | GATATAGTAGAGTCGCGGTCGTC |
| | | 323 | Reverse primer | CGATTAACTAAAATTCCTCCGAAA |
| | | 324 | Beacon | CGACATGCCCGAAAAACGCTCGCGAC CCAGCATGTCG |
| JPH3_5 | 127 | 325 | Forward primer | GGGGTAGTTTAGGTTCGGGTC |
| | | 326 | Reverse primer | ATATAATACAACCGCCAACGCC |
| | | 327 | Beacon | CGACATGCCCGCAACGCGACAACCGC AGCATGTCG |
| JPH3_67326 | 122 | 328 | Forward primer | GTAGTCGTTAGCGTCGTCGT |
| | | 317 | Reverse primer | GAAAAACAACTCAAACCCGAA |
| | | 329 | Beacon | CGACATGCGCGGTAGTCGTAGGTGGG CATGTCG |

TABLE 11-continued

Primer pairs and probes (molecular beacons) for determining the methylation status of JPH3, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| JPH3_67329 | 128 | 319 | Forward primer | GTAGGTTTAATTTTGACGACGGA |
| | | 330 | Reverse primer | GAAACCGTAACTCCACGAAC |
| | | 331 | Beacon | CGACATGCGAGGACGGTAAGGCGTACGGGCATGTCG |
| JPH3_67330 | 92 | 319 | Forward primer | GTAGGTTTAATTTTGACGACGGA |
| | | 332 | Reverse primer | ACCCTTAAAACCGATACAAACG |
| | | 331 | Beacon | CGACATGCGAGGACGGTAAGGCGTACGGGCATGTCG |
| JPH3_67331 | 90 | 313 | Forward primer | GGGGTAGGTTTAATTTTGACGAC |
| | | 314 | Reverse primer | TAAAACCGATACAAACGCCA |
| | | 331 | Beacon | CGACATGCGAGGACGGTAAGGCGTACGGGCATGTCG |
| JPH3_67332 | 115 | 333 | Forward primer | TACGGTTTAATCGGAGGACGTAG |
| | | 334 | Reverse primer | AACGAAAATAAATACCGCGAA |
| | | 335 | Beacon | CGACATGCGGGCGCGATCGGAAGTACGGCATGTCG |
| JPH3_67333 | 109 | 333 | Forward primer | TACGGTTTAATCGGAGGACGTAG |
| | | 336 | Reverse primer | AATAAATACCGCGAACCGAA |
| | | 335 | Beacon | CGACATGCGGGCGCGATCGGAAGTACGGCATGTCG |
| JPH3_67334 | 92 | 333 | Forward primer | TACGGTTTAATCGGAGGACGTAG |
| | | 337 | Reverse primer | GAACCGAACCGAAACGAAA |
| | | 335 | Beacon | CGACATGCGGGCGCGATCGGAAGTACGGCATGTCG |
| JPH3_67335 | 96 | 51 | Forward primer | TTAGATTTCGTAAACGGTGAAAAC |
| | | 52 | Reverse primer | TCTCCTCCGAAAAACGCTC |
| | | 338 | Beacon | CGACATGCGCGGTCGTCGGCGGTTTTGGCATGTCG |
| JPH3_67336 | 108 | 339 | Forward primer | TGTAATTCGGTTTTAGATTTCGT |
| | | 52 | Reverse primer | TCTCCTCCGAAAAACGCTC |
| | | 338 | Beacon | CGACATGCGCGGTCGTCGGCGGTTTTGGCATGTCG |
| JPH3_67337 | 91 | 340 | Forward primer | GTTCGTTTTCGTTTTTCGTTT |
| | | 341 | Reverse primer | CTAACCTACTAAACCGCGCC |
| | | 338 | Beacon | CGACATGCGCGGTCGTCGGCGGTTTTGGCATGTCG |
| JPH3_67338 | 97 | 342 | Forward primer | GTTTTCGTTCGTTTTTCGTTT |
| | | 341 | Reverse primer | CTAACCTACTAAACCGCGCC |
| | | 338 | Beacon | CGACATGCGCGGTCGTCGGCGGTTTTGGCATGTCG |

TABLE 11-continued

Primer pairs and probes (molecular beacons) for determining the methylation status of JPH3, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| JPH3_67339 | 120 | 343 | Forward primer | AGTAGTAGTAGTAATGCGGCGGT |
|  |  | 344 | Reverse primer | CGAACGAACGAAATACGAAC |
|  |  | 345 | Beacon | CGACATGCGCGTTTCGGGTTCGGTTCGGCATGTCG |
| JPH3_67340 | 126 | 346 | Forward primer | GGGTAGTTTAGGTTCGGGTC |
|  |  | 326 | Reverse primer | ATATAATACAACCGCCAACGCC |
|  |  | 347 | Beacon | CGACATGCGCGGGCGTTCGAGGGCGCATGTCG |

In specific embodiments, the methods of the invention employ or rely upon or utilise primers and/or probes selected from the primers and probes comprising the nucleotide sequences set forth in Table 12 below to determine the methylation status of the at least one gene. The table presents specific primer and probe combinations for certain preferred genes whose methylation status may be determined according to the methods of the invention.

TABLE 12

Primer sequences and beacon (probe) sequences

|  | SEQ ID NO | Oligo nucleotides |  |
|---|---|---|---|
| BNIP3 | 348 | forward primer | 5'-TACGCGTAGGTTTTAAGTCGC-3' |
|  | 349 | reverse primer | 5'-TCCCGAACTAAACGAAACCCCG-3' |
|  | 350 | beacon | 5'-FAM-CGACATGCCTACGACCGCGTCGCCCATTAGCATGTCG-3'-DABCYL |
| FOXE1 | 351 | forward primer | 5'-TTTGTTCGTTTTTCGATTGTTC-3' |
|  | 352 | reverse primer | 5'-TAACGCTATAAAACTCCTACCGC-3' |
|  | 353 | beacon | 5'-FAM-CGTCTCGTCGGGGTTCGGGCGTATTTTTTAGGTAGGCGAGACG-3'-DABCYL |
| JAM3 | 354 | forward primer | 5'-GGGATTATAAGTCGCGTCGC-3' |
|  | 355 | reverse primer | 5'-CGAACGCAAAACCGAAATCG-3' |
|  | 356 | beacon | 5'-FAM-CGACACGATATGGCGTTGAGGCGGTTATCGTGTCG-3'-DABCYL |
| JPH3 | 51 | forward primer | 5'-TTAGATTTCGTAAACGGTGAAAAC-3' |
|  | 52 | reverse primer | 5'-TCTCCTCCGAAAAACGCTC-3' |
|  | 53 | beacon | 5'-FAM-CGTCTGCAACCGCCGACGACCGCGACGCAGACG-3'-DABCYL |
| PHACTR3 | 357 | forward primer | TTATTTTGCGAGCGGTTTC |
|  | 358 | reverse primer | GAATACTCTAATTCCACGCGACT |
|  | 359 | beacon | CGACATGCGGGTTCGGTCGGCGCGGGGCATGTCG |

TABLE 12-continued

Primer sequences and beacon (probe) sequences

| | SEQ ID NO | Oligo nucleotides | |
|---|---|---|---|
| TFPI2 | 360 | forward primer | 5'-GTTCGTTGGGTAAGGCGTTC-3' |
| | 361 | reverse primer | 5'-CATAAAACGAACACCCGAACCG-3' |
| | 362 | beacon | 5'-FAM-CGACATGCACCGCGCACCTCCTCCCGCCAAGCATGTCG-3'-DABCYL |
| SOX17 | 363 | forward primer | 5'-GAGATGTTTCGAGGGTTGC-3' |
| | 364 | reverse primer | 5'-CCGCAATATCACTAAACCGA-3' |
| | 365 | beacon | 5'-FAM-CGACATGCGTTCGTGTTTTGGTTTGTCGCGGTTTGGCATGTCG-3'-DABCYL |
| SYNE1 | 366 | forward primer | 5'-GTTGGGTTTTCGTAGTTTTGTAGATCGC-3' |
| | 367 | reverse primer | 5'-CTACGCCCAAACTCGACG-3' |
| | 368 | beacon | 5'-FAM-CGACATGCCCCGCCCTATCGCCGAAATCGCATGTCG-3'-DABCYL |

In a further specific embodiment, the methods of the invention employ or rely upon or utilise primers selected from the primers and beacons comprising the nucleotide sequences set forth in Table 13 below to determine the methylation status of BNIP3. The table presents specific primer combinations for determining the methylation status of this gene and the primer pairs may be selected according to the table.

TABLE 13

Additional assay designs: Primer and probe sequences for determining the methylation status of BNIP3, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| BNIP3_13409 | 94 | 369 | Forward primer | AGTGTTTAGAGAGTTCGTCGGTT |
| | | 370 | Reverse primer | CGTAACGAATAAACTACGCGAT |
| | | 371 | Beacon | CGACATGCGGAGAATTCGGTTTATCGTTCGTCGCGCATGTCG |
| BNIP3_67227 | 159 | 372 | Forward primer | TTTTAGGTGGAATTTTAGTTCGC |
| | | 373 | Reverse primer | CCCTCCTACGAACATACGAAA |
| | | 374 | Beacon | CGACATGCCGTGCGGTTCGATTCGGGTTTAAGGCATGTCG |
| BNIP3_67229 | 160 | 375 | Forward primer | CGGTTTAATTGCGAGACGTAG |
| | | 376 | Reverse primer | AACGTAAAAACCCCGCGTA |
| | | 377 | Beacon | CGACATGCCGTGCGGTTCGATTCGGGCATGTCG |
| BNIP3_67231 | 107 | 378 | Forward primer | GTTTTCGGGTTTTTGTTCGT |
| | | 379 | Reverse primer | GACTCTACTCGAACCTCCGCT |
| | | 380 | Beacon | CGACATGCGGGCGTTCGTTCGTAGGAAGAAGGCATGTCG |

TABLE 13-continued

Additional assay designs: Primer and probe sequences for determining the methylation status of BNIP3, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| BNIP3_67232 | 141 | 381 | Forward primer | TGAGGACGTGTAGGGAAGC |
| | | 382 | Reverse primer | AAACGAACAAAAACCCGAAA |
| | | 383 | Beacon | CGACATGCCGAGCGGTGGGTCGGAGGCATGTCG |
| BNIP3_67233 | 153 | 384 | Forward primer | GCGTTAGAGGGTAATTGCG |
| | | 385 | Reverse primer | CTATAAATTCCTCCGACCGAAC |
| | | 386 | Beacon | CGACATGCCGCGTCGGGTTGCGGGCATGTCG |
| BNIP3_67235 | 94 | 387 | Forward primer | TTTGTATTTCGGGCGTTTC |
| | | 388 | Reverse primer | GCAACTAAAACACATCCCGC |
| | | 389 | Beacon | CGACATGCGCGATATGGCGTTAGAGGGTAATTGCGCATGTCG |
| BNIP3_67236 | 106 | 390 | Forward primer | GGTTTTTACGGAAGTCGGG |
| | | 391 | Reverse primer | AATACAAACGCGATATAAAACGAA |
| | | 392 | Beacon | CGACATGCGCGTTATTTCGTTTCGTGGACGGGCATGTCG |
| BNIP3_67239 | 151 | 393 | Forward primer | GATTTCGCGTATTGTTCGG |
| | | 394 | Reverse primer | GATCCAACTACGAAACGCA |
| | | 395 | Beacon | CGACATGCGGTTTGGATTCGGGTCGGATCGGCATGTCG |

In a further specific embodiment, the methods of the invention employ or rely upon or utilise primers selected from the primers and beacons comprising the nucleotide sequences set forth in Table 14 below to determine the methylation status of FOXE1. The table presents specific primer combinations for determining the methylation status of this gene and the primer pairs may be selected according to the table.

TABLE 14

Additional assay designs: Primer and probe sequences for determining the methylation status of FOXE1, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| FOXE1_13297 | 108 | 396 | Forward primer | TTCGTTTCGAGAAGTATTACGC |
| | | 397 | Reverse primer | GCGCTAAAAACTCAACGTCC |
| | | 398 | Beacon | CGACATGCGAGTCGTCGGTTAGCGGGTTATTTTCGGCATGTCG |
| FOXE1_13307 | 133 | 399 | Forward primer | TTCGTTTTCGGTAGTTATGGC |
| | | 400 | Reverse primer | GATCCCCTAAACTCTCCGC |
| | | 401 | Beacon | CGACATGCCGGGTTTTGGATTTTCGCGGTTGTCGGCATGTCG |
| FOXE1_13317 | 111 | 402 | Forward primer | CGGAGAGTTTAGGGGATCGT |
| | | 403 | Reverse primer | CTCTATCTACACCGCGCCA |
| | | 404 | Beacon | CGACATGCGTTTAGGTTGGTACGCGTTGGAGGGCATGTCG |

TABLE 14-continued

Additional assay designs: Primer and probe sequences for determining the methylation status of FOXE1, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| FOXE1_67265 | 118 | 405 | Forward primer | ATCGGTGTCGTTTTACGTTTC |
| | | 406 | Reverse primer | GTAAATCTCCAACCCTACGAAC |
| | | 407 | Beacon | CGACATGCGCGGAGGGAGGAGTCGGGCATGTCG |
| FOXE1_67266 | 125 | 408 | Forward primer | TAGGGAATCGGTGTCGTTTTAC |
| | | 409 | Reverse primer | CGTAAATCTCCAACCCTACGAAC |
| | | 410 | Beacon | CGACATGCCGGAGGGAGGAGTCGGTTCGGGCATGTCG |
| FOXE1_67267 | 108 | 411 | Forward primer | TGAGGTTTTTCGAGTCGGTT |
| | | 412 | Reverse primer | CCACAACGTCAAAACGAAA |
| | | 413 | Beacon | CGACATGCCGGGTTTTAGTCGATCGGGGCATGTCG |
| FOXE1_67268 | 100 | 414 | Forward primer | ACGTTCGCGTTATGATTGTC |
| | | 415 | Reverse primer | CCGACCCCTACTACCGTCT |
| | | 416 | Beacon | CGACATGCCGTAGTCGGAGGTGTTGGTTATCGGCATGTCG |
| FOXE1_67270 | 124 | 417 | Forward primer | GAGGTTATCGTCGTTGTTCGT |
| | | 397 | Reverse primer | GCGCTAAAAACTCAACGTCC |
| | | 418 | Beacon | CGACATGCCGCGGGTTGAGTCGTCGGGCATGTCG |
| FOXE1_67271 | 116 | 419 | Forward primer | TTAGGGATTATTTTCGGATTTTTC |
| | | 420 | Reverse primer | TTCTCGAAACGAACAACGAC |
| | | 421 | Beacon | CGACATGCCGTTCGGTATTAGCGCGTAAGGGGCATGTCG |
| FOXE1_67274 | 92 | 422 | Forward primer | CGGTAGAAGGGGAAGCGTT |
| | | 423 | Reverse primer | CTCATCGCCATAACCATCG |
| | | 424 | Beacon | CGACATGCGCGTGAGGCGGCGTTCGGCATGTCG |
| FOXE1_67276 | 90 | 351 | Forward primer | TTTGTTCGTTTTTCGATTGTTC |
| | | 425 | Reverse primer | CTATAAAACTCCTACCGCGCC |
| | | 426 | Beacon | CGACATGCCGGGGTTCGGGCGTATTTTTTTAGGGCATGTCG |
| FOXE1_67278 | 98 | 427 | Forward primer | TGTGCGCGTAGAAGAGGTTTC |
| | | 428 | Reverse primer | CGAAAACAAAACATAAACGACC |
| | | 429 | Beacon | CGACATGCGGTTAGAGCGAGGGTAGTTAGTATTGGGCATGTCG |
| FOXE1_67279 | 90 | 430 | Forward primer | GTGCGCGTAGAAGAGGTTTC |
| | | 431 | Reverse primer | AAAACATAAACGACCCCCG |
| | | 432 | Beacon | CGACATGCGAGCGAGGGTAGTTAGTATTGGCGGCATGTCG |

In a further specific embodiment, the methods of the invention employ or rely upon or utilise primers selected from the primers and beacons comprising the nucleotide sequences set forth in Table 15 below to determine the methylation status of JAM3. The table presents specific primer combinations for determining the methylation status of this gene and the primer pairs may be selected according to the table.

TABLE 15

Additional assay designs: Primer and probe sequences for determining the methylation status of JAM3, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| JAM3_12721 | 104 | 433 | Forward primer | TGTGTCGGTTTAGAGTATCGTTG |
| | | 434 | Reverse primer | CAATTACCATAACGACCGCC |
| | | 435 | Beacon | CGACATGCGTTATTATGGTGTCGGTTCGGTTGGG CATGTCG |
| JAM3_67314 | 108 | 433 | Forward primer | TGTGTCGGTTTAGAGTATCGTTG |
| | | 436 | Reverse primer | GCCCCAATTACCATAACGACC |
| | | 435 | Beacon | CGACATGCGTTATTATGGTGTCGGTTCGGTTGGG CATGTCG |
| JAM3_67315 | 113 | 437 | Forward primer | ATTTATGTGTCGGTTTAGAGTATCG |
| | | 436 | Reverse primer | GCCCCAATTACCATAACGACC |
| | | 435 | Beacon | CGACATGCGTTATTATGGTGTCGGTTCGGTTGGG CATGTCG |
| JAM3_67317 | 90 | 438 | Forward primer | TCGAGTTTTAGTTTTGGTTGC |
| | | 439 | Reverse primer | AAATAACGATCCTAACTCCGAAA |
| | | 440 | Beacon | CGACATGCCGGTTCGGGATTTCGGGAGGCATGTC G |
| JAM3_67318 | 133 | 441 | Forward primer | TTTAGTAAGTTTTAGCGTTTACGTC |
| | | 442 | Reverse primer | GAATAAACTCCTCCCAAACGAA |
| | | 443 | Beacon | CGACATGCGAGGGTCGTGTTTATCGTTCGGGCAT GTCG |

In a further specific embodiment, the methods of the invention employ or rely upon or utilise primers selected from the primers and beacons comprising the nucleotide sequences set forth in Table 16 below to determine the methylation status of PHACTR3. The table presents specific primer combinations for determining the methylation status of this gene and the primer pairs may be selected according to the table.

TABLE 16

Additional assay designs: Primer and probe sequences for determining the methylation status of PHACTR3, with predicted amplification product lengths shown.

| Assay name | Amplicon length | SEQ ID NO | Oligonucleotides & probes | 5' to 3' Sequences (all the beacons are 5'-FAM and 3'-DABCYL) |
|---|---|---|---|---|
| PHACTR3_67295 | 111 | 444 | Forward primer | ATTTAGGTAACGGGTTGGGC |
| | | 445 | Reverse primer | ACTCCCCGAATACAAACGAA |
| | | 446 | Beacon | CGACATGCGGTTCGAGGTAGGTGGCGTT GGCATGTCG |

TABLE 16-continued

Additional assay designs: Primer and probe sequences for determining the methylation status of PHACTR3, with predicted amplification product lengths shown.

| Assay name | Amplicon length | SEQ ID NO | Oligo nucleotides & probes | 5' to 3' Sequences (all the beacons are 5'-FAM and 3'-DABCYL) |
|---|---|---|---|---|
| PHACTR3_67296 | 128 | 447 | Forward primer | TTCGTAGAGTGATTTTAGCGTTT |
| | | 448 | Reverse primer | AACGCCACCTACCTCGAAC |
| | | 449 | Beacon | CGACATGCGCGGACGTCGGGGAGAATTTAGGGCATGTCG |
| PHACTR3_67297 | 92 | 450 | Forward primer | TAATTTGTTTTCGCGTCGG |
| | | 451 | Reverse primer | CTAAAATCACTCTACGAACGACC |
| | | 452 | Beacon | CGACATGCGGACGGGAGCGGTTGTTTCGGCATGTCG |
| PHACTR3_67298 | 118 | 453 | Forward primer | CGTTTCGGATGTTTTGATTTTAC |
| | | 454 | Reverse primer | ACTCTACGAACGACCCCGC |
| | | 455 | Beacon | CGACATGCCGGAGGACGGGAGCGGGCATGTCG |
| PHACTR3_67299 | 136 | 456 | Forward primer | TTCGTCGGTGATTTTGGTC |
| | | 454 | Reverse primer | ACTCTACGAACGACCCCGC |
| | | 457 | Beacon | CGACATGCCGTCGGTCGGGTTTATGGTCGCATGTCG |
| PHACTR3_67302 | 128 | 458 | Forward primer | ACGTTGTTACGAAATCGGG |
| | | 459 | Reverse primer | AAACGCCTAACTCCAACGAAA |
| | | 460 | Beacon | CGACATGCGGCGTACGTTTTTCGTTTTTTTGTCGGCGGCATGTCG |
| PHACTR3_67303 | 118 | 458 | Forward primer | ACGTTGTTACGAAATCGGG |
| | | 461 | Reverse primer | CTCCAACGAAACCTAACGCA |
| | | 460 | Beacon | CGACATGCGGCGTACGTTTTTCGTTTTTTTGTCGGCGGCATGTCG |
| PHACTR3_67304 | 110 | 462 | Forward primer | CGTTGTTACGAAATCGGGT |
| | | 463 | Reverse primer | GAAACCTAACGCACCTAAACG |
| | | 460 | Beacon | CGACATGCGGCGTACGTTTTTCGTTTTTTTGTCGGCGGCATGTCG |
| PHACTR3_67305 | 103 | 462 | Forward primer | CGTTGTTACGAAATCGGGT |
| | | 464 | Reverse primer | AACGCACCTAAACGCGCTA |
| | | 460 | Beacon | CGACATGCGGCGTACGTTTTTCGTTTTTTTGTCGGCGGCATGTCG |
| PHACTR3_67306 | 93 | 465 | Forward primer | GATACGAGGTAGTCGTTTTCGTT |
| | | 358 | Reverse primer | GAATACTCTAATTCCACGCGACT |
| | | 466 | Beacon | CGACATGCGCGGTTATGGGTTCGGTCGGGCATGTCG |
| PHACTR3_67308 | 124 | 467 | Forward primer | GACGTTGGGGTTATTTTGC |
| | | 358 | Reverse primer | GAATACTCTAATTCCACGCGACT |
| | | 468 | Beacon | CGACATGCGCGATACGAGGTAGTCGTTTTCGTTTTTCGGCATGTCG |

TABLE 16-continued

Additional assay designs: Primer and probe sequences for determining the methylation status of PHACTR3, with predicted amplification product lengths shown.

| Assay name | Amplicon length | SEQ ID NO | Oligo nucleotides & probes | 5' to 3' Sequences (all the beacons are 5'-FAM and 3'-DABCYL) |
|---|---|---|---|---|
| PHACTR3_67309 | 92 | 469 | Forward primer | CGTCGTTTTCGTTTAGTTCGT |
| | | 470 | Reverse primer | GCAAAATAACCCCAACGTCC |
| | | 471 | Beacon | CGACATGCGCGGAGGAGGTGGTCGAGGCATGTCG |
| PHACTR3_67310 | 133 | 472 | Forward primer | GATTGGGGATAGGAATCGC |
| | | 473 | Reverse primer | AACGACGAACGAATCGAAA |
| | | 471 | Beacon | CGACATGCGCGGAGGAGGTGGTCGAGGCATGTCG |
| PHACTR3_67311 | 113 | 472 | Forward primer | GATTGGGGATAGGAATCGC |
| | | 474 | Reverse primer | AACCCGAAACAAATAACGCT |
| | | 475 | Beacon | CGACATGCGCGGTTTTTCGAATGTAGGCGGGCATGTCG |
| PHACTR3_67312 | 101 | 472 | Forward primer | GATTGGGGATAGGAATCGC |
| | | 476 | Reverse primer | ATAACGCTAAAAACAAAACCCCG |
| | | 475 | Beacon | CGACATGCGCGGTTTTTCGAATGTAGGCGGGCATGTCG |
| PHACTR3_67313 | 92 | 472 | Forward primer | GATTGGGGATAGGAATCGC |
| | | 477 | Reverse primer | AAAACAAAACCCCGCGAAA |
| | | 475 | Beacon | CGACATGCGCGGTTTTTCGAATGTAGGCGGGCATGTCG |

In a further specific embodiment, the methods of the invention employ or rely upon or utilise primers selected from the primers and beacons comprising the nucleotide sequences set forth in Table 17 below to determine the methylation status of TFPI2. The table presents specific primer combinations for determining the methylation status of this gene and the primer pairs may be selected according to the table.

TABLE 17

Additional assay designs: Primer and probe sequences for determining the methylation status of TFPI2, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| TFPI2_12620 | 117 | 478 | Forward primer | CGGGGTGATAGTTTTCGTG |
| | | 479 | Reverse primer | CGACTTTCTACTCCAAACGACC |
| | | 480 | Beacon | CGACATGCGGGTCGGTCGGACGTTCGGCATGTCG |
| TFPI2_67243 | 98 | 481 | Forward primer | TAGAAATTGTTGGCGTTGTTTTC |
| | | 482 | Reverse primer | TACCGAACCCTACTTCTCCGT |
| | | 483 | Beacon | CGACATGCCGTATAGGAATTGGCGGTAGTTTTGCGTGGCATGTCG |

TABLE 17-continued

Additional assay designs: Primer and probe sequences for determining the methylation status of TFPI2, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| TFPI2_67244 | 124 | 484 | Forward primer | TAGTCGTCGGCGTAAGGAGC |
| | | 485 | Reverse primer | AAAACTACGAAAACAACGCCA |
| | | 486 | Beacon | CGACATGCTGGGTGCGCGTAGGGTAGCATGTCG |
| TFPI2_67245 | 120 | 487 | Forward primer | GTGTTCGTTTTATGCGGGG |
| | | 488 | Reverse primer | TCTTACACAATTTACAACGCGAA |
| | | 489 | Beacon | CGACATGCCGTTCGGTCGATTTTCGTCGGGCATGTCG |
| TFPI2_67246 | 115 | 490 | Forward primer | TTTTTGTTTTAGGCGGTTC |
| | | 491 | Reverse primer | GACGAAATAACAATCCCCGT |
| | | 489 | Beacon | CGACATGCCGTTCGGTCGATTTTCGTCGGGCATGTCG |
| TFPI2_67247 | 106 | 492 | Forward primer | TTCGTTAGGAAAAGTAGTAGAATCG |
| | | 493 | Reverse primer | GCCAAACGCTTTCTCGAAC |
| | | 494 | Beacon | CGACATGCGGGTAAGGCGTTCGAGAAAGCGGCATGTCG |
| TFPI2_67248 | 117 | 478 | Forward primer | CGGGGTGATAGTTTTCGTG |
| | | 479 | Reverse primer | CGACTTTCTACTCCAAACGACC |
| | | 495 | Beacon | CGACATGCGTCGGTCGGACGTTCGTTTCGGCATGTCG |
| TFPI2_67250 | 120 | 496 | Forward primer | GTCGTTAGTTTTTGTACGGGG |
| | | 497 | Reverse primer | GAAAATCCTAAATACGCGCAA |
| | | 498 | Beacon | CGACATGCGGGAGGTTTGCGACGATGTTTGTTGGGCATGTCG |

In a further specific embodiment, the methods of the invention employ or rely upon or utilise primers selected from the primers and beacons comprising the nucleotide sequences set forth in Table 18 below to determine the methylation status of SOX17. The table presents specific primer combinations for determining the methylation status of this gene and the primer pairs may be selected according to the table.

TABLE 18

Additional assay designs: Primer and probe sequences for determining the methylation status of SOX17, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| SOX17_66067 | 117 | 499 | Forward primer | GGCGTTAGAGTTTAGTTTCGGT |
| | | 500 | Reverse primer | TAATCCGAATCCCACGTCC |
| | | 501 | Beacon | CGACATGCGGTGTAGTTTTGGGCGCGGGCATGTCG |

TABLE 18-continued

Additional assay designs: Primer and probe sequences for determining the methylation status of SOX17, with predicted amplification product lengths shown.

| Assay name | Amplicon length | SEQ ID NO | Oligo nucleotides | 5' to 3' Sequences (all the beacons are 5'-FAM and 3'-DABCYL) |
|---|---|---|---|---|
| SOX17_66070 | 131 | 502 | Forward primer | CGGTTTAGTGATATTGCGGG |
| | | 503 | Reverse primer | ACGTAAAACTCGAACCACGAC |
| | | 504 | Beacon | CGACATGCGATGTGGTTAATGGAG CGGCGAGGGCATGTCG |
| SOX17_66071 | 110 | 505 | Forward primer | TTAGTGATATTGCGGGCGT |
| | | 506 | Reverse primer | CGACCTAAACGTAAACCTAACGA |
| | | 507 | Beacon | CGACATGCGGAGCGGCGAGGGCGG CATGTCG |
| SOX17_66073 | 92 | 508 | Forward primer | TATTGAGATGTTTCGAGGGTTGC |
| | | 509 | Reverse primer | CTAAATACGCTATAAACCAAACCG |
| | | 510 | Beacon | CGACATGCCGGTTCGAAGTCGTCG TTCGTGGCATGTCG |
| SOX17_66078 | 96 | 511 | Forward primer | TCGAGTTAAGGGCGAGTTTC |
| | | 512 | Reverse primer | TCTAAATTCTACTACGCCAACCG |
| | | 513 | Beacon | CGACATGCGGTGTGGGTTAAGGAC GAGCGTAAGGCATGTCG |
| SOX17_66079 | 91 | 511 | Forward primer | TCGAGTTAAGGGCGAGTTTC |
| | | 514 | Reverse primer | ATTCTACTACGCCAACCGCT |
| | | 515 | Beacon | CGACATGCCGGCGGTCGATGAACG TTTTTATGGGCATGTCG |
| SOX17_66080 | 117 | 516 | Forward primer | CGAATAGCGGAGTATCGGTC |
| | | 517 | Reverse primer | ACTACGCCAACCGCTTACG |
| | | 518 | Beacon | CGACATCGCGGGTCGAGTTAAGGG CGATGTCG |
| SOX17_66082 | 119 | 519 | Forward primer | TTTAGTATTTGTTTAATTCGGCGT |
| | | 520 | Reverse primer | AACGAATCCCGTATCCGAC |
| | | 521 | Beacon | CGACATGCGGATTTTGTTGCGTTA GTCGTTTGCGTTCGCATGTCG |

Each and all of these primers and probes form separate aspects of the invention. In particular, the invention relates to primer pairs selected from the primer pairs disclosed herein, including in the tables (which may comprise additional sequence over above the basic sequence listed). Further characteristics of these primers are summarized in the detailed description (experimental part) below. It is noted that variants of these sequences may be utilised in the present invention. In particular, additional sequence specific flanking sequences may be added, for example to improve binding specificity, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers and/or probes set forth in any of tables 2, 3, 4, 5 or 6. The primers and probe (including hairpin) structures may incorporate synthetic nucleotide analogues as appropriate or may be RNA or PNA based for example, or mixtures thereof.

Similarly alternative fluorescent donor and acceptor moieties/FRET pairs may be utilised as appropriate. In addition to being labelled with the fluorescent donor and acceptor moieties, the primers may include modified oligonucleotides and other appending groups and labels provided that the functionality as a primer in the methods of the invention is not compromised. Similarly alternative fluorescent donor and acceptor moieties/FRET pairs may be utilised as appropriate. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl) aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Thus, in one embodiment, said donor moiety and said acceptor moiety are selected from 5-carboxyfluorescein (FAM), 2'7'-dimethoxy-4'5'-dichloro-6-carboxyfluorescein (JOE), rhodamine, 6-carboxyrhodamine (R6G), N,N,N'-tetramethyl-6-carboxyrhodamine (TAMRA), 6-carboxy-X-rhodamine (ROX), 5-(2'-aminoethyl)aminonapthalene-1-sulfonic acid (EDANS), anthranilamide, coumarin, terbium chelate derivatives, Malachite green, Reactive Red 4, DABCYL, tetramethyl rhodamine, pyrene butyrate, eosine nitrotyrosine, ethidium, and Texas Red. In a further embodiment, said donor moiety is selected from fluorescein, 5-carboxyfluorescein (FAM), rhodamine, 5-(2'-aminoethyl)aminonapthalene-1-sulfonic acid (EDANS), anthranilamide, coumarin, terbium chelate derivatives, Malachite green, and Reactive Red 4, and said acceptor moiety is selected from DABCYL, rhodamine, tetramethyl rhodamine, pyrene butyrate, eosine nitrotyrosine, ethidium, and Texas Red.

In one particular embodiment, said donor moiety is fluorescein or a derivative thereof, and said acceptor moiety is DABCYL. In specific embodiments, the fluorescein derivative comprises, consists essentially of or consists of 6-carboxy fluorescein.

For all aspects and embodiments of the invention, the primers and in particular the stem loop/hairpin structures, and/or the probes (as appropriate upon the form of detection employed) may be labelled with donor and acceptor moieties during chemical synthesis of the primers or probes or the label may be attached following synthesis using any suitable method. Many such methods are available and well characterised in the art.

It is noted that the specific exemplified probe types (such as the hairpin probe type employed in tables 7 and 9) may be replaced as appropriate with a different probe (or primer) type as appropriate. Equivalents are discussed herein and may be utilised as appropriate.

In a further embodiment, bisulphite sequencing is utilised in order to determine the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein). Primers may be designed for use in sequencing through the important CpG islands in the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein). Thus, primers may be designed in both the sense and antisense orientation to direct sequencing across the promoter region of the relevant gene or genes.

In one embodiment, in which the NDRG4 and/or NDRG2 gene is sequenced, bisulphite sequencing may be carried out by using sequencing primers which comprise, consist essentially of or consist of the following sequences, and which may be used in isolation or in combination to sequence both strands:

NDRG4 primers

SEQ ID NO: 570
5'-gatyggggtgttttttaggttt-3' (forward)

wherein "Y" represents a pyrimidine mucleotide

SEQ ID NO: 6
5'-craacaaccaaaaaccccctc-3' (reverse)

Wherein "r" represents a purine nucleotide.
NDRG2 primers

SEQ ID NO: 522
5'-tttgttggttatttttttttattttt-3' (forward)

SEQ ID NO: 523
5'-cccccaaactcaataataaaaac-3' (reverse)

These sequencing primers form a further aspect of the invention, with suitable variants being included within the scope of the invention (the discussion of which applies mutatis mutandis here).

Other nucleic acid amplification techniques, in addition to PCR (which includes real-time versions thereof and variants such as nested PCR), may also be utilised, as appropriate, to detect the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein). Such amplification techniques are well known in the art, and include methods such as NASBA (Compton, 1991), 3SR (Fahy et al., 1991) and Transcription Mediated Amplification (TMA). Other suitable amplification methods include the ligase chain reaction (LCR) (Barringer et al, 1990), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technlology, and nick displacement amplification (WO 2004/067726). This list is not intended to be exhaustive; any nucleic acid amplification technique may be used provided the appropriate nucleic acid product is specifically amplified. Thus, these amplification techniques may be tied in to MSP and/or bisulphite sequencing techniques for example.

Sequence variation that reflects the methylation status at CpG dinucleotides in the original genomic DNA offers two approaches to primer design. Both primer types may be utilised in the methods of the invention either alone or in combination. Firstly, primers may be designed that themselves do not cover any potential sites of DNA methylation. Sequence variations at sites of differential methylation are located between the two primers. Such primers are used in bisulphite genomic sequencing, COBRA and Ms-SnuPE for example. Secondly, primers may be designed that anneal specifically with either the methylated or unmethylated version of the converted sequence. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not, which in turn indicates whether the DNA had been methylated or not.

Another way to distinguish between modified and unmodified DNA is to use oligonucleotide probes which may also be specific for certain products. Such probes may be hybridized directly to modified DNA or to amplification products of modified DNA. Oligonucleotide probes can be labelled using any detection system known in the art. These include but are not limited to fluorescent moieties, radio-isotope labelled moieties, bioluminescent moieties, luminescent moieties, chemiluminescent moieties, enzymes, substrates, receptors, or ligands.

In the MSP technique, amplification is achieved with the use of primers specific for the sequence of the gene whose methylation status is to be assessed. In order to provide specificity for the nucleic acid molecules, primer binding sites corresponding to a suitable region of the sequence may be selected. The skilled reader will appreciate that the nucleic acid molecules may also include sequences other than primer binding sites which are required for detection of the methylation status of the gene, for example RNA Polymerase binding sites or promoter sequences may be required for isothermal amplification technologies, such as NASBA, 3SR and TMA.

TMA (Gen-probe Inc.) is an RNA transcription amplification system using two enzymes to drive the reaction, namely RNA polymerase and reverse transcriptase. The TMA reaction is isothermal and can amplify either DNA or RNA to produce RNA amplified end products. TMA may be combined with Gen-probe's Hybridization Protection Assay (HPA) detection technique to allow detection of products in a single tube. Such single tube detection is a preferred method for carrying out the invention.

Whilst the genes (in particular promoters) of the invention appear to be unmethylated in normal tissues, and thus the detection of methylation (or indeed a lack of methylation) in these genes is readily observable as being significant in terms of a cancer diagnosis and also in selecting suitable treatment regimens and for determining the likelihood of successful treatment or resistance to treatment with certain anti-cancer agents etc, when determining methylation status, it may be beneficial to include suitable controls in order to ensure the method chosen to assess this parameter is working correctly and reliably. For example, suitable controls may include assessing the methylation status of a gene known to be methylated. This experiment acts as a positive control to ensure that false negative results are not obtained (i.e. a conclusion of a lack of methylation is made even though the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may, in fact, be methylated). The gene may be one which is known to be methylated in the sample under investigation or it may have been artificially methylated, for example by using a suitable methyltransferase enzyme, such as SssI methyltransferase. In one specific embodiment, the NDRG4/NDRG2 subfamily gene, preferably the NDRG4 and/or NDRG2 gene, may be assessed in normal lymphocytes, following treatment with SssI methyltransferase, as a positive control.

Additionally or alternatively, suitable negative controls may be employed with the methods of the invention. Here, suitable controls may include assessing the methylation status of a gene known to be unmethylated or carrying out an amplification in the absence of DNA (for example by using a water only sample). The former experiment acts as a negative control to ensure that false positive results are not obtained (i.e. a conclusion of methylation is made even though the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein, such as at least one gene selected from OSMR, SFRP1, NDRG4, GATA5, ADAM23, JPH3, SFRP2 and APC in one specific embodiment) may, in fact, be unmethylated). The gene may be one which is known to be unmethylated in the sample under investigation or it may have been artificially demethylated, for example by using a suitable DNA methyltransferase inhibitor, such as those discussed in more detail below. In one specific embodiment, the NDRG4/NDRG2 subfamily gene, in particular the NDRG4 and/or NDRG2 gene, may be assessed in normal lymphocytes as a negative control, since it has been shown for the first time herein that the NDRG4 and/or NDRG2 gene is unmethylated in normal tissues.

The application of the methods of present invention to extremely small amounts of abnormally-methylated DNA, that are released into collected fluids, in particular stools, may require the generation and amplification of a DNA library before testing for methylation of any specific gene. Suitable methods on whole genome amplification and libraries generation for such amplification (e.g. Methylplex and Enzyplex technology, Rubicon Genomics) are described in US2003/0143599, WO2004/081225 and WO2004/081183 for example. In addition, WO2005/090507 describes library generation/amplification methods that require either bisulfite conversion or non-bisulfite based application. Bisulfite treatment may occur before or after library construction and may require the use of adaptors resistant to bisulfite conversion. Meth-DOP-PCR (Di Vinci et al, 2006), a modified degenerate oligonucleotide-primed PCR amplification (DOP-PCR) that is combined with MSP, provides another suitable method for specific detection of methylation in small amounts of DNA. Improved management of patient care may require these existing methods and techniques to supplement the methods of the invention.

As discussed in the experimental section, epigenetic silencing resulting in methylation of the NDRG4/NDRG2 subfamily gene has been shown in a number of gastrointestinal cancers such as colorectal cancer and/or gastric cancer, stomach and oesophageal cancers, in particular oesophageal carcinomas. Thus, in specific embodiments, the invention provides for a method of diagnosing a gastrointestinal cancer, such as colorectal cancer and/or gastric cancer and/or oesophageal cancer or predisposition to a gastrointestinal cancer, such as colorectal cancer and/or gastric cancer and/or oesophageal cancer comprising detecting the methylation status of the NDRG4/NDRG2 subfamily gene, wherein methylation of the gene is indicative for a gastrointestinal cancer, such as colorectal cancer and/or gastric cancer and/or oesophageal cancer, or predisposition to a gastrointestinal cancer, such as colorectal cancer and/or gastric cancer and/or oesophageal cancer. Preferably, the gene is NDRG2, or NDRG4, or a combination of NDRG2 and NDRG4.

Whilst the epigenetic change, in particular methylation status, of any of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17 and PHACTR3 and JAM3 (in all permutations and combinations including panels as discussed herein, such as at least one gene selected from GATA4, OSMR, NDRG4, GATA5, SFRP1, ADAM23, JPH3, SFRP2, APC and MGMT) may be determined in order to diagnose a gastrointestinal cancer, such as colorectal cancer and/or gastric cancer and/or oesophageal cancer or a predisposition thereto. In specific embodiments, the at least one gene may be selected from GATA4, OSMR, NDRG4 and SFRP2, in particular where faecal samples are utilized. Detecting an epigenetic change, in particular methylation, in these genes results in a particularly sensitive and specific diagnostic method. In a further embodiment, where plasma or serum samples are utilised, the at least one gene may be selected from OSMR, SFRP1, NDRG4, GATA5, ADAM23, JPH3, SFRP2 and APC and particularly selected from OSMR, NDRG4, GATA5 and ADAM23, in particular where plasma or serum samples are utilised. Detecting an epigenetic change, in particular methylation, in these genes results in a particularly sensitive and specific diagnostic method.

Additionally or alternatively, the at least one gene may be selected from TFPI2, BNIP3, FOXE1, SYNE1, SOX17, PHACTR3 and JAM3, such as from TFPI2, BNIP3, FOXE1, SYNE1 and SOX17, in particular TFPI2.

In embodiments in which tissue samples are utilised, the methods may comprise, consist essentially of or consist of detecting an epigenetic change in a panel of genes comprising OSMR, GATA4 and ADAM23 or OSMR, GATA4 and GATA5, wherein detection of the epigenetic change in at least one of the genes in the panel is indicative of a predisposition to, or the incidence of, colorectal cancer. The tissue sample may comprise, consist essentially of or consist of a colon and/or rectal and/or appendix sample for example, as discussed herein above.

In embodiments where faecal samples are employed, the at least one gene may be selected from GATA4, OSMR, NDRG4, GATA5, SERP1, ADAM23, JPH3, SFRP2, APC and MGMT. in addition, or alternatively, the at least one gene may be selected from TFPI2, BNIP3, FOXE1, SYNE1, SOX17, PHACTR3, and JAM3, such as from TFPI2, FOXE1, SYNE1, SOZ17, PHACTR3 and JAM3, in particular TFPI2.

Moreover, in order to improve the sensitivity of the methods of the invention the methods may comprise detecting an epigenetic change in a panel of genes comprising at least two, three, four, five or six of the genes, wherein detection of an epigenetic change in at least one of the genes in the panel is indicative of a predisposition to, or the incidence of, cancer and in particular gastrointestinal cancers as defined herein, such as colorectal cancer. The panel of genes may comprise/consist essentially of or consist of two, three, four, five or six genes.

Certain panels of genes have been found to result in particularly sensitive methods for detecting a gastrointestinal cancer, such as colorectal cancer and/or gastric cancer and/or oesophageal cancer or a predisposition thereto—especially colorectal cancer. Accordingly, in one embodiment, the panel of genes comprises, consists essentially of or consists of GATA4 and OSMR, GATA4 and NDRG4, GATA4 and SFRP2, OSMR and NDRG4, OSMR and SFRP2, NDRG4 and SFRP2, APC and SFRP2, APC and OSMR, APC and GATA4, APC and NDRG4, MGMT and OSMR, MGMT and GATA4, MGMT and NDRG4, MGMT and SFRP2, MGMT and APC, SFRP1 and MGMT, SFRP1 and OSMR, SFRP1 and GATA4, SFRP1 and NDRG4, SFRP1 and SFRP2, SFRP1 and APC, GATA5 and SFRP1, GATA5 and MGMT, GATA5 and OSMR, GATA5 and GATA4, GATA5 and NDRG4, GATA5 and SFRP2 or GATA5 and APC. Suitable panels incorporating other genes such as ADAM23 and/or JPH3 are also envisaged in the present invention. These embodiments are of particular applications to faecal test samples.

Further useful panels of genes comprise, consist essentially of or consists of SFRP1, SFRP2 and APC or SFRP2, OSMR and APC. Further panels of genes comprise, consist essentially of or consist of GATA4, OSMR and NDRG4, GATA4, OSMR and SFRP2, GATA4, NDRG4 and SFRP2 or OSMR, NDRG4 and SFRP2. One specific four gene panel consists of GATA4, OSMR, NDRG4 and SFRP2. One specific panel of at least six genes comprises, consists essentially of or consists of NDRG4, OSMR, SFRP1, ADAM23, GATA5 and MGMT. These panels may usefully be applied to faecal test samples in certain embodiments.

In a further specific embodiment, the panel of genes comprises, consists essentially of or consists of OSMR, GATA4 and ADAM23 or OSMR, GATA4 and GATA5. This embodiment applies in particular to tissue samples, which may be colon, rectal or appendix samples for example, as discussed herein.

In certain embodiments, the panel of genes comprises, consists essentially of or consists of OSMR, NDRG4, GATA5 and ADAM23, where blood based samples and in particular plasma or serum samples are utilised.

Thus, the invention provides a method of detecting a predisposition to, or the incidence of, early stage colorectal cancer and in particular stage 0 to II colorectal cancer in a blood sample, or derivative thereof such as a plasma or serum sample (preferably a plasma sample) comprising detecting an epigenetic change in at least one gene selected from OSMR, NDRG4, GATA5 and ADAM23, wherein detection of the epigenetic change is indicative of a predisposition to, or the incidence of, early stage colorectal cancer and in particular stage 0 to II colorectal cancer. This method may be applied to a panel consisting of these four genes.

It is noted that for each gene, it may be possible to detect an epigenetic change, in particular methylation of the gene, in a plurality of locations within the same gene. Thus, for example, a gene may incorporate more than one CpG island, or multiple sites within the same CpG island may be investigated as appropriate. As shown in the detailed description (experimental part) below, for example, OSMR can be assessed at two discrete locations, both providing useful diagnostically relevant results. The respective targets are designated herein as OSMR3 and OSMR4. In one embodiment, the panel of genes comprises, consists essentially of or consists of both OSMR3 and OSMR4. When OSMR is referred to herein, as for all other genes, reference is made to an investigation of an epigenetic change, in particular methylation which is relevant to colorectal cancer. Thus, the panels of genes in the present invention may incorporate assessment of multiple sites within the same gene as appropriate. Primers investigating multiple sites within the same genes are set forth in the tables above, see particularly tables 2 to 18 (and especially tables 5 to 11 and 13 to 18).

As discussed in greater detail herein, the detection of an epigenetic change in each of the panel of genes may be carried out in a single reaction. Many suitable techniques allowing multiplexing are available and may be utilised in the present invention. Most depend upon use of suitable fluorescent molecules having distinguishable emission spectra. The skilled person can readily select from the many fluorophores available to determine which can be used in a multiplexing context.

In one embodiment, a universal quencher is utilised together with suitable fluorophore donors each having a distinguishable emission wavelength maximum. A particularly useful quencher is DABCYL. Together with a suitable quencher such as DABCYL the following fluorophores may each be utilised to allow multiplexing: Coumarin (emission maximum of 475 nm), EDANS (491 nm), fluorescein (515 nm), Lucifer yellow (523 nm), BODIPY (525 nm), Eosine (543 nm), tetramethylrhodamine (575 nm) and texas red (615 nm) (Tyagi et al., Nature Biotechnology, Vol. 16, Jan. 1998; 49-53).

It is noted that the methylation status of additional genes may also be determined in order to supplement the methods of the invention. No gene has been found to be epigenetically silenced in every similar tumour. For this reason, it may be advantageous to target multiple DNA alterations to attain high rates of tumour detection. Thus, in one embodiment of the methods of the invention, the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is analysed in combination with the methylation status of at least one other gene involved in the establishment of cancer. The at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may be combined with at least two other genes involved in the establishment of cancer. The at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) may be combined with and at least three, four, five or six other genes involved in the establishment of cancer. For colorectal cancer, the other genes involved in the establishment of cancer may be selected from the group consisting of SFRP1, SFRP2, GATA-4, GATA-5, CHFR, APC(2), MGMT, p16, Vimentin, p14, RASSF1a, RAB32, SEPTIN-9, RASSF2A, TMEFF2, NGFR or SMARCA3. However, any gene involved in the establishment of colorectal cancer may be utilized in combination with the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in the methods of present invention.

Genes that become methylated early in the process of carcinogenesis are not only ideal for screening purposes, but also interesting targets for early cancer detection and for monitoring the progression or outcome of cancers. In a further aspect, the invention provides for a method of cancer prognosis (prognosis to cancer) comprising detecting epigenetic silencing of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein epigenetic silencing of the gene is indicative for cancer development. Preferably, epigenetic silencing is detected by determination of the methylation status and/or measurement of expression level of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein). In one embodiment, the subject is suffering from advanced adenomas or at risk for developing AJCC stage I, II, III or IV cancer. In another embodiment, the outcome is the survival of the subject after a surgical resection, e.g. a noncurative or curative surgical resection.

Early detection of epigenetic silencing of one of more genes may provide justification for more definitive follow up of patients who have molecular, but not yet all the pathological or clinical, features associated with the malignancy. Identification of cancer at its earliest stage while it is still localized and readily treatable may improve the clinical outcome in patients.

Methods with a prognostic value should allow for the specific detection of tumours and not detect (benign) adenomas, and thus provide for a differential diagnosis between advanced adenoma versus benign adenoma. As shown in the detailed description (experimental part), gene promoter hypermethylation of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) was observed at a higher frequency in adenomas with concurrent colorectal cancer when compared to adenomas from patients that did not have colorectal cancer. This prognostic value is included within the definition of diagnosis.

In a related aspect, the invention provides a method for determining the histopathological stage of cancer and in particular gastrointestinal cancer, such as colorectal cancer in a sample comprising detecting an epigenetic change in at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein detection of the epigenetic change is indicative of the histopathological stage of the cancer, such as colorectal cancer for example. All embodiments of the methods of the invention are hereby incorporated as appropriate and are not repeated for reasons of conciseness. The epigenetic change is generally one causing gene silencing. Preferably, epigenetic silencing is detected by determination of the methylation status and/or measurement of expression levels of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) and the methylation status and/or expression level of the gene or genes is correlated to a histopathological stage of cancer. In this method, a sample is obtained from a subject suffering from, or suspected of suffering from any appropriate cancer in accordance with this invention, such as colorectal cancer for example. The methylation level of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), the expression level of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), or a combination thereof is determined and correlated to a histopathological stage of the cancer. The "stage" of a cancer is a descriptor (usually numbers I to IV) of how much the cancer has spread. The stage often takes into account the size of a tumour, how deep it has penetrated, whether it has invaded adjacent organs, if and how many lymph nodes it has metastasized to, and whether it has spread to distant organs. Staging of cancer is important because the stage at diagnosis is the biggest predictor of survival, and treatments are often changed based on the stage. As aforementioned, the description of suitable methods for determining epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) apply mutatis mutandis to these aspects of the invention and are not repeated here simply for reasons of conciseness.

In a specific embodiment, the invention provides a method for determining the histopathological stage of a gastrointestinal cancer, such as colorectal cancer and/or gastric cancer and/or oesophageal cancer or a predisposition thereto in a tissue or blood sample, or derivative thereof such as a plasma or serum sample. The most suitable genes and combinations of genes are described hereinabove for these specific test samples (at least one gene selected from OSMR, SFRP1, NDRG4, GATA5, ADAM23, JPH3, SFRP2 and APC for blood samples for example) and are not repeated for reasons of conciseness.

In a further specific embodiment, the invention provides a method for predicting or monitoring progression of an adenoma (to a carcinoma), in particular in the context of gastrointestinal cancers such as colorectal cancer, comprising determining the methylation status of an NDRG2/NDRG4 subfamily gene and in particular the NDRG4 gene in a suitable test sample, wherein an elevated or increased level of methylation indicates that the adenoma is more likely to progress to a carcinoma (than if the level of methylation is lower). This embodiment applies particularly to the region of the NDRG4 gene which is amplified using primer set 1 as set out in table 2 above. Thus, in one embodiment, these methods employ primer set 1 in order to determine the methylation status of the NDRG4 gene. As is discussed below, primer pair 1 allows distinguishing of adenomas that progress to cancer from those that will not progress. This is highly important for cancer screening. The test sample may be any suitable sample, as discussed extensively above. However, the sample is generally a suitable tissue sample, in particular an adenoma sample.

In a related embodiment, detecting increased levels of methylation towards the transcription start site of the NDRG4 gene may also be useful for monitoring the progression of cancer, and in particular gastrointestinal cancers such as colorectal cancer (CRC). As is shown herein, based upon the results obtained, it is predicted that spreading of methylation from more 5' regions of the promoter towards the transcription start site correlates with cancer progression (for example from adenoma to carcinoma). Thus, the invention provides a method for predicting or monitoring progression of a gastrointestinal cancer, such as CRC, comprising determining the methylation status of an NDRG2/NDRG4 subfamily gene in a suitable test sample, wherein an elevated or increased level of methylation towards the transcription start site indicates that the cancer is more progressed than if the level of methylation is lower. The transcription start site and promoter sequence are known from the published gene sequence information. Primer set 1 and 2 as defined herein may be utilised as appropriate in these methods. Primer set 1 is used to determine the methylation status of the NDRG4 gene closer to the transcription start site than primer set 2. Thus, a comparison of such results may be useful in these methods.

As stated herein the methods of the invention for diagnostic, prognostic, or personalised medicinal care are preferentially used in connection with a gastrointestinal cancer, such as colorectal cancer and/or gastric cancer and/or oesophageal cancer. A number of techniques are currently available for detection of colorectal cancer. These include:
Faecal occult blood tests (Guaiac and immunochemical)
Colonoscopy and/or sigmoidoscopy
X-ray after double-contrast barium enema or CT-colonography
Faecal DNA test (PreGen-Plus®)

More accurate screening, surveillance of higher-risk patients and improved management of patient care may advantageously employ these existing methods and techniques to supplement the methods of the invention.

Faecal DNA testing is an emerging technology in screening for colorectal cancer. Premalignant adenomas and cancers shed DNA markers from their cells which are not degraded during the digestive process and remain stable in the stool. Capture, followed by amplification, for example using the Polymerase Chain Reaction, amplifies the DNA to detectable levels for assay. The faecal DNA integrity assay has been proposed as a useful tool for the detection of colorectal cancer. The presence of high-molecular-weight DNA fragments in stool is associated with colorectal cancer and may be related to disease-associated differences in the regulation of proliferation and apoptosis. Detecting colorectal cancer by testing stool for DNA may alternatively be based on identifying oncogene mutations characteristic of colorectal neoplasia that are detectable in exfoliated epithelial cells in the stool. While neoplastic bleeding is intermittent, epithelial shedding is continuous, potentially making stool-based DNA testing (also known as fecal DNA [f-DNA]) testing more sensitive than other methods. Commercially available stool-based DNA tests for colorectal cancer include PreGen-Plus™ (EXACT Sciences Corporation, Marlborough, Mass. 01752 USA) which is a single test that identifies the presence of 23 different microsatellite (MSI) mutations known to be associated with CRC, including mutations in BAT-26. Additionally, 21 other point mutations in other genes associated with CRC are included in this test: adenomatous polyposis coli (APC), K-ras, and protein and molecular size 53,000 daltons (p53). This test is also designed to detect long DNA fragments, which have been specifically associated with cells called non-apoptotic colonocytes, which are common in CRC.

Accordingly, molecular screening of faecal samples focused on oncogene mutations and/or DNA integrity may complement the methods of present invention. In specific embodiments, the methods of the invention are used in combination with detecting DNA integrity, or at least one DNA oncogene mutation, or a combination of both detecting DNA integrity and at least one DNA oncogene mutation in the sample in order to detect a predisposition to, or the incidence of, colorectal cancer. The methods may be carried out on a faecal sample. In one embodiment the method may also include the step of obtaining and/or processing the sample.

Testing can be performed diagnostically or in conjunction with a therapeutic regimen. Epigenetic loss of function of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) can be rescued by the use of DNA demethylating agents and/or DNA methyltransferase inhibitors. Testing can be used to determine what therapeutic or preventive regimen to employ on a patient and be used to monitor efficacy of a therapeutic regimen.

Accordingly, the invention also provides a method for predicting the likelihood of successful treatment of a cancer as defined herein and in particular gastrointestinal cancer, such as colorectal cancer and/or gastric cancer and/or oesophageal cancer with a DNA demethylating agent and/or a DNA methyltransferase inhibitor and/or HDAC inhibitor comprising detecting an epigenetic change in at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein detection of the epigenetic change is indicative that the likelihood of successful treatment is higher than if the epigenetic modification is not detected. Alternatively, the method comprises measurement of expression levels of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein a reduced level of expression indicates the likelihood of successful treatment of cancer is higher than if the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is expressed at a higher level. For the avoidance of doubt it is stated that the description of suitable methods (sample types, cancer types, panels of genes etc.) for determining epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) apply mutatis mutandis to these aspects of the invention and are not repeated here simply for reasons of conciseness.

In an opposite scenario, the invention provides a method for predicting the likelihood of resistance to treatment of colorectal cancer with a DNA demethylating agent and/or DNA methyltransferase inhibitor and/or HDAC inhibitor comprising detecting an epigenetic change in at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein detection of the epigenetic change is indicative that the likelihood of resistance to treatment is lower than if the epigenetic modification is not detected.

Alternatively, the method comprises measurement of expression levels of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein a higher level of expression indicates the likelihood of resistance to treatment of cancer is higher than if the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is expressed at a reduced level.

Thus, the patient population may be selected for treatment on the basis of their methylation status with respect to the relevant at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein—such as where the at least one gene is selected from GATA4, OSMR, NDRG4 and SFRP2 or selected from OSMR, NDRG4, GATA5 and ADAM23 where tissues or bodily fluid and in particular faecal or blood based samples and in particular plasma samples are utilised), which leads to down regulation of gene expression of the corresponding gene. This leads to a much more focussed and personalised form of medicine and thus leads to improved success rates since patients will be treated with drugs which are most likely to be effective. The description of suitable methods for determining epigenetic silencing of the at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3 apply mutatis mutandis to these aspects of the invention and are not repeated here simply for reasons of conciseness.

In certain aspects, epigenetic loss of function of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in adenoma can identify the need for treatment. Subjects having a disease such as colon neoplasia may be assayed for methylation of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein). Alternatively, the subject may be undergoing routine screening and may not necessarily be suspected of having a disease such as colon neoplasia. Detecting methylation of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in an adenoma can be used to improve sensitivity and/or specificity for detecting a colon neoplasia, since such advanced adenoma may indicate that the probable course of the adenoma is development to a carcinoma. In such case, preventive treatment may be recommended and involve resection of the adenoma.

Accordingly, the invention provides a method for predicting suitable treatment of an adenoma obtained from a subject, comprising determining the methylation status of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in an adenoma, wherein if the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is methylated, in particular hypermethylated, the need for treatment of the adenoma is identified. Preferably, the treatment comprises resection of the adenoma.

In an opposite scenario, the invention provides a method for predicting suitable treatment of an adenoma obtained from a subject, comprising determining the methylation status of at least one gene selected from at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in an adenoma, wherein if the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is unmethylated or methylated to a lesser degree, it is decided that there is no need of resection of the adenoma. The description of suitable methods for determining epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) apply mutatis mutandis to these aspects of the invention and are not repeated here simply for reasons of conciseness. The adenomas are typically of colonic origin in certain embodiments.

The invention further provides for a method of selecting a suitable treatment regimen for cancer or predisposition to cancer comprising determining epigenetic silencing of a NDRG4/2 family gene in a sample obtained from a subject, wherein if the gene is epigenetically silenced, in particular hypermethylated or reduced expressed, a DNA demethylating agent and/or a DNA methyltransferase inhibitor and/or a HDAC inhibitor is selected for treatment.

In an opposite scenario, the invention provides for a method of selecting a suitable treatment regimen for cancer or predisposition to cancer comprising determining the methylation status and/or expression level of a NDRG4/2 family gene in a sample obtained from a subject, wherein if the gene is unmethylated or higher expressed, treatment with a DNA demethylating agent and/or a DNA methyltransferase inhibitor and/or a HDAC inhibitor is contra-indicated. Thus, alternative treatment should be explored.

In a related aspect, the invention also provides a method of selecting a suitable treatment regimen for cancer, in particular a gastrointestinal cancer such as colorectal cancer (as defined herein), comprising detecting an epigenetic change in at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), wherein detection of the epigenetic change results in selection of a DNA demethylating agent and/or a DNA methyltransferase inhibitor and/or a HDAC inhibitor for treatment and wherein if the epigenetic change is not detected, a DNA demethylating agent and/or a DNA methyltransferase inhibitor and/or a HDAC inhibitor is not selected for treatment. In the event that the epigenetic change is not detected (for example through gene expression detection or any other suitable method), alternative treatments should be explored. The description of suitable methods for determining epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) apply mutatis mutandis to these aspects of the invention and are not repeated here simply for reasons of conciseness. In embodiments where blood and in particular plasma or serum samples are utilised, the at least one gene may be selected from OSMR, SFRP1, NDRG4, GATA5, ADAM23, JPH3, SFRP2 and APC. Suitable panels in this context comprise, consist essentially of or consist of OSMR, NDRG4, GATA5 and ADAM23. Additionally or alternatively, the at least one gene may be selected from TFPI2, BNIP3, FOXE1, SYNE1, SOX17, PHACTR3 and JAM3, such as from TFPI2, BNIP3, FOXE1, SYNE1 and SOX17, in particular TFPI2.

In embodiments where faecal samples are employed, the at least one gene may be selected from GATA4, OSMR, NDRG4, GATA5, SERP1, ADAM23, JPH3, SFRP2, APC and MGMT. In addition, or alternatively, the at least one gene may be selected from TFPI2, BNIP3, FOXE1, SYNE1, SOX17, PHACTR3, and JAM3, such as from TFPI2, FOXE1, SYNE1, SOZ17, PHACTR3 and JAM3, in particular TFPI2. Suitable panels, as defined herein, are also envisaged, such as a panel comprising, consisting essentially of or consisting of OSMR, NDRG4, GATA4 and SFRP2 for example.

In embodiments in which tissue samples are utilised, the methods may comprise, consist essentially of or consist of detecting an epigenetic change in a panel of genes comprising OSMR, GATA4 and ADAM23 or OSMR, GATA4 and GATA5. The tissue sample may comprise, consist essentially of or consist of a colon and/or rectal and/or appendix sample.

In another aspect, the invention provides for a method of treating cancer and in particular colorectal cancer in a subject comprising administration of a DNA demethylating agent and/or a HDAC inhibitor and/or a DNA methyltransferase inhibitor wherein the subject has been selected for treatment on the basis of a method of the invention. Accordingly, the description of suitable methods for determining epigenetic silencing of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) apply mutatis mutandis to these aspects of the invention and are not repeated here simply for reasons of conciseness. Thus, in embodiments where blood and in particular plasma or serum samples are utilised, the at least one gene may be selected from OSMR, SFRP1, NDRG4, GATA5, ADAM23, JPH3, SFRP2 and APC. Suitable panels in this context comprise, consist essentially of or consist of OSMR, NDRG4, GATA5 and ADAM23.

Additionally or alternatively, the at least one gene may be selected from TFPI2, BNIP3, FOXE1, SYNE1, SOX17, PHACTR3 and JAM3, such as from TFPI2, BNIP3, FOXE1, SYNE1 and SOX17, in particular TFPI2.

In embodiments where faecal samples are employed, the at least one gene may be selected from GATA4, OSMR, NDRG4, GATA5, SERP1, ADAM23, JPH3, SFRP2, APC and MGMT. In addition, or alternatively, the at least one gene may be selected from TFPI2, BNIP3, FOXE1, SYNE1, SOX17, PHACTR3, and JAM3, such as from TFPI2, FOXE1, SYNE1, SOZ17, PHACTR3 and JAM3, in particular TFPI2. Suitable panels, as defined herein, are also envisaged, such as a panel comprising, consisting essentially of or consisting of OSMR, NDRG4, GATA4 and SFRP2 for example.

In embodiments in which tissue samples are utilised, the methods may comprise, consist essentially of or consist of detecting an epigenetic change in a panel of genes comprising OSMR, GATA4 and ADAM23 or OSMR, GATA4 and GATA5. The tissue sample may comprise, consist essentially of or consist of a colon and/or rectal and/or appendix sample.

Thus, for the patient population where the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is methylated, which leads to decreased gene expression, this type of treatment is recommended. This method is referred to hereinafter as the "method of treatment" aspect of the invention.

In a related aspect, the invention also provides for the use of a DNA demethylating agent and/or a DNA methyltransferase inhibitor and/or HDAC inhibitor (in the manufacture of a medicament for use) in treating cancer, and in particular a gastrointestinal cancer, such as colorectal cancer and/or gastric cancer and/or oesophageal cancer in a subject, wherein the subject has been selected for treatment on the basis of the methods of the invention. Likewise, the invention provides a DNA demethylating agent and/or a DNA methyltransferase inhibitor and/or HDAC inhibitor for use in treating cancer, and in particular a gastrointestinal cancer, such as colorectal cancer and/or gastric cancer and/or oesophageal cancer in a subject, wherein the subject has been selected for treatment on the basis of the methods of the invention.

For all of the relevant methods (pharmacogenetic methods, treatment regimen methods and methods of treatment) of the invention, the DNA demethylating agent may be any agent capable of up regulating transcription of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein—such as at least one gene selected from GATA4, OSMR, NDRG4, GATA5 and ADAM23). A preferred DNA demethylating agent comprises, consists essentially of or consists of a DNA methyltransferase inhibitor. The DNA methyltransferase inhibitor may be any suitable inhibitor of DNA methyltransferase which is suitable for treating cancer in the presence of methylation of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein—such as at least one gene selected from OSMR, NDRG4, GATA5 and ADAM23). As is shown in the experimental section below, methylation of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein such as at least one gene selected from OSMR, NDRG4, GATA5 and ADAM23) is linked to colorectal cancer and so preventing this methylation is predicted to help to treat a gastrointestinal cancer, such as colorectal cancer and/or gastric cancer and/or oesophageal cancer.

The DNA methyltransferase inhibitor may, in one embodiment, be one which reduces expression of DNMT genes, such as suitable antisense molecules, or siRNA molecules which mediate RNAi for example. The design of a suitable siRNA molecule is within the capability of the skilled person and suitable molecules can be made to order by commercial entities (see for example, www.ambion.com). In embodiments, the DNA methyltransferase gene is (human) DNMT1.

Alternatively, the agent may be a direct inhibitor of DNMTs. Examples include modified nucleotides such as phosphorothioate modified oligonucleotides (FIG. 6 of Villar-Garea, A. And Esteller, M. DNA demethylating agents and chromatin-remodelling drugs: which, how and why? Current Drug Metabolism, 2003, 4, 11-31) and nucleosides and nucleotides such as cytidine analogues. Suitable examples of cytidine analogues include 5-azacytidine, 5-aza-2'-deoxycytidine, 5-fluouro-2'-deoxycytidine, pseudoisocytidine, 5,6-dihydro-5-azacytidine, 1-β-D-arabinofuranosyl-5-azacytosine (known as fazabarine) (see FIG. 4 of Villar-Garea, A. And Esteller, M. DNA demethylating agents and chromatin-remodelling drugs: which, how and why? Current Drug Metabolism, 2003, 4, 11-31).

In another embodiment, the DNA methyltransferase inhibitor comprises Decitabine. Full details of this drug can be found at www.supergen.com for example.

Additional DNMT inhibitors include S-Adenosyl-Methionine (SAM) related compounds like ethyl group donors such as L-ethionine and non-alkylating agents such as S-adenosyl-homocysteine (SAH), sinefungin, (S)-6-methyl-6-deaminosine fungin, 6-deaminosinefungin, N4-adenosyl-N4-methyl-2,4-diaminobutanoic acid, 5'-methylthio-5'-deoxyadenosine (MTA) and 5'-amino-5'-deoxyadenosine (Villar-Garea, A. And Esteller, M. DNA demethylating agents and chromatin-remodelling drugs: which, how and why? Current Drug Metabolism, 2003, 4, 11-31).

Further agents which may alter DNA methylation and which may, therefore, be useful in the present compositions include organohalogenated compounds such as chloroform etc, procianamide, intercalating agents such as mitomycin C, 4-aminobiphenyl etc, inorganic salts of arsenic and selenium and antibiotics such as kanamycin, hygromycin and cefotaxim (Villar-Garea, A. And Esteller, M. DNA demethylating agents and chromatin-remodelling drugs: which, how and why? Current Drug Metabolism, 2003, 4, 11-31).

Useful DNMT inhibitors in the present invention comprise, consists essentially of or consists of 5-azacytidine and/or zebulaine.

As discussed above, one challenge faced by researchers investigating colorectal cancer is the diversity of DNA present in stool samples. The DNA of interest represents only a very small percentage of the total DNA isolated from stool. Therefore, along with the exploration of suitable DNA markers, techniques for improved DNA isolation and enrichment of the human DNA component from faecal samples are required for more sensitive cancer detection.

Most techniques for improved sensitivity of cancer detection from faecal samples focus on improvements in recovery of target human DNA from the total DNA. The inventors have successfully improved the sensitivity of detection of colorectal cancer in faecal samples by increasing the amount of DNA used in the detection reactions. Increasing the amount of DNA in the detection reaction goes along with an increase in substances co-purified with the DNA.

An increase in the amount of impurities may be expected to result in PCR-inhibition, and therefore an increased level of input DNA in the detection reaction has not been previously explored for improving the sensitivity of cancer detection in faecal samples.

Accordingly, in a further aspect, the invention provides a method of processing a faecal sample to isolate and prepare DNA for use in detecting a predisposition to, or the incidence of, colorectal cancer in a faecal sample comprising:
(a) isolating DNA from the faecal sample
(b) subjecting at least 2.5 µg of the isolated DNA per amplification reaction required to treatment with a reagent which selectively modifies unmethylated cytosine residues in the DNA contained in the sample to produce detectable modified residues but which does not modify methylated cytosine residues
(c) amplifying the treated isolated DNA.

Thus, the inventors have found that by including at least 2.5 g of isolated DNA in the reagent treatment step for every downstream amplification that is required, improved detection methods using stool samples are achieved. The amount of DNA is expressed per amplification reaction required in particular to allow for multiple parallel reactions to be carried out on the same sample. For example, test and control samples can then be run in parallel. Also, where detection of an epigenetic change, preferably methylation, in at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) is not carried out in the same reaction (by use of appropriate fluorophores for example) each of a panel of genes may be assessed in a separate reaction. Thus a single starting sample may need to be split into a plurality of sub-samples, as required. This improves the accuracy of the results obtained by minimizing inter-sample variations. The amount of isolated DNA per amplification reaction is at least approximately 2.5 µg, 3 µg, 4 µg, 5 µg, 7.5 µg, 10 µg etc. to improve sensitivity, and is most preferably approximately 2.5 µg.

In one embodiment, the method further comprises, preferably prior to isolation of DNA from the sample, adding a homogenization buffer to the faecal sample. Any suitable buffer may be utilized. Useful buffers are commercially available, for example from Amresco.

The reagent which selectively modifies unmethylated cytosine residues in the DNA contained in the sample to produce detectable modified residues but which does not modify methylated cytosine residues the reagent preferably comprises, consists essentially of or consists of a bisulphite reagent. Suitable reagents are discussed herein, which discussion applies mutatis mutandis. In specific embodiments, the bisulphite reagent comprises, consists essentially of or consists of sodium bisulphite.

In a specific embodiment, between treatment of the isolated DNA with the reagent and amplification of the treated isolated DNA, the treated isolated DNA is concentrated. Any suitable DNA concentration method may be utilised. For example, a DNA-binding reagent may be utilised in order to concentrate DNA from the sample. DNA-binding reagents may be selected from DNA-binding buffers, DNA-binding filters, DNA-binding columns etc. and may require use of a centrifugation step. Suitable kits are commercially available, such as the ZYMO Clean and Concentrator Kit available from Zymo Research.

In order to achieve the necessary recovery of DNA from the faecal sample, the faecal sample may be at least approximately 4 g in weight. The faecal sample may be anywhere between approximately 2 g and 10 g in weight and is most preferably around 4 g in weight.

The methods of the invention may thus include steps such as:
obtaining and processing a stool sample from the subject under test, wherein preferably around (at least) 4 g stool is obtained
adding homogenization buffer, preferably directly after defecation (the subject may add this themselves). The buffer may be added at any suitable ratio, such as at 1:7 for example
isolating DNA from the stool sample. As mentioned above, any suitable DNA isolation technique may be employed. This may involve (a double) low speed centrifugation. Isolation may require RNase A and Proteinase K treatment followed by DNA extraction, for example by phenol/chloroform extraction. Other DNA purification techniques can be used, as discussed herein
subjecting the obtained DNA to bisulphite conversion, such as subjecting at least 18 to 32 µg DNA to bisulphite conversion or subjecting at least 2.5 µg DNA to bisulphite conversion for each PCR reaction to be done (input expressed per PCR reaction for reason of multiplexing as discussed earlier)
concentrating the amount of bisulphite treated DNA obtained from the at least 18 to 32 µg untreated DNA
amplifying the amount of bisulphite converted DNA. The amount to be amplified may be equivalent to 10 to 2.5 µg unconverted DNA (this equals the amounts for 4 marker panels down to use of a single marker).

The sensitivity of the methods for processing a faecal sample may be improved further by combining them with known methods for isolating DNA from a faecal sample. For example, the human DNA component may be purified from a stool sample using streptavidin-bound magnetic beads (Dong et al., 2001; Ahlquist et al., 2000). In a further embodiment, an electrophoresis-driven separation of target DNA sequences, using oligonucleotide capture probes immobilized in an acrylamide gel (Whitney et al., 2004) may be utilised in order to purify human DNA from the stool sample. In a still further embodiment, which may be used in the alternative or in combination with earlier embodiments, faecal samples may be frozen as quickly as possible after collection in order to preserve DNA integrity. As discussed above, DNA integrity may also be usefully tested in terms of diagnosing colorectal cancer. Additionally or alternatively, stabilization buffer may be added to the faecal samples before transport of the samples (Olson et al., 2005). In a yet further complementary embodiment, Methyl-binding domain (MBD) protein may be utilised to enrich methylated human DNA from a faecal sample, in order to specifically improve sensitivity for detecting methylated DNA markers in the sample (Zou et al., Clin Chem. 2007 September; 53(9):1646-51).

In specific aspects, the methods of processing a faecal sample according to the invention are combined with the other methods of the invention in order to provide improved diagnosis, histopathological analysis, pharmaogenomic analysis etc. of colorectal cancer. Accordingly, all embodiments of the methods of the invention apply mutatis mutandis Thus, the methods of the invention can be performed on the amplified treated DNA to provide particularly sensitive methods relating to colorectal cancer for example.

In a still further aspect, the invention provides a method of determining the methylation status of at least one gene in a blood sample, in particular a blood plasma or serum sample, comprising:
(a) isolating DNA from a blood plasma or serum sample
(b) subjecting the isolated DNA to treatment with a reagent which selectively modifies unmethylated cytosine residues in the DNA contained in the sample to produce detectable modified residues but which does not modify methylated cytosine residues
(c) amplifying the treated isolated DNA in order to determine the methylation status of at least one gene, characterised in that 0.07 to 0.72 ml blood plasma or serum sample equivalent of DNA is used per amplification reaction.

The methods thus utilise small volumes in the amplification reactions yet still maintain high sensitivity and specificity of detection. Thus, as discussed herein, a single blood sample may be advantageously utilised to determine the methylation status of a panel of genes in one embodiment. The volumes may be anywhere between around 0.07 and around 0.72 ml blood plasma or serum equivalent, and as discussed below preferably plasma equivalent, of DNA per amplification reaction. In specific embodiments, between around 0.07, 0.10, 0.15 and 0.50, 0.60, 0.70 ml, such as between 0.07 and 0.15, 0.16, 0.17, 0.18 or 0.19 ml blood plasma or serum equivalent of DNA is used per amplification reaction. In a specific embodiment, substantially the same selected volumes of blood plasma or serum sample, equivalent of DNA is used for each amplification reaction carried out. Thus, where multiple amplifications are carried out based upon a single blood sample taken from a subject, each amplification will utilise 0.07 to 0.72 ml blood plasma or serum sample, equivalent of DNA.

The blood plasma or serum sample may be derived from whole blood or any suitable plasma or serum containing parts/fractions thereof as appropriate. In specific embodiments, the blood plasma or serum sample comprises, consist essentially of or consists of plasma. The blood sample, from which the plasma or serum is derived may be collected using any suitable method. Many such methods are well known in the art. In one embodiment, the methods of the invention also incorporate the step of obtaining the blood sample and/or the plasma or serum sample from whole blood. Any appropriate blood sample may be utilised in the methods of the invention, provided it contains sufficient (free floating) DNA. In a specific embodiment, the volume of the blood sample, or derivative thereof that is utilised in the methods is around 5 to 15 ml, such as 10 ml.

Blood samples, or derivatives thereof and in particular plasma or serum samples, may be stored prior to use in the methods of the invention once obtained. They may be frozen, for example, at a suitable temperature. Suitable temperatures may be between around 0° C., −1° C., −2° C., −3° C., −4° C. and −20° C., −30° C., −40° C., −50° C., −60° C., −70° C., −80° C., −90° C. etc., such as around −80° C. They may also be stored at other temperatures, such as at 4° C. or at room temperature depending upon their form. In one specific embodiment, plasma or serum is dried to allow storage at non-freezing temperatures. The drying may comprise lyophilization for example, although other dehydration techniques may be employed. Where plasma or serum is stored at temperatures greater (i.e. warmer) than freezing, and in particular greater than −80° C., antimicrobial agents such as antibiotics may be added to the sample to prevent spoiling.

In one embodiment, stabilizers are added to the blood sample, or derivative thereof, in particular serum or plasma. This is particularly relevant where the sample is not frozen. In one specific embodiment, where the sample is serum, stabilizers such as stabilizers selected from EDTA and/or citrate and/or heparin are employed. In a further embodiment, where the sample is plasma, stabilizers such as stabilizers selected from citrate and/or heparin may be utilised.

It is preferred that the blood plasma or serum sample comprises, consists essentially of or consists of a plasma sample. Plasma may be derived from whole blood by any suitable means. In one embodiment, the plasma sample is obtained by centrifugation of whole blood. Centrifugation may be carried out at any suitable speed and for any suitable period of time and under any suitable conditions as may be determined by one skilled in the art. For example, centrifugation may be carried out at between around 1000 and 3000 g. Centrifugation may be carried out for between around 1, 2, 3, 4, or 5 and 10, 11, 12, 13, 14 or 15 minutes for example. Centrifugation may be carried out at low temperatures, such as between around 0 and 5° C., for example 4° C., to maintain integrity of the sample. Multiple centrifugation steps may be employed in order to obtain the plasma sample. In a specific embodiment, two centrifugation steps are employed to obtain the plasma sample.

It has been shown that sensitivity of the methods of the invention may be improved by excluding samples with a plasma (or serum) volume less than around 1 to 3 ml and in particular around 2 ml (such as 1.5 to 2.5 ml) prior to isolating DNA. Thus, the methods may comprise determining the volume of plasma (or serum) obtained from a blood sample prior to DNA isolation. If the volume of the plasma (or serum) obtained from the blood sample is less than around 1 to 3 ml and in particular around 2 ml (such as 1.5 to 2.5 ml), the sample is excluded from further assessment.

As stated herein, the methods are useful for determining the methylation status of at least one gene. By "determining the methylation status" is meant determining the presence or absence of 5-methylcytosine ("5-mCyt") at one or a plurality of (functionally relevant) CpG dinucleotides within the DNA sequence of the at least one gene. In particular, aberrant methylation, which may be referred to as hypermethylation, of the at least one gene may be detected. Typically, the methylation status is determined in one or more CpG islands in the at least one gene. These CpG islands are often found in the promoter region of the gene(s). Thus, CpG dinucleotides are typically concentrated in the promoter regions and exons of human genes and the methylation status of these CpG residues is of functional importance to whether the at least one gene is expressed. Since CpG dinucleotides susceptible to methylation are typically concentrated in the promoter region, exons and introns of human genes, promoter, exon and intron regions may be assessed in order to determine the methylation status of the at least one gene. A "promoter" is a region extending typically between approximately 1 Kb, 500 bp or 150 to 300 bp upstream from the transcription start site. The CpG island may surround or be positioned around the transcription start site of the at least one gene.

The methods of the invention involve isolating/extracting/purifying DNA from the blood plasma or serum sample. Any suitable DNA isolation technique may be utilised, as discussed herein, which discussion applies here mutatis mutandis. Likewise, suitable methods and kits for isolating DNA from blood samples which are commercially available are discussed and exemplified herein, which discussion applies here mutatis mutandis (see table 1). Thus, as can be derived from the table, DNA isolation may be carried out using silica-membranes, isopropanol or magnetic bead based methods for example.

The methods of the invention may also, as appropriate, incorporate quantification of isolated/extracted/purified DNA in the sample. Quantification of the DNA in the sample may be achieved using any suitable means. Quantitation of nucleic acids may, for example, be based upon use of a spectrophotometer, a fluorometer or a UV transilluminator. Examples of suitable techniques are described in standard texts such as Molecular Cloning—A Laboratory Manual (Third Edition), Sambrook and Russell (see in particular Appendix 8 therein). In one embodiment, kits such as the Picogreen® dsDNA quantitation kit available from Molecular Probes, Invitrogen may be employed to quantify the DNA.

The methods of this aspect of the invention (and other aspects of the invention which involve certain types of methylation detection) rely upon a reagent which selectively modifies unmethylated cytosine residues in the DNA contained in the sample to produce detectable modified residues but which does not modify methylated cytosine residues. Any suitable reagent may be utilised in the methods of the invention. Examples include bisulphite, hydrogen sulphite and disulphite reagents and suitable mixtures thereof. In an embodiment of the invention, the reagent comprises, consists essentially of or consists of a bisulphite reagent. In particular, the reagent may comprise, consist essentially of or consist of sodium bisulphite.

In a specific embodiment, following treatment of the isolated DNA with the reagent, and preferably between treatment of the isolated DNA with the reagent and amplification of the treated isolated DNA, the treated isolated DNA is concentrated. Any suitable DNA concentration method may be utilised. For example, a DNA-binding reagent may be utilised in order to concentrate DNA from the sample. DNA-binding reagents may be selected from DNA-binding buffers, DNA-binding filters, DNA-binding columns etc. and may require use of a centrifugation step. Suitable kits are commercially available, such as the ZYMO Clean and Concentrator Kit available from Zymo Research.

In one specific embodiment, the at least one gene whose methylation status is determined is selected from OSMR, SFRP1, NDRG4, GATA5, ADAM23, JPH3, SFRP2 and APC. As is discussed in detail herein, the methylation status of these genes in blood plasma or serum samples is correlated with the incidence of cancer and in particular colorectal cancer. Details of these genes are provided herein which discussion applies to this aspect mutatis mutandis.

In a specific embodiment, the at least one gene is selected from OSMR, NDRG4, GATA5 and ADAM23 since these four genes have been shown to be particularly reliably linked to the incidence of colorectal cancer using blood derived samples, in particular plasma sample.

Also, these genes have been shown to be linked to early stage colorectal cancer. Accordingly, the invention provides a method of determining the methylation status of at least one gene selected from OSMR, NDRG4, GATA5 and ADAM23 in a blood sample, in particular a blood plasma or serum sample, comprising:

(a) isolating DNA from a blood plasma or serum sample
(b) subjecting the isolated DNA to treatment with a reagent which selectively modifies unmethylated cytosine residues in the DNA contained in the sample to produce detectable modified residues but which does not modify methylated cytosine residues
(c) amplifying the treated isolated DNA in order to determine the methylation status of at least one gene, characterised in that 0.07 to 0.72 ml blood plasma or serum sample equivalent of DNA is used per amplification reaction.

This method may be utilised in order to diagnose early stage colorectal cancer, in particular stage 0 to II colorectal cancer. It may also be used to stage colorectal cancer—detection of methylated gene or genes indicates an early stage of cancer. Corresponding methods and kits are also envisaged. These methods may additionally or alternatively be usefully applied applied to determine the methylation status of at least one gene selected from TFPI2, BNIP3, FOXE1, SYNE1, SOX17, PHACTR3 and JAM3, such as from TFPI2, BNIP3, FOXE1, STNE1 and SOX17, in particular TFPI2.

Moreover, in order to improve the sensitivity of the methods of the invention the methods may comprise determining the methylation status of a panel of genes comprising at least two, three, four, five or six (of the) genes. Thus, in one embodiment, the at least one gene forms part of a panel of genes comprising at least two, three, four, five or six genes, wherein the methylation status of each of the genes is determined. The panel of genes may comprise, consist essentially of or consist of two, three, four, five or six genes. Suitable panels are discussed herein in respect of other aspects of the invention. That discussion and those embodiments apply here mutatis mutandis.

In specific embodiments, the panel of genes comprises, consists essentially of or consists of OSMR, NDRG4, GATA5 and ADAM23. This panel may be useful in the diagnosis of early stage colorectal cancer, such as stage 0 to II colorectal cancer.

It is noted that for each gene, it may be possible to determine the methylation status of the gene, in a plurality of locations within the same gene (as discussed herein). Thus, for example, a gene may incorporate more than one CpG island, or multiple sites within the same CpG island may be investigated as appropriate.

As discussed in greater detail herein, the determination of the methylation status of each of the panel of genes may be carried out in a single reaction. Many suitable techniques allowing multiplexing are available and may be utilised in the present invention. Most depend upon use of suitable fluorescent molecules having distinguishable emission spectra. The skilled person can readily select from the many fluorophores available to determine which can be used in a multiplexing context.

In one embodiment, a universal quencher is utilised together with suitable fluorophore donors each having a distinguishable emission wavelength maximum. One suitable quencher is DABCYL. Together with a suitable quencher such as DABCYL the following fluorophores may each be utilised to allow multiplexing: Coumarin (emission maximum of 475 nm), EDANS (491 nm), fluorescein (515 nm), Lucifer yellow (523 nm), BODIPY (525 nm), Eosine (543 nm), tetramethylrhodamine (575 nm) and texas red (615 nm) (Tyagi et al., Nature Biotechnology, Vol. 16, Jan. 1998; 49-53).

As discussed above, the methylation status of additional genes may also be determined in order to supplement the methods of the invention. Other genes involved in the establishment of colorectal cancer may be selected from the group consisting of CHFR, MGMT, p16, Vimentin, p14, RASSF1a, RAB32, SEPTIN-9, RASSF2A, ALX4 and SMARCA3.

The final step of the methods of the invention involve amplifying the treated isolated DNA in order to determine the methylation status of at least one gene. As discussed above, this amplification utilises 0.07 to 0.72 ml blood plasma or serum sample, equivalent of DNA per amplification reaction. Any suitable amplification technique may be utilised. In a specific embodiment, the amplifying step comprises, consists essentially of or consists of the polymerase chain reaction (PCR). It should be noted that whilst PCR is a preferred amplification method, to include variants on the basic technique such as nested PCR, equivalents may also be included within the scope of the invention. Examples include without limitation isothermal amplification techniques such as NASBA, 3SR, TMA and triamplification, all of which are well known in the art and commercially available. Other suitable amplification methods without limitation include the ligase chain reaction (LCR) (Barringer et al, 1990), MLPA, selective amplification of target polynucleotide sequences (U.S. Pat. No. 6,410,276), consensus sequence primed polymerase chain reaction (U.S. Pat. No. 4,437,975), invader technology (Third Wave Technologies, Madison, Wis.), strand displacement technology, arbitrarily primed polymerase chain reaction (WO90/06995) and nick displacement amplification (WO2004/067726).

Various amplification based assays for determining the methylation status of at least one gene are known in the art, and can be used in conjunction with the present invention. These assays (including techniques such as methylation specific PCR) are described in greater detail herein, which description applies here mutatis mutandis and is not repeated simply for reasons of conciseness.

In specific embodiments, the methods of the invention employ or rely upon or utilise primers and/or probes selected from the primers and probes comprising the nucleotide sequences set forth in the relevant tables above (such as tables 2 to 18 and in particular tables 4 to 10) to determine the methylation status of the at least one gene. The tables present specific primer and probe combinations for certain preferred genes whose methylation status may be determined according to the methods of the invention.

Sequence variation that reflects the methylation status at CpG dinucleotides in the original genomic DNA offers two approaches to primer design. Both primer types may be utilised in the methods of the invention as discussed in detail herein, which discussion applies mutatis mutandis here. Suitable probes may also be employed, as described herein.

When determining methylation status, it may be beneficial to include suitable controls in order to ensure the method chosen to assess this parameter is working correctly and reliably. Suitable (positive and negative) controls are discussed in detail herein, which discussion applies mutatis mutandis.

As can be derived from the discussion and examples herein, the methylation status of the at least one gene may be correlated with the incidence of a disease for specific genes and specific diseases. Accordingly, the methods of the invention may be used in order to detect a predisposition to, or the incidence of, any disease for which gene methylation plays a role. In a specific embodiment, the disease comprises a cell proliferative disorder, although in principle any disease may be diagnosed according to these methods provided that gene methylation can be determined in an appropriate blood plasma or serum sample. The cell proliferative disorder may comprise, consist essentially of or consist of cancer for example. In particular, the cancer may comprise, consist essentially of or consist of a gastrointestinal cancer, such as colorectal cancer and/or gastric cancer and/or oesophageal cancer and in particular colorectal cancer for example. Further specific gastrointestinal cancers are discussed above and each may be applicable to the present methods. As discussed herein, the methods may have particular application to early stage colorectal cancer, such as stage 0 to II colorectal cancer.

The invention also provides kits which may be used in order to carry out the methods of the invention. The kits may incorporate any of the various features, aspects and embodiments mentioned in connection with the various methods (and uses) of the invention above.

Thus, a kit is provided for:
(a) predicting the likelihood of successful treatment of cancer (as defined herein) and in particular a gastrointestinal cancer, such as colorectal cancer and/or gastric cancer and/or oesophageal cancer and/or the likelihood of resistance to treatment of cancer and in particular a gastrointestinal cancer, such as colorectal cancer and/or gastric cancer and/or oesophageal cancer with a DNA damaging agent and/or a DNA methyltransferase inhibitor and/or a HDAC inhibitor, and/or
(b) selecting a suitable treatment regimen for cancer and in particular a gastrointestinal cancer, such as colorectal cancer and/or gastric cancer and/or oesophageal cancer and/or
(c) diagnosing cancer and in particular a gastrointestinal cancer, such as colorectal cancer and/or gastric cancer and/or oesophageal cancer or a predisposition thereto, and/or
(d) determining the histopathological stage of cancer and in particular a gastrointestinal cancer, such as colorectal cancer and/or gastric cancer and/or oesophageal cancer or a predisposition thereto in a sample comprising carrier means containing therein a set of primers for use in detecting the methylation status of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein, in particular with respect to the methods of the invention). For example in one specific embodiment, the kit comprises carrier means containing therein a set of primers for use in detecting the methylation status of at least one gene selected from OSMR, SFRP1, NDRG4, GATA5, ADAM23, JPH3, SFRP2 and APC. Any of the NDRG2/NDRG4-family genes may be assessed using the kits of the invention. A more detailed discussion of family members is provided above.

Thus, the kit may include suitable primers for determining whether the NDRG2/NDRG4-family gene and preferably the NDRG4 and/or NDRG2 gene is methylated. These primers may comprise any of the primers discussed in detail in respect of the various methods of the invention which may be employed in order to determine the methylation status of the NDRG2/NDRG4-family gene and preferably the NDRG4 and/or NDRG2 gene. Thus, the primers in the kit may comprise, consist essentially of, or consist of primers for the purposes of amplifying methylated or unmethylated DNA (following bisulphite treatment). In one embodiment, the primers in the kit comprise, consist essentially of, or consist of primers which are capable of amplifying methylated and/or unmethylated DNA following bisulfite treatment which DNA comprises, consists essentially of, or consists of the nucleotide sequence set forth as SEQ ID NO: 524 and/or SEQ ID NO: 525.

The kit may alternatively or additionally employ bisulphite sequencing in order to determine the methylation status the NDRG2/NDRG4-family gene and in particular the NDRG4 and/or NDRG2 gene. Thus, the kit may comprise primers for use in sequencing through the important CpG islands in the NDRG2/NDRG4-family gene, in particular the NDRG4 and/or NDRG2 gene. Thus, primers may be designed in both the sense and antisense orientation to direct sequencing across the promoter region of the gene. In one embodiment, the primers in the kit comprise, consist essentially of, or consist of primers which are capable of sequencing of DNA following bisulfite treatment which DNA comprises, consists essentially of, or consists of the nucleotide sequence set forth as SEQ ID NO: 524 and/or SEQ ID NO: 525. Suitable primers are discussed herein in greater detail.

Similarly, the invention provides a kit for detecting a predisposition to, or the incidence of, a gastrointestinal cancer, such as colorectal cancer and/or gastric cancer and/or oesophageal cancer and in particular colorectal cancer in a sample comprising:
(a) means for detecting an epigenetic change in at least one gene selected from an NDRG2/NDRG4 subfamily gene (in particular NDRG4), GATA4, OSMR, GATA5, SFRP1, ADAM23, JPH3, SFRP2, APC, and MGMT, and/or at least one gene selected from TFPI2, BNIP3, FOXE1, SYNE1, SOX17, PHACTR3 and JAM3 (in all permutations and combinations including panels as discussed herein)
(b) means for processing a faecal sample.

As discussed in more detail above, the at least one genemay be selected from GATA4, OSMR, NDRG4 and SFRP2 since these genes provide a particularly sensitive indication of colorectal cancer. The at least one gene may be selected from TFPI2, FOXE1, SYNE1, SOX17, PHACTR3 and JAM3, in particular TFPI2.

The kit may comprise means for detecting an epigenetic change in a panel of genes comprising at least two, three, four, five or six of the genes, wherein detection of an epigenetic change in at least one of the genes in the panel is indicative of a predisposition to, or the incidence of, colorectal cancer or is used in one of the other application as discussed above. In one embodiment, the panel of genes comprises two, three, four, five or six genes.

In specific embodiments, the panel of genes comprises, consists essentially of or consists of GATA4 and OSMR, GATA4 and NDRG4, GATA4 and SFRP2, OSMR and NDRG4, OSMR and SFRP2 or NDRG4 and SFRP2. In a more specific embodiment, the panel of genes comprises, consists essentially of or consists of GATA4, OSMR and NDRG4, GATA4, OSMR and SFRP2, GATA4, NDRG4 and SFRP2 or OSMR, NDRG4 and SFRP2. Further panels comprise, consist essentially of or consist of GATA4, OSMR, NDRG4 and SFRP2.

An alternative panel of genes comprises, consists essentially of or consists of NDRG4, OSMR, SFRP1, ADAM23, GATA5 and MGMT. The skilled person would appreciate that other combinations and permutations may be formed as appropriate, as discussed in respect of the methods of the invention.

In one embodiment, the means for processing a faecal sample comprise a sealable vessel for collection of a faecal sample. Additionally or alternatively, the means for processing a faecal sample in the kit comprises a homogenization buffer. The means for processing a faecal sample may further or alternatively comprise reagents for extraction/isolation/concentration/purification of DNA. Suitable reagents are known in the art and comprise, consist essentially of or consist of alcohols such as ethanol and isopropanol for precipitation of DNA. Salt-based precipitation may require high concentrations of salts to precipitate contaminants. The salt may comprise, consist essentially of or consist of potassium acetate and/or ammonium acetate for example. Organic solvents may also be included in the kits to extract contaminants from cell lysates. Thus, in one embodiment, the means for processing the faecal sample comprise, consist essentially of or consist of phenol, chloroform and isoamyl alcohol to extract the DNA. Suitable combinations of reagents are envisaged as appropriate.

As discussed herein, which discussion applies mutatis mutandis, sensitivity of detection may be improved by increasing the quantity of DNA in the sample. Accordingly, in one embodiment the means for processing a faecal sample comprises, consists essentially of or consists of primers for directing amplification of DNA in the sample. Any suitable primers which amplify the at least one gene selected from GATA4, OSMR, NDRG4, GATA5, SFRP1, ADAM23, JPH3, SFRP2, APC, MGMT, TFPI2, BNIP3, FOXE1, SYNE1, SOX17, PHACTR3 and JAM3 may be utilised. The primers may not discriminate between methylated and unmethylated DNA (i.e. the primer binding sites lies outside of the CpG islands) thus providing a general increase in the amount of DNA prior to determining whether the methylated form of the gene or genes is present in the sample.

Similarly, the invention provides a kit for detecting a predisposition to, or the incidence of, a gastrointestinal cancer, such as colorectal cancer and/or gastric cancer and/or oesophageal cancer and in particular colorectal cancer in a sample comprising:
(a) means for detecting an epigenetic change in at least one gene selected from OSMR, SFRP1, NDRG4, GATA5, ADAM23, JPH3, SFRP2 and APC and/or at least one gene selected from TFPI2, BNIP3, FOXE1, SYNE1, SOX17, PHACTR3 and JAM3.
(b) means for processing a blood sample or derivative thereof.

As discussed in more detail above, the at least one gene may be selected from OSMR, NDRG4 GATA5 and ADAM23 since these genes provide a particularly sensitive indication of colorectal cancer in blood samples, or derivatives thereof and in particular plasma. The at least one gene may be selected from TFPI2, BNIP3, FOXE1, SYNE1, and SOX17, in particular TFPI2.

The kit may comprise means for detecting an epigenetic change in a panel of genes comprising at least two, three, four, five or six of the genes, wherein detection of an epigenetic change in at least one of the genes in the panel is indicative of a predisposition to, or the incidence of, colorectal cancer or is used in one of the other application as discussed above. In one embodiment, the panel of genes comprises two, three, four, five or six genes.

In one embodiment, the panel of genes comprises, consists essentially of or consists of OSMR, NDRG4, GATA5 and ADAM23. This kit may be used to diagnose early stage colorectal cancer, in particular stage 0 to II colorectal cancer.

In one embodiment, the means for processing a blood sample or derivative thereof comprises, consists essentially of or consists of a sealable vessel for collection of a blood sample. The means for processing a blood sample or derivative thereof may further or alternatively comprises consists essentially of or consists of a reagents for extraction/isolation/concentration/purification of DNA. Suitable reagents are known in the art and comprise, consist essentially of or consist of alcohols such as ethanol and isopropanol for precipitation of DNA. Salt-based precipitation may require high concentrations of salts to precipitate contaminants. The salt may comprise, consist essentially of or consist of potassium acetate and/or ammonium acetate for example. Organic solvents may also be included in the kits to extract contaminants from cell lysates. Thus, in one embodiment, the means for processing the blood sample or derivative thereof comprise, consist essentially of or consist of phenol, chloroform and isoamyl alcohol to extract the DNA. Suitable combinations of reagents are envisaged as appropriate. The means for processing a blood sample or derivative thereof may comprise, consist essentially of or consist of isopropanol, magnetic beads or a silica-based membrane for isolating DNA. The means for processing a blood sample or derivative thereof may comprise, consist essentially of or consist of a kit as shown in table 1.

The means for processing a blood sample or derivative thereof, in particular plasma or serum sample may comprise consist essentially of or consist of one or more stabilizers. In one embodiment, stabilizers are included in the kit to be added to the blood sample, or derivative thereof. This is particularly relevant where the sample is not frozen. In one specific embodiment, where the sample is serum, stabilizers such as stabilizers selected from EDTA and/or citrate and/or heparin are included. In a further embodiment, where the sample is plasma, stabilizers such as stabilizers selected from citrate and/or heparin may be included. Antimicrobial agents such as antibiotics may be also be included in the kits of the invention prevent spoiling (of serum and plasma samples).

Similarly, the invention provides a kit for detecting a predisposition to, or the incidence of, a gastrointestinal cancer, such as colorectal cancer and/or gastric cancer and/or oesophageal cancer and in particular colorectal cancer in a sample comprising:
(a) means for detecting an epigenetic change in at least one gene selected from GATA4, OSMR, NDRG4, GATA5, SFRP1, ADAM23, JPH3, SFRP2, APC and MGMT
(b) means for processing a tissue sample, in particular a colon, rectal or appendix sample.

The kit may comprise means for detecting an epigenetic change in a panel of genes comprising at least two, three, four, five or six of the genes, wherein detection of an epigenetic change in at least one of the genes in the panel is indicative of a predisposition to, or the incidence of, a gastrointestinal cancer, such as colorectal cancer and/or gastric cancer and/or oesophageal cancer and in particular colorectal cancer or is used in one of the other applications as discussed above. In one embodiment, the panel of genes comprises two, three, four, five or six genes.

In specific embodiments, the panel of genes comprises, consists essentially of or consists of OSMR, GATA4 and ADAM23 or OSMR, GATA4 and GATA5.

These kits may also be useful in predicting the likelihood of successful treatment of a gastrointestinal cancer, such as colorectal cancer and/or gastric cancer and/or oesophageal cancer and in particular colorectal cancer and/or the likelihood of resistance to treatment of a gastrointestinal cancer, such as colorectal cancer and/or gastric cancer and/or oesophageal cancer and in particular colorectal cancer with a DNA damaging agent and/or a DNA methyltransferase inhibitor and/or a HDAC inhibitor, and/or selecting a suitable treatment regimen for a gastrointestinal cancer, such as colorectal cancer and/or gastric cancer and/or oesophageal cancer and in particular colorectal cancer and/or determining the histopathological stage of a gastrointestinal cancer, such as colorectal cancer and/or gastric cancer and/or oesophageal cancer and in particular colorectal cancer in a sample, as discussed in respect of the methods of the invention (which discussion applies mutatis mutandis).

In a further embodiment, applicable to all relevant kits of the invention, the means for detecting an epigenetic change in the panel of genes enable the detection to be carried out in a single reaction. Multiplexing is made possible for example through use of appropriate fluorophores having separable emission spectra. TaqMan probes, Molecular Beacons, Scorpions, etc . . . , as discussed herein, allow multiple markers to be measured in the same sample (multiplex PCR), since fluorescent dyes with different emission spectra may be attached to the different probes. Accordingly, suitably labelled probes and primers are encapsulated by the kits of the invention.

In a particularly preferred embodiment, the epigenetic change which is detected using the kits of the invention is methylation. Many suitable reagents for methylation detection are known in the art, and are discussed herein (which discussion applies here mutatis mutandis). In particular, hypermethylation of the promoter region of the gene(s) may be detected using the kits of the invention. Thus, the means for detecting methylation may comprise methylation specific PCR primers. Suitable primers may be selected from the primers comprising, consisting essentially of or consisting of the nucleotide sequences presented in any one of tables 2 to 18 as appropriate depending upon the kit and gene or genes concerned.

The kit may also include means for carrying out the methylation specific PCR in real time or at end point. The means for carrying out the methylation specific PCR/amplification in real time or at end point may comprise hairpin primers (Amplifluor), hairpin probes (Molecular Beacons), hydrolytic probes (Taqman), FRET probe pairs (Lightcycler), primers incorporating a hairpin probe (Scorpion), fluorescent dyes (SYBR Green etc.), DzyNA primers or oligonucleotide blockers for example. Suitable probes may be selected from the probes comprising, consisting essentially of or consisting of the nucleotide sequences presented in tables 2 to 18 as appropriate for the respective genes. All appropriate combinations are envisaged by the invention. Primers and probes for detecting a suitable reference gene, such as beta-actin are displayed in some of these tables (3 and 4).

The end-point PCR fluorescence detection technique can use the same approaches as widely used for Real Time PCR-TaqMan assay, Molecular Beacons, Scorpion etc. Accordingly, the kits of the invention may, in certain embodiments, include means for carrying out end-point methylation specific PCR. The means for carrying out end-point methylation specific PCR/amplification may comprise primers and/or probes as explained for PCR/amplification in Real-time.

In the real-time and end-point detection embodiments, the probes for detection of amplification products may simply be used to monitor progress of the amplification reaction in real-time and/or they may also have a role in determining the methylation status of the at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), themselves. Thus, the probes may be designed in much the same fashion as the primers to take advantage of sequence differences following treatment with a suitable reagent such as sodium bisulphite dependent upon the methylation status of the appropriate cytosine residues (found in CpG dinucleotides).

The probes may comprise any suitable probe type for real-time detection of amplification products as discussed above. Notably, however, with the AMPLIFLUOR and SCORPION embodiments, the probes are an integral part of the primers which are utilised. The probes are typically fluorescently labelled, although other label types may be utilised as appropriate (such as mass labels or radioisotope labels). These probes are also suitable for end-point detection.

The kits of the invention may be kits for use in MSP and in particular in a real-time or end point detection version of MSP.

The kits of the invention may incorporate reagents for quantification of DNA such as those found in the Picogreen® dsDNA quantitation kit available from Molecular Probes, Invitrogen.

The kits of the invention may, additionally or alternatively comprise, consist essentially of or consist of a reagent which selectively modifies unmethylated cytosine residues in the DNA contained in the sample to produce detectable modified residues but which does not modify methylated cytosine residues. The reagent preferably comprises, consists essentially of or consists of a bisulphite reagent. The bisulphite reagent most preferably comprises, consists essentially of or consists of sodium bisulphite. This reagent is capable of converting unmethylated cytosine residues to uracil whereas methylated cytosines remain unconverted. This difference in residue may be utilised to distinguish between methylated and unmethylated nucleic acid in a downstream process, such as PCR using primers which distinguish between cytosine and uracil (cytosine pairs with guanine, whereas uracil pairs with adenine). The reagent may be incorporated as the means for processing a faecal sample or means for processing a blood sample or derivative thereof depending upon the kit in question.

As discussed with respect to the methods of the invention, suitable controls may be utilised in order to act as quality control for the methods. Accordingly, in one embodiment, the kit of the invention further comprises, consists essentially of or consists of one or more control nucleic acid molecules of which the methylation status is known. These (one or more) control nucleic acid molecules may include both nucleic acids which are known to be, or treated so as to be, methylated and/or nucleic acid molecules which are known to be, or treated so as to be, unmethylated. One example of a suitable internal reference gene, which is generally unmethylated, but may be treated so as to be methylated, is β-actin.

Furthermore, the kit of the invention may further comprise, consist essentially of or consist of primers for the amplification of the control nucleic acid. These primers may be the same primers as those utilised to monitor methylation in the test sample in specific embodiments. Thus, the control nucleic acid may comprise at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), for example taken from normal tissues in which it is known to be unmethylated. The control nucleic acid may additionally comprise at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein) in methylated form, for example as methylated by a methyltransferase enzyme such as SssI methyltransferase for example.

Suitable probes and/or oligonucleotide blockers for use in determining the methylation status of the control nucleic acid molecules may also be incorporated into the kits of the invention. The probes may comprise any suitable probe type for real-time detection of amplification products. The discussion provided above applies mutatis mutandis.

The kits of the invention may additionally include suitable buffers and other reagents for carrying out the claimed methods of the invention. Thus, the discussion provided in respect of the methods of the invention as to the requirements for determination of the methylation status of at least one gene selected from an NDRG2/NDRG4 subfamily gene (in particular NDRG4), GATA4, OSMR, GATA5, SFRP1, ADAM23, JPH3, SFRP2, APC, MGMT, TFPI2, BNIP3, FOXE1, SYNE1, SOX17, PHACTR3 and JAM3 (in all permutations and combinations including panels as discussed herein), apply mutatis mutandis here.

In specific embodiments, the kit of the invention further comprises, consists essentially of, or consists of nucleic acid amplification buffers. Suitable reagents may be selected from $(NH_4)_2SO_4$, Tris (pH 8.8), $MgCl_2$, β-mercaptoethanol and stock solutions of dNTPs. Reagents may be supplied at any suitable concentration.

The kit may also additionally comprise, consist essentially of or consist of enzymes to catalyze nucleic acid amplification. Thus, the kit may also additionally comprise, consist essentially of or consist of a suitable polymerase for nucleic acid amplification. Examples include those from both family A and family B type polymerases, such as Taq (such as the commercially available Jumpstart DNA Taq polymerase), Pfu, Vent etc.

The various components of the kit may be packaged separately in separate compartments or may, for example be stored together where appropriate.

The kit may also incorporate suitable instructions for use, which may be printed on a separate sheet or incorporated into the kit packaging for example.

In one specific aspect, the methods and kits of the invention may be combined with the other methods and kits of the invention in order to provide improved diagnosis, histopathological analysis, pharmacogenomic analysis etc.

of a gastrointestinal cancer, such as colorectal cancer and/or gastric cancer and/or oesophageal cancer and in particular colorectal cancer.

Accordingly, all embodiments of the methods and kits of the invention apply mutatis mutandis to the respective aspects of the invention.

The invention will now be described with respect to the following non-limiting examples.

DETAILED DESCRIPTION OF THE INVENTION

Brief Description of the Drawings

FIG. 3a shows methylated NDRG4 sequence (SEQ ID NO: 524)(NM_020465:-1000 to +1000 relative to TSS) Bisulfite sequence primers in mid-grey; Flank primers for the nested MSP are underlined; Methylated MSP primers in light-grey; Unmethylated primers in dark-grey and light-grey FIG. 3b shows methylated NDRG2 sequence (SEQ ID NO: 525). Bisulfite sequence primers in mid-grey; Flank primers for the nested MSP are underlined; Methylated MSP primers in light-grey; Unmethylated primers in dark-grey and light-grey

EXPERIMENTAL SECTION

Figure 1A:
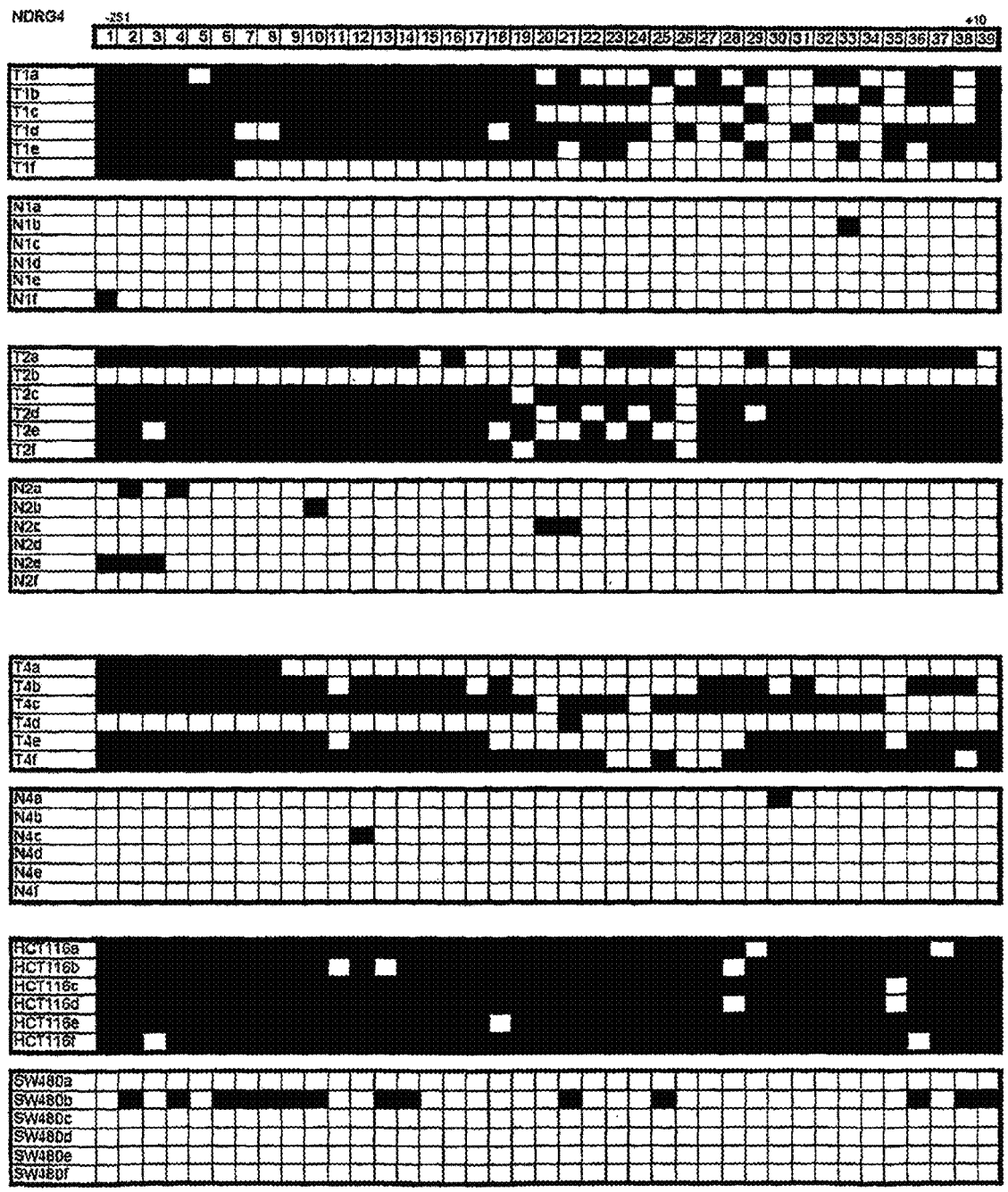
FIG. 1a. NDRG4: Bisulfite sequencing of colorectal cancer tissue (T), normal colon mucosa (N), the methylated colorectal cancer cell line (HCT116) and the unmethylated cell line SW480. White and black squares represent methylated and unmethylated CpG dinucleotides in NDRG4 respectively. Each row represents a single clone. Location of the CpG are relative to the transcription start site. The location of the MSP primers is positions 20 to 23 and 31 to 34 respectively.
Figure 1B:
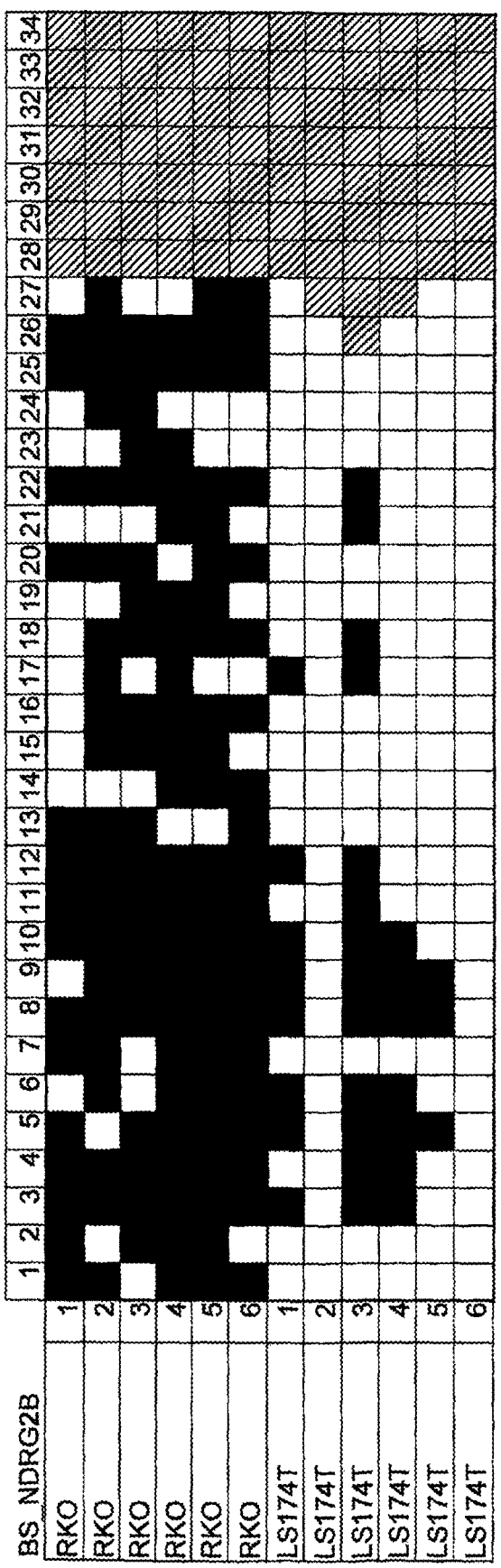
FIG. 1b. NDRG2: Bisulfite sequencing of colon carcinoma cell lines (RKO and LS174T). White and black squares represent methylated and unmethylated CpG dinucleotides in NDRG2B respectively.

1) NDRG Experiments
Cell Culture

Colon cancer cell lines LS174T, HCT116, HT29, RKO, CaCo2, Colo205, SW48 and SW480 were used for MSP, bisulfite sequencing and real time (reexpression) RT-PCR (1 MM DAC and 300 nM TSA).

Study Population

Formalin-fixed, paraffin-embedded colon mucosa tissue of colorectal cancer patients and controls over 50 years of age was retrospectively collected from the archive of the dept. of Pathology of the University Hospital Maastricht. Approval was obtained by the Medical Ethical Committee (MEC) of the Maastricht University and the University Hospital Maastricht. If present, also normal and adenoma tissue was collected from these cases. The control group consists of histologically normal biopsy material from patients undergoing endoscopy because of non-specific abdominal complaints, adenoma biopsies from patients which did not develop colorectal cancers within 5-10 years.

Colorectal cancers patients and controls were excluded if being diagnosed with additional cancers other than non-melanoma skin cancer.

Methylation-Specific PCR

DNA methylation in the CpG islands of the gene promoter was determined by bisulfite treatment of genomic DNA with sodium bisulfite followed by MSP. Briefly, bisulfite modification of genomic DNA was carried using the EZ DNA methylation kit (Zymo Research). MSP analysis on DNA retrieved from formalin-fixed, paraffin embedded tissue was facilitated by first amplifying the DNA with flanking PCR primers which amplify bisulfite-modified DNA but do not make the distinction between methylated or unmethylated DNA. This PCR product was used as a template for the MSP reaction. All PCRs were performed with controls for unmethylated DNA (DNA from normal lymfocytes), methylated DNA (normal lymphocyte DNA treated in vitro with SssI methyltransferase (New England Biolabs)), and a control without DNA. Ten µl of each MSP reaction were directly loaded onto 2% agarose visualized under UV illumination. Primer sequences and PCR conditions, are specified in Table 19.

Alternatively, DNA methylation was determined by QMSP.

TABLE 19

NDRG4 and NDRG2b MSP primers

| SEQ ID No | Gene | Primer name | Sequence 5'-3 | Size | Ann. Temp. | Cycles | Posn.* |
|---|---|---|---|---|---|---|---|
| 5 | NDRG4 | Flank F | ggttygttygggattagttttagg | 155 bp | 56 | 35 | -144 |
| 6 | NDRG4 | Flank R | craacaaccaaaaacccctc | | | | +10 |
| 7 | NDRG4 | U sense | gattagttttaggtttggtattgttttgt | 100 bp | 66 | 25 | -133 |
| 8 | NDRG4 | U antisense | aaaaccaaactaaaaacaatacacca | | | | -34 |
| 9 | NDRG4 | M sense | tttaggttcggtatcgtttcgc | 88 bp | 66 | 25 | -126 |
| 10 | NDRG4 | M antisense | cgaactaaaaacgatacgccg | | | | -39 |
| 20 | NDRG2 | Flank F | YGTTTTTTATTTATAGYGGTTTTT | | | | |
| 21 | NDRG2 | Flank R | TCCTAATACCTCTCCTCTCTTTACTAC | | | | |
| 22 | NDRG2 | U sense | TTTTATTTATAGTGGTTTTTTGTATTTTTT | | | | |
| 23 | NDRG2 | U antisense | TCTCCTCTCTTTACTACATCCCAACA | | | | |
| 24 | NDRG2 | M sense | TTTATAGCGGTTTTTCGTATTTTTC | | | | |
| 25 | NDRG2 | M antisense | CCTCTCTTTACTACGTCCCGACG | | | | |

*Position relative to transcription start site

Bisulfite Genomic Sequencing

Genomic DNA was isolated using the Wizard Genomic DNA Purification kit (Promega, Leiden, the Netherlands). Bisulfite modification of genomic DNA was carried out using the EZ DNA methylation kit (Zymo Research). PCR products were subcloned using the TA cloning kit (Invitrogen, Breda, the Netherlands) and single colonies were selected and sequenced. Primer sequences and PCR conditions are specified in Table 20.

TABLE 20

NDRG4 and NDRG2b bisulfite sequencing primers

| SEQ ID NO | Gene | Primer name | Sequence 5'-3 | Size | Ann. Temp. | Cycles | Position |
|---|---|---|---|---|---|---|---|
| 569 | NDRG4 | F | gatygggtgtttttaggttt | 262 bp | 64 | 40 | -251 |
| 6 | NDRG4 | R | craacaaccaaaaacccctc | | | | +10 |
| 522 | NDRG2 | F | TTTGTTGGTTATTTTTTTTTATTTTT | | | | |
| 523 | NDRG2 | R | CCCCCAAACTCAATAATAAAAAC | | | | |

Real-Time RT-PCR

Total RNA isolation was isolated by use of the Rneasy Mini kit (Qiagen) cDNA synthesis using the Iscript cDNA synthesis kit (Bio-Rad). Quantitative real-time reverse transcription-PCR was done using SYBR Green PCR Master Mix (Applied Biosystems, Nieuwekerk a/d IJssel, the Netherlands). Primers and PCR conditions are specified in Table 21.

TABLE 21

NDRG4 Real time RT-PCR primers

| SEQ ID NO | Gene | Primer name | Sequence 5'-3 | Size | Ann. Temp. | Cycles |
|---|---|---|---|---|---|---|
| 1 | NDRG4 | F | cctgaggagaagccgctg | 101 bp | 60 | 40 |
| 2 | NDRG4 | R | atgtcatgttccttccagtctgt | | | |

Expression Analysis of NDRG4

Figure 2:
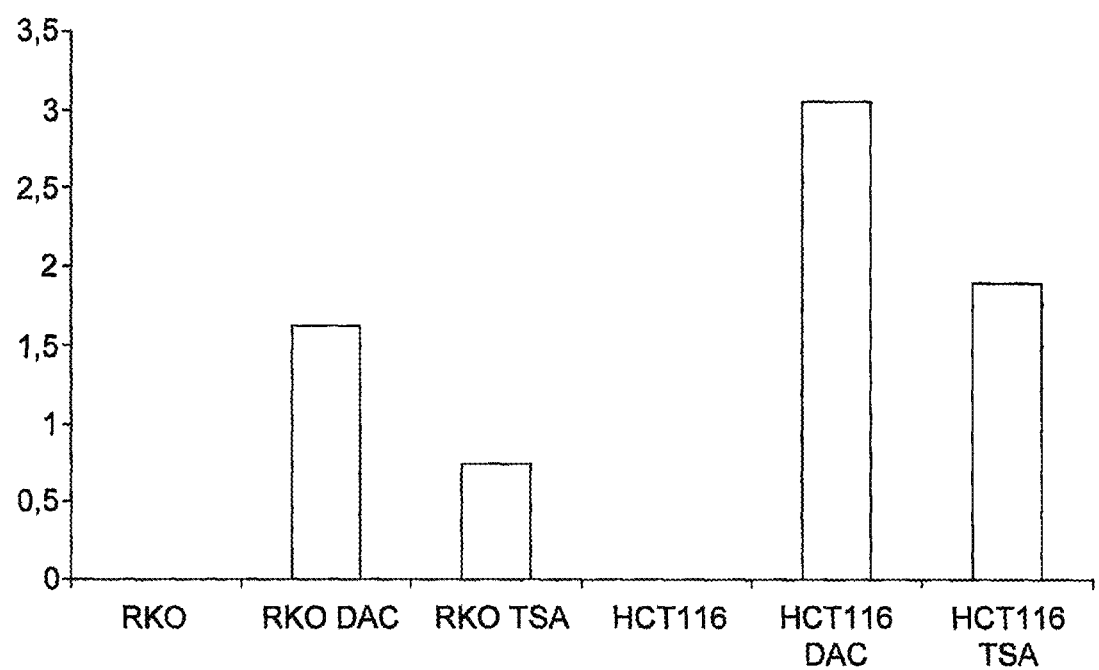
FIG. 2 shows relative expression of NDRG4 after treatment with DAC and TSA compared to untreated cell lines. Cyclophilin was used as a reference gene for expression normalisation.

Expression of the NDRG4 gene was determined by real-time reverse-transcription PCR (RT-PCR). The NDRG4 gene was found to be well expressed in normal colon cell lines, whereas it was not expressed in the colon cancer cell lines. Since this on its own did not indicate that the silencing is epigenetic, the RKO and HCT116 cell lines were treated with the reagent DAC (5'dazacytidine) and TSA. Relative expression of NDRG4 after treatment with DAC and TSA was compared to untreated cell lines. Cyclophilin was used as a reference gene for expression normalisation. FIG. 2 shows that treatment resulted in a reactivation of NDRG4 expression, providing evidence for epigenetic silencing of the gene in colon cancer cells.

CpG Island Methylation Status Analysis of NDRG4 and NDRG2

Having observed that the silencing of NDRG4 expression was reversed after treatment with DAC and TSA, the association between the transcriptional inactivation and the putative epigenetic aberration was further investigated. The NDRG CpG island methylation status was established by PCR analysis of bisulfite-modified genomic DNA, which induces chemical conversion of unmethylated, but not methylated, cytosine to uracil, using the procedures as specified.

Table V shows that NDRG4 CpG island methylation analysed by MSP was observed in the cancer cell lines LS174T, HCT116, HT29, RKO, CaCO2 and SW48, whereas it was absent in the unmethylated cell line SW480.

Similarly, NDRG2 CpG island methylation analysed by MSP with different primer sets (a to d) was observed in most of the cancer cell lines. In all cancer cell lines LS174T, HCT116, HT29, RKO, CaCO2 and SW48, NDRG2 CpG island methylation was observed with primer sets b of table 19.

Following the demonstration of the epigenetic loss of function of NDRG4 in cancer-cell lines, we assessed the prevalence of NDRG4 CpG island promoter hypermethylation in cancer patients. As expected, NDRG4 CpG island promoter hypermethylation was absent in normal mucosa from patients without cancer. As indicated in Table 23, NDRG4 CpG island promoter hypermethylation was observed with different frequency among each class of neoplasm. NDRG4 was methylated in 76% of the 88 investigated carcinoma tissues and in 57% of 57 adenomas with concurrent colorectal cancer. In adenomas from patients that did not have colorectal cancer (low-grade dysplastic non-progressed adenomas), NDRG4 methylation was significantly lower (14%), indicating the prognostic value of this NDRG4 methylation towards colorectal cancer development

TABLE 23

Prevalence of NDRG4 methylation in colorectal tissue

| | Methylation (%) |
|---|---|
| Morphologically normal mucosa adjacent to tumor tissue | 2.5 (n = 82) |
| Adenomas from patients also presenting a colorectal carcinoma | 57 (n = 57) |
| Carcinoma tissue | 76 (n = 88) |
| Normal mucosa from patients without cancer | 0 (n = 27) |
| Adenomas from patients that did not develop colorectal cancer (low-grade dysplastic non-progressed adenomas) | 14 (n = 51) |

NDRG4 Methylation Compared to Methylation of Other Markers

Figure 4:
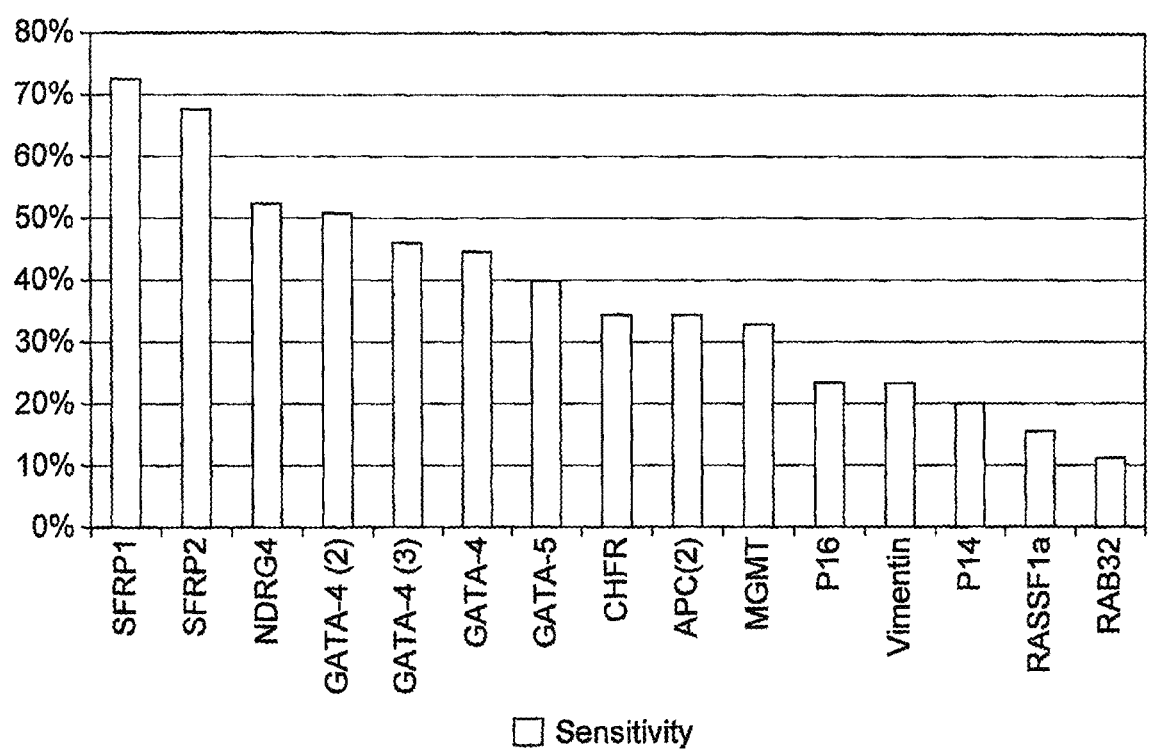
FIG. 4 shows sentivity of different markers, with 100% specificity. X axis=: % positive in real time QMSP; Y axis=: different markers. Case: n=65 carcinoma's; Controls: n=33 histologically normal resection ends.

Samples from resected tumors and histologically normal resection were tested for hypermethylation of 13 genes. Representative results are shown in FIG. 4. The highest methylation was obtained for SFRP1, SFRP2, NDRG4, GATA4 and GATA5. All showed a sensitivity >40% for 100% specificity. We tested the ability of the NDRG4 methylation marker to improve the sensitivity of cancer detection with a number of methylation markers selected on their ability to detect colorectal cancer. The other genes were selected from the group consisting of SFRP1, SFRP2, GATA-4, GATA-5, CHFR, APC(2), MGMT, p16, Vimentin,

TABLE 22

Methylation status of colorectal cancer cell lines (analysed by MSP)

| | LS174T | HCT116 | HT29 | RKO | CaC02 | Colo205 | SW48 | SW480 |
|---|---|---|---|---|---|---|---|---|
| NDRG4 | M | M | M | M | M | M | M | U |
| NDRG2 a | U | U | U | U | U | U | U | / |
| NDRG2b | U | M | U | M | M | M | M | / |
| NDRG2c | U | M | U | M | M | M | M | U? |
| NDRG2d (a) | U | M | U | M | M | U | U | M | p14, RASSF1a and RAB32. In a first instance, the ability of NDRG4 to complement SFRP1 was analysed. 30% of colon carcinoma samples (n=18) for which SFRP1 failed to be hypermethylated, showed hypermethylation for NDRG4 (n=6). Similarly, carcinoma samples which failed to be detected by way of SFRP2, GATA4, or GATA5 methylation analysis, showed hypermethylation for NDRG4. In fact, the combination of NDRG4 with any of the methylation markers from FIG. 4 improved diagnosis of cancer NDRG-4 MSP on Other Cancer Types (Methylated Cancers)

NDRG-4 methylation was assessed on other cancer types showing hypermethylation for certain genes. These cancer types comprised melanoma, clear cell kidney cancer, ovarian carcinoma, prostate cancer, breast cancer and gastric cancer. The results were as follows:

Melanoma: 0 out of 8 samples were methylated for NDRG4
Clear cell kidney cancer: only 1 out of 10 samples was methylated for NDRG4
Ovarium carcinoma: 0 out of 20 samples were methylated for NDRG4
Prostate cancer: 0 out of 10 samples were methylated for NDRG4
Breast cancer: 0/7 lobular cancers and 0/9 Ductal cancers were methylated for NDRG4

In contrast to these results, in all of the 6 gastric cancers tested methylation for NDRG4 was observed. This seems to indicate that NDRG4 is a type-specific cancer methylation marker and is preferably used to detect colon cancer and/or gastric cancer.

REFERENCES

Akey, D. T., Akey, J. M., Zhang, K., Jin, L., 2002. Genomics, 80:376-384.
Angela Di Vinci, Ilaria Gelvi, Barbara Banelli, Ida Casciano, Giorgio Allemanni and Massimo Romani. Laboratory Investigation (2006) 1-7
Barringer K J, Orgel L, Wahl G, Gingeras T R. Gene. 1990 Apr. 30; 89(1):117-22
Boggs B. A., Cheung P, Heard E, Spector D L, Chinault A C, Allis C D. Nat. Genet. 2002, 30: 73-76.
Compton, J. Nature. 1991 Mar. 7; 350(6313):91-2.
Cottrell, S., Distler, J., Goodman, N., Mooney, S., Kluth, A., Olek, A., Schwope, I., Tetzner, R., Ziebarth, H., Berlin, K. Nucleic Acid Res. 2004, 32:E10.
Cross, S H et al. Nature Genetics 1994, 6, 236-244;
Deng Y, Yao L, Chau L, Ng S Svb, Peng Y, Liu X, Au W S, Wang J, Li F, Ji S, Han H, Nie X, Li Q, Kung H F, Leung S Y, Lin M C. Int J Cancer. 2003, 106(6):984.
Eads, C. A., Danenberg, K. D., Kawakami, K, Saltz, L. B., Blake C., shibata, D; Danenberg, P. V. and Laird P. W. Nucleic acid Res. 2000, 28: E32
Fahy E, Kwoh D Y, Gingeras T R. PCR Methods Appl. 1991 August; 1(1):25-33
Furuichi Y, Wataya Y, Hayatsu H, Ukita T. Biochem Biophys Res Commun. 1970 Dec. 9; 41(5):1185-91
Guan R J, Ford H L, Fu Y, Li Y, Shaw L M, Pardee A B. Cancer Res. 2000, 60(3):749-55.
Herman J G, Graff J R, Myohanen S, Nelkin B D, Baylin S B. Proc. Natl. Acad. Sci. USA. 1996: 93(18):9821-9826
Hu X L, Liu X P, Lin S X, Deng Y C, Liu N, Li X, Yao L B. World J Gastroenterol. 2004, 10(23):3518-21
Johnstone R. W. Nat. Rev. Drug Discov. 2002, 1: 287-299.
Jones P A and Baylin S B Nat. Rev. Genet. 2002, 3: 415-428.
Jorgensen, H F., Adie, K., Chaubert, P. and Bird A. Nucleic Acids Research, 2006, Vol. 34, No. 13 e96
Kondo Y, shen L, Issa J P Mol. Cell. Biol. 2003, 23: 206-215.
Lund A H, and van Lohuizen M. Genes Dev. 2004, 18: 2315-2335.
Lusis E A, Watson M A, Chicoine M R, Lyman M, Roerig P, Reifenberger G, Gutmann D H, Perry A. Cancer Res. 2005, 65(16):7121-6.
Mitchelmore C, Buchmann-Moller S, Rask L, West M J, Troncoso J C, Jensen N A. Neurobiol Dis. 2004, 16(1): 48-58
Nishimoto S, Tawara J, Toyoda H, Kitamura K, Komurasaki T. Eur J Biochem. 2003 June; 270(11):2521-31
Qu X, Zhai Y, Wei H, Zhang C, Xing G, Yu Y, He F. Mol Cell Biochem. 2002, 229(1-2):35-44.
Rand K., Qu, W., Ho, T., Clark, S. J., Molloy, P. Methods. 2002, 27:114-120.
Sasaki, M., Anast, J., Bassett, W., Kawakami, T., Sakuragi, N., and Dahiya, R. Biochem. Biophys. Res. Commun. 2003, 209: 305-309.
Shiio Y, Eisenman R N Proc. Natl. Acad. Sci. USA. 2003, 100: 7357-7362.
Shiraisi, M et al. Biol Chem. 1999, 380(9):1127-1131
Zhao W, Tang R, Huang Y, Wang W, Zhou Z, Gu S, Dai J, Ying K, Xie Y, Mao Y. Biochim Biophys Acta. 2001, 1519(1-2):134-138;

2) Experiments on Faecal DNA

Example 1

Materials and Methods in Relation to Faecal DNA
Sample Collection and Processing A standardized multicenter screening trial (The Netherlands) was initiated in 2006. In this trial, non symptomatic subjects aged 50 or above are screened with colonoscopy, FOBT and real-time MSP using DNA from stool and blood. In addition, prospectively collected stool samples from multiple centers (Germany and The Netherlands) were used. In these trials, symptomatic patients, attending a Gastroenterology clinic and ultimately diagnosed with CRC, provided a stool sample for use in real-time MSP. From the ongoing trials 147 stool samples were available for the present study. 3 main categories of stool samples were used: 67 samples with no suspicious findings, 58 adenomas and 22 samples from patients covering all stages of CRC, with 90% representing early stage disease.

After defecation in a special bucket, patients added 250 ml of stool homogenization buffer (Amresco, Solon, Ohio, USA) to the sample. Samples were shipped to the laboratory and further processed within 72 hours after defecation. Stool homogenization buffer was added to a ratio 1:7, and the samples were homogenized and aliquoted in portions of 32 ml.

DNA Extraction from Stool

Single aliquots (32 ml containing the equivalent of 4 g of stool) were centrifuged for 5 minutes at 2540 rcf at 20° C. The supernatant was retained and centrifuged a second time (10 minutes at 16500 rcf at 4° C.). 22 ml of the supernatant obtained following the second centrifugation step was incubated with 5 µl Rnase A for 60 minutes at 37° C. Total DNA was then SodiumAcetate (pH 5.2)—isopropanol precipitated and washed with 70% ethanol. The DNA was resuspended in 4 ml 1×TE (pH 7.4). 400 µl 10× buffer (240 mM EDTA (pH=8.0), 750 mM NaC), 400 µl 10% SDS, and 20 µl Proteinase K (20 mg/ml) was added and the samples were incubated at 48° C. overnight at constant shaking (225 RPM). After centrifugation (3000 RCF for 30 seconds at room temperature), 5 ml of Phenol: Chloroform: Isoamyl-alcohol (25:24:1, v/v; Invitrogen) was added and incubated for 10 minutes at room temperature shaking at 225 RPM and centrifuged for 5 minutes at 3000 RCF. The aqueous layer was transferred to a new tube containing 5 ml of Phenol: Chloroform: Isoamylalcohol. Again, the samples were incubated for 10 minutes at room temperature shaking at 225 RPM and centrifuged for 5 minutes at 3000 RCF at room temperature. The aqueous layer was transferred to a new tube and DNA was precipitated by adding 500 µl 7.5 M Ammonium Acetate, 5 µl glycogen and 10 ml of cold 100% Ethanol (−20° C.), further incubated at −20° C. for at least 1 hour and centrifuged at 15000 RCF for 30 minutes at 4° C. Pellets were washed with 3.5 ml freshly prepared 70% Ethanol and air dried. Pellets were finaly resuspended in 2 ml of LoTE pH 8.0 and stored at −80° C., until further processing. Average yield of DNA was 462 µg (ranging from 46-2127 µg; SD 420)

DNA Modification

An upscaled DNA modification step was applied to 32 µg of the obtained DNA. 16 Aliquots of 2 µg of DNA were subjected to bisulfite modification in 96-wells format on a pipetting robot (Tecan), using the EZ-96DNA Methylation kit (Zymo Research), according to the manufacturer's protocol. Basically, aliquots of 45 µl were mixed with 5 µl of M-Dilution Buffer and incubated at 37° C. for 15 minutes shaking at 1100 rpm. Then 100 µl of the diluted CT Conversion Reagent was added and samples were incubated at 70° C. for 3 hours, shaking at 1100 rpm in the dark. After conversion, the samples were desalted by incubation on ice for 10 minutes and addition of 400 µl of M-Binding buffer. The samples were loaded on a Zymo-Spin I Column in a collection tube and after centrifugation washed with 200 µl of M-Wash Buffer. 200 µl of M-Desulphonation Buffer was put onto the column and incubated at room temperature for 15 minutes. After centrifugation of the columns, they were washed twice with 200 µl of M-Wash Buffer. Finally, the DNA was washed from the column in 50 µl Tris-HCl 1 mM pH8.0 and stored at −80° C., until further processing.

DNA Concentration

Bisulfite treated DNA is concentrated using the ZYMO Clean and Concentrator Kit (Zymo Research). To each aliquot of DNA 100 µl of DNA Binding Buffer was added. The equivalent of ~6 µg of DNA (quantified before bisulfite treatment) was transferred to a Zymo-Spin™ Column in a collection tube. (16 wells with bisulfite treated DNA per sample are divided over 5 Zymo-Spin™ columns.) The tubes were centrifuged at >10,000 rpm for 30 seconds and washed twice with 200 µl of wash buffer. The DNA was eluted of the column by adding 6 µl of 1 mM Tris-HCl, pH=8.0, incubated for 1 minute and centrifugation at >10,000 rpm for 30 seconds. The eluates of columns with the same sample were pooled. The resulting chemical treated DNA was used as template for real-time MSP.

DNA Amplification

Real-time MSP was applied on a 7900HT fast real-time PCR system (Applied Biosystems). 2.4 µl of the modified DNA (equivalent to 2.5 µg unconverted DNA) was added to a PCR mix (total volume 12 µl) containing buffer (16.6 mM (NH4)2SO4, 67 mM Tris (pH 8.8), 6.7 mM MgCl2, 10 mM β-mercaptoethanol), dNTPs (5 mM), forward primer (6 ng), reverse primer (18 ng), molecular beacon (0.16 µM), BSA (0.1 µg), and Jumpstart DNA Taq polymerase (0.4 units; Sigma Aldrich). The primer sequences and molecular beacon sequences used for each of the genes are summarized in table 1. Cycle program used was as follows: 5 minutes 95° C., followed by 45 cycles of 30 seconds 95° C., 30 seconds 57° C. (51° C. for APC), and 30 seconds 72° C., followed by 5 minutes 72° C. A standard curve (2×106–20 copies) was included to determine copy numbers of unknown samples by interpolation of their Ct values to the standard curve.

Results

Marker Identification and Validation in Colon Tissue Samples.

Assay Validity Rate in Tissue and Stool:

230 FFPE and 147 stool samples were processed using real-time MSP. The real-time MSP assays produced valid results in 99% of the FFPE and stool samples.

Marker Selection in Colon Tissue:

Based on re-expression, 224 different gene assays representing 145 gene promotors were tested on the Base5 methylation profiling platform (data not shown, see reference 1 for details). The 37 most differentially methylated gene sequences assessing 29 gene promoters were validated on retrospectively collected tumors from 65 colorectal cancer patients (all stages) and 74 distant resection ends (histopathologically normal) using real-time MSP. Several markers reliably detected CRC in those tissue samples (data not shown). The results were confirmed on an independent test set containing 39 tissue controls (non-cancerous), 34 carcinomas and 16 adenomas. Several combinations of the tested markers reliably detected CRC with high specificity and sensitivity.

Figure 5:
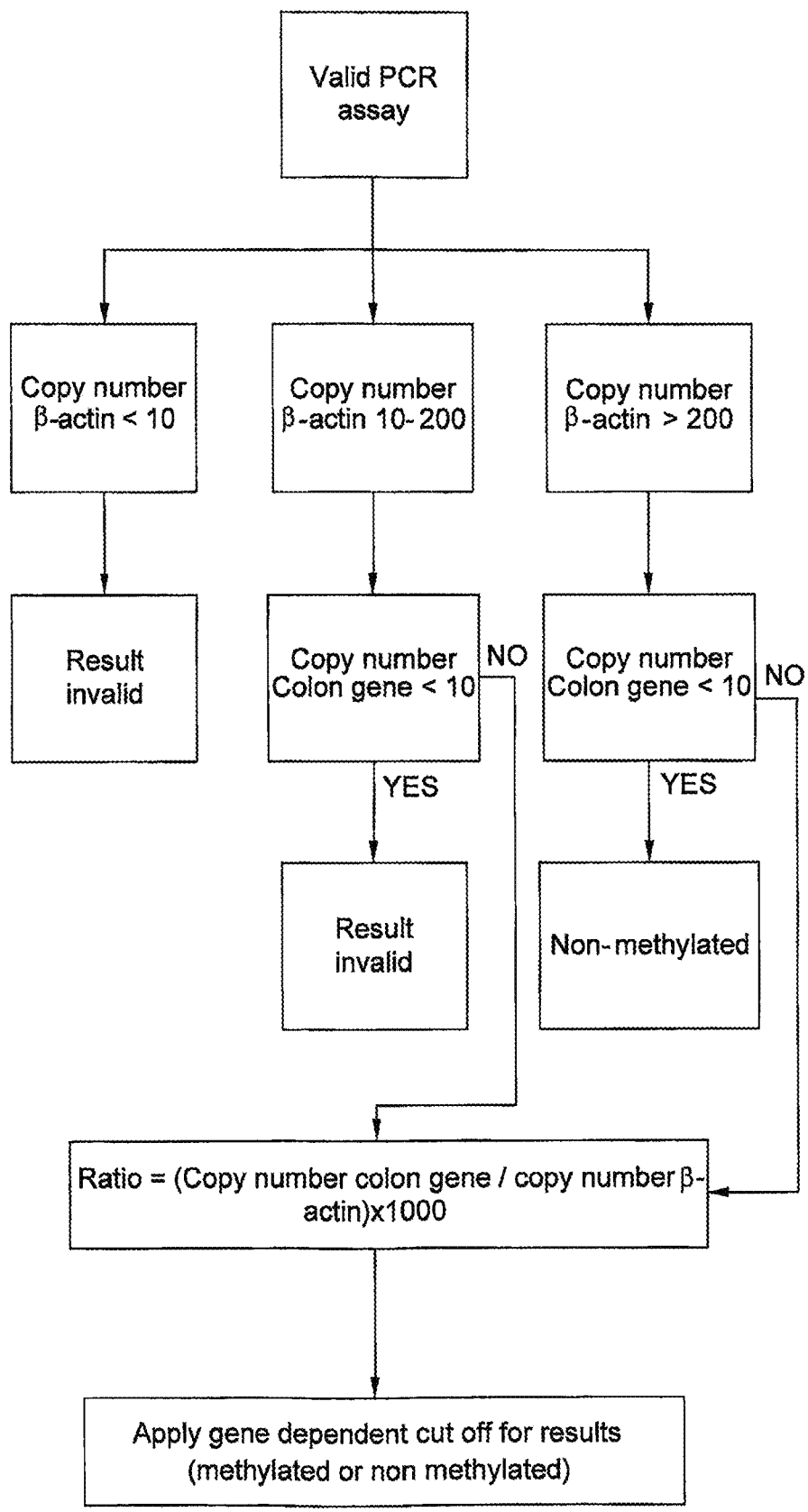
FIG. 5 shows a decision tree for determination of the methylation status of the gene of interest linked to colorectal cancer in clinical samples (real-time MSP).
Figure 6:
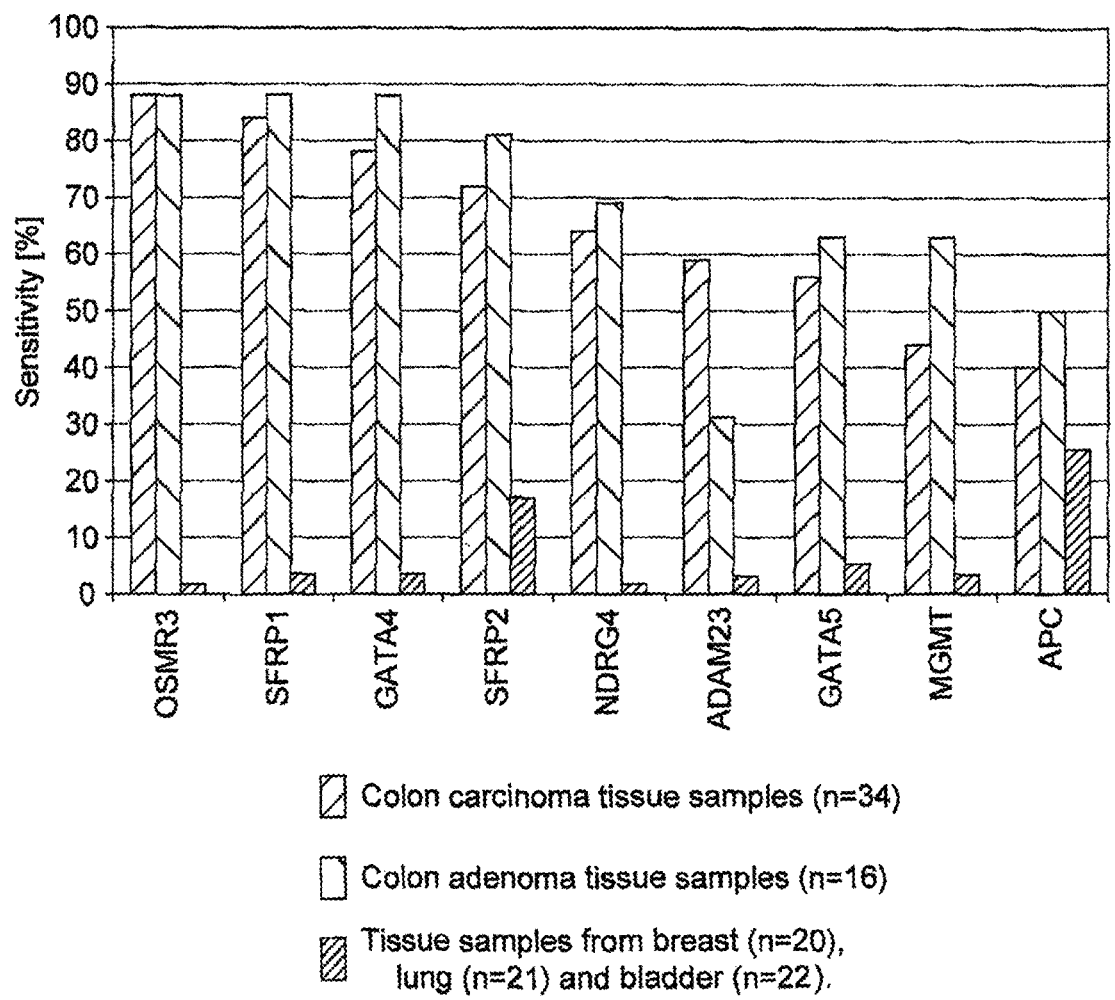
FIG. 6 presents results of real-time MSP carried out on 9 different genes for 34 colon carcinoma tissue samples, 16 colon adenoma tissue samples and 63 breast (20), lung (21) and bladder (22) cancer samples. Sensitivity performance for each gene is shown wherein the analytical cut-off was set to give 100% specificity (based on the non-cancerous controls).

The ten best performing markers GATA5, GATA4, SFRP1, SFRP2, APC, MGMT, NDRG4, OSMR, JPH3 and ADAM23 were validated with primer sets and beacon probes as specified in Table 24. In addition to the colon test genes, the independent reference gene β-Actin (ACT) was also measured. The ratios between the colon test genes and ACT were calculated, and are the test result of the assay. The samples were classified as methylated, non-methylated, or invalid based on the decision tree shown in FIG. 5.

The individual performance of the ten markers is shown in Table 25. Dependent on the cutoff applied, different sensitivities were obtained for the individual markers. For 100% specificity of the marker, sensitivities (%) ranged from 56 to 66 for GATA5, 78 to 82 GATA4, 84 to 92 for SFRP1, 72 to 84 for SFRP2, 40 to 46 for APC, 44 for MGMT, 64 to 66 for NDRG4, 88 for OSMR, 82 for JPH3 and 50 for ADAM23.

TABLE 24

Primers sequences and beacon sequences

| SEQ ID NO: | | | |
|---|---|---|---|
| 26 | β-Actin | forward primer | 5'-TAGGGAGTATATAGGTTGGGGAAGTT-3' |
| 27 | | reverse primer | 5'-AACACACAATAACAAACACAAATTCAC-3' |

TABLE 24-continued

Primers sequences and beacon sequences

| SEQ ID NO: | | | |
|---|---|---|---|
| 28 | | beacon | 5'-FAM-CGACTGCGTGTGGGGTGGTGATGGAGGAGGTTTAGGCAGTCG-3'-DABCYL |
| 29 | GATA4 | forward primer | 5'-AGGTTAGTTAGCGTTTTAGGGTC-3' |
| 30 | | reverse primer | 5'-ACGACGACGAAACCTCTCG-3' |
| 31 | | beacon | 5'-FAM-CGACATGCCTCGCGACTCGAATCCCCGACCCAGCATGTCG-3'-DABCYL |
| 32 | GATA5 | forward primer | 5'-AGTTCGTTTTTAGGTTAGTTTTCGGC-3' |
| 33 | | reverse primer | 5'-CCAATACAACTAAACGAACGAACCG-3' |
| 34 | | beacon | 5'-FAM-CGACATGCGTAGGGAGGTAGAGGGGTTCGGGATTCCGTAGCATGTCG-3'-DABCYL |
| 35 | SFRP1 | forward primer | 5'-TGTAGTTTTCGGAGTTAGTGTCGCGC-3' |
| 36 | | reverse primer | 5'-CCTACGATCGAAAACGACGCGAACG-3' |
| | | beacon | 5'-FAM-CGACATGCTCGGGAGTCGGGGCGTATTTAGTTCGTAGCGGCATGTCG-3'-DABCYL |
| 38 | SFR2 | forward primer | 5'-GGGTCGGAGTTTTTCGGAGTTGCGC-3' |
| 39 | | reverse primer | 5'-CCGCTCTCTTCGCTAAATACGACTCG-3' |
| 40 | | beacon | 5'-FAM-CGACATGCGGTGTTTCGTTTTTTCGCGTTTTAGTCGTCGGGCATGTCG-3'-DABCYL |
| 17 | NDRG4 | forward primer | 5'-GTATTTTAGTCGCGTAGAAGGC-3' |
| 18 | | reverse primer | 5'-AATTTAACGAATATAAACGCTCGAC-3' |
| 19 | | beacon | 5'-FAM-CGACATGCCCGAACGAACCGCGATCCCTGCATGTCG-3'-DABCYL |
| 41 | APC | forward primer | 5'-GAACCAAAACGCTCCCCAT-3' |
| 42 | | reverse primer | 5'-TTATATGTCGGTTACGTGCGTTTATAT-3' |
| 43 | | beacon | 5'-FAM-CGTCTGCCCCGTCGAAAACCCGCCGATTAACGCAGACG-3'-DABCYL |
| 44 | ADAM23 | forward primer | 5'-GAAGGACGAGAAGTAGGCG-3' |
| 45 | | reverse primer | 5'-CTAACGAACTACAACCTTACCGA-3' |
| 46 | | beacon | 5'-FAM-CGACATGCCCCCGACCCGCACGCCGCCCTGCATGTCG-3'-DABCYL |
| 47 | OSMR(3) | forward primer | 5'-TTTGGTCGGGGTAGGAGTAGC-3' |

TABLE 24-continued

Primers sequences and beacon sequences

| SEQ ID NO: | | | |
|---|---|---|---|
| 48 | | reverse primer | 5'-CGAACTTTACGAACAACGAAC-3' |
| 49 | | beacon | 5'-FAM-CGACATGCCCGTACCCCGCGCAGCATGTCG-3'-DABCYL |
| 47 | OSMR(4) | forward primer | 5'-TTTGGTCGGGGTAGGAGTAGC-3' |
| 50 | | reverse primer | 5'-AAAAACTTAAAAACCGAAAACTCG-3' |
| 49 | | beacon | 5'-FAM-CGACATGCCCGTACCCCGCGCAGCATGTCG-3'-DABCYL |
| 51 | JPH3 | forward primer | 5'-TTAGATTTCGTAAACGGTGAAAAC-3' |
| 52 | | reverse primer | 5'-TCTCCTCCGAAAAACGCTC-3' |
| 53 | | beacon | 5'-FAM-CGTCTGCAACCGCCGACGACCGCGACGCAGACG-3'-DABCYL |
| 54 | MGMT | forward primer | 5'-TTTCGACGTTCGTAGGTTTTCGC-3' |
| 55 | | reverse primer | 5'-GCACTCTTCCGAAAACGAAACG-3' |
| 56 | | beacon | 5'-FAM-CGTCTCGCGTGCGTATCGTTTGCGATTTGGTGAGTGTTTGGGGCGAGACG-3'-DABCYL |

TABLE 25

Individual performance of markers on adenoma and carcinoma colorectal tissue samples

| Gene* | Cases (adenoma + carcinoma) | Controls | Cut off ratio** | Sensitivity (%) | Specificity (%) |
|---|---|---|---|---|---|
| GATA5 | 50 | 39 | 12 (5) | 56 (66) | 100 |
| GATA4 | 50 | 39 | 17 (12) | 78 (82) | 100 |
| SFRP1 | 50 | 39 | 47 (25) | 84 (92) | 100 |
| SFRP2 | 50 | 39 | 28 (9) | 72 (84) | 100 |
| APC | 50 | 39 | 16 (5) | 40 (46) | 100 |
| MGMT | 50 | 39 | 18 | 44 | 100 |
| NDRG4 | 50 | 39 | 7 (1) | 64 (66) | 100 |
| OSMR (3) | 50 | 39 | 47 | 88 | 100 |
| JPH3 | 50 | 39 | 55 (75) | 82 (82) | 95 (100) |
| ADAM23 | 50 | 39 | 2 | 50 | 100 |

*(3) reflects the primer combinations used for assessing methylation of the OSMR gene
**In case two sets of cut off ratio were assessed, the second set and its corresponding sensitivity is indicated between ( ).

Complementarity of Markers

The different markers were tested on their complementarity. Several combinations of the tested markers reliably detected CRC with high specificity and sensitivity. Results are summarized in Table 26. For 100% specificity, sensitivities (%) ranged between 90 to 98 for combinations of two markers. A sensitivity of 100% was obtained for the 3-marker combinations SFRP1+SFRP2+APC and SFRP2+OSMR+APC.

TABLE 26

Complementarity of markers on adenoma and carcinoma colorectal tissue samples

| Genes* | Sensitivity** | Specificity |
|---|---|---|
| NDRG4 + OSMR (4) | 90% | 100% |
| SFRP2 + APC | 92% | 100% |
| APC + OSMR (3) | 92% | 100% |
| MGMT + OSMR (3) | 92% | 100% |
| OSMR (3) + OSMR (4) | 92% | 100% |
| SFRP1 + APC | 94% | 100% |
| SFRP1 + GATA-4 | 94% | 100% |
| SFRP1 + NDRG4 | 94% | 100% |
| SFRP1 + OSMR (3) | 94% | 100% |
| SFRP1 + OSMR (4) | 94% | 100% |
| GATA-4 + OSMR (4) | 94% | 100% |
| NDRG4 + OSMR (3) | 94% | 100% |
| GATA-5 + SFRP1 | 96% | 100% |
| GATA-5 + OSMR (3) | 96% | 100% |
| SFRP2 + OSMR (4) | 96% | 100% |
| GATA-4 + OSMR (3) | 96% | 100% |
| SFRP1 + SFRP2 | 98% | 100% |
| SFRP2 + OSMR (3) | 98% | 100% |
| SFRP1 + SFRP2 + APC | 100% | 100% |
| SFRP2 + OSMR (3) + APC | 100% | 100% |

*(3) and (4) reflect the primer combinations used for assessing methylation of the OSMR gene
**Sensitivity corresponding to the second cutoff set specified between ( ) in Table 25.

Performance of Markers on Adenoma and Carcinoma Tissue Samples

Important for early cancer detection is the performance of the markers on early stage cancers. Therefore, the 50 cancer cases from the test set were further divided into 2 diagnosis groups: carcinomas and adenomas. Results are summarized in table 27 and 28. Sensitivity for carcinomas ranged from 35% to 88% for detection of colorectal cancer whereas sensitivity for adenomas ranged from 31% to 88% both with a corresponding specificity of 100%. These results indicate that the selected set of genes are highly specific for colorectal cancer and include some promising early stage detection markers.

TABLE 27

Performance of the markers on carcinoma samples

| Gene* | Carcinoma | Controls | Cut off ratio | Sensitivity | Specificity |
|---|---|---|---|---|---|
| GATA5 | 34 | 39 | 12 | 53 | 100 |
| GATA4 | 34 | 39 | 17 | 74 | 100 |
| SFRP1 | 34 | 39 | 47 | 82 | 100 |
| SFRP2 | 34 | 39 | 28 | 68 | 100 |
| APC | 34 | 39 | 16 | 35 | 100 |
| MGMT | 34 | 39 | 18 | 35 | 100 |
| NDRG4 | 34 | 39 | 7 | 62 | 100 |
| OSMR (3) | 34 | 39 | 47 | 88 | 100 |
| JPH3 | 34 | 39 | 55 | 82 | 100 |
| ADAM23 | 34 | 39 | 2 | 59 | 100 |

*(3) reflects the primer combinations used for assessing methylation of the OSMR gene

TABLE 28

Performance of the markers on adenoma samples

| Gene* | adenoma | Controls | Cut off ratio | Sensitivity | Specificity |
|---|---|---|---|---|---|
| GATA5 | 16 | 39 | 12 | 63 | 100 |
| GATA4 | 16 | 39 | 17 | 88 | 100 |
| SFRP1 | 16 | 39 | 47 | 88 | 100 |
| SFRP2 | 16 | 39 | 28 | 81 | 100 |
| APC | 16 | 39 | 16 | 50 | 100 |
| MGMT | 16 | 39 | 18 | 63 | 100 |
| NDRG4 | 16 | 39 | 7 | 69 | 100 |
| OSMR (3) | 16 | 39 | 47 | 88 | 100 |
| JPH3 | 16 | 39 | 55 | 81 | 100 |
| ADAM23 | 16 | 39 | 2 | 31 | 100 |

*(3) reflects the primer combinations used for assessing methylation of the OSMR gene Performance of Markers in Fecal Samples Nine of the best performing methylation markers in tissue (GATA4, GATA5, SFRP1, SFRP2, NDRG4, APC, ADAM23, OSMR3, and JPH3) were chosen to be evaluated in fecal samples. β-Actin copy numbers were also quantified as a control for sample quality and DNA yield. Methylated copies of these genes were quantified in all available stool samples by real-time MSP on a 7900HT fast real-time PCR system (Applied Biosystems).

The individual performance of the 9 genes (Actin, SFRP2, GATA5, GATA4, APC, SFRP1, NDRG4, OSMR3 and ADAM23) in fecal samples from adenoma's and colorectal cancers is shown in Table 29. A specificity of 100% was obtained for most of the genes, except for SFRP2. The best performing genes in fecal samples from patients with CRC corresponded to GATA4 with 73% sensitivity, SFRP1 with 67% sensitivity, OSMR3 with 67% sensitivity, and NDRG4 with 60% sensitivity, all with a corresponding specificity of 100%.

TABLE 29

Performance of the markers in fecal samples

| | Number | Act | SFRP 2 | GATA5 | GATA4 | APC | SFRP1 | NDRG4 | OSMR (3) | Adam23 |
|---|---|---|---|---|---|---|---|---|---|---|
| cutoff (copies) | of samples | 200 | 1 | 1 | 4 | 1 | 1 | 0 | 10 | 1 |
| Sens adenoma | 13 | 15% | 38% | 0% | 15% | 8% | 8% | 15% | 8% | 0% |
| Sens CRC | 15 | 67% | 67% | 27% | 73% | 47% | 67% | 60% | 67% | 40% |
| Spec | 19 | 95% | 84% | 100% | 100% | 100% | 100% | 100% | 100% | 100% |

Performance of Marker Combination Panels in Fecal Samples

Four candidate methylation markers were found to result in the best sensitivity and specificity in stool samples: GATA4, SFRP2, NDRG4, OSMR. β-Actin copy numbers were also quantified as a control for sample quality and DNA yield. The performance of combination panels of these 4 methylation markers was investigated. Methylated copies of these genes were quantified in all available stool samples by real-time MSP on a 7900HT fast real-time PCR system (Applied Biosystems). Table 30 shows the results and lists the cut-off (copies) applied. For instance for the most sensitive marker combination panel SFRP2+GATA4+NDRG4+OSMR, cutoff values of the individual markers were SFRP2=2; GATA4=4; NDRG4=0.1 and OSMR=10. This combination panel had 95% specificity, 87% sensitivity for CRC, and 46% sensitivity for adenomas. The preferred 2-marker combination NDRG4+GATA4 had a 100% specificity, a sensitivity of 73% for CRC, and a 33% sensitivity for adenomas.

TABLE 30

Performance of marker combinations

Cutoff (copies) and performance of combination panels *

|  | SFRP2 + GATA4 + NDRG4 | SFRP2 + NDRG4 | SFRP2 + GATA4 + NDRG4 + OSMR (3) | SFRP2 + NDRG4 + OSMR (3) | NDRG4 + OSMR (3) | NDRG4 + GATA4 |
|---|---|---|---|---|---|---|
| SFRP 2 cp | 1 | 1 | 1 | 1 | (—) | (—) |
| GATA4 cp | 4 | (—) | 4 | (—) | (—) | 4 |
| NDRG4 cp | 0 | 0 | 0 | 0 | 0 | 0 |
| OSMR (3) | (—) | (—) | 10 | 10 | 10 | (—) |
| Sens adenoma | 46% | 46% | 46% | 46% | 23% | 33% |
| Sens CRC | 80% | 73% | 87% | 80% | 80% | 73% |
| Specificity | 95% | 95% | 95% | 95% | 95% | 100% |

* Marker not used in the combination panel is indicated by (—)

The performance of the most sensitive marker combination panel SFRP2+GATA4+NDRG4+OSMR was evaluated for the different UICC stages. Results are summarized in Table 31.

TABLE 31

Performance of combination panel SFRP2 + GATA4 + NDRG4 + OSMR for different UICC stages

| UICC stage | Neg | Pos | Total |
|---|---|---|---|
| ? |  | 1 | 1 |
| I | 1 | 4 | 5 |
| II |  | 4 | 4 |
| III | 1 | 3 | 4 |
| IV |  | 1 | 1 |
| Total samples | 2 | 13 | 15 |

Example 2

Based on re-expression, 224 different gene assays representing 145 gene promotors were tested on the Base5 methylation profiling platform (data not shown, see reference 2 for details). The 37 most differentially methylated gene sequences assessing 29 gene promoters were validated on retrospectively collected tumors from 65 colorectal cancer patients (all stages) and 74 distant resection ends (histopathologically normal) using real-time MSP. Several markers reliably detected CRC in those tissue samples (data not shown). The results were confirmed on an independent test set containing 59 samples from patients with cancer other than CRC (20 breast, 21 lung and 22 bladder cancer samples covering stages I-III), 39 non-cancerous controls, 34 carcinomas and 16 adenomas. After testing the non-CRC tissue samples, we had 59 results because 4 were invalid. The individual performance of the 9 best performing tissue markers is shown in FIG. 2, when the analytical cut-off was set to give 100% specificity (based on the 39 non-cancerous controls). The most tissue specific markers include: NDRG4, OSMR, SFRP1, ADAM23, GATA5 and MGMT.

REFERENCES

Ahlquist D A, Skoletsky J E, Boynton K A, Harrington J J, Mahoney D W, Pierceall W E, Shuber A P. Colorectal cancer screening by detection of altered human DNA in stool: feasibility of a multi-target assay panel. Gastroenterology 2000, 119:1219-1227

Baylin, S. B., Belinsky, S. A. & Herman, J. G. Aberrant methylation of gene promoters in cancer-concepts, misconcepts, and promise. J. Natl Cancer Inst. 92, 1460-1461 (2000).

Belshaw N J, Elliott G O, Williams E A, et al. Use of DNA from human stools to detect aberrant CpG island methylation of genes implicated in colorectal cancer. Cancer Epidemiol Biomarkers Prev 2004; 13:1495ˆ501.

Boynton K A, Summerhayes I C, Ahlquist D A, Shuber A P. DNA integrity as a potential marker for stool-based detection of colorectal cancer. Clin Chem 2003, 49:1058-1065

W. D. Chen, Z. J. Han, J. Skoletsky, J. Olson, J. Sah, L. Myeroff, P. Platzer, S. Lu, D. Dawson, J. Willis, T. P. Pretlow, J. Lutterbaugh, L. Kasturi, J. K. Willson, J. S. Rao, A. Shuber and S. D. Markowitz. Detection in fecal DNA of colon cancer specific methylation of the nonexpressed vimentin gene. J Natl Cancer Inst 97 (2005), 1124-1132.

Dong S M, Traverso G, Johnson C, Geng L, Favis R, Boynton K, Hibi K, Goodman S N, D'Allessio M, Paty P, Hamilton S R, Sidransky D, Barany F, Levin B, Shuber A, Kinzler K W, Vogelstein B, Jen J. Detecting colorectal cancer in stool with the use of multiple genetic targets. J Natl Cancer Inst. 2001 Jun. 6; 93(11):858-65

P. A. Jones and S. B. Baylin. The fundamental role of epigenetic events in cancer. Nat Rev Genet 3 (2002), 415-428.

P. W. Laird. Early detection: The power and the promise of DNA methylation markers. Nat Rev Cancer 3 (2003), 253-266.

K. Lenhard, G. T. Bommer, S. Asutay, R. Schauer, T. Brabletz, B. Goke, R. Lamerz and F. T. Kolligs. Analysis of promoter methylation in stool: a novel method for the detection of colorectal cancer, Clin Gastroenterol Hepatol 3 (2005), 142-149.

Leung W K, To K F, Man E P, Chan M W, Bai A H, Hui A J, Chan F K, Lee J F, Sung J J. Detection of epigenetic changes in fecal DNA as a molecular screening test for colorectal cancer: a feasibility study. Clin Chem. 2004 November; 50(11):2179-82.

H. M. Muller, M. Oberwalder, H. Fiegl, M. Morandell, G. Goebel, M. Zitt, M. Muhlthaler, D. Ofner, R. Margreiter and M. Widschwendter. Methylation changes in faecal DNA: a marker for colorectal cancer screening? Lancet 363 (2004), 1283-1285.

Olson J, Whitney D H, Durkee K, Shuber A P. DNA Stabilization Is Critical for Maximizing Performance of Fecal DNA-Based Colorectal Cancer Tests Diagn Mol Pathol. 2005 September; 14(3):183-91.

Z. Petko, M. Ghiassi, A. Shuber, J. Gorham, W. Smalley, M. K. Washington, S. Schultenover, S. Gautam, S. D. Markowitz and W. M. Grady. Aberrantly methylated CDKN2A, MGMT, and MLH1 in colon polyps and in fecal DNA from patients with colorectal polyps. Clin Cancer Res 11 (2005), 1203-1209.

Sidransky, D. Nucleic acid-based methods for the detection of cancer. Science 278, 1054-1058 (1997)

Straub, J. et al., AB-104-AACRMD (2007), poster presented September 2007 at the AACR meeting "Molecular Diagnostics in Cancer Therapeutic Development: Maximizing Opportunities for Personalized Treatment.

Whitney D, Skoletsky J, Moore K, Boynton K, Kann L, Brand R, Syngal S, Lawson M, Shuber A. Enhanced Retrieval of DNA from Human Fecal Samples Results in Improved Performance of Colorectal Cancer Screening Test. J Mol Diagn. 2004 November; 6(4):386-95

Zou et al., Clin Chem. 2007 September; 53(9):1646-51. A novel method to capture methylated human DNA from stool: implications for colorectal cancer screening.

3) Experiments on Plasma DNA

Materials and Methods in Relation to Plasma DNA

Sample Collection and Processing

Plasma samples were collected from multiple centers in Germany, The Netherlands and Belgium.

10 ml of blood was obtained per individual using EDTA Vacutainer™ tubes. Individuals with no suspicious findings, adenomas or carcinomas based on colonoscopy were enrolled in the present study. Within 4 hrs from the blood drawing, the plasma fraction was separated from the cell fraction by centrifugation at 1500 g for 15 min (4° C.). The plasma was transferred to new tubes and once again centrifuged (1500 µg, 15 min, 4° C.), after which the supernatant was transferred to new tubes and stored at −80° C. until further use. Samples were shipped on dry ice.

Plasma samples from patients with stages I-IV of colorectal cancers and different controls belonging to the following groups were enrolled in this study. Tables 32 and 33 gives an overview of the collected samples sets.

Colorectal cancer group: patients with pathologically confirmed colorectal cancer with stage I to IV (according to the UICC stage grouping)

Adenomas

Non-cancer controls: patients without cancerous disease

Cancer controls: patients with carcinomas other than colorectal cancer

TABLE 32

Plasma training set 1

| Diagnosis group | Sample volume | Number of samples | Notes |
|---|---|---|---|
| Colorectal cancers | 1.2 to 4.5 ml of plasma (corresponding to 0.07 to 0.27 plasma equivalent of DNA per PCR) | 42 | StageI-IV Grade 1-3 (81% stage I-III) |
| Non-cancer controls | | 34 | Symptomatic patients with non-acute conditions |
| Cancer controls | 4 to 6 ml of plasma (corresponding to 0.24 to 0.36 plasma equivalent of DNA per PCR) | 25 | Predominantly ovarian and prostate cancers |

TABLE 33

Plasma training set 2

| Diagnosis group | Sample volume | Number of samples | Notes |
|---|---|---|---|
| Colorectal cancers | 1.3 to 4.3 ml of plasma (corresponding to 0.16 to 0.52 plasma equivalent of DNA per PCR) | 78 | StageI-IV Grade 1-3 (76% stage I-III) |
| Adenomas | | 49 | |
| Non-cancer controls | | 64 | Symptomatic patients with non-acute conditions |
| Cancer controls | 4 to 6 ml of plasma (corresponding to 0.48 to 0.72 plasma equivalent of DNA per PCR) | 25 | Predominantly ovarian and prostate cancers |

DNA Isolation from Plasma Samples

DNA isolation from plasma samples (1.2 to 6 ml) was performed using an upscaled phenol-chloroform DNA isolation method using the 15 ml of Heavy Phase lock Gel tubes (PLG tubes) (Eppendorf, cat #0032 005.152) or alternatively the ChargeSwitch® gDNA 1 ml serum kit from Invitrogen (cat #CS11040).

Phenol-Chloroform Procedure

Plasma samples were thawed and 1/10 volume of 10× buffer (240 mM EDTA (pH=8.0), 750 mM NaCl), 1/10 volume of 10% SDS and 5 µl of Proteinase K (20 mg/ml stock solution) per 1 ml of sample (e.g. 15 µl for 3 ml of sample) was added to each plasma sample. This mixture was incubated overnight at 48° C. at constant shaking (200 RPM).

Subsequently the PLG tube was centrifuged at 2500 RCF for 3 min, sample mixture and approximately the same volume of phenol/chloroform (Invitrogen, cat #15593049) were added to it. This solution was briefly vortexed, mixed for 10 min using a tube rocker at room temperature and centrifuged for 5 min at 2500 RCF. In case the retrieved sample volume was ≤4 ml, an equal volume of phenol/chloroform was added. The upper aqueous layer was phenol/chloroform-treated for a second time.

DNA was precipated from the the upper aqueous layer by adding 5 µl glycogen, 1/10 volume of 7.5 M Ammonium Acetate and 2-2.5 volumes of cold (−20° C.) 100% ethanol. Tubes were gently inverted and incubated at −20° C. for at least 1 h, followed by a centrifugation step at 17000 RCF for 30 min (4° C.). Ethanol was carefully removed by pipetting. Pellets were washed with 2 ml freshly prepared 70% ethanol, vortexed gently and submitted to a centrifugation step at 17000 RCF for 15 min at 4° C. After careful removal of the remaining ethanol, pellets were air dried and resuspended in 45 µl of LoTE pH 8.0. The isolated DNA is stored at −80° C. until further processing. This method allowed an average DNA recovery of 120 ng per ml of plasma.

ChargeSwitch® gDNA 1 ml Serum Kit

Plasma samples are thawed and DNA is isolated using the ChargeSwitch® gDNA 1 ml serum kit according to the manufacturer's instructions with the exception that the procedure is upscaled for larger sample volumes using the MagnaBot® large volume magnetic separation device from Promega (Cat #V3471). Results are presented in Table 41.

DNA Modification

The complete content of DNA isolated in above procedure was subjected to sodium bisulfite treatment (BT) using the EZ-96 DNA Methylation kit from Zymo Research (Cat #D5003) performed on a pipetting robot (Tecan Freedom EVOII, Roma, Liha, Mca, Te-Vacs). Briefly, 45 µl of plasma DNA sample was mixed with 5 µl of M-Dilution Buffer (provided in kit) and incubated at 37° C. for 15 min shaking at 1100 RPM. This mixture was further incubated with 100 µl of diluted CT conversion reagent (provided in kit) shaking at 70° C. for 3 hours (protected from light). Subsequently the modified DNA was desalted and desulfonated according to manufacturer's instructions and eluted in either 40 µl or 20 µl of Tris-HCl 1 mM pH8.0, depending on the applied concentration procedure. The eluted material was stored at −80° C. until further processing.

DNA Amplification

Real-time MSP was performed on a 7900HT fast real-time PCR cycler from Applied Biosystems. 2.4 µl of the modified DNA was added to a PCR mix (total volume 12 µl) containing home-made buffer solution (final concentrations are summarized: 16.6 mM $(NH_4)_2SO_4$, 67 mM Tris (pH 8.8), 6.7 mM MgCl2, 10 mM β-mercaptoethanol), dNTPs (5 mM; Amersham Biosciences cat #27-2035-02), methylation specific forward primer (6 ng), methylation specific reverse primer (18 ng), molecular beacon (0.16 µM) and Jumpstart DNA Taq polymerase (0.4 units; Sigma Cat #D9307).

Cycling conditions are specified in Table 34.

A standard curve was included ($9.6\times10^5$–9.6 copies) to determine copy numbers of unknown samples by interpolation of their Ct values to the standard curve.

TABLE 34

Cycling profile

| | | | |
|---|---|---|---|
| 1 | Activation | 95° C. | 5 min |
| 2 | Denaturation | 95° C. | 30 sec |
| 3 | Annealing and data collection | 57° C. (51° C. for APC) | 30 sec |
| 4 | extension | 72° C. | 30 sec |
| 5 | cycling | Repeat step 2 to 4, 45 times | |

Results

Marker Identification and Validation in Tissue and Plasma Samples.

Assay Validity Rate in Tissue and Plasma:

293 FFPE and 317 plasma samples were processed using real-time MSP (Table 35). The real-time MSP assays produced valid results in 98% of the FFPE samples and in 100% of the plasma samples.

TABLE 35

Summary of samples evaluated by real-time MSP

| Sample Sets | Sample Types | Sample Numbers | Valid Tests [%] |
|---|---|---|---|
| Tissue Training Set | Cancer | 65 | 65/65 [100] |
| | Controls | 76 | 74/76 [97] |
| Tissue Test Set | Total | 141 | 139/141 [99] |
| | CRC | 34 | 34/34 [100] |
| | Controls | 39 | 39/39 [100] |
| | Other Cancers | 63 | 59/63 [94] |
| | Adenomas | 16 | 16/16 [100] |
| Tissue Sets combined | Total | 152 | 148/152 [97] |
| | CRC | 99 | 99/99 [100] |
| | Controls | 115 | 113/115 [98] |
| | Other Cancers | 63 | 59/63 [94] |
| | Adenomas | 16 | 16/16 [100] |
| Plasma Training set (1) | Total | 293 | 287/293 [98] |
| | Cancer | 42 | 42/42 [100] |
| | Controls | 34 | 34/34 [100] |
| | Other cancers | 25 | 25/25 [100] |
| Plasma Training set (2), increased | Total | 101 | 101/101 [100] |
| | Cancer | 78 | 78/78 [100] |
| | Adenoma | 49 | 49/49 [100] |
| | Controls | 64 | 64/64 [100] |
| | Other cancers | 25 | 25/25 [100] |
| plasma equivalent of DNA per real-time MSP assay | Total | 216 | 216/216 [100] |
| Plasma Sets combined | Cancer | 120 | 120/120 [100] |
| | Adenoma | 49 | 49/49 [100] |
| | Controls | 98 | 98/98 [100] |
| | Other cancers | 50 | 50/50 [100] |
| | Total | 317 | 317/317 [100] |

Marker Identification

Using re-expression profiles of colon cancerous cell lines, candidate genes were identified and the most promising markers (224 different gene assays representing 145 gene promoters) were tested on tissue using the BaseS methylation profiling platform (data not shown, see Straub, J. et al for details). Promoter sequences were linked with gene expression to identify epigenetically silenced genes. An established pharmacologic unmasking strategy (5-aza-2'-deoxycytidine (DAC) and trichostatin A (TSA)) for re-expression analysis of epigenetically targeted genes was combined with proprietary advanced bioinformatics tools to identify genes prone to promoter methylation.

Marker Selection in Colon Tissue

Figure 7:
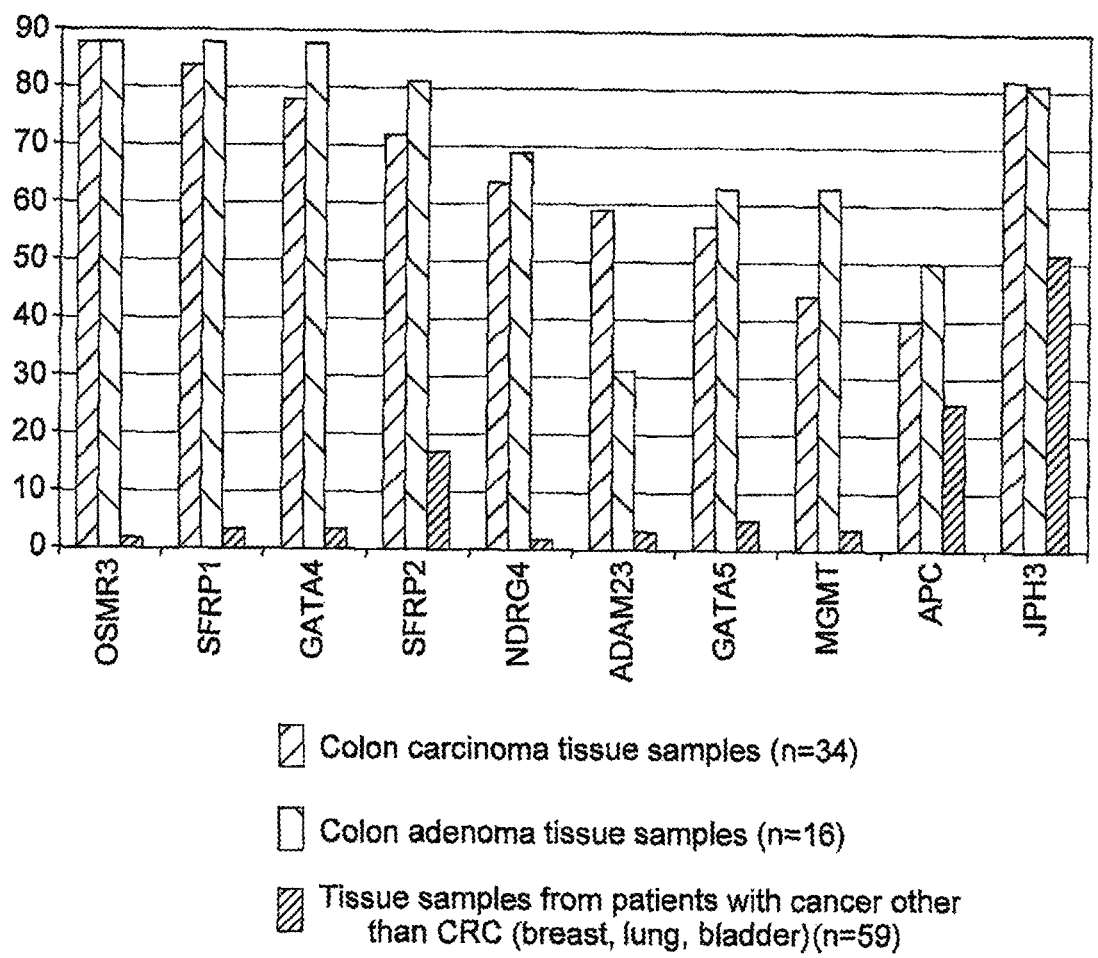
FIG. 7 presents results of real-time MSP carried out on 10 different genes for 34 colon carcinoma tissue samples, 16 colon adenoma tissue samples and 59 samples from patients with cancer other than CRC. Sensitivity performance for each gene is shown wherein the analytical cut-off was set to give 100% specificity (based on the non-cancerous controls), except for JPH3 where 95% specificity was obtained.

Marker candidates identified by re-expression were screened using 37 real-time methylation specific PCR (real-time MSP) assays. These assays were used to assess the methylation status of 29 gene promoters in 293 formalin-fixed paraffin-embedded (FFPE) tissue samples collected from various clinics. Samples included 99 carcinomas of various stages, 16 adenomas, 63 samples from patients with cancer other than CRC (20 breast [stages I-III], 22 bladder [stages I-III], 21 lung [stages I and II]), 39 samples from patients with no evidence of cancer and 76 distant resection ends (histopathologically normal) from CRC patients. These samples were divided into training and independent test sets, and used to select the gene methylation assays best able to discriminate between cancerous and non-cancerous samples. The training set included retrospectively collected tumors from 65 colorectal cancer patients (all stages) and 74 distant resection ends. Using the 10 best performing genes the results were confirmed on an independent test set containing 59 samples from patients with cancer other than CRC, 39 non-cancerous controls and 50 cancer cases (34 carcinomas and 16 adenomas). The individual performance of the 10 best performing tissue markers OSMR, SFRP1, GATA4, SFRP2, NDRG4, ADAM23, GATA5, MGMT, APC and JPH3 is shown in FIG. 7, when the analytical cut-off was set to give 100% specificity, except for JPH3 where a specificity of 95% was obtained (based on the 39 non-cancerous controls). Corresponding primer and beacon sequences are summarized in Table 3 (above). In addition to the colon test genes, the independent reference gene β-Actin (ACT) was also measured. The ratios between the colon test genes and ACT were calculated, and are the test result of the assay. The samples were classified as methylated, non-methylated, or invalid based on the decision tree shown in FIG. 5.

Complementarity of Markers

The different markers were tested on their complementarity. Several marker combinations reliably detected CRC with high specificity and sensitivity. Results of the best 2 marker combinations are summarized in Table 36. For 100% specificity, sensitivities ranged between 94 to 100%.

TABLE 36

Performance of 2 combinations of the markers reliably detecting CRC and adenomas when using real-time MSP (tissue test set: 34 carcinomas, 16 adenomas, 39 controls)

| Samples | # detected/tested | Sensitivity % [95% CI] | Specificity % (# detected/tested) |
|---|---|---|---|
| Panel 1 (OSMR, GATA4, ADAM23) | | | |
| 34 carcinomas 39 controls | 33/34 | 97 [91-100] | 100 (0/39) |
| 16 adenomas 39 controls | 16/16 | 100 | 100 (0/39) |
| 50 neoplasms (34 carcinomas and 16 adenomas) 39 controls | 49/50 | 98 [94-100] | 100 (0/39) |
| Panel 2 (OSMR, GATA4, GATA5) | | | |
| 34 carcinomas 39 controls | 32/34 | 94 [86-100] | 100 (0/39) |
| 16 adenomas 39 controls | 16/16 | 100 | 100 (0/39) |
| 50 neoplasms (34 carcinomas and 16 adenomas) 39 controls | 48/50 | 96 [90-100] | 100 (0/39) |

Marker Testing in Plasma

Eight of the best performing markers in tissue were assessed (OSMR, SFRP1, NDRG4, GATA5, ADAM23, JPH3, SFRP2 and APC) on 101 available plasma samples from multiple centers (plasma training set 1: Table 32). These plasma samples included 34 samples with no suspicious findings, 25 samples from patients with cancers other than colon cancer and 42 samples from patients covering all stages of CRC, with 81% representing stages I-III of disease.

DNA was isolated following the upscaled phenol-chloroform procedure; subsequently the whole DNA sample was modified as described above. The plasma training set 1 was eluted in 40 μl of BT elution volume of which 2.4 μl was subjected to real-time MSP, the 2.4 μl of eluted DNA corresponds to an equivalent of 0.07 to 0.36 ml of original plasma sample which went into the isolation procedure (=0.07 to 0.36 plasma equivalent of DNA per PCR).

Figure 8:
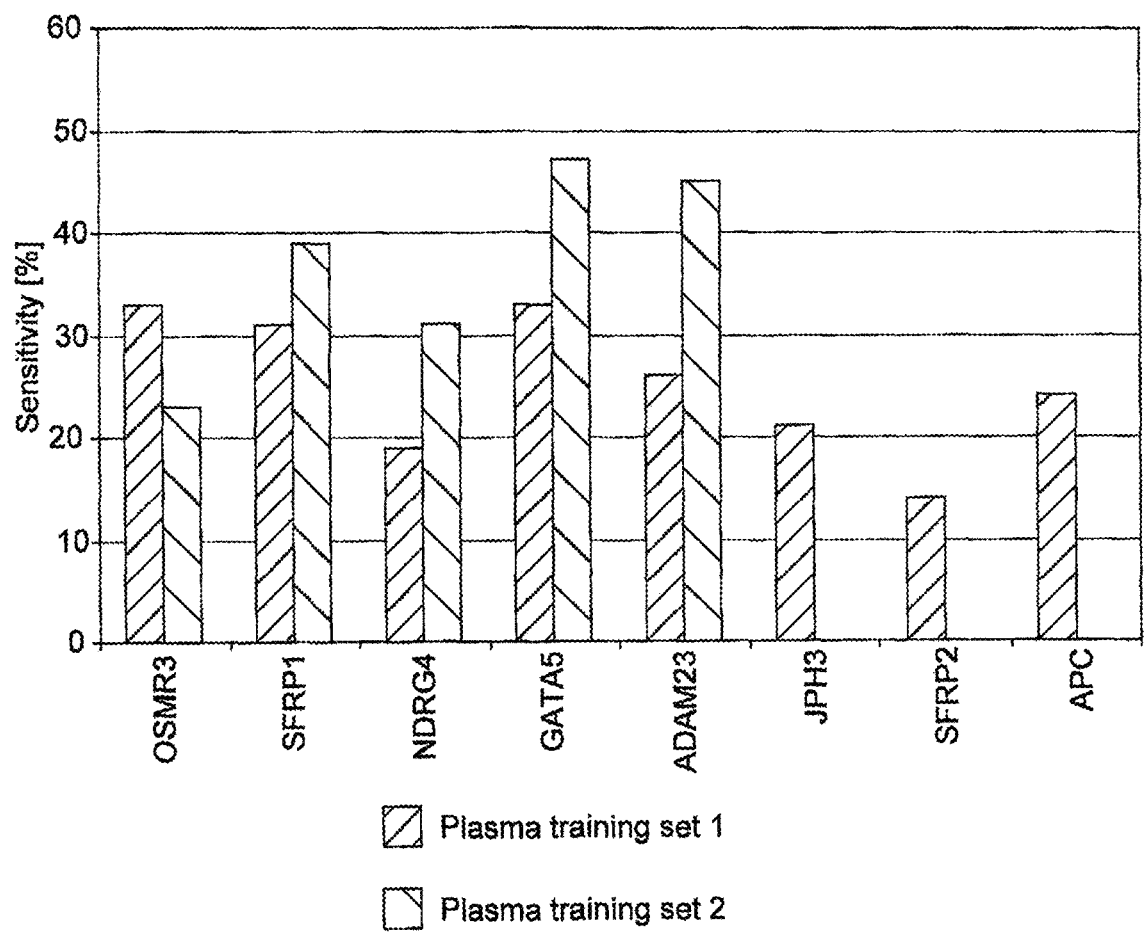
FIG. 8 presents results of real-time MSP carried out on 8 different genes for plasma training set 1 and 5 different genes for plasma training set 2. Plasma training set 1 includes 34 samples with no suspicious findings, 25 samples from patients with cancers other than colon and 42 samples from patients covering all stages of CRC, with 81% representing stages I-III of disease. Plasma training set 2 was tested on 64 samples with no suspicious findings, 49 adenomas, 25 samples from patients with cancer other than colon cancer and 78 samples from patients covering all stages of CRC, with 76% representing stages I-III of disease.

The individual performance (% sensitivity) of the 8 gene assays in plasma samples is shown in FIG. 8, sensitivity values ranging from 14 to 33%. Corresponding specificity values are displayed in Table 37. Obtained specificity values ranged from 97 to 100%.

Five of the best performing markers in training set 1 were further studied with an additional, independent sample set prospectively collected from multiple centers (plasma training set 2: Table 33). Reducing the number of gene assays from 8 to 5 resulted in fewer assays per sample and a greater aliquot of plasma equivalent of DNA was added per PCR reaction. The modified DNA from sample set 2 was more concentrated by eluting in 20 μl instead of 40 μl of BT elution volume. 2.4 μl eluted DNA from sample set 2 was further processed through real-time MSP, this corresponds to 0.16 to 0.72 ml plasma equivalent of DNA per PCR depending on the plasma volume prior to DNA isolation.

The plasma samples of training set 2 included 64 samples with no suspicious findings, 49 adenomas, 25 samples from patients with cancers other than colon cancer and 78 samples from patients covering all stages of CRC, with 76% representing stages I-III of disease. The individual performance (% sensitivity) of the 5 gene assays is shown in FIG. 8 with corresponding specificity values displayed in Table 37. Specificity values ranged from 96 to 99%, with sensitivity ranging from 23 to 47%.

Four candidate methylation markers were found to result in the best sensitivity and specificity in plasma samples: OSMR, NDRG4, GATA5 and ADAM23; performance of this plasma panel is shown in Table 38. Performance characteristics (stages I-III CRC) of this panel of 4 methylation genes demonstrated 73% sensitivity and 92% specificity when optimized for sensitivity, whereas 64% sensitivity and 98% specificity was obtained when optimizing for specificity. Sensitivity can be further improved (from 64% to 68%) when samples with a plasma volume less than 2 ml prior to DNA isolation are excluded from analysis. Results are presented in Table 39.

TABLE 37

Individual gene assay performance displaying % specificity for both plasma training sets and % sensitivity for adenomas in plasma training set 2

| | OSMR | SFRP1 | NDRG4 | GATA5 | ADAM23 | JPH3 | SFRP2 | APC |
|---|---|---|---|---|---|---|---|---|
| % Specificity (all 59 controls), plasma set 1 | 100 | 98 | 100 | 97 | 98 | 97 | 97 | 97 |

TABLE 37-continued

Individual gene assay performance displaying % specificity for both plasma training sets and % sensitivity for adenomas in plasma training set 2

|  | OSMR | SFRP1 | NDRG4 | GATA5 | ADAM23 | JPH3 | SFRP2 | APC |
|---|---|---|---|---|---|---|---|---|
| % Specificity (all 89 controls), plasma set 2: increased plasma equivalent of DNA per real-time MSP assay | 99 | 96 | 99 | 99 | 97 | N/A | N/A | N/A |
| % Sensitivity adenomas plasma set 2: increased plasma equivalent of DNA per real-time MSP assay | 2 | 2 | 0 | 6 | 2 | N/A | N/A | N/A |

TABLE 38

Performance of a plasma marker panel using real-time MSP (independent of recovered plasma volume prior to DNA isolation)

| Sample sets | Sample groups | Sensitivity % (# detected/# total) [95% CI] | Specificity % (# detected/# total) [95% CI] |
|---|---|---|---|
| | | Plasma panel (optimized for sensitivity) OSMR, NDRG4, GATA5 and ADAM23 | |
| Plasma training set 1 | Stages I-III CRC All Stages CRC All Controls | 50 (17/34) 60 (25/42) [45-83] | 97 (2/59) [93-100] |
| Plasma training set 2 (increased plasma equivalent of DNA per real-time MSP assay) | Stages I-III CRC All Stages CRC Adenomas All Controls | 73 (43/59) 73 (57/78) [63-83] 12 (6/49) | 92 (7/89) [86-98] |
| | | Plasma panel (optimized for specificity) OSMR, NDRG4, GATA5 and ADAM23 | |
| Plasma training set 1 | Stages I-III CRC All Stages CRC All Controls | N/A | N/A |
| Plasma training set 2 (increased plasma equivalent of DNA per real-time MSP assay) | Stages I-III CRC All Stages CRC Adenomas All Controls | 64 (38/59) 64 (50/78) [53-75] 6 (3/49) | 98 (2/89) [95-100] |

TABLE 39

Performance of a plasma marker panel using real-time MSP using at least 2 ml of plasma prior to DNA isolation

| Sample sets | Sample groups | Sensitivity % (# detected/# total) [95% CI] | Specificity % (# detected/# total) [95% CI] |
|---|---|---|---|
| | | Plasma panel (optimized for sensitivity) OSMR, NDRG4, GATA5 and ADAM23 | |
| Plasma training set 2 (increased plasma equivalent of DNA per real-time MSP assay) | Stages I-III CRC All Stages CRC Adenomas All Controls | 73 (41/56) 74 (54/73) [64-84] 12 (6/49) | 92 (7/89) [86-98] |
| | | Plasma panel (optimized for specificity) OSMR, NDRG4, GATA5 and ADAM23 | |
| Plasma training set 2 (increased plasma equivalent of DNA per real-time MSP assay) | Stages I-III CRC All Stages CRC Adenomas All Controls | 68 (38/56) 67 (49/73) [56-76] 6 (3/49) | 98 (2/89) [95-100] |

Average DNA Recovery Yield from Plasma Samples

Plasma DNA (collected after double centrifugation step) from colorectal cancer patients was isolated according to the phenol/chloroform procedure and quantified using the PicoGreen dsDNA quantitation kit from Molecular Probes. The average plasma DNA recovery yield was 117 ng/ml of plasma, with a range of 41 to 384 ng/ml (data obtained from 25 patients).

TABLE 40

Average DNA recovery yield plasma samples

| Sample | ng/ml plasma |
|---|---|
| 1 | 41 |
| 2 | 66 |
| 3 | 264 |
| 4 | 163 |
| 5 | 54 |
| 6 | 121 |
| 7 | 87 |
| 8 | 107 |
| 9 | 53 |
| 10 | 121 |
| 11 | 88 |
| 12 | 201 |
| 13 | 53 |
| 14 | 47 |
| 15 | 384 |
| 16 | 87 |
| 17 | 115 |
| 18 | 107 |
| 19 | 70 |
| 20 | 72 |
| 21 | 122 |
| 22 | 146 |
| 23 | 71 |
| 24 | 195 |
| 25 | 94 |

Phenol/Chloroform Procedure Versus ChargeSwitch® Using Plasma Samples

This experiment was carried out to show the isolation of DNA from plasma by using the method of this invention. Plasma volumes ranging from 2.5 to 6 ml were processed according to the above discussed upscaled phenol/chloroform and ChargeSwitch® isolation procedure. Plasma derived from ovarian, prostate and colon blood samples were investigated. The objective was to isolate DNA (according to both methods) and further process the samples in parallel through bisuphite treatment and β-Actin real-time MSP to address the sample quality and DNA yield. The corresponding β-Actin copies for both isolation procedures are summarized in Table 16.

TABLE 41

β-Actin copies phenol/chloroform versus ChargeSwitch ® isolation procedure

| Sample number | Sample origin | Plasma volume (ml) | B-Actin copies Phenol | B-Actin copies ChargeSwitch |
|---|---|---|---|---|
| 1 | ovarian cancer | 6.0 | 4349 | 863 |
| 2 | ovarian cancer | 6.0 | 2710 | 466 |
| 3 | ovarian cancer | 6.0 | 3922 | 967 |
| 4 | ovarian cancer | 6.0 | 758 | 490 |
| 5 | ovarian cancer | 6.0 | 4201 | 423 |
| 6 | ovarian cancer | 6.0 | 2644 | 139 |
| 7 | ovarian cancer | 6.0 | 1472 | 187 |
| 8 | prostate cancer | 2.6 | 145 | 7 |
| 9 | colon cancer | 2.5 | 317 | 52 |
| 10 | pos control cell line | N/A | 8702 | 1314 |

Updated Results for Plasma Training Set 2.

Corrected information was received from the clinics about plasma training set 2. For plasma training set 2: the cancer cases remained the same, a new category of "unknown" was created, the number of controls was 52 (instead of former 64) and the adenoma cases were 39 (instead of former 49). This allowed re-classification of sample types as provided in Table 42. Since the corrected information classified a number of unknown cancer cases (controls) as early stage cancers, additional conclusions on detection of early stage cancers could be drawn. As shown in table 43, the plasma panel allowed very sensitive detection (70%) of early stage samples. Improved detection could be obtained by excluding samples with a plasma volume less than 2 ml (Table 44)

TABLE 42

Summary of samples tested by real-time MSP and evaluablility rate

| Sample sets | Sample types | Sample numbers | Valid tests [%] |
|---|---|---|---|
| Tissue training set | CRC | 65 | 65/65 [100] |
|  | Controls | 76 | 74/76 [97] |
|  | Total | 141 | 139/141 [99] |
| Tissue test set | CRC | 34 | 34/34 [100] |
|  | Controls | 39 | 39/39 [100] |
|  | Other Cancers | 63 | 59/63 [94] |
|  | Adenomas | 16 | 16/16 [100] |
|  | Total | 152 | 148/152 [97] |
| Tissue sets combined | CRC | 99 | 99/99 [100] |
|  | Controls | 115 | 113/115 [98] |
|  | Other Cancers | 63 | 59/63 [94] |
|  | Adenomas | 16 | 16/16 [100] |
|  | Total | 293 | 287/293 [98] |
| Plasma training set (1) | CRC | 42 | 42/42 [100] |
|  | Controls | 34 | 34/34 [100] |
|  | Other cancers | 25 | 25/25 [100] |
|  | Total | 101 | 101/101 [100] |
| Plasma training set (2) | CRC | 78 | 78/78 [100] |
|  | Adenoma | 39 | 49/49 [100] |
|  | Controls | 52 | 64/64 [100] |
|  | Other cancers | 25 | 25/25 [100] |
|  | Unknown | 22 | 22/22 [100] |
|  | Total | 216 | 216/216 [100] |
| Plasma sets combined | CRC | 120 | 120/120 [100] |
|  | Adenoma | 39 | 49/49 [100] |
|  | Controls | 86 | 98/98 [100] |
|  | Other cancers | 50 | 50/50 [100] |
|  | Unknown | 22 | 22/22 [100] |
|  | Total | 317 | 317/317 [100] |

TABLE 43

Performance characteristics of a 4-gene marker panel using plasma set 2

| Sample groups (plasma training set 2) | Plasma panel OSMR, GATA5, NDRG4 and ADAM23 | | | |
|---|---|---|---|---|
| | optimized for sensitivity | | optimized for specificity | |
| | Sensitivity % (# detected/# total) [95% CI] | Specificity % (# detected/# total) [95% CI] | Sensitivity % (# detected/# total) [95% CI] | Specificity % (# detected/# total) [95% CI] |
| Early stages CRC (0-II) | 70% (23/33) [54-86] | 92% (6/77) [86-98] | 58% (19/33) [41-75] | 99% (1/77) [96-100] |
| All stages CRC | 73% (57/78) [63-83] | | 64% (50/78) [53-75] | |
| Adenomas Controls | 10% (4/39) | | 5% (2/39) | |

TABLE 44

Performance characteristics of a 4-gene marker panel using plasma set 2

| Sample groups (plasma training set 2) | Plasma panel OSMR, GATA5, NDRG4 and ADAM23 | | | |
|---|---|---|---|---|
| | optimized for sensitivity | | optimized for specificity | |
| | Sensitivity % (# detected/# total) [95% CI] | Specificity % (# detected/# total) [95% CI] | Sensitivity % (# detected/# total) [95% CI] | Specificity % (# detected/# total) [95% CI] |
| Early stages CRC (0-II) | 70% (23/33) [54-86] | 92% (6/77) [86-98] | 58% (19/33) [41-75] | 99% (1/77) [96-100] |
| All stages CRC | 74% (54/73) [64-84] | | 67% (49/73) [56-78] | |
| Adenomas Controls | 10% (4/39) | | 5% (2/39) | |

REFERENCES

Baylin, S. B., Belinsky, S. A. & Herman, J. G. Aberrant methylation of gene promoters in cancer—concepts, misconcepts, and promise. J. Natl Cancer Inst. 92, 1460-1461 (2000).

Catherine Lofton-Day et al, poster presented April 2007 at the AACR Annual meeting 2007, Los Angelos, USA: "Clinical case-control study in plasma shows that the DNA methylation biomarker, Septin 9, detects 70% of Stage I-III colorectal cancer patients"

W. M. Grady, A. Rajput, J. D. Lutterbaugh and S. D. Markowitz, Detection of aberrantly methylated hMLH1 promoterDNA in the serum of patients with microsatellite unstable colon cancer, Cancer Res 61 (2001), 900-902

P. A. Jones and S. B. Baylin. The fundamental role of epigenetic events in cancer. Nat Rev Genet 3 (2002), 415-428.

P. W. Laird. Early detection: The power and the promise of DNA methylation markers. Nat Rev Cancer 3 (2003), 253-266.

Leung W K, To K F, Man E P, Chan M W, Bai A H, Hui A J, Chan F K, Sung J J. Quantitative detection of promoter hypermethylation in multiple genes in the serum of patients with colorectal cancer. Am J Gastroenterol. 2005 October; 100(10):2274-9

Nakayama G, Hibi K, Nakayama H, Kodera Y, Ito K, Akiyama S, Nakao A. A highly sensitive method for the detection of p16 methylation in the serum of colorectal cancer patients. Anticancer Res. 2007 May-June; 27(3B): 1459-63

Straub, J. et al., AB-104-AACRMD (2007), poster presented September 2007 at the AACR meeting "Molecular Diagnostics in Cancer Therapeutic Development: Maximizing Opportunities for Personalized Treatment.

Yamaguchi S, Asao T, Nakamura J, Ide M, Kuwano H. High frequency of DAP-kinase gene promoter methylation in colorectal cancer specimens and its identification in serum.

Cancer Letters, 2003 May 8; 194(1): 99-105

Hong-Zhi Zou, Bao-Ming Yu2, Zhi-Wei Wang, Ji-Yuan Sun, Hui Cang, Fei Gao, Dong Hua Li, Ren Zhao, Guo-Guang Feng and Jing Yi. Detection of aberrant p16 methylation in the serum of colorectal cancer patients. Clin Cancer Res. Vol. 8, 188-191, January 2002.

4) N-Myc Downstream Regulated Gene 4 (NDRG4) Promoter Methylation is a Sensitive and Specific Biomarker for Colorectal Cancer Abstract Background and aims: N-Myc downstream regulated gene 4 (NDRG4), a gene involved in cellular differentiation and neurite formation, is one of the four members of the NDRG family. Here we address the role of NDRG4 promoter methylation in CRC (CRC).

Methods: NDRG4 promoter methylation was analyzed in CRC cell lines, well characterised series of normal colon mucosa, colorectal adenomas, carcinomas and other neoplasias using methylation specific PCR (MSP) and bisulfite sequencing. NDRG4 promoter methylation was also analyzed in fecal DNA of CRC patients and controls using quantitative MSP. Loss of heterozygosity (LOH) mapping of the NDRG4 locus and mutation analysis using direct sequencing of NDRG4 coding exons and their flanking intronic regions were performed. NDRG4 mRNA and protein expression was studied using RT-PCR and immunohistochemistry respectively.

Results: NDRG4 promoter methylation is observed in 7/8 CRC cell lines. The prevalence of NDRG4 promoter methylation in CRC tissue is 86% (71/83) compared to 4% (2/48) in normal colon mucosa. A second, independent series of CRCs confirmed the high prevalence (69%, 127/183) of NDRG4 methylation. NDRG4 methylation was also observed in 81% (13/16) of oesophageal adenocarcinomas and 77% (17/22) of gastric cancers while no or little methylation was observed in skin (0/8), kidney (1/10), ovary (0/20), prostate (0/10), breast (0/16) and oesophageal squamous cell cancers (0/12). NDRG4 promoter methylation can be detected in fecal DNA of 76% (16/21) of CRC patients, while only 3% (2/67) of control patients tested positive yielding a sensitivity of 76% and a specificity of 97%. No mutations were found and 30.5% of tumors showed LOH on the NDRG4 locus. Expression of NDRG4 is decreased at the RNA and protein level in CRC when compared to normal tissue.

Conclusions: NDRG4 is frequently methylated in CRC cell lines, colorectal adenomas and carcinomas and other adenocarcinomas of the gastrointestinal tract. NDRG4 promoter methylation in fecal DNA can be used as a sensitive and specific biomarker for the detection of CRC.

Introduction

Previous microarray experiments to identify genes which are epigenetically regulated in tumor endothelial cells revealed 81 genes that are downregulated in tumor endothelial cells and reexpressed after 5-aza-2'-deoxycytidine (DAC) and trichostatin A (TSA) treatment. Silencing of these genes in tumor-endothelial cells was associated with promoter histone H3 deacetylation and loss of H3 lysine 4 methylation, however did not involve DNA methylation of promoter CpG islands. Interestingly, 21 of these 81 genes (26%) have been reported to be hypermethylated and silenced in various tumor types suggesting that many of the identified gene promoters have the potential to be regulated by promoter methylation in tumor cells (Hellebrekers, Melotte et al. 2007). Amongst the identified CpG island containing genes is N-myc downregulated gene-4 (NDRG4), also known as Smap-8 and Bdm1. NDRG4 is part of the NDRG family which consists of four members, NDRG1, -2, -3 and -4 which have an amino acid sequence homology of 57-65% (Zhou, Kokame et al. 2001; Qu, Zhai et al. 2002). Phylogenetic analysis verified two subfamilies, one consisting of NDRG1 and -3 and the other consisting of NDRG-2 and -4 (Qu, Zhai et al. 2002). NDRG1 is the most extensively studied member of the NDRG family. Expression of NDRG1 is often downregulated in cancer cells (van Belzen, Dinjens et al. 1997; Kurdistani, Arizti et al. 1998; Guan, Ford et al. 2000; Bandyopadhyay, Pai et al. 2003; Bandyopadhyay, Pai et al. 2004; Shah, Kemeny et al. 2005) and upregulated by DAC treatment (Guan, Ford et al. 2000; Bandyopadhyay, Pai et al. 2004). In addition, NDRG2 has also been described as candidate tumor suppressor gene (Deng, Yao et al. 2003; Lusis, Watson et al. 2005) and reported to be methylated in meningiomas (Lusis, Watson et al. 2005) and different cancer cell lines (Liu, Wang et al. 2007). So far, the function of NDRG3 and NDRG4 in cancer has not been addressed. The NDRG4 gene is located on chromosome 16q21-q22.3, spans 26 kb and contains 17 exons covering the entire sequence of three cDNA isoforms NDRG4-B, NDRG4-Bvar and NDRG4-H. NDRG4 mRNA is predominantly present in the cytoplasm. At present, expression of NDRG4 has only been described in brain and heart using Northern blot analysis. The molecular characterization of NDRG4 and the role of this protein in the nervous system has mainly been investigated in the rat (Nakada, Hongo et al. 2002; Ohki, Hongo et al. 2002; Maeda, Hongo et al. 2004; Hongo, Watanabe et al. 2006). NDRG4 protein may participate in processes that lead to cellular differentiation and neurite formation (Ohki, Hongo et al. 2002).

Here, we report NDRG4 to be expressed in normal colon mucosa and downregulated in colon cancer tissue. In addition, NDRG4 promoter methylation, loss of heterozygosity (LOH) and mutational inactivation were examined. We identified the NDRG4 promoter as being frequently methylated in CRC and other neoplasias of the gastrointestinal tract and investigated its potential as a biomarker in stool of CRC patients and controls.

Materials and Methods

Cell Lines, Study Population and Tissues

CRC cell lines HT29, SW480, Caco2, Colo205, RKO, LS174T, HCT116 and SW480 were cultured in DMEM (Invitrogen) supplemented with 10% heat-inactivated fetal calf serum (Hyclone). To investigate reexpression of NDRG4 following inhibition of DNA methyltransferases, HCT116 and RKO were treated with 1 μM DAC (Sigma).

Figure 9:
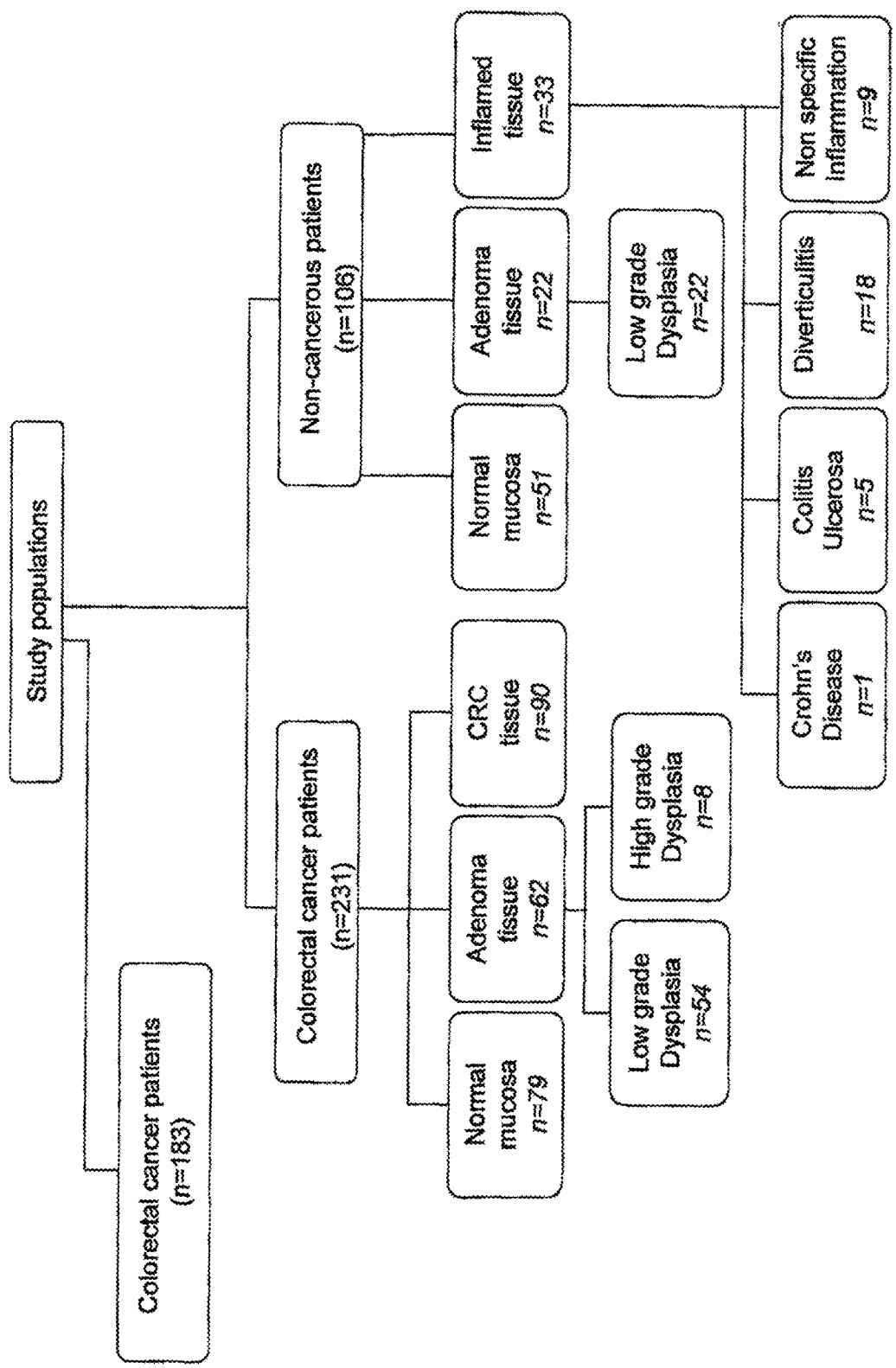
FIG. 9 is an overview of the NDRG4 study showing the patient groups which were investigated.

NDRG4 promoter methylation was investigated in well-characterized series of colorectal carcinomas, adenomas and controls (FIG. 9). The first series consists of formalin-fixed, paraffin-embedded CRCs (n=90) of patients over 50 years of age which were retrospectively collected from the archive of the dept. of Pathology of the University Hospital Maastricht. When present, also normal (n=79) and adenoma (n=60) tissue was collected from these patients. Histologically normal biopsy material from patients undergoing endoscopy for non-specific abdominal complaints (n=51), adenoma biopsies (n=22) from patients who did not develop CRC within 10 years, and resected colon mucosa of patients with various inflammatory bowel conditions (n=33) were selected as control tissue. This last group includes Crohn's disease (n=1), colitis ulcerosa (n=6), non-specific inflammation (n=9) and diverticulitis (n=18). A second independent series of CRCs (n=200) was randomly selected from the prospective Netherlands Cohort Study on diet and cancer (NLCS), which has been described in detail elsewhere (van den Brandt, Goldbohm et al. 1990; Brink, de Goeij et al. 2003). Series characteristics are shown in supplemental table 1 In addition, archival, formalin-fixed, paraffin-embedded skin—(n=8), kidney—(n=10), ovary—(n=10), prostate—(n=10), breast—(n=15), stomach—(n=22) and oesophagus (n=28) cancer tissue was analyzed for NDRG4 promoter methylation. This study was approved by the Medical Ethical Committee (MEC) of the Maastricht University and the University Hospital Maastricht.

TABLE 45

Series characteristics

|  | Age* | Sex† | Location‡ Proximal | Location‡ Distal |
|---|---|---|---|---|
| CRC+ | | | | |
| Normal tissue | 71.0 ± 8.6 | 41/38 | 40/75 (53%) | 35/75 (47%) |
| Adenoma tissue | 71.7 ± 7.9 | 32/30 | 26/59 (44%) | 33/59 (56%) |
| Carcinoma tissue | 71.5 ± 8.3 | 44/46 | 49/88 (56%) | 39/88 (44%) |
| CRC− | | | | |
| Normal tissue | 65.2 ± 9.0 | 22/29 | 13/39 (33%) | 26/39 (67%) |
| Adenoma tissue | 63.1 ± 7.6 | 16/6 | 6/18 (33%) | 12/18 (67%) |
| Inflamed tissue | 65.3 ± 10.1 | 14/19 | 10/26 (39%) | 16/26 (62%) |
| P-value | <0.001 | NS | NS | |

|  | Carcinoma tissue |  | CRC+ Adenoma tissue | CRC− Adenoma tissue |
|---|---|---|---|---|
| Histological type | | Histological type | | |
| Adenocarcinoma | 72/90 (80%) | | 39/62 (63%) | 16/22 (73%) |
| Mucinous carcinoma | 18/90 (20%) | Tubular | 22/62 (36%) | 6/22 (27%) |
| | | Tubulovillous | 1/62 (2%) | 0/22 (0%) |
| | | Villous | | |
| Differentiation: | | Dysplasia | | |
| Poor | 8/90 (9%) | Lowgrade | 54/62 (87%) | 22/22 (100%) |
| Moderate | 70/90 (78%) | Highgrade | 8/62 (13%) | 0/22 (0%) |
| Well | 12/90 (13%) | | | |
| TNM stage: | | | | |
| I | 13/90 (14%) | | | |
| II | 29/90 (32%) | | | |
| III | 36/90 (40%) | | | |
| IV | 12/90 (13%) | | | |

Table 4.5: Patient characteristics NDRG4b
*years ± SD, analyzed by One-way ANOVA
†Male/Female, analyzed by Pearson's $\chi^2$
‡analyzed by Pearson's $\chi^2$. Location could not be traced for all samples explaining different total sample numbers
CRC+: colorectal cancer patients
CRC−: patients without colorectal cancer
NS: not significant
TNM stage: 'Tumour Node Metastasis' Staging DNA-Isolation from Tissues and Cell Lines A 5 µm section of each tissue block was stained with haematoxylin and eosin and revised by a pathologist (AdB). Five sections of 20 µm were deparaffinated prior to DNA-isolation. DNA was extracted from these tissue samples and from cell lines using the Puregene DNA isolation kit (Gentra systems) according to the manufacturers instructions. In brief, cell lysis solution and proteinase K (20 mg/ml, Qiagen) were added to the tissue samples and incubated overnight at 55° C. Subsequently, DNA was extracted for 72 h at 37° C., protein was removed, and DNA was precipitated using 100% 2-propanol. Finally, DNA was rehydrated in hydration buffer.

Collection and Preparation of Fecal DNA

Colonoscopy negative control stool samples (n=67) were obtained from a population of healthy subjects over 50 years of age which are being screened within the framework of a workplace-based community CRC screening study at the University Hospital Maastricht. The Medical Ethical Committee (MEC) of the Maastricht University, the University Hospital Maastricht and the Dutch 'Wet op Bevolkingsonderzoek' (WBO) is approving this screening study. Stool samples from colonoscopy confirmed CRC patients (n=21) covering all CRC stages were collected at the Free University Medical Center in Amsterdam. For recovery of human DNA, whole stool samples were homogenized in a 7 excess volume of stool homogenization buffer (Exact sciences, Marlborough, Mass., USA) and aliquoted in portions of 32 ml containing the equivalent of 4 g of stool each. Single aliquots were centrifuged and the supernatants were incubated with 80 units per ml RNase A for 60 minutes at 37° C. Total DNA was then precipitated using sodium acetate isopropanol (PH 5.2), washed with 70% ethanol and resuspended in 4 ml 1×TE (pH 7.4). 400 µl 10× buffer (240 mM EDTA (pH 8.0), 750 mM NaC), 400 µl 10% SDS and 20 µl Proteinase K (20 mg/ml) was added, samples were incubated overnight at 48° C. at constant shaking and centrifuged the next day. Additionally, 5 ml of phenol-chloroform-isoamylalcohol was added and samples were incubated for 10 minutes at RT before centrifugation. The phenol-chloroform-isoamylalcohol extraction was repeated, the aqueous layer was subsequently transferred in a new tube, DNA was precipitated, washed and pellets were resuspended in 2 ml of LoTE (pH 8.0).

Sodium Bisulfite Conversion, Methylation-Specific PCR and Sodium Bisulfite Sequencing Sodium bisulfite modification of 500 ng genomic DNA was performed using the EZ DNA methylation kit (ZYMO research Co., Orange, Calif.) according to the manufacturer's instructions. NDRG4 MSP analysis on bisulfite treated DNA retrieved from cell lines and formalin-fixed, paraffin embedded tissue was facilitated by first amplifying the DNA with flanking PCR primers which amplify bisulfite-modified DNA but do not discriminate between methylated or unmethylated DNA. This PCR product was used as a template for the MSP reaction (Herman, Graff et al. 1996; van Engeland, Weijenberg et al. 2003). Flank primers, MSP primers and PCR conditions are listed in table 2 (see above). All PCRs were performed with controls for unmethylated DNA (DNA from normal lymphocytes), methylated DNA (normal lymphocyte DNA treated in vitro with SssI methyltransferase (New England Biolabs), and a control without DNA. Ten µl of each MSP reaction were directly loaded onto 2% agarose gel and visualized under UV illumination. For sequencing of sodium bisulfite-converted DNA, PCR products were amplified and cloned using the TOPO-TA cloning kit (Invitrogen, Breda, the Netherlands). Single colonies were picked and sequenced using an automated sequencer (Applied Biosystems, Foster City, Calif.). Primer sequences used are SEQ ID NO: 569 5'-GATYGGGGTGTTTTT-TAGGTTT-3' (sense primer) and SEQ ID NO: 6 5'-CRAACAACCAAAAACCCCTC-3' (antisense primer).

Quantitative MSP

Quantitative real-time MSP was performed using a 7900HT real-time PCR system (Applied Biosystems). 2.4 µl of the modified DNA (equivalent to 2.5 µg unconverted DNA) was added to a PCR mix (total volume 12 µl) containing buffer (16.6 mM (NH4)2SO4, 67 mM Tris (pH 8.8), 6.7 mM MgCl2, 10 mM β-mercaptoethanol), dNTPs (5 mM), forward primer (6 ng), reverse primer (18 ng), molecular beacon (0.16 µM), BSA (0.1 µg), and Jumpstart DNA Taq polymerase (0.4 units; Sigma Aldrich). The PCR program was as follows: 5 minutes 95° C., followed by 45 cycles of 30 seconds 95° C., 30 seconds 57° C., and 30 seconds 72° C., followed by 5 minutes 72° C. Primer sequences used are SEQ ID NO: 17 5'-GTATTT-TAGTCGCGTAGAAGGC-3' (forward primer), SEQ ID NO: 18 5'-AATTTAACGAATATAAACGCTCGAC-3' (reverse primer) and SEQ ID NO: 19 5'-FAM-CGA-CATGCCCGAACGAACCGCGATCCCTGCATGTCG-3'-DABCYL (molecular beacon). A standard curve ($2 \times 10^{6-20}$ copies) was included to determine copy numbers of unknown samples by interpolation of their Ct values to the standard curve.

Loss of Heterozygosity Analysis

Allelic status was analyzed by PCR amplification with specific primer pairs flanking polymorphic microsatellite loci. The fluorescent dye-labeled microsatellite markers DS16S3089 (forward primer: SEQ ID NO: 526 AGCCCTGCCTGATGAA; reverse primer: SEQ ID NO: 527 TGTGTGGGTAGCACCAA) and DS16S3071 (forward primer: SEQ ID NO: 528 AGCTCTCTGATGGGCAGTG; reverse primer: SEQ ID NO: 529 TGGAAGATAGCCCC-CAAAT) located on 16q21-22 were selected from genome public database. DS16S3089 is situated 1.9 Mb downstream of NDRG4 and DS16S3071 1.8 Mb upstream of NDRG4. Matched tumor/normal DNA samples were amplified by PCR in a 15 µl volume containing 0.25 mM dNTP, 0.3 µM primers, 1.5 mM MgCl2 and 0.04 units Taqpolymerase (platinum, Invitrogen) using 50 ng DNA as template. The reaction mixture was subjected to 3 min of denaturing at 95° C. and 30 cycles of 95° C. for 1 min, 60° C. annealing temperature for 1 min and 72° C. for 1 min followed by a final extension step at 72° C. for 10 min. PCR products were sequenced using an automated sequencer (Applied Biosystems, Foster City, Calif.) and analyzed using Genemapper software version 4.0 (Applied Biosystems). Only genotypes demonstrating two different sizes, i.e. heterozygous MS alleles, were used for evaluating allelic status. The allelic ratio was calculated as (N1/N2)/(T1/T2) for the ratio of area values of tumor (T) versus the normal (N) alleles. LOH was defined as an allelic ratio more than 1.35 and less than 0.67.

Mutation Analysis

The NDRG4 coding exons and their flanking intronic regions were individually amplified using genomic DNA extracted from paraffine embedded colonic adenocarcinoma tissue. Mutation analysis was examined using the nested PCR approach. The outside PCR was performed with 125 ng genomic DNA, 50 pmol of each forward and reverse primer and 1 units of TaqPolymerase mixture (Invitrogen). DNA amplification was done on a thermal cycler using Thermo-Fast 96-well plates (Corning) starting with an initial denaturation step at 95° C. for 3 min, followed by 35 cycles of denaturation at 95° C. for 30s, annealing with an specific temperature for each primer for 30s and extension at 72° C. for 30 sec. An additional final extension of 72° C. for 5 min was added. Following the outside PCR an inside PCR was done using the same conditions as the outside PCR. PCR primer sets for each exon, including intron-exon boundary, are provided in detail in supplemental table 3. DNA was purified using the Millipore multiscreen 96 wells plate (Millipore). PCR products were amplified using the Big-Dye® Terminator v1.1 Cycle sequencing kit and amplified products were sequenced using an ABI 3730 DNA Analyzer (Applied Biosystems, Foster City, Calif.).

TABLE 46

NDRG4 mutation analysis primer sequences and PCR conditions.

| Exon No. | Primer | SEQ ID NO | Sense primer | SEQ ID NO | Antisense primer | Annealing temperature |
|---|---|---|---|---|---|---|
| 2 | Outside | 530 | CCCAGCCCCGACTTGC | 531 | CTAAGACCTCAAAGGCGCG | 56 |
|  | Inside | 532 | TGTCCTTCTCCGCCCGG | 531 | CTAAGACCTCAAAGGCGCG | 62 |
| 3 | Outside | 533 | CCCCTCTGTTTGCCTTCC | 534 | CTGGCCAGGTGGGGTG | 56 |
|  | Inside | 533 | CCCCTCTGTTTGCCTTCC | 535 | GCCAGGTGGGGTGAGGG | 62 |
| 4 | Outside | 536 | CTGCGTCACCTCATTCCC | 537 | TCACCGCTCTGGCTGATG | 56 |
|  | Inside | 538 | GAGGAGCCAAGAGCGGAG | 537 | TCACCGCTCTGGCTGATG | 62 |

TABLE 46-continued

NDRG4 mutation analysis primer sequences and PCR conditions.

| Exon No. | Primer | SEQ ID NO | Sense primer | SEQ ID NO | Antisense primer | Annealing temperature |
|---|---|---|---|---|---|---|
| 5 | Outside | 539 | CCCCTCTGCTCAGCCATAG | 540 | GCTGGAGACAGGCAGAGGG | 56 |
|   | Inside | 539 | CCCCTCTGCTCAGCCATAG | 541 | GGAGACAGGCAGAGGGGG | 56 |
| 6 | Outside | 542 | GTAGGTACCCTGAGCCCCC | 543 | ACCCCTGGGCCCTAGC | 56 |
|   | Inside | 544 | CCCTCTGCCTGTCTCCAGC | 543 | ACCCCTGGGCCCTAGC | 62 |
| 7 | Outside | 545 | GGAAATGGCACCCCTAGC | 546 | GGGGGCATGGGGAGAC | 56 |
|   | Inside | 547 | GCACCCCTAGCCCTAGAGT | 546 | GGGGGCATGGGGAGAC | 56 |
| 8 | Outside | 548 | CCTTGAAGACTTTACAGAGTGTTTC | 549 | GTATACCCACCCCACCCC | 56 |
|   | Inside | 550 | CTGCACCCATCCTGGCC | 549 | GTATACCCACCCCACCCC | 62 |
| 9 | Outside | 551 | GGGGTGGGGTGGGTATAC | 552 | GCTGGGAGGGGCAAATC | 56 |
|   | Inside | 551 | GGGGTGGGGTGGGTATAC | 553 | GGCAAATCCCAGATCACCC | 62 |
| 10 | Outside | 554 | GCCTCCATCCATCTCCCTG | 555 | GGCTGCTGATCCCACCC | 56 |
|    | Inside | 556 | CATGCCTCCATCCATCTCC | 555 | GGCTGCTGATCCCACCC | 62 |
| 11 + 12 | Outside | 557 | CACCTCTGCCTCTGCCCC | 558 | CCCCAGTGAGCCCACAGC | 56 |
|         | Inside | 559 | CCTCTGCCCCTCCCCC | 558 | CCCCAGTGAGCCCACAGC | 62 |
| 13 | Outside | 560 | TGCCTTGGCAATGGGG | 561 | CAGGGCTGGGGAAGAAAG | 56 |
|    | Inside | 562 | CTTGGCAATGGGGGTGG | 561 | CAGGGCTGGGGAAGAAAG | 62 |
| 14 + 15 | Outside | 563 | GGAGCTTGTCCTGGAGTGAG | 564 | GTGGGGTGGAAATGTACTCAC | 56 |
|         | Inside | 565 | TGGAGTGAGGGCCCTGC | 564 | GTGGGGTGGAAATGTACTCAC | 62 |
| 16 | Outside | 566 | TGCCCGCCAGTCCTCAG | 567 | TAAAGGGAACATGAGCCGG | 56 |
|    | Inside | 568 | CAGTCCTCAGGCCCATCC | 567 | TAAAGGGAACATGAGCCGG | 56 |

*Number of cycles in each case was 35

Quantitative Reverse Transcriptase PCR

Total RNA from cell lines, normal mucosa and tumor tissue was isolated using the Rneasy Mini kit (Qiagen) following the manufacturers instructions. Possible genomic DNA contaminations were removed by DNAse treatment with the RNase-free DNAse set (Qiagen). cDNA synthesis using the Iscript cDNA synthesis kit (Bio-Rad) was performed. Quantitative real-time (RT-PCR) was performed using SYBR Green PCR master mix (Applied Biosystems, Nieuwekerk a/d IJssel, The Netherlands). Realtime RT-PCR mixes were composed of 1×iQ SYBR Green Supermix (Bio-Rad), 400 nM of the forward (SEQ ID NO: 3 5'-GGCCTTCTGCATGTAGTGATCCG-3') and reverse (SEQ ID NO: 4 5'-GGTGATCTCCTGCATGTCCTCG-3') primer and cDNA corresponding to 30 ng total RNA per reaction. As standard control, primers targeted against cyclophilin A were used. Reactions were run using the iCycler (Bio-Rad) for 40 cycles at a Tm of 60° C. The comparative Ct method was used to calculate differences in mRNA expression. To do so, the Ct value of each sample was normalized to the reference gene ([delta]Ct=Ct,sample−Ct,cyclo). Next, the fold difference in expression was calculated as $2^{-[delta][delta]Ct}$, with [delta] [delta]Ct=[delta]Ct,sample1−[delta]Ct,control.

Immunohistochemistry

Immunohistochemistry was performed on formalin-fixed, paraffin embedded tissue sections (5 m) of normal colon mucosa and CRC tissue. Sections were deparaffinized in xylene, rehydrated and incubated with 1% methanol for 30 minutes to inactivate the endogenous peroxidase. After blocking, sections were stained with the NDRG4 monoclonal antibody (Abnova Corporation), 1:6000 diluted in Tris-buffered saline (TBS) with 0.1% Tween and 0.5% bovine serum albumin (BSA) and incubated for 60 minutes. Sections were incubated with the secondary antibody poly-HRP-GAM/R/R IgG (Immunologic, Immunovision Technologies) and staining was visualized as a brown precipitate using DAB substrate chromogen (Dako) followed by haematoxylin counterstaining. Sections incubated without the primary antibody served as a negative control.

Data Analysis

We used the Pearson's $\chi^2$ or Fisher's Exact test and the One-way ANOVA, Kruskal-Wallis or Mann-Witney test where appropriate to compare non-parametric and categorical data respectively. Paired samples within the group of cases were analyzed using the McNemar test and the paired T-test to compare non-parametric and categorical data respectively. Logistic regression analysis was used to compare categorical data adjusted for age and location of the tissue since significant differences in age and location of the different tissues were observed between CRC cases and controls. All quoted p-values are two-sided, and a p-value 0.05 or lower was considered statistically significant. All statistical tests were corrected for multiple comparisons using the Bonferroni method. Data analysis was done using SPSS software (version 12.0.1).

Results

NDRG4 Promoter Methylation and Expression in CRC Cell Lines

Figure 10:
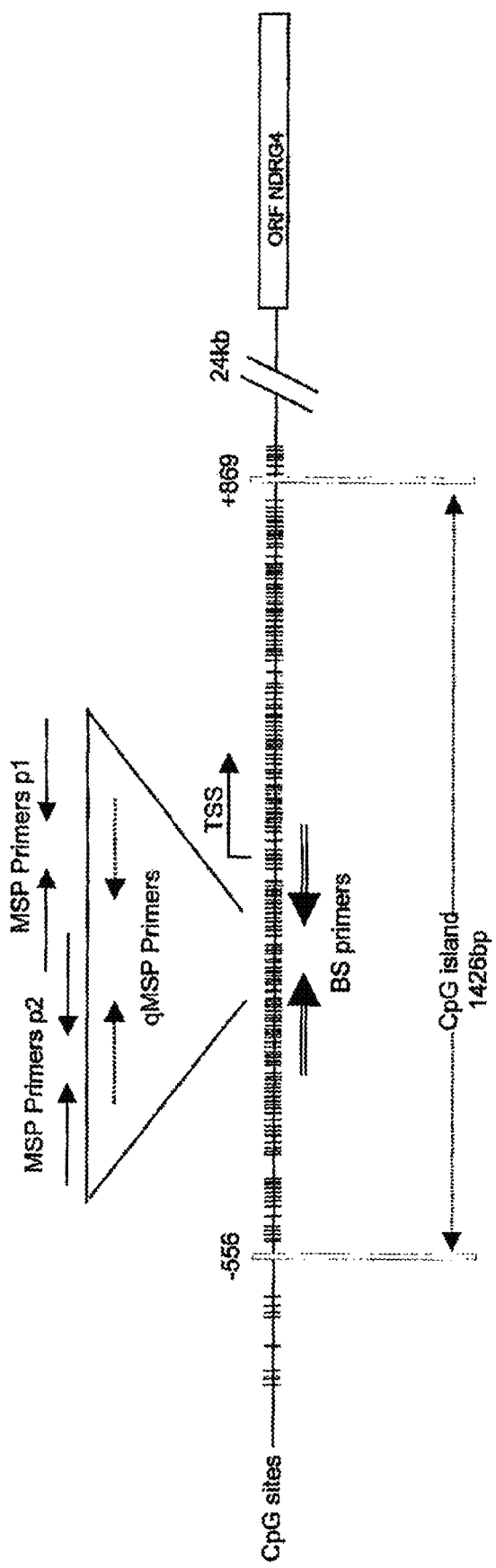
FIG. 10 shows a schematic representation of the promoter region of NDRG4. A dense CpG island from −556 to +869 relative to the transcription start site (TSS) (indicated by a curved arrow) is shown. Locations of CpG dinucleotides (represented by 1), ORF NDRG4 (as indicated with a grey rectangle) and the region of the hypermethylated fragment identified by Methylation Specific PCR (MSP), Quantative MSP (qMSP) and Bisulfite sequencing (BS) primers are indicated.
Figure 11A:
FIG. 11a shows results of methylation specific PCR (MSP) with primer pair 2 to detect DNA methylation in eight different CRC cell lines.
Figure 11B:
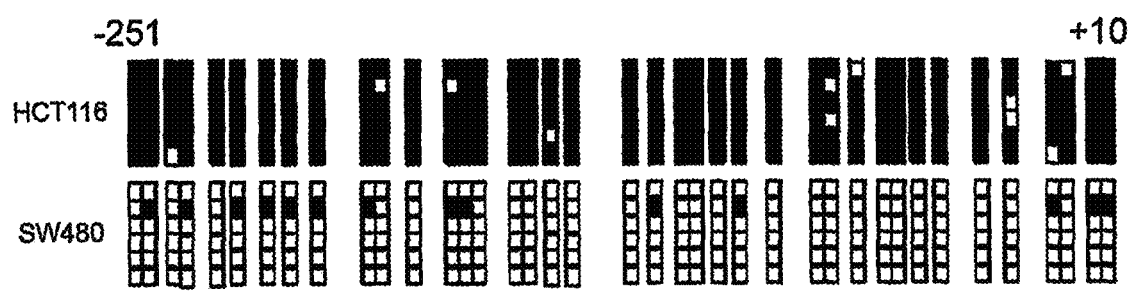
FIG. 11b shows bisulfite sequencing of two CRC cell lines, namely HCT116 and SW480. Six different clones were sequenced. Each row represents an individual cloned allele that was sequenced following sodium bisulfite DNA modification. Each box indicate a CpG dinucleotide (black box; methylated CpG site, white box; unmethylated CpG site)
Figure 11C:
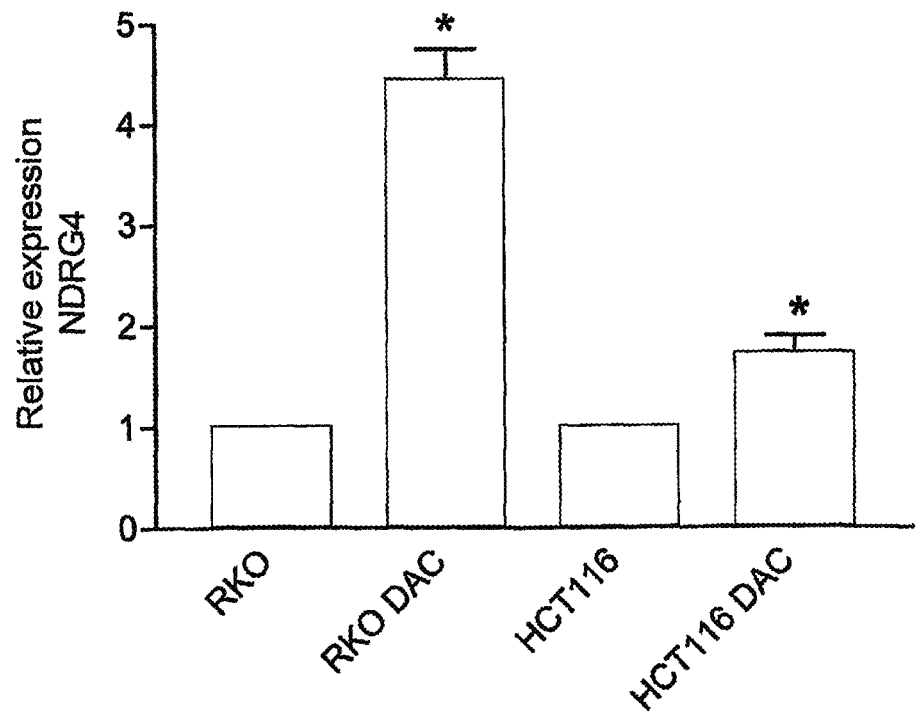
FIG. 11c shows NDRG4 expression in colon cancer cell lines (RKO and HCT116) after treatment with the methylation inhibitor 5-aza-2'-doxycytidine (DAC).

The structure of the NDRG4 gene shows a dense CpG island (GC content >60%, ratio of observed CpG/expected CpG >0.6 and minimum length 200 bp (Gardiner-Garden and Frommer 1987)) located −556 to +869 relative to the transcription start site as shown in FIG. 10. To assay this region for potential methylation we designed two different MSP primer pairs (1 and 2) amplifying overlapping fragments in the CpG island. These primers were initially used to investigate eight CRC cell lines (LS174, HCT116, HT29, RKO, CACO2, COLO2, SW48 and SW480) for DNA methylation. All cell lines except SW480 were methylated as analyzed by MSP using both primer pairs as shown in FIG. 11a. To further investigate the pattern of CpG island methylation we performed sodium bisulfite sequencing of HCT116 and SW480. The promoter region spanning 39 CpG sites was PCR-amplified using sodium bisulfite-modified genomic DNA as template and six clones of each cell lines were sequenced. Bisulfite sequencing confirmed MSP data in that HCT116 showed almost complete methylation at 39 sites as depicted in FIG. 11b, whereas SW480 showed almost no methylated CpG sites. Endogenous NDRG4 mRNA levels in CRC cell lines HCT116 and RKO were significant increased after treatment with DAC (FIG. 11c).

Methylation of NDRG4 in Normal and CRC Tissue

Figure 12A:
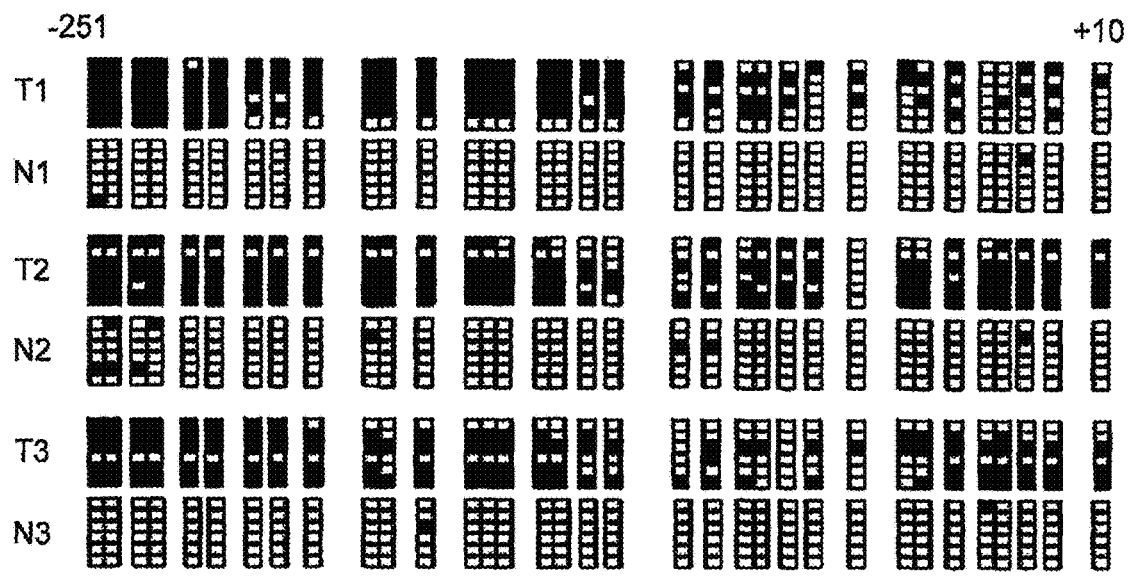
FIG. 12a shows bisulfite sequencing of three cases of cancers (T) and their matched normal non malignant mucosa tissue (N). Six different clones were sequenced.

Methylation of NDRG4 was confirmed in three pairs of primary tumors and matched normal colonic mucosa by sodium bisulfite sequencing. The results depicted in FIG. 12a show dense methylation of the three tumor samples while almost no methylation was observed in the normal colon mucosa. Interestingly, the density of methylation was higher in the upstream region of the NDRG4 CpG island when compared to more downsteam region as shown in FIG. 12a.

Subsequently, the methylation status of NDRG4 was investigated in colorectal carcinoma, adenoma and normal colorectal mucosa using two different primer pairs (1 and 2). The methylation frequencies using both primer pairs are depicted in table 47. A significant difference (table 47, p=0.042 10-7) was observed in methylation frequencies in normal mucosa of the control group (2/48 (4%)) compared to cancer tissue of CRC patients (71/83 (86%)) using primer pair 2. In addition, we compared NDRG4 promoter methylation in adjacent normal mucosa tissue of CRC patients (9/78 (12%)) and the normal mucosa of non-cancerous patients (2/48 (4%) but did not find a significant difference among these two groups (table 47). Furthermore, to investigate NDRG4 methylation in premalignant lesions, we compared adenomas obtained from CRC patients that developed synchronously or metachronously to the tumour and adenomas obtained from patients that did not develop CRC after 10 years of follow-up. We observed a higher prevalence of NDRG4 methylation in adenomas from CRC patients although these differences did not reach statistical significance (table 47).

TABLE 47

Methylation frequencies (%) of normal, adenoma, carcinoma tissue from CRC patients and normal, adenoma tissue of non-cancerous patients. Methylation differences are analyzed by logistic regression adjusted for age (NDRG4p1, p2) and location (NDRG4 p1)

| | Carcinoma Controls | | | Normal tissue | | | Adenoma tissue | | |
|---|---|---|---|---|---|---|---|---|---|
| | tissue | normal | P | controls | CRC+ | P | Controls | CRC+ | P |
| NDRG4 p1 | 71% | 0% | $0.02 \times 10^{-2}$ | 0% | 3% | NS | 13% | 41% | NS |
| NDRG4 p2 | 86% | 4% | $0.042 \times 10^{-7}$ | 4% | 12% | NS | 55% | 66% | NS |

Abbreviations: CRC+, colorectal cancer patients; P, P-value; NS, not significant To confirm the high prevalence of NDRG4 promoter methylation in CRC, we analyzed a second independent series of 183 CRC samples. Comparable to the results of the first study series we observed that 70% (127/183) of CRC patients presented NDRG4 methylation.

Further analysis of the clinicopathologic features of patients with primary CRC with regard to NDRG4 promoter methylation did not reveal any association with age at diagnosis, sex, location of the tumor or the TNM stage for both independent series using primer 2 (table 49). To investigate NDRG4 promoter methylation during cancer progression we compared the frequency of methylation from normal mucosa to adenoma and carcinoma tissues in patients for which all the three tissues were available (table 48). Our results show that NDRG4 is significantly (table 48, p<0.02 10-2) more frequently methylated in carcinomas (84%) compared to normal mucosa adjacent to the tumor (16%). In addition to the carcinomas, adenoma samples from CRC patients also exhibit significantly (table 48, p<0.03 10-3) higher NDRG4 methylation frequencies (61%) compared to normal colon samples (14%). Finally, NDRG4 methylation was increased in carcinoma tissues (81%) compared to adenoma samples (63%) although this enhancement was not significant (primer pair 2, table 48).

TABLE 48

NDRG4 Methylation frequencies (%) of carcinoma tissue, adenoma and normal tissue from colorectal cancer patients. Methylation differences were analyzed by Mc Nemar test.

| CRC patients | Normal tissue | Adenoma tissue | P | Normal tissue | Carcinoma tissue | P | Adenoma tissue | Carcinoma tissue | P |
|---|---|---|---|---|---|---|---|---|---|
| NDRG 4 p1 | 0% | 34% | 0.003 | 0% | 73% | $0.01 \times 10^{-4}$ | 39% | 76% | 0.012 |
| NDRG 4 p2 | 14% | 61% | $<0.03 \times 10^{-3}$ | 16% | 84% | $<0.02 \times 10^{-2}$ | 63% | 81% | NS |

Frequencies may vary because of missing data for some variables.

Abbreviations: CRC+, colorectal cancer patients; P, P-value; NS, not significant The different series were analyzed using two different primer pairs 1 and 2 amplifying overlapping fragments in the CpG island, as depicted in FIG. 10. Using primer pair 1 we observed overall the same results compared to primer pair 2 however we found an increase of NDRG4 methylation for all the subgroups using primer pair 2 compared to primer pair 1. Interestingly, we found a significant difference (table 2, p=0.012) in promoter methylation in adenomas of CRC patients (55/77 (41%)) compared to the carcinomas (55/77 (71%)) which was not observed using primer pair 2. In addition, comparing the NDRG4 methylation status of adenomas obtained from CRC patients that developed synchronously or metachronously to the tumour (24/58(41%)) and adenomas obtained from patients that did not develop CRC (4/31 (13%) we observed a enormous increase of NDRG4 methylation in adenomas from CRC patients using primer pair 1 although these differences also did also not reach statistical significance. Further analysis of the clinicopathologic features of patients with primary CRC with regard to NDRG4 promoter methylation for both independent series did not reveal any association with age at diagnosis, sex or the TNM stage. However, we did find a significant correlation between promoter methylation and the location of the tumor using primer pair 1 (table 49, p=0.034).

TABLE 49

Prevalence (%) of promoter methylation of NDRG4 in relation to clinicopathological features of carcinoma tissue for two independent series. Methylation differences were analyzed by chi-square

| Characteristics | % methylation NDRG4p1 | % methylation NDRG4p2 | % methylation NDRG4p2 Independent series |
|---|---|---|---|
| TNM stage* | | | |
| I | 15% | 16% | 23% |
| II | 33% | 32% | 33% |
| III | 40% | 41% | 30% |
| IV | 13% | 11% | 13% |
| P | NS | NS | NS |
| Tumor Location‡ | | | |
| proximal | 65% | 56% | 37% |
| distal | 35% | 44% | 63% |
| P | 0.034 | NS | NS |

TABLE 49-continued

Prevalence (%) of promoter methylation of NDRG4 in relation to clinicopathological features of carcinoma tissue for two independent series. Methylation differences were analyzed by chi-square

| Characteristics | % methylation NDRG4p1 | % methylation NDRG4p2 | % methylation NDRG4p2 Independent series |
|---|---|---|---|
| Sex* | | | |
| Male | 42% | 48% | 55% |
| Female | 58% | 52% | 44% |
| P | NS | NS | NS |
| Age at diagnosis§ | | | |
| <=mean | 40% | 48% | 48% |
| >mean | 60% | 52% | 52% |
| P | NS | NS | NS |

Abbreviations:
P, P-value;
NS, not significant

NDRG4 Promoter Methylation in Other Neoplasias

Next, we asked whether NDRG4 promoter methylation is present in other tumor tissues. Therefore 119 primary tumor specimens covering 7 different tumor types were analyzed using MSP primer pair 2. No or little methylation was found in skin (0/8, 0%), kidney (1/10, 10%), ovary (0/20, 0%), prostate (0/10, 0%) and breast (lobular (0/7, 0%) and ductal (0/9, 0%)) carcinomas. In contrast, NDRG4 promoter was frequently methylated in adenocarcinomas of the esophagus (13/16, 81%), while no methylation was found in esophageal squamous cancers (0/12, 0%). Both diffuse type (8/11, 73%) and intestinal type (9/11, 82%) carcinomas of the stomach were frequently methylated while the normal mucosa of the stomach did not show any methylation (0/5, 0%).

NDRG4 Promoter Methylation in Fecal DNA

The high prevalence of NDRG4 promoter methylation in CRC and the absence of methylation in normal colon mucosa suggest that NDRG4 promoter methylation could be a sensitive and specific biomarker for non-invasive detection of CRC. Therefore, we developed a quantitative MSP assay using molecular beacon technology and analyzed fecal DNA of 21 CRC patients and 67 healthy controls. NDGR4 promoter methylation could be detected in 16/21 CRC patients yielding a 76% sensitivity for the detection of CRC. Only 2/67 (3%) of healthy controls tested positive for NDRG4 methylation, which resulted in a clinical specificity for the assay of 97%. Stool samples were obtained from CRC patients covering all different TNM stages. The assay had a 75% sensitivity among CRC patients with early stage colon cancer (stage I and II) and 80% of sensitivity among later stage patients (stage III and IV).

NDRG4 RNA and Protein Expression

Figure 12B:
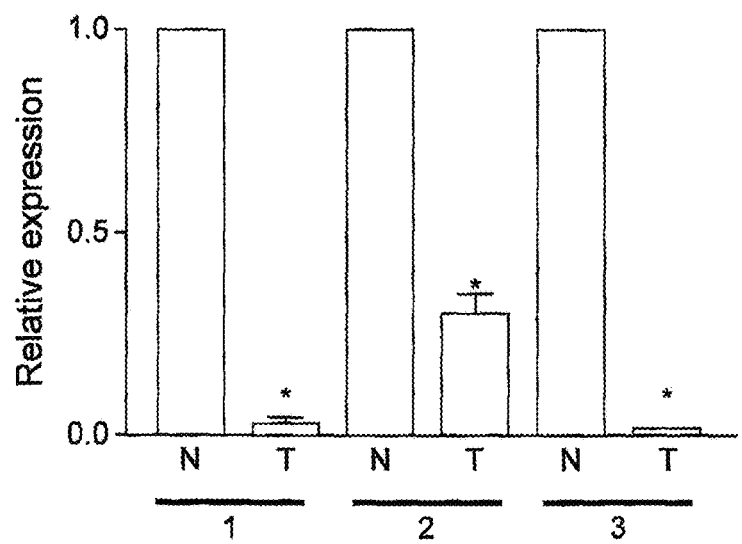
FIG. 12b shows levels of NDRG4 transcript expression measured by realtime PCR in colon cancer tissue (labelled for T) and matched normal colon tissue samples (labelled for N) for three different persons. For each patient, levels of NDRG4 expression in the normal mucosa tissue were set to equal 1. The experiments were performed three times.

To analyse whether methylation of the promoter CpG island of NDRG4 is associated with gene silencing we investigated mRNA expression of NDRG4 in CRC cell lines, three pairs of CRC tissues and matching normal colon mucosa. In all three CRCs, mRNA levels were significantly downregulated (97, 70% and 98% respectively) when compared to normal colon mucosa (FIG. 12b).

Figure 12C:
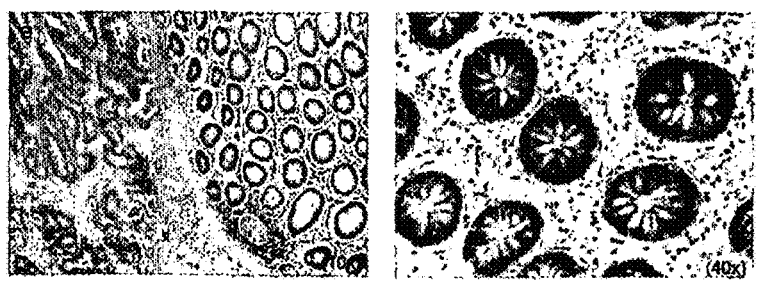
FIG. 12c shows localization of NDRG4 expression. Immunohistochemical staining of NDRG4 in normal mucosa and colon tumor shows no staining in cancer cells but clear staining in the nuclei of normal epithelial cells.

To investigate the protein expression of NDRG4 in both normal colonic mucosa and colon cancers, we performed NDRG4 immunohistochemistry demonstrating the presence of NDRG4 protein expression in the cytoplasm of normal colon mucosa while protein expression is lost in half of CRCs (FIG. 12c). Subsequently, we performed immunohistochemical analysis of NDRG4 expression on 19 CRC samples. Eleven of these patients had a methylated NDRG4 promoter. However, we could not find a significant association between NDRG4 promoter methylation and NDRG4 expression (data not shown). This observation suggests that other mechanisms might lead to NDRG4 inactivation.

Loss of Heterozygosity and Mutation Analysis of the NDRG4 Gene in CRC

Macrodissected CRC tissue and corresponding normal tissues of 86 CRC patients were analyzed using the microsatellite markers DS16S3089 and DS16S3071. The two markers showed a heterozygosity of 77.4% and 35.4% respectively. Of these, 59 cases were informative; 18 tumors (30.5%) showed LOH with at least one marker on chromosome 16q.

Twelve primary CRC and CRC cell lines HCT116 and SW480 were analyzed for NDRG4 mutations. No inactivating mutations within the coding region of the NDRG4 gene were detected in 12 colorectal carcinomas. However, we found one novel nonsynonymous mutation in the SW480 cell line (40662A→AG Ile65Val). As part of the mutational analysis, 2 previously reported SNPs (NCBI SNP database) were detected. One SNP was observed in 1/12 CRC patients (43760G→GG Val224Val refSNP rs 17821543). The second SNP was observed in 9/12 CRC patients (48311A→AG Ser354Ser refSNP rs 42945).

Discussion

The progression of CRC from small benign colorectal adenomas to larger and more dysplastic lesions takes several decades and identifying early stages would improve management and treatment of this disease (Brenner and Rennert 2005). Colonoscopy is currently the best technique for detecting CRC or its precursor lesions from the age of 50 years onwards. Testing for the presence of fecal occult blood (FOBT) as preselection for colonoscopy is the only non-invasive screening method with proven effectiveness, reducing both the incidence and the risk of death from CRC when used programmatically.

However, both sensitivity and specificity of FOBT is low and therefore there is an urgent need for more sensitive and specific non-invasive screening tests. A promising option is analyzing (expression of) cancer-specific molecules such as DNA, RNA and protein in blood and tissue. First attempts to detect genetic alterations are promising (Dong, Traverso et al. 2001; Traverso, Shuber et al. 2002) although still need improvement. Markers of choice have been TP53, K-ras and APC mutations and in addition BAT-26 instability and long DNA (a marker for non-apoptotic shedding of epithelial colonocytes). Recently, CpG island hypermethylation can also be used as a (prognostic) marker for non-invasive detection of CRC in different biological samples (Esteller 2003; Chen, Han et al. 2005; Ebert, Model et al. 2006). Over the last years, several genes have been described to be methylated in CRC using different techniques.

Here we used MSP, quantitative MSP and bisulfite sequencing to analyse NDRG4 as a biomarker for the early detection of colorectal and other gastrointestinal cancers. (ARRAY) The NDRG4 promoter CpG island was demonstrated to be methylated in two independent large series of CRC cases. In the first series we included normal mucosa of non-cancerous patients since the normal mucosa from the CRC patients is situated within the same bowel segment as the tumor and can be contaminated with malignant cells or a field-effect could have change the molecular signature of this cell as described for MGMT (issa, 2005). Nevertheless, by performing statistical analysis we could not find any significantly difference in methylation between these two groups. Chronic inflammation has previously been shown to accelerate DNA methylation in normal tissues (Issa, Ahuja et al. 2001).

Therefore additional screens with inflamed colon mucosa are expected in a screening setting. In our study population, inclusion of inflamed mucosa to the normal mucosa of control patients slightly reduced the specificity of NDRG4 from 96% to 94%. Because we found a difference in the density of methylation in the promoter area of NDRG4 by bisulfite sequencing, we used two different primer sets to investigated the methylation status of NDRG4. Interestingly, using primer pair 2, we found 86% of methylation in carcinoma tissue while only 71% was observed by use of primer pair 1. This increased detection of methylation using primer pair 2 was observed for all the subgroups of this series as shown in table 47. Primer pair 2 is situated more to the 5'region of the gene. The frequencies of methylation were lower near the transcription start site. We hypothesize that NDRG4 hypermethylation initially occurs at the 5' end of the NDRG4 CpG island and spreads towards the transcription start site before ultimately shutting down NDRG4 mRNA expression, as has also been observed for RUNX3 (Turker 2002; Homma, Tamura et al. 2006). In addition, we found a significant difference (p=0.012) in methylation frequency using primer pair 1, between adenoma tissue and carcinoma tissue within the group of CRCs. Therefore, we speculated, that spreading of DNA methylation in the promoter area of NDRG4 towards the transcription start site occurs during cancer progression.

Remarkably, using primer pair 1, hypermethylation was more frequently present in progressed adenomas from the CRC patients (41%) when compared to the non progressing adenomas of the CRC-patients (13%). The capacity to distinguish adenomas that progress to cancer from those that will not progress is highly important for CRC screening (Hermsen, Postma et al. 2002). Whereas this difference can not be made macroscopically, endoscopic screening strategies aiming to detect and remove all adenomas will be inherently unspecific. The majority of adenomas removed would not have progressed to cancer because only a small percentage of these benign precursor lesions will progress into a carcinoma (Lengauer, Kinzler et al. 1998). These data might indicate that NDRG4 promoter methylation in adenoma tissue (in the region we investigated) is a possible risk factor for developing a colon tumor.

Recently, it has been reported that promoter methylation can be detected in biological fluids such as blood, urine or stool and may allow early diagnosis of various cancers, including CRC. Some studies have shown that methylation of one gene promoter can be used as a screening method for fecal DNA methylation detection. For example, promoter methylation of SFR2, Vimentin and HIC1 can be detected in fecal DNA of CRC patients with a sensitivity of 77%, 43% and 42% respectively and a specificity of 77%, 90% and 95% respectively (Muller, Oberwalder et al. 2004; Chen, Han et al. 2005; Lenhard, Bommer et al. 2005). NDRG4 methylation in fecal DNA as a single marker can differentiate cancer from controls with a sensitivity of 76% and a specificity of 97%.

In order to be a specific biomarker for CRC, analysis of tissue specificity was performed; we found NDRG4 methylation in other tumors of the gastrointestinal tract, namely oesophagus and gastric cancers. This data indicate that methylation of NDRG4 may serve as a marker for other gastrointestinal tumors as well.

We next studied whether methylation of NDRG4 is associated with downregulation of NDRG4 RNA and protein expression. So far, the expression of NDRG4 has only been documented in the brain and heart by use of Northern blotting. We observed expression of NDRG4 in normal colon tissue and downregulation in al three tumor tissues. Subsequently, we performed immunohistochemical analysis of NDRG4 expression on 19 CRC samples from the CRC patients for which paraffin-embedded tissues were available. Eleven of these patients had a methylated NDRG4 promoter. However, we could not find a significant association between NDRG4 promoter methylation and NDRG4 expression. Some tumors had a methylated NDRG4 promoter although still expressed NDRG4 protein. The methylation that we detected using MSP might reflect methylation of only a few cancer cells or methylation of only one of two NDRG4 alleles (and absence in the other). Nevertheless, some tumors lack expression of NDRG4 protein while no promoter methylation was observed. This observation suggests that other mechanisms might lead to NDRG4 inactivation. No mutations were found, indicating that mutational inactivation of the NDRG4 gene might not play a mayor role in CRC. Our results confirmed previous data on NDRG4 mutation studies (Sjoblom, Jones et al. 2006). However, LOH at 16q is seen in about 30% of the CRC cases. Frequent LOH of 16q had previously been described in a wide variety of solid tumor types as breast (Rakha, Green et al. 2006), liver (Sakai, Nagahara et al. 1992; Bando, Nagai et al. 2000), prostate (Elo, Harkonen et al. 1997), ovarian (Kawakami, Staub et al. 1999) and Wilms' tumors (Mason, Goodfellow et al. 2000) but until now it has not been described in CRC. Because NDRG4 is downregulated in most of the colon cancer cells compared to normal colonic epithelial cells we hypotheses that NDRG4 has a tumor suppressor function in cancer.

In conclusion, we are the first group who described a role for NDRG4 in cancer and our data indicate that NDRG4 is a potential novel marker for CRC with a very high sensitivity and specificity of 76% and 100% respectively. Although the sensitivity and specificity of NDRG4 as a marker alone is already very high, the diagnostic accuracy of NDRG4 may be enhanced by the addition of other markers analyzed in patients with CRC as well. This may augment the ability to identify patients with cancer in a multipanel methylation-based diagnostic test.

REFERENCES

Bando, K., H. Nagai, et al. (2000). "Identification of a 1.-Mb common region at 16q24.1-24.2 deleted in hepatocellular carcinoma." Genes Chromosomes Cancer 28(1): 38-44.

Bandyopadhyay, S., S. K. Pai, et al. (2003). "The Drg-1 gene suppresses tumor metastasis in prostate cancer." Cancer Res 63(8): 1731-6.

Bandyopadhyay, S., S. K. Pai, et al. (2004). "Role of the putative tumor metastasis suppressor gene Drg-1 in breast cancer progression." Oncogene 23(33): 5675-81.

Brenner, D. E. and G. Rennert (2005). "Fecal DNA biomarkers for the detection of colorectal neoplasia: attractive, but is it feasible?" J Natl Cancer Inst 97(15): 1107-9.

Brink, M., A. F. de Goeij, et al. (2003). "K-ras oncogene mutations in sporadic colorectal cancer in The Netherlands Cohort Study." Carcinogenesis 24(4): 703-10.

Chen, W. D., Z. J. Han, et al. (2005). "Detection in fecal DNA of colon cancer-specific methylation of the nonexpressed vimentin gene." J Natl Cancer Inst 97(15): 1124-32.

Deng, Y., L. Yao, et al. (2003). "N-Myc downstream-regulated gene 2 (NDRG2) inhibits glioblastoma cell proliferation." Int J Cancer 106(3): 342-7.

Dong, S. M., G. Traverso, et al. (2001). "Detecting colorectal cancer in stool with the use of multiple genetic targets." J Natl Cancer Inst 93(11): 858-65.

Ebert, M. P., F. Model, et al. (2006). "Aristaless-like homeobox-4 gene methylation is a potential marker for colorectal adenocarcinomas." Gastroenterology 131(5): 1418-30.

Elo, J. P., P. Harkonen, et al. (1997). "Loss of heterozygosity at 16q24.1-q24.2 is significantly associated with metastatic and aggressive behavior of prostate cancer." Cancer Res 57(16): 3356-9.

Esteller, M. (2003). "Relevance of DNA methylation in the management of cancer." Lancet Oncol 4(6): 351-8.

Gardiner-Garden, M. and M. Frommer (1987). "CpG islands in vertebrate genomes." J Mol Biol 196(2): 261-82.

Guan, R. J., H. L. Ford, et al. (2000). "Drg-1 as a differentiation-related, putative metastatic suppressor gene in human colon cancer." Cancer Res 60(3): 749-55.

Hellebrekers, D. M., V. Melotte, et al. (2007). "Identification of epigenetically silenced genes in tumor endothelial cells." Cancer Res 67(9): 4138-48.

Herman, J. G., J. R. Graff, et al. (1996). "Methylation-specific PCR: a novel PCR assay for methylation status of CpG islands." Proc Natl Acad Sci USA 93(18): 9821-6.

Hermsen, M., C. Postma, et al. (2002). "Colorectal adenoma to carcinoma progression follows multiple pathways of chromosomal instability." Gastroenterology 123(4): 1109-19.

Homma, N., G. Tamura, et al. (2006). "Spreading of methylation within RUNX3 CpG island in gastric cancer." Cancer Sci 97(1): 51-6.

Hongo, S., T. Watanabe, et al. (2006). "Ndrg4 enhances NGF-induced ERK activation uncoupled with Elk-1 activation." J Cell Biochem 98(1): 185-93.

Issa, J. P., N. Ahuja, et al. (2001). "Accelerated age-related CpG island methylation in ulcerative colitis." Cancer Res 61(9): 3573-7.

Kawakami, M., J. Staub, et al. (1999). "Involvement of H-cadherin (CDH13) on 16q in the region of frequent deletion in ovarian cancer." Int J Oncol 15(4): 715-20.

Kurdistani, S. K., P. Arizti, et al. (1998). "Inhibition of tumor cell growth by RTP/rit42 and its responsiveness to p53 and DNA damage." Cancer Res 58(19): 4439-44.

Lengauer, C., K. W. Kinzler, et al. (1998). "Genetic instabilities in human cancers." Nature 396(6712): 643-9.

Lenhard, K., G. T. Bommer, et al. (2005). "Analysis of promoter methylation in stool: a novel method for the detection of colorectal cancer." Clin Gastroenterol Hepatol 3(2): 142-9.

Liu, N., L. Wang, et al. (2007). "Promoter methylation, mutation, and genomic deletion are involved in the decreased NDRG2 expression levels in several cancer cell lines." Biochem Biophys Res Commun 358(1): 164-169.

Lusis, E. A., M. A. Watson, et al. (2005). "Integrative genomic analysis identifies NDRG2 as a candidate tumor suppressor gene frequently inactivated in clinically aggressive meningioma." Cancer Res 65(16): 7121-6.

Maeda, A., S. Hongo, et al. (2004). "Genomic organization, expression, and comparative analysis of noncoding region of the rat Ndrg4 gene." Gene 324: 149-58.

Mason, J. E., P. J. Goodfellow, et al. (2000). "16q loss of heterozygosity and microsatellite instability in Wilms' tumor." J Pediatr Surg 35(6): 891-6; discussion 896-7.

Muller, H. M., M. Oberwalder, et al. (2004). "Methylation changes in faecal DNA: a marker for colorectal cancer screening?" Lancet 363(9417): 1283-5.

Nakada, N., S. Hongo, et al. (2002). "Molecular characterization of NDRG4/Bdm1 protein isoforms that are differentially regulated during rat brain development." Brain Res Dev Brain Res 135(1-2): 45-53.

Ohki, T., S. Hongo, et al. (2002). "Inhibition of neurite outgrowth by reduced level of NDRG4 protein in antisense transfected PC12 cells." Brain Res Dev Brain Res 135(1-2): 55-63.

Qu, X., Y. Zhai, et al. (2002). "Characterization and expression of three novel differentiation-related genes belong to the human NDRG gene family." Mol Cell Biochem 229(1-2): 35-44.

Rakha, E. A., A. R. Green, et al. (2006). "Chromosome 16 tumor-suppressor genes in breast cancer." Genes Chromosomes Cancer 45(6): 527-35.

Sakai, K., H. Nagahara, et al. (1992). "Loss of heterozygosity on chromosome 16 in hepatocellular carcinoma." J Gastroenterol Hepatol 7(3): 288-92.

Shah, M. A., N. Kemeny, et al. (2005). "Drg1 expression in 131 colorectal liver metastases: correlation with clinical variables and patient outcomes." Clin Cancer Res 11(9): 3296-302.

Sjoblom, T., S. Jones, et al. (2006). "The consensus coding sequences of human breast and colorectal cancers." Science 314(5797): 268-74.

Traverso, G., A. Shuber, et al. (2002). "Detection of APC mutations in fecal DNA from patients with colorectal tumors." N Engl J Med 346(5): 311-20.

Turker, M. S. (2002). "Gene silencing in mammalian cells and the spread of DNA methylation." Oncogene 21(35): 5388-93.

van Belzen, N., W. N. Dinjens, et al. (1997). "A novel gene which is up-regulated during colon epithelial cell differentiation and down-regulated in colorectal neoplasms." Lab Invest 77(1): 85-92.

van den Brandt, P. A., R. A. Goldbohm, et al. (1990). "A large-scale prospective cohort study on diet and cancer in The Netherlands." J Clin Epidemiol 43(3): 285-95.

van Engeland, M., M. P. Weijenberg, et al. (2003). "Effects of dietary folate and alcohol intake on promoter methylation in sporadic colorectal cancer: the Netherlands cohort study on diet and cancer." Cancer Res 63(12): 3133-7.

Zhou, R. H., K. Kokame, et al. (2001). "Characterization of the human NDRG gene family: a newly identified member, NDRG4, is specifically expressed in brain and heart." Genomics 73(1): 86-97.

5) Additional Real-Time MSP Assays Tested on Plasmid Material for NDRG4 and OSMR Genes Plasmid material corresponding to a promoter region of NDRG4 and OSMR gene was used to test additional assay designs. The plasmid for the standard curve was generated as follows: the promoter sequence as defined by the primers is PCR amplified and cloned (using suitable isolated and bisulphite modified cell line DNA). The sequence is verified by sequencing and compared to the published promoter sequence. A serial dilution of either NDRG4 or OSMR plasmid material ($2\times10^6$ to $2\times10^1$ copies/5 µl) was loaded in duplicate. 5 µl of plasmid dilution or buffer (non template control) was added to a 20 µl PCR mix containing the specified primer and beacon detector sequences as previously described. Results were generated using the SDS 2.2 software from Applied Biosystems with automatic baseline and threshold settings. Data were exported as Ct values (cycle number at which the amplification curves cross the threshold value, set automatically by the software).

NDRG4

Initial real-time results for 2 different NDRG4 assay designs are presented in table 50 and 51. The primer and beacon combinations used for the respective assays NDRG4_1a and NDRG4_1b were previously described. Underscore 1a and 1b reflect the different primer and/or beacon combinations used for assessing the methylation status of the NDRG4 gene. NDRG4_1a corresponds to the preferred NDRG4 assay design, also simply referred to as NDRG4 (see Table 4). Comparable results were obtained for both assay designs. Clinical sample data provided in this invention are generated using the preferred NDRG4 assay design (=NDRG4=NDRG4_1 a)

TABLE 50

Realtime MSP results obtained for NDRG4_1a assay on plasmid material.
Resulting standard curve (y = −3.3321x + 39.862; R2 = 0.9991) corresponds to a PCR efficiency of 100%.

| Assay | Task | Ct | Quantity | Log copies | Duplicate Ct | Average Ct | ΔCt |
|---|---|---|---|---|---|---|---|
| NDRG4_1a | Standard | 18.82 | 2000000 | 6.30 | 18.92 | 18.87 | 0.09 |
| NDRG4_1a | Standard | 22.09 | 200000 | 5.30 | 22.22 | 22.15 | 0.13 |
| NDRG4_1a | Standard | 25.42 | 20000 | 4.30 | 25.47 | 25.45 | 0.06 |
| NDRG4_1a | Standard | 28.86 | 2000 | 3.30 | 28.94 | 28.90 | 0.08 |
| NDRG4_1a | Standard | 32.58 | 200 | 2.30 | 32.48 | 32.53 | 0.10 |
| NDRG4_1a | Standard | 34.92 | 20 | 1.30 | 35.64 | 35.28 | 0.71 |
| NDRG4_1a | NTC | Undetermined | 0 | | Undetermined | Undeter. | Undeter. |

TABLE 51

Real time MSP results obtained for NDRG4_1b assay on plasmid material. Resulting standard curve (y = −3.4181x + 40.991; R2 = 0.9991) corresponds to a PCR efficiency of 99.2%.

| Assay | Task | Ct | Quantity | Log copies | Duplicate Ct | Average Ct | ΔCt |
|---|---|---|---|---|---|---|---|
| NDRG4_1b | Standard | 19.48 | 2000000 | 6.30 | 19.59 | 19.53 | 0.12 |
| NDRG4_1b | Standard | 22.93 | 200000 | 5.30 | 22.92 | 22.92 | 0.01 |
| NDRG4_1b | Standard | 26.26 | 20000 | 4.30 | 26.18 | 26.22 | 0.08 |
| NDRG4_1b | Standard | 29.65 | 2000 | 3.30 | 29.67 | 29.66 | 0.02 |
| NDRG4_1b | Standard | 32.82 | 200 | 2.30 | 32.83 | 32.82 | 0.01 |
| NDRG4_1b | Standard | 36.75 | 20 | 1.30 | 36.91 | 36.83 | 0.16 |
| NDRG4_1b | NTC | Undetermined | 0 | | Undetermined | Undet | Undet |

OSMR

Initial real-time results for 3 different OSMR assay designs are presented in below Tables 52 to 54. The primer and beacon combinations used for the respective assays OSMR_1, OSMR_3 [=OMSR (3)] and OSMR_4 [=OSMR (4)] were previously described. Underscore 1, 3 and 4 reflect the different primer and/or beacon combinations used for assessing the methylation status of the OSMR gene. Comparable results were obtained for all three assay designs.

TABLE 52

Real time MSP result obtained for OSMR_1 assays on plasmid material. Resulting standard curve (y = −3.3326x + 41.136; R2 = 0.9993) corresponds to a PCR efficiency of 99.6%.

| Assay | Task | Ct | Quantity | Log copies | Duplicate Ct | Average Ct | ΔCt |
|---|---|---|---|---|---|---|---|
| OSMR_1 | Standard | 20.04 | 2000000 | 6.30 | 20.14 | 20.09 | 0.09 |
| OSMR_1 | Standard | 23.48 | 200000 | 5.30 | 23.41 | 23.44 | 0.07 |
| OSMR_1 | Standard | 26.73 | 20000 | 4.30 | 26.85 | 26.79 | 0.12 |
| OSMR_1 | Standard | 30.13 | 2000 | 3.30 | 30.26 | 30.19 | 0.13 |
| OSMR_1 | Standard | 33.55 | 200 | 2.30 | 33.93 | 33.74 | 0.38 |
| OSMR_1 | Standard | 36.54 | 20 | 1.30 | 36.58 | 36.56 | 0.04 |
| OSMR_1 | NTC | Undetermined | 0 | | Undetermined | Undet | Undet |

TABLE 52

Real time MSP result obtained for OSMR_3 assays on plasmid material. Resulting standard curve (y = −3.3909x + 38.398; R2 = 0.9999) corresponds to a PCR efficiency of 97.2%.

| Assay | Task | Ct | Quantity | Log copies | Duplicate Ct | Average Ct | ΔCt |
|---|---|---|---|---|---|---|---|
| OSMR_3 | Standard | 16.93 | 2000000 | 6.30 | 17.16 | 17.04 | 0.23 |
| OSMR_3 | Standard | 20.41 | 200000 | 5.30 | 20.29 | 20.35 | 0.12 |
| OSMR_3 | Standard | 23.97 | 20000 | 4.30 | 23.83 | 23.90 | 0.14 |
| OSMR_3 | Standard | 27.22 | 2000 | 3.30 | 27.16 | 27.19 | 0.06 |
| OSMR_3 | Standard | 30.51 | 200 | 2.30 | 30.67 | 30.59 | 0.16 |
| OSMR_3 | Standard | 34.18 | 20 | 1.30 | 33.77 | 33.98 | 0.41 |
| OSMR_3 | NTC | 38.13 | 0 | | Undetermined | Undet | Undet |

TABLE 54

Real time MSP result obtained for OSMR_4 assays on plasmid material. Resulting standard curve (y = −3.2795x + 38.77; R2 = 0.9997) corresponds to a PCR efficiency of 100.8%

| Assay | Task | Ct | Quantity | Log copies | Duplicate Ct | Average Ct | ΔCt |
|---|---|---|---|---|---|---|---|
| OSMR_4 | Standard | 18.24 | 2000000 | 6.30 | 17.90 | 18.07 | 0.33 |
| OSMR_4 | Standard | 21.56 | 200000 | 5.30 | 21.05 | 21.31 | 0.51 |
| OSMR_4 | Standard | 24.79 | 20000 | 4.30 | 24.64 | 24.72 | 0.15 |

TABLE 54-continued

Real time MSP result obtained for OSMR_4 assays on plasmid material. Resulting standard curve (y = −3.2795x + 38.77; R2 = 0.9997) corresponds to a PCR efficiency of 100.8%

| Assay | Task | Ct | Quantity | Log copies | Duplicate Ct | Average Ct | ΔCt |
|---|---|---|---|---|---|---|---|
| OSMR_4 | Standard | 28.24 | 2000 | 3.30 | 27.91 | 28.08 | 0.33 |
| OSMR_4 | Standard | 31.37 | 200 | 2.30 | 31.18 | 31.28 | 0.19 |
| OSMR_4 | Standard | 34.63 | 20 | 1.30 | 34.12 | 34.37 | 0.50 |
| OSMR_4 | NTC | Undetermined | 0 | | Undetermined | Undet | Undet |

6) Testing and Validation of Further CRC Markers in Bodily Fluid Test Samples

New markers added: BNIP3, FOXE1, JAM3, PHACTR3, TPFI2, SOX17 and SYNE1 (and also JPH3 stool data). Suitable primers and probes for determining the methylation status of these genes are set forth in Tables 12 (and 13 to 18) above.

Methods and Results
Clinical Samples

Samples were collected from centers in Germany and The Netherlands

TABLE 55

Samples for DNA extraction from plasma (blood origin)

| type | Sample Numbers |
|---|---|
| Normal | 10 |
| Colorectal Cancer stage III | 6 |
| Colorectal Cancer stage IV | 4 |

TABLE 56

Samples for DNA extraction from stool

| type | Sample Numbers |
|---|---|
| Control (Normal) | 7 |
| Case (Colorectal Cancer) | 1 |
| Case (Colorectal Cancer) | 6 |

Marker Testing on Clinical Samples

Experiments were performed as previously described. Briefly DNA was extracted from stool and/or plasma followed by bisulfite treatment. Samples were tested by real-time MSP assays, using 384 well plates with a 12 μl final volume. The template volume is 2.4 μl with a mix volume of 9.6 μl. Results were generated using the SDS 2.2 software (Applied Biosystems), exported as Ct values (cycle number at which the amplification curves cross the threshold value, set automatically by the software). Copy numbers are extrapolated using a standard curve.

The individual performance of the 8 gene assays TFPI2, BNIP3, FOXE1, SYNE1, SOX17, PHACTR3, JAM3 and JPH3 in plasma and stool samples is shown in Table XV (except for JPH3: stool data only). Sensitivity values for plasma and stool are ranging from 30 to 70% and 0 to 57% respectively with a corresponding specificity of a 100%. When optimizing for sensitivity, 80% sensitivity for TFPI2 and 50% sensitivity for PHACTR3 is obtained in plasma samples with a corresponding specificity of 90%. It is observed that for some markers (TFPI2, BNIP3, FOXE1, SYNE1 and SOX17) sensitivity of colorectal cancer detection is higher when using plasma samples compared to stool samples.

TABLE 57

Individual gene performance: Sensitivity and specificity of TFPI2, BNIP3, FOXE1, SYNE1, SOX17, PHACTR3, JAM3 markers on stool and plasma samples. Sensitivity and specificity results for the JPH3 marker were only obtained for stool using this sample set, plasma data were enabled earlier with a different sample set.

| | optimized for Specificity | | | optimized for Sensitivity | | |
|---|---|---|---|---|---|---|
| | Specificity | Sensitivity | cutoff | Specificity | Sensitivity | cutoff |
| TFPI2 Stool | 100 | 57 | 10 | | | |
| TFPI2 Plasma | 100 | 70 | 1 | 90 | 80 | 0 |
| BNIP3 Stool | 100 | 0 | 7 | | | |
| BNIP3 Plasma | 100 | 30 | 0 | | | |
| FOXE1 Stool | 100 | 57 | 0 | | | |
| FOXE1 Plasma | 100 | 60 | 0 | | | |
| SYNE1 Stool | 100 | 57 | 2 | | | |
| SYNE1 Plasma | 100 | 60 | 0 | | | |
| SOX17 Stool | 100 | 57 | 30 | | | |
| SOX17 Plasma | 100 | 60 | 2 | | | |
| PHACTR3 Stool | 100 | 43 | 8 | | | |
| PHACTR3 Plasma | 100 | 40 | 2 | 90 | 50 | 0 |
| JAM3 Stool | 100 | 43 | 1 | | | |
| JAM3 Plasma | 100 | 30 | 1 | | | |
| JPH3 Stool | 100 | 14 | 20 | | | |
| JPH3 Plasma | see previous colon results | | | | | |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

SEQUENCE LISTING

<160> NUMBER OF SEQ ID NOS: 569

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
cctgaggaga agccgctg					18

<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2
atgtcatgtt ccttccagtc tgt				23

<210> SEQ ID NO 3
<211> LENGTH: 23
<212> TYPE: DNA
<213> ORGANISM: Artificial
<220> FEATURE:
<223> OTHER INFORMATION: Primer

<400> SEQUENCE: 3
ggccttctgc atgtagtgat ccg				23

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
ggtgatctcc tgcatgtcct cg				22

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
ggttygttyg ggattagttt tagg				24

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
craacaacca aaaccccctc					20

<210> SEQ ID NO 7
<211> LENGTH: 29
<212> TYPE: DNA
<213> ORGANISM: Artificial

```
<220> FEATURE:
<223> OTHER INFORMATION: Primer

<400> SEQUENCE: 7
gattagtttt aggtttggta ttgttttgt                                29

<210> SEQ ID NO 8
<211> LENGTH: 26
<212> TYPE: DNA
<213> ORGANISM: Artificial
<220> FEATURE:
<223> OTHER INFORMATION: Primer

<400> SEQUENCE: 8
aaaaccaaac taaaaacaat acacca                                   26

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
tttaggttcg gtatcgtttc gc                                       22

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
cgaactaaaa acgatacgcc g                                        21

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11 atygggggtgt tttttaggtt t                                       21

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
ataccraacc taaaactaat ccc                                      23

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
gggtgttttt taggtttcgc gtcgc                                    25
```

```
<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
cctaaaacta atcccaaaca aacca                                              25

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15 tttttaggt ttcgcgtcgc                                                     20

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
aaactaatcc cgaacgaacc g                                                  21

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
gtattttagt cgcgtagaag gc                                                 22

<210> SEQ ID NO 18
<211> LENGTH: 25
<212> TYPE: DNA
<213> ORGANISM: Artificial
<220> FEATURE:
<223> OTHER INFORMATION: Primer

<400> SEQUENCE: 18
aatttaacga atataaacgc tcgac                                              25

<210> SEQ ID NO 19
<211> LENGTH: 36
<212> TYPE: DNA
<213> ORGANISM: Artificial
<220> FEATURE:
<223> OTHER INFORMATION: Molecular Beacon Probe

<400> SEQUENCE: 19
cgacatgccc gaacgaaccg cgatccctgc atgtcg                                  36

<210> SEQ ID NO 20
<211> LENGTH: 24
<212> TYPE: DNA
<213> ORGANISM: Artificial
<220> FEATURE:
<223> OTHER INFORMATION: Primer
```

```
<400> SEQUENCE: 20 ygtttttttat ttatagyggt tttt                                         24

<210> SEQ ID NO 21
<211> LENGTH: 27
<212> TYPE: DNA
<213> ORGANISM: Artificial
<220> FEATURE:
<223> OTHER INFORMATION: Primer

<400> SEQUENCE: 21
tcctaatacc tctcctctct ttactac                                       27

<210> SEQ ID NO 22
<211> LENGTH: 30
<212> TYPE: DNA
<213> ORGANISM: Artificial
<220> FEATURE:
<223> OTHER INFORMATION: Primer

<400> SEQUENCE: 22
ttttatttat agtggttttt tgtattttt                                     30

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
tctcctctct ttactacatc ccaaca                                        26

<210> SEQ ID NO 24
<211> LENGTH: 25
<212> TYPE: DNA
<213> ORGANISM: Artificial
<220> FEATURE:
<223> OTHER INFORMATION: Primer

<400> SEQUENCE: 24
tttatagcgg tttttcgtat ttttc                                         25

<210> SEQ ID NO 25
<211> LENGTH: 23
<212> TYPE: DNA
<213> ORGANISM: Artificial
<220> FEATURE:
<223> OTHER INFORMATION: Primer

<400> SEQUENCE: 25
cctctcttta ctacgtcccg acg                                           23

<210> SEQ ID NO 26
<211> LENGTH: 26
<212> TYPE: DNA
<213> ORGANISM: Artificial
<220> FEATURE:
<223> OTHER INFORMATION: Primer

<400> SEQUENCE: 26
tagggagtat ataggttggg gaagtt                                        26

<210> SEQ ID NO 27
```

```
<211> LENGTH: 27
<212> TYPE: DNA
<213> ORGANISM: Artificial
<220> FEATURE:
<223> OTHER INFORMATION: Primer

<400> SEQUENCE: 27
aacacacaat aacaaacaca aattcac                                         27

<210> SEQ ID NO 28
<211> LENGTH: 42
<212> TYPE: DNA
<213> ORGANISM: Artificial
<220> FEATURE:
<223> OTHER INFORMATION: Molecular Beacon Probe

<400> SEQUENCE: 28
cgactgcgtg tggggtggtg atggaggagg tttaggcagt cg                        42

<210> SEQ ID NO 29
<211> LENGTH: 23
<212> TYPE: DNA
<213> ORGANISM: Artificial
<220> FEATURE:
<223> OTHER INFORMATION: Primer

<400> SEQUENCE: 29
aggttagtta gcgttttagg gtc                                             23

<210> SEQ ID NO 30
<211> LENGTH: 19
<212> TYPE: DNA
<213> ORGANISM: Artificial
<220> FEATURE:
<223> OTHER INFORMATION: Primer

<400> SEQUENCE: 30
acgacgacga aacctctcg                                                  19

<210> SEQ ID NO 31
<211> LENGTH: 40
<212> TYPE: DNA
<213> ORGANISM: Artificial
<220> FEATURE:
<223> OTHER INFORMATION: Molecular Beacon Probe

<400> SEQUENCE: 31
cgacatgcct cgcgactcga atccccgacc cagcatgtcg                           40

<210> SEQ ID NO 32
<211> LENGTH: 26
<212> TYPE: DNA
<213> ORGANISM: Artificial
<220> FEATURE:
<223> OTHER INFORMATION: Primer

<400> SEQUENCE: 32
agttcgtttt taggttagtt ttcggc                                          26

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
```
ccaatacaac taaacgaacg aaccg                                    25

<210> SEQ ID NO 34
<211> LENGTH: 45
<212> TYPE: DNA
<213> ORGANISM: Artificial
<220> FEATURE:
<223> OTHER INFORMATION: Molecular Beacon Probe

<400> SEQUENCE: 34
cgacatgcgt agggaggtag agggttcggg attcgtagca tgtcg              45

<210> SEQ ID NO 35
<211> LENGTH: 26
<212> TYPE: DNA
<213> ORGANISM: Artificial
<220> FEATURE:
<223> OTHER INFORMATION: Primer

<400> SEQUENCE: 35
tgtagttttc ggagttagtg tcgcgc                                   26

<210> SEQ ID NO 36
<211> LENGTH: 25
<212> TYPE: DNA
<213> ORGANISM: Artificial
<220> FEATURE:
<223> OTHER INFORMATION: Primer

<400> SEQUENCE: 36
cctacgatcg aaaacgacgc gaacg                                    25

<210> SEQ ID NO 37
<211> LENGTH: 47
<212> TYPE: DNA
<213> ORGANISM: Artificial
<220> FEATURE:
<223> OTHER INFORMATION: Molecular Beacon Probe

<400> SEQUENCE: 37
cgacatgctc gggagtcggg gcgtatttag ttcgtagcgg catgtcg            47

<210> SEQ ID NO 38
<211> LENGTH: 25
<212> TYPE: DNA
<213> ORGANISM: Artificial
<220> FEATURE:
<223> OTHER INFORMATION: Primer

<400> SEQUENCE: 38
gggtcggagt ttttcggagt tgcgc                                    25

<210> SEQ ID NO 39
<211> LENGTH: 26
<212> TYPE: DNA
<213> ORGANISM: Artificial
<220> FEATURE:
<223> OTHER INFORMATION: Primer

<400> SEQUENCE: 39
ccgctctctt cgctaaatac gactcg                                   26

<210> SEQ ID NO 40
<211> LENGTH: 48
<212> TYPE: DNA

```
<213> ORGANISM: Artificial
<220> FEATURE:
<223> OTHER INFORMATION: Molecular Beacon Probe

<400> SEQUENCE: 40
cgacatgcgg tgtttcgttt tttcgcgttt tagtcgtcgg gcatgtcg        48

<210> SEQ ID NO 41
<211> LENGTH: 19
<212> TYPE: DNA
<213> ORGANISM: Artificial
<220> FEATURE:
<223> OTHER INFORMATION: Primer

<400> SEQUENCE: 41
gaaccaaaac gctccccat                                         19

<210> SEQ ID NO 42
<211> LENGTH: 27
<212> TYPE: DNA
<213> ORGANISM: Artificial
<220> FEATURE:
<223> OTHER INFORMATION: Primer

<400> SEQUENCE: 42
ttatatgtcg gttacgtgcg tttatat                                27

<210> SEQ ID NO 43
<211> LENGTH: 38
<212> TYPE: DNA
<213> ORGANISM: Artificial
<220> FEATURE:
<223> OTHER INFORMATION: Molecular Beacon Probe

<400> SEQUENCE: 43
cgtctgcccc gtcgaaaacc cgccgattaa cgcagacg                    38

<210> SEQ ID NO 44
<211> LENGTH: 19
<212> TYPE: DNA
<213> ORGANISM: Artificial
<220> FEATURE:
<223> OTHER INFORMATION: Primer

<400> SEQUENCE: 44
gaaggacgag aagtaggcg                                         19

<210> SEQ ID NO 45
<211> LENGTH: 23
<212> TYPE: DNA
<213> ORGANISM: Artificial
<220> FEATURE:
<223> OTHER INFORMATION: Primer

<400> SEQUENCE: 45
ctaacgaact acaaccttac cga                                    23

<210> SEQ ID NO 46
<211> LENGTH: 37
<212> TYPE: DNA
<213> ORGANISM: Artificial
<220> FEATURE:
<223> OTHER INFORMATION: Molecular Beacon Probe

<400> SEQUENCE: 46
cgacatgccc ccgacccgca cgccgccctg catgtcg                     37
```

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47
tttggtcggg gtaggagtag c                                              21

<210> SEQ ID NO 48
<211> LENGTH: 22
<212> TYPE: DNA
<213> ORGANISM: Artificial
<220> FEATURE:
<223> OTHER INFORMATION: Primer

<400> SEQUENCE: 48
cgaactttac gaacgaacga ac                                             22

<210> SEQ ID NO 49
<211> LENGTH: 32
<212> TYPE: DNA
<213> ORGANISM: Artificial
<220> FEATURE:
<223> OTHER INFORMATION: Molecular Beacon Probe

<400> SEQUENCE: 49
cgacatgccc gtaccccgcg cgcagcatgt cg                                  32

<210> SEQ ID NO 50
<211> LENGTH: 24
<212> TYPE: DNA
<213> ORGANISM: Artificial
<220> FEATURE:
<223> OTHER INFORMATION: Primer

<400> SEQUENCE: 50
aaaaacttaa aaaccgaaaa ctcg                                           24

<210> SEQ ID NO 51
<211> LENGTH: 24
<212> TYPE: DNA
<213> ORGANISM: Artificial
<220> FEATURE:
<223> OTHER INFORMATION: Primer

<400> SEQUENCE: 51
ttagatttcg taaacggtga aaac                                           24

<210> SEQ ID NO 52
<211> LENGTH: 19
<212> TYPE: DNA
<213> ORGANISM: Artificial
<220> FEATURE:
<223> OTHER INFORMATION: Primer

<400> SEQUENCE: 52
tctcctccga aaacgctc                                                  19

<210> SEQ ID NO 53
<211> LENGTH: 33
<212> TYPE: DNA
<213> ORGANISM: Artificial
<220> FEATURE:

<223> OTHER INFORMATION: Molecular Beacon Probe

<400> SEQUENCE: 53
cgtctgcaac cgccgacgac cgcgacgcag acg                              33

<210> SEQ ID NO 54
<211> LENGTH: 23
<212> TYPE: DNA
<213> ORGANISM: Artificial
<220> FEATURE:
<223> OTHER INFORMATION: Primer

<400> SEQUENCE: 54
tttcgacgtt cgtaggtttt cgc                                         23

<210> SEQ ID NO 55
<211> LENGTH: 22
<212> TYPE: DNA
<213> ORGANISM: Artificial
<220> FEATURE:
<223> OTHER INFORMATION: Primer

<400> SEQUENCE: 55
gcactcttcc gaaaacgaaa cg                                          22

<210> SEQ ID NO 56
<211> LENGTH: 50
<212> TYPE: DNA
<213> ORGANISM: Artificial
<220> FEATURE:
<223> OTHER INFORMATION: Molecular Beacon Probe

<400> SEQUENCE: 56
cgtctcgcgt gcgtatcgtt tgcgatttgg tgagtgtttg gggcgagacg            50

<210> SEQ ID NO 57
<211> LENGTH: 36
<212> TYPE: DNA
<213> ORGANISM: Artificial
<220> FEATURE:
<223> OTHER INFORMATION: Molecular Beacon Probe

<400> SEQUENCE: 57
cgacatgcag ggatcgcggt tcgttcgggc atgtcg                           36

<210> SEQ ID NO 58
<211> LENGTH: 23
<212> TYPE: DNA
<213> ORGANISM: Artificial
<220> FEATURE:
<223> OTHER INFORMATION: Primer

<400> SEQUENCE: 58
ggtattttag tcgcgtagaa ggc                                         23

<210> SEQ ID NO 59
<211> LENGTH: 21
<212> TYPE: DNA
<213> ORGANISM: Artificial
<220> FEATURE:
<223> OTHER INFORMATION: Primer

<400> SEQUENCE: 59
gaatataaac gctcgacccg c                                           21

```
<210> SEQ ID NO 60
<211> LENGTH: 46
<212> TYPE: DNA
<213> ORGANISM: Artificial
<220> FEATURE:
<223> OTHER INFORMATION: Molecular Beacon Probe

<400> SEQUENCE: 60
cgacatgcgc ggttcgttcg ggattagttt taggttcggc atgtcg          46

<210> SEQ ID NO 61
<211> LENGTH: 39
<212> TYPE: DNA
<213> ORGANISM: Artificial
<220> FEATURE:
<223> OTHER INFORMATION: Molecular Beacon Probe

<400> SEQUENCE: 61
cgtacccgcg tttatattcg ttaaatttac gcgggtacg                   39

<210> SEQ ID NO 62
<211> LENGTH: 19
<212> TYPE: DNA
<213> ORGANISM: Artificial
<220> FEATURE:
<223> OTHER INFORMATION: Primer

<400> SEQUENCE: 62
tagtcgcgta gaaggcgga                                         19

<210> SEQ ID NO 63
<211> LENGTH: 23
<212> TYPE: DNA
<213> ORGANISM: Artificial
<220> FEATURE:
<223> OTHER INFORMATION: Primer

<400> SEQUENCE: 63
gactacaaaa acgaaaaccg aac                                    23

<210> SEQ ID NO 64
<211> LENGTH: 31
<212> TYPE: DNA
<213> ORGANISM: Artificial
<220> FEATURE:
<223> OTHER INFORMATION: Molecular Beacon Probe

<400> SEQUENCE: 64
cgacatcggg tacgttttcg cggcgatgtc g                           31

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
ctacaaaaac gaaaaccgaa c                                      21

<210> SEQ ID NO 66
<211> LENGTH: 23
<212> TYPE: DNA
<213> ORGANISM: Artificial
<220> FEATURE:
<223> OTHER INFORMATION: Molecular Beacon Probe
```

<400> SEQUENCE: 66
cgtttcgcgg gtcgagcgaa acg                                             23

<210> SEQ ID NO 67
<211> LENGTH: 21
<212> TYPE: DNA
<213> ORGANISM: Artificial
<220> FEATURE:
<223> OTHER INFORMATION: Primer

<400> SEQUENCE: 67
cgaaaaccga actaaaaacg a                                               21

<210> SEQ ID NO 68
<211> LENGTH: 43
<212> TYPE: DNA
<213> ORGANISM: Artificial
<220> FEATURE:
<223> OTHER INFORMATION: Molecular beacon Probe

<400> SEQUENCE: 68
cgacatgccg cggttcgttc gggattagtt ttagggcatg tcg                       43

<210> SEQ ID NO 69
<211> LENGTH: 19
<212> TYPE: DNA
<213> ORGANISM: Artificial
<220> FEATURE:
<223> OTHER INFORMATION: Primer

<400> SEQUENCE: 69
tttcgttcgt ttatcgggt                                                  19

<210> SEQ ID NO 70
<211> LENGTH: 23
<212> TYPE: DNA
<213> ORGANISM: Artificial
<220> FEATURE:
<223> OTHER INFORMATION: Primer

<400> SEQUENCE: 70
cgaacctaaa actaatcccg aac                                             23

<210> SEQ ID NO 71
<211> LENGTH: 36
<212> TYPE: DNA
<213> ORGANISM: Artificial
<220> FEATURE:
<223> OTHER INFORMATION: Molecular Beacon Probe

<400> SEQUENCE: 71
cgacacgcgt agaaggcgga agttacgcgc gtgtcg                               36

<210> SEQ ID NO 72
<211> LENGTH: 27
<212> TYPE: DNA
<213> ORGANISM: Artificial
<220> FEATURE:
<223> OTHER INFORMATION: Primer

<400> SEQUENCE: 72
ggtttcgtag cgtatttagt atagttc                                         27

<210> SEQ ID NO 73
<211> LENGTH: 20

```
<212> TYPE: DNA
<213> ORGANISM: Artificial
<220> FEATURE:
<223> OTHER INFORMATION: Primer

<400> SEQUENCE: 73
gtaacttccg ccttctacgc                                                    20

<210> SEQ ID NO 74
<211> LENGTH: 42
<212> TYPE: DNA
<213> ORGANISM: Artificial
<220> FEATURE:
<223> OTHER INFORMATION: Molecular Beacon Probe

<400> SEQUENCE: 74
cgacatgcgc ggatcgatcg gggtgttttt tagggcatgt cg                           42

<210> SEQ ID NO 75
<211> LENGTH: 23
<212> TYPE: DNA
<213> ORGANISM: Artificial
<220> FEATURE:
<223> OTHER INFORMATION: Primer

<400> SEQUENCE: 75
gagttgtttt tgtcgtttcg ttt                                                23

<210> SEQ ID NO 76
<211> LENGTH: 19
<212> TYPE: DNA
<213> ORGANISM: Artificial
<220> FEATURE:
<223> OTHER INFORMATION: Primer

<400> SEQUENCE: 76
aacaccttca tctcgacgc                                                     19

<210> SEQ ID NO 77
<211> LENGTH: 31
<212> TYPE: DNA
<213> ORGANISM: Artificial
<220> FEATURE:
<223> OTHER INFORMATION: Molecular Beacon Probe

<400> SEQUENCE: 77
cgacatgcgg ttcggtcgag cgcgcatgtc g                                       31

<210> SEQ ID NO 78
<211> LENGTH: 24
<212> TYPE: DNA
<213> ORGANISM: Artificial
<220> FEATURE:
<223> OTHER INFORMATION: Primer

<400> SEQUENCE: 78
gttgtgagtt gttttttgtcg tttc                                              24

<210> SEQ ID NO 79
<211> LENGTH: 45
<212> TYPE: DNA
<213> ORGANISM: Artificial
<220> FEATURE:
<223> OTHER INFORMATION: Molecular Beacon Probe

<400> SEQUENCE: 79
```
cgacatgccg ttgtttcgac gtcgttattt agagtcggca tgtcg           45

<210> SEQ ID NO 80
<211> LENGTH: 25
<212> TYPE: DNA
<213> ORGANISM: Artificial
<220> FEATURE:
<223> OTHER INFORMATION: Primer

<400> SEQUENCE: 80 tttagtatt tttatttcgg cgttc                                  25

<210> SEQ ID NO 81
<211> LENGTH: 20
<212> TYPE: DNA
<213> ORGANISM: Artificial
<220> FEATURE:
<223> OTHER INFORMATION: Primer

<400> SEQUENCE: 81
ctactcctac cgcttcgctc                                       20

<210> SEQ ID NO 82
<211> LENGTH: 28
<212> TYPE: DNA
<213> ORGANISM: Artificial
<220> FEATURE:
<223> OTHER INFORMATION: Molecular Beacon Probe

<400> SEQUENCE: 82
cgacatcgcg ctcctctccc cgatgtcg                              28

<210> SEQ ID NO 83
<211> LENGTH: 25
<212> TYPE: DNA
<213> ORGANISM: Artificial
<220> FEATURE:
<223> OTHER INFORMATION: Primer

<400> SEQUENCE: 83
cggtgtttta gtatttttat ttcgg                                 25

<210> SEQ ID NO 84
<211> LENGTH: 21
<212> TYPE: DNA
<213> ORGANISM: Artificial
<220> FEATURE:
<223> OTHER INFORMATION: Primer

<400> SEQUENCE: 84
aactactcct accgcttcgc t                                     21

<210> SEQ ID NO 85
<211> LENGTH: 30
<212> TYPE: DNA
<213> ORGANISM: Artificial
<220> FEATURE:
<223> OTHER INFORMATION: Molecular Beacon Probe

<400> SEQUENCE: 85
cgacatcggt tttgggtggc ggcgatgtcg                            30

<210> SEQ ID NO 86
<211> LENGTH: 19
<212> TYPE: DNA
<213> ORGANISM: Artificial

<220> FEATURE:
<223> OTHER INFORMATION: Primer

<400> SEQUENCE: 86
ctctcctacc gctccgctc                                                    19

<210> SEQ ID NO 87
<211> LENGTH: 31
<212> TYPE: DNA
<213> ORGANISM: Artificial
<220> FEATURE:
<223> OTHER INFORMATION: Molecular Beacon Probe

<400> SEQUENCE: 87
cgacatcgct cctctccccg actcgatgtc g                                      31

<210> SEQ ID NO 88
<211> LENGTH: 31
<212> TYPE: DNA
<213> ORGANISM: Artificial
<220> FEATURE:
<223> OTHER INFORMATION: Molecular Beacon Probe

<400> SEQUENCE: 88
cgacatgccg aacgcgctac cccgcatgtc g                                      31

<210> SEQ ID NO 89
<211> LENGTH: 21
<212> TYPE: DNA
<213> ORGANISM: Artificial
<220> FEATURE:
<223> OTHER INFORMATION: Primer

<400> SEQUENCE: 89
cgagtcgttt tagttttcgg t                                                 21

<210> SEQ ID NO 90
<211> LENGTH: 19
<212> TYPE: DNA
<213> ORGANISM: Artificial
<220> FEATURE:
<223> OTHER INFORMATION: Primer

<400> SEQUENCE: 90
tactcacaaa taccgcccg                                                    19

<210> SEQ ID NO 91
<211> LENGTH: 34
<212> TYPE: DNA
<213> ORGANISM: Artificial
<220> FEATURE:
<223> OTHER INFORMATION: Molecular Beacon Probe

<400> SEQUENCE: 91
cgacatcgga aagtggcggt cggttgcgat gtcg                                   34

<210> SEQ ID NO 92
<211> LENGTH: 20
<212> TYPE: DNA
<213> ORGANISM: Artificial
<220> FEATURE:
<223> OTHER INFORMATION: Primer

<400> SEQUENCE: 92
ttcggtgaat tttaggaggc                                                   20

-continued

<210> SEQ ID NO 93
<211> LENGTH: 19
<212> TYPE: DNA
<213> ORGANISM: Artificial
<220> FEATURE:
<223> OTHER INFORMATION: Primer

<400> SEQUENCE: 93
tcgaacgacg aacacgaaa                                              19

<210> SEQ ID NO 94
<211> LENGTH: 30
<212> TYPE: DNA
<213> ORGANISM: Artificial
<220> FEATURE:
<223> OTHER INFORMATION: Molecular Beacon Probe

<400> SEQUENCE: 94
cgacatgcgc ggggtgggtg cggcatgtcg                                  30

<210> SEQ ID NO 95
<211> LENGTH: 23
<212> TYPE: DNA
<213> ORGANISM: Artificial
<220> FEATURE:
<223> OTHER INFORMATION: Primer

<400> SEQUENCE: 95
ttcgggttgg agtatttatt agc                                         23

<210> SEQ ID NO 96
<211> LENGTH: 20
<212> TYPE: DNA
<213> ORGANISM: Artificial
<220> FEATURE:
<223> OTHER INFORMATION: Primer

<400> SEQUENCE: 96
cgaacttcca atcttcgacc                                             20

<210> SEQ ID NO 97
<211> LENGTH: 34
<212> TYPE: DNA
<213> ORGANISM: Artificial
<220> FEATURE:
<223> OTHER INFORMATION: Molecular Beacon Probe

<400> SEQUENCE: 97
cgacatgcgg cggtggcggt gggtcggcat gtcg                             34

<210> SEQ ID NO 98
<211> LENGTH: 21
<212> TYPE: DNA
<213> ORGANISM: Artificial
<220> FEATURE:
<223> OTHER INFORMATION: Primer

<400> SEQUENCE: 98
gatttttcgg ggtttacgaa g                                           21

<210> SEQ ID NO 99
<211> LENGTH: 22
<212> TYPE: DNA
<213> ORGANISM: Artificial
<220> FEATURE:
<223> OTHER INFORMATION: Primer

<400> SEQUENCE: 99
gaaacttaac gacaaaaacg ca                                    22

<210> SEQ ID NO 100
<211> LENGTH: 41
<212> TYPE: DNA
<213> ORGANISM: Artificial
<220> FEATURE:
<223> OTHER INFORMATION: Molecular Beacon Probe

<400> SEQUENCE: 100
cgacatgcgt ttagttgtat tggttcgggt ttcgcatgtc g               41

<210> SEQ ID NO 101
<211> LENGTH: 21
<212> TYPE: DNA
<213> ORGANISM: Artificial
<220> FEATURE:
<223> OTHER INFORMATION: Primer

<400> SEQUENCE: 101
ggtttgtatt cggattcggt c                                     21

<210> SEQ ID NO 102
<211> LENGTH: 21
<212> TYPE: DNA
<213> ORGANISM: Artificial
<220> FEATURE:
<223> OTHER INFORMATION: Primer

<400> SEQUENCE: 102
tcgataacaa cgtcctacac g                                     21

<210> SEQ ID NO 103
<211> LENGTH: 43
<212> TYPE: DNA
<213> ORGANISM: Artificial
<220> FEATURE:
<223> OTHER INFORMATION: Molecular Beacon Primer

<400> SEQUENCE: 103
cgacatgcga aggtgggttt gcggtttggg aggtcgcatg tcg             43

<210> SEQ ID NO 104
<211> LENGTH: 20
<212> TYPE: DNA
<213> ORGANISM: Artificial
<220> FEATURE:
<223> OTHER INFORMATION: Primer

<400> SEQUENCE: 104
tagggtgcgg gtttgtattc                                       20

<210> SEQ ID NO 105
<211> LENGTH: 19
<212> TYPE: DNA
<213> ORGANISM: Artificial
<220> FEATURE:
<223> OTHER INFORMATION: Primer

<400> SEQUENCE: 105
aacaacgtcc tacacgacc                                        19

<210> SEQ ID NO 106

```
<211> LENGTH: 44
<212> TYPE: DNA
<213> ORGANISM: Artificial
<220> FEATURE:
<223> OTHER INFORMATION: Molecular Beacon Probe

<400> SEQUENCE: 106
cgacatgcgt atttatcgaa ggtgggtttg cggtttgcat gtcg                    44

<210> SEQ ID NO 107
<211> LENGTH: 23
<212> TYPE: DNA
<213> ORGANISM: Artificial
<220> FEATURE:
<223> OTHER INFORMATION: Primer

<400> SEQUENCE: 107
tagttggtgt agtagaggtc ggc                                          23

<210> SEQ ID NO 108
<211> LENGTH: 20
<212> TYPE: DNA
<213> ORGANISM: Artificial
<220> FEATURE:
<223> OTHER INFORMATION: Primer

<400> SEQUENCE: 108
gacctaaatc tcgcttccgt                                              20

<210> SEQ ID NO 109
<211> LENGTH: 39
<212> TYPE: DNA
<213> ORGANISM: Artificial
<220> FEATURE:
<223> OTHER INFORMATION: Molecular Beacon Probe

<400> SEQUENCE: 109
cgacatgccg agggagattg gagtgagttt cgcatgtcg                         39

<210> SEQ ID NO 110
<211> LENGTH: 20
<212> TYPE: DNA
<213> ORGANISM: Artificial
<220> FEATURE:
<223> OTHER INFORMATION: Primer

<400> SEQUENCE: 110
tatagcgtgg tgttggtcgt                                              20

<210> SEQ ID NO 111
<211> LENGTH: 19
<212> TYPE: DNA
<213> ORGANISM: Artificial
<220> FEATURE:
<223> OTHER INFORMATION: Primer

<400> SEQUENCE: 111
ctaaatctcg cttccgtcc                                               19

<210> SEQ ID NO 112
<211> LENGTH: 40
<212> TYPE: DNA
<213> ORGANISM: Artificial
<220> FEATURE:
<223> OTHER INFORMATION: Molecular Beacon Probe

<400> SEQUENCE: 112
```
cgacatgcgc gagggagatt ggagtgagtt tcgcatgtcg        40

<210> SEQ ID NO 113
<211> LENGTH: 23
<212> TYPE: DNA
<213> ORGANISM: Artificial
<220> FEATURE:
<223> OTHER INFORMATION: Primer

<400> SEQUENCE: 113
ggtgtcgagg tttttaaggt ttc        23

<210> SEQ ID NO 114
<211> LENGTH: 22
<212> TYPE: DNA
<213> ORGANISM: Artificial
<220> FEATURE:
<223> OTHER INFORMATION: Primer

<400> SEQUENCE: 114
tcactttcta acgaaaacga ct        22

<210> SEQ ID NO 115
<211> LENGTH: 38
<212> TYPE: DNA
<213> ORGANISM: Artificial
<220> FEATURE:
<223> OTHER INFORMATION: Molecular Beacon Probe

<400> SEQUENCE: 115
cgacatgcgg gacgggatgg gttttttgcgg gcatgtcg        38

<210> SEQ ID NO 116
<211> LENGTH: 21
<212> TYPE: DNA
<213> ORGANISM: Artificial
<220> FEATURE:
<223> OTHER INFORMATION: Primer

<400> SEQUENCE: 116
gtagtttcgg agttgggtgt c        21

<210> SEQ ID NO 117
<211> LENGTH: 20
<212> TYPE: DNA
<213> ORGANISM: Artificial
<220> FEATURE:
<223> OTHER INFORMATION: Primer

<400> SEQUENCE: 117
aaaaacgact cttcccgatt        20

<210> SEQ ID NO 118
<211> LENGTH: 36
<212> TYPE: DNA
<213> ORGANISM: Artificial
<220> FEATURE:
<223> OTHER INFORMATION: Molecular Beacon Probe

<400> SEQUENCE: 118
cgacatgcga gggacgggat gggttttttgc atgtcg        36

<210> SEQ ID NO 119
<211> LENGTH: 20
<212> TYPE: DNA

<213> ORGANISM: Artificial
<220> FEATURE:
<223> OTHER INFORMATION: Primer

<400> SEQUENCE: 119
gactcttccc gattacaacg					20

<210> SEQ ID NO 120
<211> LENGTH: 37
<212> TYPE: DNA
<213> ORGANISM: Artificial
<220> FEATURE:
<223> OTHER INFORMATION: Molecular Beacon Probe

<400> SEQUENCE: 120
cgacatgcga gggacgggat gggtttttgg catgtcg					37

<210> SEQ ID NO 121
<211> LENGTH: 19
<212> TYPE: DNA
<213> ORGANISM: Artificial
<220> FEATURE:
<223> OTHER INFORMATION: Primer

<400> SEQUENCE: 121
ttttgcgtta aagggtcgg					19

<210> SEQ ID NO 122
<211> LENGTH: 22
<212> TYPE: DNA
<213> ORGANISM: Artificial
<220> FEATURE:
<223> OTHER INFORMATION: Primer

<400> SEQUENCE: 122 cgaaaccttaaaaacctcgaca					22

<210> SEQ ID NO 123
<211> LENGTH: 44
<212> TYPE: DNA
<213> ORGANISM: Artificial
<220> FEATURE:
<223> OTHER INFORMATION: Molecular Beacon Probe

<400> SEQUENCE: 123
cgacatgccg gggtttaaaa ggtagtttcg gagttggcat gtcg					44

<210> SEQ ID NO 124
<211> LENGTH: 19
<212> TYPE: DNA
<213> ORGANISM: Artificial
<220> FEATURE:
<223> OTHER INFORMATION: Primer

<400> SEQUENCE: 124
gatgtcgttg cgttcgttt					19

<210> SEQ ID NO 125
<211> LENGTH: 20
<212> TYPE: DNA
<213> ORGANISM: Artificial
<220> FEATURE:
<223> OTHER INFORMATION: Primer

<400> SEQUENCE: 125
ccgaaacctt aaaacctcg					20

<210> SEQ ID NO 126
<211> LENGTH: 41
<212> TYPE: DNA
<213> ORGANISM: Artificial
<220> FEATURE:
<223> OTHER INFORMATION: Molecular Beacon Probe

<400> SEQUENCE: 126
cgacatgccg gcggggtttt aaaggtagtt tcggcatgtc g            41

<210> SEQ ID NO 127
<211> LENGTH: 19
<212> TYPE: DNA
<213> ORGANISM: Artificial
<220> FEATURE:
<223> OTHER INFORMATION: Primer

<400> SEQUENCE: 127
gttttgcgga tgtcgttgc            19

<210> SEQ ID NO 128
<211> LENGTH: 19
<212> TYPE: DNA
<213> ORGANISM: Artificial
<220> FEATURE:
<223> OTHER INFORMATION: Primer

<400> SEQUENCE: 128
tagggttttt gcggatgtc            19

<210> SEQ ID NO 129
<211> LENGTH: 21
<212> TYPE: DNA
<213> ORGANISM: Artificial
<220> FEATURE:
<223> OTHER INFORMATION: Primer

<400> SEQUENCE: 129
tcgagattgt ggagttttcg t            21

<210> SEQ ID NO 130
<211> LENGTH: 20
<212> TYPE: DNA
<213> ORGANISM: Artificial
<220> FEATURE:
<223> OTHER INFORMATION: Primer

<400> SEQUENCE: 130
taaaaacctc gtactccgcc            20

<210> SEQ ID NO 131
<211> LENGTH: 36
<212> TYPE: DNA
<213> ORGANISM: Artificial
<220> FEATURE:
<223> OTHER INFORMATION: Molecular Beacon Probe

<400> SEQUENCE: 131
cgacatcggt ttgggaggtc gtgtaggacg atgtcg            36

<210> SEQ ID NO 132
<211> LENGTH: 23
<212> TYPE: DNA
<213> ORGANISM: Artificial
<220> FEATURE:

<223> OTHER INFORMATION: Primer

<400> SEQUENCE: 132
gtaacccaat cctaaactac cga                                              23

<210> SEQ ID NO 133
<211> LENGTH: 20
<212> TYPE: DNA
<213> ORGANISM: Artificial
<220> FEATURE:
<223> OTHER INFORMATION: Primer

<400> SEQUENCE: 133
ggtttgtatt cggattcggt                                                  20

<210> SEQ ID NO 134
<211> LENGTH: 20
<212> TYPE: DNA
<213> ORGANISM: Artificial
<220> FEATURE:
<223> OTHER INFORMATION: Primer

<400> SEQUENCE: 134
acccttcgat aacaacgtcc                                                  20

<210> SEQ ID NO 135
<211> LENGTH: 42
<212> TYPE: DNA
<213> ORGANISM: Artificial
<220> FEATURE:
<223> OTHER INFORMATION: Molecular Beacon Probe

<400> SEQUENCE: 135
cgacatgccg tatttatcga aggtgggttt gcgggcatgt cg                          42

<210> SEQ ID NO 136
<211> LENGTH: 22
<212> TYPE: DNA
<213> ORGANISM: Artificial
<220> FEATURE:
<223> OTHER INFORMATION: Primer

<400> SEQUENCE: 136
gtttcgagat tgtggagttt tc                                               22

<210> SEQ ID NO 137
<211> LENGTH: 22
<212> TYPE: DNA
<213> ORGANISM: Artificial
<220> FEATURE:
<223> OTHER INFORMATION: Primer

<400> SEQUENCE: 137
gataacaacg tcctacacga cc                                               22

<210> SEQ ID NO 138
<211> LENGTH: 39
<212> TYPE: DNA
<213> ORGANISM: Artificial
<220> FEATURE:
<223> OTHER INFORMATION: Molecular Beacon Probe

<400> SEQUENCE: 138
cgacatgccg aaggtgggtt tgcggtttgg ggcatgtcg                              39

```
<210> SEQ ID NO 139
<211> LENGTH: 19
<212> TYPE: DNA
<213> ORGANISM: Artificial
<220> FEATURE:
<223> OTHER INFORMATION: Primer

<400> SEQUENCE: 139
ttattcgttt cgtttcggg                                                    19

<210> SEQ ID NO 140
<211> LENGTH: 22
<212> TYPE: DNA
<213> ORGANISM: Artificial
<220> FEATURE:
<223> OTHER INFORMATION: Primer

<400> SEQUENCE: 140
aaacccacct tcgataaata cg                                                22

<210> SEQ ID NO 141
<211> LENGTH: 38
<212> TYPE: DNA
<213> ORGANISM: Artificial
<220> FEATURE:
<223> OTHER INFORMATION: Molecular Beacon Probe

<400> SEQUENCE: 141
cgacatcgtt tttggtaggg aggttcggat cgatgtcg                               38

<210> SEQ ID NO 142
<211> LENGTH: 23
<212> TYPE: DNA
<213> ORGANISM: Artificial
<220> FEATURE:
<223> OTHER INFORMATION: Primer

<400> SEQUENCE: 142
cggggtgtta tttaggttta ttc                                               23

<210> SEQ ID NO 143
<211> LENGTH: 23
<212> TYPE: DNA
<213> ORGANISM: Artificial
<220> FEATURE:
<223> OTHER INFORMATION: Primer

<400> SEQUENCE: 143
aatacgaaaa ctccacaatc tcg                                               23

<210> SEQ ID NO 144
<211> LENGTH: 40
<212> TYPE: DNA
<213> ORGANISM: Artificial
<220> FEATURE:
<223> OTHER INFORMATION: Molecular Beacon Probe

<400> SEQUENCE: 144
cgacatgcgt ttttggtagg gaggttcgga tcgcatgtcg                             40

<210> SEQ ID NO 145
<211> LENGTH: 20
<212> TYPE: DNA
<213> ORGANISM: Artificial
<220> FEATURE:
<223> OTHER INFORMATION: Primer
```

<400> SEQUENCE: 145 cgttttggt agggaggttc                                                  20

<210> SEQ ID NO 146
<211> LENGTH: 19
<212> TYPE: DNA
<213> ORGANISM: Artificial
<220> FEATURE:
<223> OTHER INFORMATION: Primer

<400> SEQUENCE: 146
atccgaatac aaacccgca                                                  19

<210> SEQ ID NO 147
<211> LENGTH: 44
<212> TYPE: DNA
<213> ORGANISM: Artificial
<220> FEATURE:
<223> OTHER INFORMATION: Molecular Beacon Probe

<400> SEQUENCE: 147
cgacatgccg tgggggagga tgaggggagc gtttcggcat gtcg                       44

<210> SEQ ID NO 148
<211> LENGTH: 19
<212> TYPE: DNA
<213> ORGANISM: Artificial
<220> FEATURE:
<223> OTHER INFORMATION: Primer

<400> SEQUENCE: 148
aaacccgcac cctacgaaa                                                  19

<210> SEQ ID NO 149
<211> LENGTH: 22
<212> TYPE: DNA
<213> ORGANISM: Artificial
<220> FEATURE:
<223> OTHER INFORMATION: Primer

<400> SEQUENCE: 149
attagtgtag ttagacgggc gg                                              22

<210> SEQ ID NO 150
<211> LENGTH: 20
<212> TYPE: DNA
<213> ORGANISM: Artificial
<220> FEATURE:
<223> OTHER INFORMATION: Primer

<400> SEQUENCE: 150
gactcaacca ccaaacacga                                                 20

<210> SEQ ID NO 151
<211> LENGTH: 33
<212> TYPE: DNA
<213> ORGANISM: Artificial
<220> FEATURE:
<223> OTHER INFORMATION: Molecular Beacon Probe

<400> SEQUENCE: 151
cgacatgcgt gggtttcggg gagtcgcatg tcg                                  33

<210> SEQ ID NO 152
<211> LENGTH: 22

```
<212> TYPE: DNA
<213> ORGANISM: Artificial
<220> FEATURE:
<223> OTHER INFORMATION: Primer

<400> SEQUENCE: 152
aaactacgaa acctcaacga cc                                          22

<210> SEQ ID NO 153
<211> LENGTH: 30
<212> TYPE: DNA
<213> ORGANISM: Artificial
<220> FEATURE:
<223> OTHER INFORMATION: Molecular Beacon Probe

<400> SEQUENCE: 153
cgacatgcgg tggcggtggg tcgcatgtcg                                  30

<210> SEQ ID NO 154
<211> LENGTH: 20
<212> TYPE: DNA
<213> ORGANISM: Artificial
<220> FEATURE:
<223> OTHER INFORMATION: Primer

<400> SEQUENCE: 154
gttacgggag ttttgcgttt                                             20

<210> SEQ ID NO 155
<211> LENGTH: 19
<212> TYPE: DNA
<213> ORGANISM: Artificial
<220> FEATURE:
<223> OTHER INFORMATION: Primer

<400> SEQUENCE: 155
cgattcctct ccctcgaat                                              19

<210> SEQ ID NO 156
<211> LENGTH: 38
<212> TYPE: DNA
<213> ORGANISM: Artificial
<220> FEATURE:
<223> OTHER INFORMATION: Molecular Beacon Probe

<400> SEQUENCE: 156
cgacatgcga gtttatgtcg ggtaggtgtc gcatgtcg                         38

<210> SEQ ID NO 157
<211> LENGTH: 23
<212> TYPE: DNA
<213> ORGANISM: Artificial
<220> FEATURE:
<223> OTHER INFORMATION: Primer

<400> SEQUENCE: 157
aatcgtgttt cgttcgtatt ttc                                         23

<210> SEQ ID NO 158
<211> LENGTH: 19
<212> TYPE: DNA
<213> ORGANISM: Artificial
<220> FEATURE:
<223> OTHER INFORMATION: Primer

<400> SEQUENCE: 158
```
gatatactcc gaacccgcc                                                        19

<210> SEQ ID NO 159
<211> LENGTH: 40
<212> TYPE: DNA
<213> ORGANISM: Artificial
<220> FEATURE:
<223> OTHER INFORMATION: Molecular Beacon Probe

<400> SEQUENCE: 159
cgacatgcgc ggagtagttt cgtaggttgc gggcatgtcg                                 40

<210> SEQ ID NO 160
<211> LENGTH: 22
<212> TYPE: DNA
<213> ORGANISM: Artificial
<220> FEATURE:
<223> OTHER INFORMATION: Primer

<400> SEQUENCE: 160
gcgatttagg ttagggaatc gt                                                    22

<210> SEQ ID NO 161
<211> LENGTH: 41
<212> TYPE: DNA
<213> ORGANISM: Artificial
<220> FEATURE:
<223> OTHER INFORMATION: Molecular Beacon Probe

<400> SEQUENCE: 161
cgacatgccg gtgagggttg tatggaggcg tcggcatgtc g                               41

<210> SEQ ID NO 162
<211> LENGTH: 20
<212> TYPE: DNA
<213> ORGANISM: Artificial
<220> FEATURE:
<223> OTHER INFORMATION: Primer

<400> SEQUENCE: 162
tttcggtggg gttttagtc                                                        20

<210> SEQ ID NO 163
<211> LENGTH: 22
<212> TYPE: DNA
<213> ORGANISM: Artificial
<220> FEATURE:
<223> OTHER INFORMATION: Primer

<400> SEQUENCE: 163
gattccctaa cctaaatcgc ct                                                    22

<210> SEQ ID NO 164
<211> LENGTH: 44
<212> TYPE: DNA
<213> ORGANISM: Artificial
<220> FEATURE:
<223> OTHER INFORMATION: Molecular Beacon Probe

<400> SEQUENCE: 164
cgacatgcgc gttagaaatg cgtgtgggta ggaggcgcat gtcg                            44

<210> SEQ ID NO 165
<211> LENGTH: 21
<212> TYPE: DNA
<213> ORGANISM: Artificial

```
<220> FEATURE:
<223> OTHER INFORMATION: Primer

<400> SEQUENCE: 165
atttcggtgg ggtttttagt c                                              21

<210> SEQ ID NO 166
<211> LENGTH: 19
<212> TYPE: DNA
<213> ORGANISM: Artificial
<220> FEATURE:
<223> OTHER INFORMATION: Primer

<400> SEQUENCE: 166
cacacgcatt tctaacgcc                                                 19

<210> SEQ ID NO 167
<211> LENGTH: 39
<212> TYPE: DNA
<213> ORGANISM: Artificial
<220> FEATURE:
<223> OTHER INFORMATION: Molecular Beacon Probe

<400> SEQUENCE: 167
cgacatgcct cttcccgaat ccccgaaaac cgcatgtcg                           39

<210> SEQ ID NO 168
<211> LENGTH: 19
<212> TYPE: DNA
<213> ORGANISM: Artificial
<220> FEATURE:
<223> OTHER INFORMATION: Primer

<400> SEQUENCE: 168
gggttttatc gtcgcgtgt                                                 19

<210> SEQ ID NO 169
<211> LENGTH: 23
<212> TYPE: DNA
<213> ORGANISM: Artificial
<220> FEATURE:
<223> OTHER INFORMATION: Primer

<400> SEQUENCE: 169
ccgaaaacta acctaaaaac gaa                                            23

<210> SEQ ID NO 170
<211> LENGTH: 33
<212> TYPE: DNA
<213> ORGANISM: Artificial
<220> FEATURE:
<223> OTHER INFORMATION: Molecular Beacon Probe

<400> SEQUENCE: 170
cgacatgccc cgaccccgct caccggcatg tcg                                 33

<210> SEQ ID NO 171
<211> LENGTH: 20
<212> TYPE: DNA
<213> ORGANISM: Artificial
<220> FEATURE:
<223> OTHER INFORMATION: Primer

<400> SEQUENCE: 171
ggggtttacg gggtttttatc                                               20
```

```
<210> SEQ ID NO 172
<211> LENGTH: 23
<212> TYPE: DNA
<213> ORGANISM: Artificial
<220> FEATURE:
<223> OTHER INFORMATION: Primer

<400> SEQUENCE: 172
cgaaaactaa cctaaaaacg aac                                            23

<210> SEQ ID NO 173
<211> LENGTH: 38
<212> TYPE: DNA
<213> ORGANISM: Artificial
<220> FEATURE:
<223> OTHER INFORMATION: Molecular Beacon Probe

<400> SEQUENCE: 173
cgacatgcga taatcccgac cccgctcacc gcatgtcg                            38

<210> SEQ ID NO 174
<211> LENGTH: 23
<212> TYPE: DNA
<213> ORGANISM: Artificial
<220> FEATURE:
<223> OTHER INFORMATION: Primer

<400> SEQUENCE: 174
ttgtttagaa atcgaggaaa tcg                                            23

<210> SEQ ID NO 175
<211> LENGTH: 19
<212> TYPE: DNA
<213> ORGANISM: Artificial
<220> FEATURE:
<223> OTHER INFORMATION: Primer

<400> SEQUENCE: 175
cgacgataaa accccgtaa                                                 19

<210> SEQ ID NO 176
<211> LENGTH: 35
<212> TYPE: DNA
<213> ORGANISM: Artificial
<220> FEATURE:
<223> OTHER INFORMATION: Molecular Beacon Probe

<400> SEQUENCE: 176
cgacatgcga gtttcgggtg cggttacgca tgtcg                               35

<210> SEQ ID NO 177
<211> LENGTH: 24
<212> TYPE: DNA
<213> ORGANISM: Artificial
<220> FEATURE:
<223> OTHER INFORMATION: Primer

<400> SEQUENCE: 177
tgtggtttcg tttgtttaga aatc                                           24

<210> SEQ ID NO 178
<211> LENGTH: 40
<212> TYPE: DNA
<213> ORGANISM: Artificial
<220> FEATURE:
<223> OTHER INFORMATION: Molecular Beacon Probe
```

```
<400> SEQUENCE: 178
cgacatgcga gtttcgggtg cggttacgta acgcatgtcg                           40

<210> SEQ ID NO 179
<211> LENGTH: 19
<212> TYPE: DNA
<213> ORGANISM: Artificial
<220> FEATURE:
<223> OTHER INFORMATION: Primer

<400> SEQUENCE: 179
cccgtaaacc ccctcgtta                                                  19

<210> SEQ ID NO 180
<211> LENGTH: 42
<212> TYPE: DNA
<213> ORGANISM: Artificial
<220> FEATURE:
<223> OTHER INFORMATION: Molecular Beacon Probe

<400> SEQUENCE: 180
cgacatgccg cggggttttc gttagtgtat ttcggcatgt cg                        42

<210> SEQ ID NO 181
<211> LENGTH: 25
<212> TYPE: DNA
<213> ORGANISM: Artificial
<220> FEATURE:
<223> OTHER INFORMATION: Primer

<400> SEQUENCE: 181
cgtttgttta gaaatcgagg aaatc                                           25

<210> SEQ ID NO 182
<211> LENGTH: 21
<212> TYPE: DNA
<213> ORGANISM: Artificial
<220> FEATURE:
<223> OTHER INFORMATION: Primer

<400> SEQUENCE: 182
cataaaaacg accgactcga a                                               21

<210> SEQ ID NO 183
<211> LENGTH: 44
<212> TYPE: DNA
<213> ORGANISM: Artificial
<220> FEATURE:
<223> OTHER INFORMATION: Molecular Beacon Probe

<400> SEQUENCE: 183
cgacatgcgg ggttttcgtt agtgtatttc gttttagcat gtcg                      44

<210> SEQ ID NO 184
<211> LENGTH: 25
<212> TYPE: DNA
<213> ORGANISM: Artificial
<220> FEATURE:
<223> OTHER INFORMATION: Primer

<400> SEQUENCE: 184
ttcgtatttc gttatttatt cggtt                                           25

<210> SEQ ID NO 185
```

```
<211> LENGTH: 20
<212> TYPE: DNA
<213> ORGANISM: Artificial
<220> FEATURE:
<223> OTHER INFORMATION: Primer

<400> SEQUENCE: 185
gaaactataa aaccccccgca                                                20

<210> SEQ ID NO 186
<211> LENGTH: 45
<212> TYPE: DNA
<213> ORGANISM: Artificial
<220> FEATURE:
<223> OTHER INFORMATION: Molecular Beacon Probe

<400> SEQUENCE: 186
cgacatgccg ggttttttcga tggtagcgtt ttgtacggca tgtcg              45

<210> SEQ ID NO 187
<211> LENGTH: 21
<212> TYPE: DNA
<213> ORGANISM: Artificial
<220> FEATURE:
<223> OTHER INFORMATION: Primer

<400> SEQUENCE: 187
cgagttttcg ttaggtcgtt t                                         21

<210> SEQ ID NO 188
<211> LENGTH: 19
<212> TYPE: DNA
<213> ORGANISM: Artificial
<220> FEATURE:
<223> OTHER INFORMATION: Primer

<400> SEQUENCE: 188
actcgactca cacccgaac                                            19

<210> SEQ ID NO 189
<211> LENGTH: 41
<212> TYPE: DNA
<213> ORGANISM: Artificial
<220> FEATURE:
<223> OTHER INFORMATION: Molecular Beacon Probe

<400> SEQUENCE: 189
cgacatgcgt acgtttcggg cgtcggtttt tcggcatgtc g                   41

<210> SEQ ID NO 190
<211> LENGTH: 19
<212> TYPE: DNA
<213> ORGANISM: Artificial
<220> FEATURE:
<223> OTHER INFORMATION: Primer

<400> SEQUENCE: 190
cgcgagtttt cgttaggtc                                            19

<210> SEQ ID NO 191
<211> LENGTH: 23
<212> TYPE: DNA
<213> ORGANISM: Artificial
<220> FEATURE:
<223> OTHER INFORMATION: Primer

<400> SEQUENCE: 191
```

```
cgaacaaata aaacaacatc gaa                                            23

<210> SEQ ID NO 192
<211> LENGTH: 19
<212> TYPE: DNA
<213> ORGANISM: Artificial
<220> FEATURE:
<223> OTHER INFORMATION: Primer

<400> SEQUENCE: 192
tcgggatttt ggaggtttc                                                 19

<210> SEQ ID NO 193
<211> LENGTH: 19
<212> TYPE: DNA
<213> ORGANISM: Artificial
<220> FEATURE:
<223> OTHER INFORMATION: Primer

<400> SEQUENCE: 193
ctacgaatac cgctacgcc                                                 19

<210> SEQ ID NO 194
<211> LENGTH: 43
<212> TYPE: DNA
<213> ORGANISM: Artificial
<220> FEATURE:
<223> OTHER INFORMATION: Molecular Beacon Probe

<400> SEQUENCE: 194
cgacatgcgg gatttcgtcg gtttttttggc gtagggcatg tcg                     43

<210> SEQ ID NO 195
<211> LENGTH: 47
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 195
agcgatgcgt tcgagcatcg cnttttttcga tgttgtttta tttgttc                 47

<210> SEQ ID NO 196
<211> LENGTH: 22
<212> TYPE: DNA
<213> ORGANISM: Artificial
<220> FEATURE:
<223> OTHER INFORMATION: Primer

<400> SEQUENCE: 196
ataactatct acgcccaacc ga                                             22

<210> SEQ ID NO 197
<211> LENGTH: 25
<212> TYPE: DNA
<213> ORGANISM: Artificial
<220> FEATURE:
<223> OTHER INFORMATION: Primer
```

<400> SEQUENCE: 197 ttttcgatg ttgttttatt tgttc                                    25

<210> SEQ ID NO 198
<211> LENGTH: 44
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 198
agcgatgcgt tcgagcatcg cnataactat ctacgcccaa ccga              44

<210> SEQ ID NO 199
<211> LENGTH: 47
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 199
agcgatgcgt tcgagcatcg cnttcgtgta gttttatgta gaggtcg           47

<210> SEQ ID NO 200
<211> LENGTH: 21
<212> TYPE: DNA
<213> ORGANISM: Artificial
<220> FEATURE:
<223> OTHER INFORMATION: Primer

<400> SEQUENCE: 200
gctataacga cgaaactcga a                                       21

<210> SEQ ID NO 201
<211> LENGTH: 25
<212> TYPE: DNA
<213> ORGANISM: Artificial
<220> FEATURE:
<223> OTHER INFORMATION: Primer

<400> SEQUENCE: 201
ttcgtgtagt tttatgtaga ggtcg                                   25

<210> SEQ ID NO 202
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil

```
<220> FEATURE:
<221> NAME/KEY: misc_feature
<222> LOCATION: (22)..(22)
<223> OTHER INFORMATION: n is a, c, g, or t

<400> SEQUENCE: 202
agcgatgcgt tcgagcatcg cngctataac gacgaaactc gaa                43

<210> SEQ ID NO 203
<211> LENGTH: 42
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 203
agcgatgcgt tcgagcatcg cnttaggcgt tagaaatgcg tg                 42

<210> SEQ ID NO 204
<211> LENGTH: 20
<212> TYPE: DNA
<213> ORGANISM: Artificial
<220> FEATURE:
<223> OTHER INFORMATION: Primer

<400> SEQUENCE: 204
caccgaaaat acgaacgaaa                                          20

<210> SEQ ID NO 205
<211> LENGTH: 20
<212> TYPE: DNA
<213> ORGANISM: Artificial
<220> FEATURE:
<223> OTHER INFORMATION: Primer

<400> SEQUENCE: 205
ttaggcgtta gaaatgcgtg                                          20

<210> SEQ ID NO 206
<211> LENGTH: 42
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 206
agcgatgcgt tcgagcatcg cncaccgaaa atacgaacga aa                 42

<210> SEQ ID NO 207
<211> LENGTH: 45
<212> TYPE: DNA
<213> ORGANISM: Artificial
<220> FEATURE:
```

```
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 207
agcgatgcgt tcgagcatcg cnggtcgtta agtttgggtt tattc          45

<210> SEQ ID NO 208
<211> LENGTH: 23
<212> TYPE: DNA
<213> ORGANISM: Artificial
<220> FEATURE:
<223> OTHER INFORMATION: Primer

<400> SEQUENCE: 208
aaaactacat aaaaacgccg cta                                  23

<210> SEQ ID NO 209
<211> LENGTH: 23
<212> TYPE: DNA
<213> ORGANISM: Artificial
<220> FEATURE:
<223> OTHER INFORMATION: Primer

<400> SEQUENCE: 209
ggtcgttaag tttgggttta ttc                                  23

<210> SEQ ID NO 210
<211> LENGTH: 45
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 210
agcgatgcgt tcgagcatcg cnaaaactac ataaaaacgc cgcta          45

<210> SEQ ID NO 211
<211> LENGTH: 19
<212> TYPE: DNA
<213> ORGANISM: Artificial
<220> FEATURE:
<223> OTHER INFORMATION: Primer

<400> SEQUENCE: 211
ataaaaacgc cgctaccgc                                       19

<210> SEQ ID NO 212
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
```

<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 212
agcgatgcgt tcgagcatcg cnataaaaac gccgctaccg c          41

<210> SEQ ID NO 213
<211> LENGTH: 45
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 213
agcgatgcgt tcgagcatcg cncgttaagt ttgggtttat tcggt          45

<210> SEQ ID NO 214
<211> LENGTH: 19
<212> TYPE: DNA
<213> ORGANISM: Artificial
<220> FEATURE:
<223> OTHER INFORMATION: Primer

<400> SEQUENCE: 214
ctaccgcgaa acaactccg          19

<210> SEQ ID NO 215
<211> LENGTH: 23
<212> TYPE: DNA
<213> ORGANISM: Artificial
<220> FEATURE:
<223> OTHER INFORMATION: Primer

<400> SEQUENCE: 215
cgttaagttt gggtttattc ggt          23

<210> SEQ ID NO 216
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 216
agcgatgcgt tcgagcatcg cnctaccgcg aaacaactcc g          41

<210> SEQ ID NO 217
<211> LENGTH: 44
<212> TYPE: DNA

```
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 217
agcgatgcgt tcgagcatcg cngtttagaa atcgaggaaa tcgc          44

<210> SEQ ID NO 218
<211> LENGTH: 21
<212> TYPE: DNA
<213> ORGANISM: Artificial
<220> FEATURE:
<223> OTHER INFORMATION: Primer

<400> SEQUENCE: 218
gacttccata aaaacgaccg a          21

<210> SEQ ID NO 219
<211> LENGTH: 22
<212> TYPE: DNA
<213> ORGANISM: Artificial
<220> FEATURE:
<223> OTHER INFORMATION: Primer

<400> SEQUENCE: 219
gtttagaaat cgaggaaatc gc          22

<210> SEQ ID NO 220
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 220
agcgatgcgt tcgagcatcg cngacttcca taaaaacgac cga          43

<210> SEQ ID NO 221
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 221
agcgatgcgt tcgagcatcg cncataaaaa cgaccgactc gaa          43
```

<210> SEQ ID NO 222
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 222
agcgatgcgt tcgagcatcg cntttgcgtg gtcgtaaggt c                41

<210> SEQ ID NO 223
<211> LENGTH: 19
<212> TYPE: DNA
<213> ORGANISM: Artificial
<220> FEATURE:
<223> OTHER INFORMATION: Primer

<400> SEQUENCE: 223
aaataaaccc cgaaccgaa                                         19

<210> SEQ ID NO 224
<211> LENGTH: 19
<212> TYPE: DNA
<213> ORGANISM: Artificial
<220> FEATURE:
<223> OTHER INFORMATION: Primer

<400> SEQUENCE: 224
tttgcgtggt cgtaaggtc                                         19

<210> SEQ ID NO 225
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 225
agcgatgcgt tcgagcatcg cnaaataaac cccgaaccga a                41

<210> SEQ ID NO 226
<211> LENGTH: 45
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)

<223> OTHER INFORMATION: n is a, c, g, or t

<400> SEQUENCE: 226
agcgatgcgt tcgagcatcg cncggggttt tcgttagtgt atttc        45

<210> SEQ ID NO 227
<211> LENGTH: 22
<212> TYPE: DNA
<213> ORGANISM: Artificial
<220> FEATURE:
<223> OTHER INFORMATION: Primer

<400> SEQUENCE: 227
aaaccgactt ccataaaaac ga        22

<210> SEQ ID NO 228
<211> LENGTH: 23
<212> TYPE: DNA
<213> ORGANISM: Artificial
<220> FEATURE:
<223> OTHER INFORMATION: Primer

<400> SEQUENCE: 228
cggggttttc gttagtgtat ttc        23

<210> SEQ ID NO 229
<211> LENGTH: 44
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 229
agcgatgcgt tcgagcatcg cnaaaccgac ttccataaaa acga        44

<210> SEQ ID NO 230
<211> LENGTH: 24
<212> TYPE: DNA
<213> ORGANISM: Artificial
<220> FEATURE:
<223> OTHER INFORMATION: Primer

<400> SEQUENCE: 230
gtgttaagag tgcgtagtaa gacg        24

<210> SEQ ID NO 231
<211> LENGTH: 21
<212> TYPE: DNA
<213> ORGANISM: Artificial
<220> FEATURE:
<223> OTHER INFORMATION: Primer

<400> SEQUENCE: 231
gaaacgaacg tacaaaaacg a        21

<210> SEQ ID NO 232
<211> LENGTH: 47
<212> TYPE: DNA
<213> ORGANISM: Artificial

```
<220> FEATURE:
<223> OTHER INFORMATION: Molecular Beacon Probe

<400> SEQUENCE: 232
cgacatgccg aaactataaa tcaactacga aacaaacgcg catgtcg          47

<210> SEQ ID NO 233
<211> LENGTH: 23
<212> TYPE: DNA
<213> ORGANISM: Artificial
<220> FEATURE:
<223> OTHER INFORMATION: Primer

<400> SEQUENCE: 233
ttaagtaaac gttgggtaga ggc                                    23

<210> SEQ ID NO 234
<211> LENGTH: 20
<212> TYPE: DNA
<213> ORGANISM: Artificial
<220> FEATURE:
<223> OTHER INFORMATION: Primer

<400> SEQUENCE: 234
ctcgataact tttccgacga                                        20

<210> SEQ ID NO 235
<211> LENGTH: 38
<212> TYPE: DNA
<213> ORGANISM: Artificial
<220> FEATURE:
<223> OTHER INFORMATION: Molecular Beacon Probe

<400> SEQUENCE: 235
cgacatgccg aggagggaa cgggttgttg gcatgtcg                     38

<210> SEQ ID NO 236
<211> LENGTH: 22
<212> TYPE: DNA
<213> ORGANISM: Artificial
<220> FEATURE:
<223> OTHER INFORMATION: Primer

<400> SEQUENCE: 236
tgttcgttcg ttcgtaaagt tc                                     22

<210> SEQ ID NO 237
<211> LENGTH: 23
<212> TYPE: DNA
<213> ORGANISM: Artificial
<220> FEATURE:
<223> OTHER INFORMATION: Primer

<400> SEQUENCE: 237
tacaatttcc cgtcttacta cgc                                    23

<210> SEQ ID NO 238
<211> LENGTH: 42
<212> TYPE: DNA
<213> ORGANISM: Artificial
<220> FEATURE:
<223> OTHER INFORMATION: Molecular Beacon Probe

<400> SEQUENCE: 238
cgacatgcgc ggtcgttttt tttcgggatt gaaggcatgt cg               42
```

```
<210> SEQ ID NO 239
<211> LENGTH: 21
<212> TYPE: DNA
<213> ORGANISM: Artificial
<220> FEATURE:
<223> OTHER INFORMATION: Primer

<400> SEQUENCE: 239
cacaacccga actttacgaa c                                              21

<210> SEQ ID NO 240
<211> LENGTH: 37
<212> TYPE: DNA
<213> ORGANISM: Artificial
<220> FEATURE:
<223> OTHER INFORMATION: Molecular Beacon Probe

<400> SEQUENCE: 240
cgacatgcgc ggggtacgga gtttcggtcg catgtcg                              37

<210> SEQ ID NO 241
<211> LENGTH: 21
<212> TYPE: DNA
<213> ORGANISM: Artificial
<220> FEATURE:
<223> OTHER INFORMATION: Primer

<400> SEQUENCE: 241
acgttgggta gaggcggtat c                                              21

<210> SEQ ID NO 242
<211> LENGTH: 22
<212> TYPE: DNA
<213> ORGANISM: Artificial
<220> FEATURE:
<223> OTHER INFORMATION: Primer

<400> SEQUENCE: 242 ataactttc cgacgaacga ac                                              22

<210> SEQ ID NO 243
<211> LENGTH: 38
<212> TYPE: DNA
<213> ORGANISM: Artificial
<220> FEATURE:
<223> OTHER INFORMATION: Molecular Beacon Probe

<400> SEQUENCE: 243
cgacatgcac ccatcccgac taaacgcgac gcatgtcg                             38

<210> SEQ ID NO 244
<211> LENGTH: 22
<212> TYPE: DNA
<213> ORGANISM: Artificial
<220> FEATURE:
<223> OTHER INFORMATION: Primer

<400> SEQUENCE: 244
gtatagtacg gggttcgttc gt                                             22

<210> SEQ ID NO 245
<211> LENGTH: 19
<212> TYPE: DNA
<213> ORGANISM: Artificial
<220> FEATURE:
<223> OTHER INFORMATION: Primer
```

```
<400> SEQUENCE: 245
actcgtaaaa cccttcgcc                                                19

<210> SEQ ID NO 246
<211> LENGTH: 35
<212> TYPE: DNA
<213> ORGANISM: Artificial
<220> FEATURE:
<223> OTHER INFORMATION: Molecular Beacon Probe

<400> SEQUENCE: 246
cgacatgcgg tagggcgcga gtagagcgca tgtcg                              35

<210> SEQ ID NO 247
<211> LENGTH: 19
<212> TYPE: DNA
<213> ORGANISM: Artificial
<220> FEATURE:
<223> OTHER INFORMATION: Primer

<400> SEQUENCE: 247
ggtagaggcg gtatcgagg                                                19

<210> SEQ ID NO 248
<211> LENGTH: 37
<212> TYPE: DNA
<213> ORGANISM: Artificial
<220> FEATURE:
<223> OTHER INFORMATION: Molecular Beacon Probe

<400> SEQUENCE: 248
cgacatgcgg gatgggttgc gaagttgtcg catgtcg                            37

<210> SEQ ID NO 249
<211> LENGTH: 19
<212> TYPE: DNA
<213> ORGANISM: Artificial
<220> FEATURE:
<223> OTHER INFORMATION: Primer

<400> SEQUENCE: 249
acgttgggta gaggcggta                                                19

<210> SEQ ID NO 250
<211> LENGTH: 34
<212> TYPE: DNA
<213> ORGANISM: Artificial
<220> FEATURE:
<223> OTHER INFORMATION: Molecular Beacon Probe

<400> SEQUENCE: 250
cgacacgcgt ttagtcggga tgggttgcgt gtcg                               34

<210> SEQ ID NO 251
<211> LENGTH: 19
<212> TYPE: DNA
<213> ORGANISM: Artificial
<220> FEATURE:
<223> OTHER INFORMATION: Primer

<400> SEQUENCE: 251
cggtatcgag gaggggaac                                                19

<210> SEQ ID NO 252
```

```
<211> LENGTH: 19
<212> TYPE: DNA
<213> ORGANISM: Artificial
<220> FEATURE:
<223> OTHER INFORMATION: Primer

<400> SEQUENCE: 252
aaatccgaca acttcgcaa                                                  19

<210> SEQ ID NO 253
<211> LENGTH: 44
<212> TYPE: DNA
<213> ORGANISM: Artificial
<220> FEATURE:
<223> OTHER INFORMATION: Molecular Beacon Probe

<400> SEQUENCE: 253
cgacatgcgt tgttgtattt tcggtcgcgt ttagtcgcat gtcg                       44

<210> SEQ ID NO 254
<211> LENGTH: 40
<212> TYPE: DNA
<213> ORGANISM: Artificial
<220> FEATURE:
<223> OTHER INFORMATION: Molecular Beacon Probe

<400> SEQUENCE: 254
cgacatgccg ggttgttgta ttttcggtcg cggcatgtcg                            40

<210> SEQ ID NO 255
<211> LENGTH: 20
<212> TYPE: DNA
<213> ORGANISM: Artificial
<220> FEATURE:
<223> OTHER INFORMATION: Primer

<400> SEQUENCE: 255
taggtaggta ggtcgggggc                                                 20

<210> SEQ ID NO 256
<211> LENGTH: 21
<212> TYPE: DNA
<213> ORGANISM: Artificial
<220> FEATURE:
<223> OTHER INFORMATION: Primer

<400> SEQUENCE: 256
cgaaaataca acaacccgtt c                                               21

<210> SEQ ID NO 257
<211> LENGTH: 35
<212> TYPE: DNA
<213> ORGANISM: Artificial
<220> FEATURE:
<223> OTHER INFORMATION: Molecular Beacon Probe

<400> SEQUENCE: 257
cgacatgcgt tgggtagagg cggtatcgca tgtcg                                35

<210> SEQ ID NO 258
<211> LENGTH: 18
<212> TYPE: DNA
<213> ORGANISM: Artificial
<220> FEATURE:
<223> OTHER INFORMATION: Primer

<400> SEQUENCE: 258
```
ttcgtgcgtt tttggtcg                                                         18

<210> SEQ ID NO 259
<211> LENGTH: 19
<212> TYPE: DNA
<213> ORGANISM: Artificial
<220> FEATURE:
<223> OTHER INFORMATION: Primer

<400> SEQUENCE: 259
cgaactttac gaacgaacg                                                        19

<210> SEQ ID NO 260
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 260
agcgatgcgt tcgagcatcg cnagagtgcg tagtaagacg gga                             43

<210> SEQ ID NO 261
<211> LENGTH: 21
<212> TYPE: DNA
<213> ORGANISM: Artificial
<220> FEATURE:
<223> OTHER INFORMATION: Primer

<400> SEQUENCE: 261
acgtacaaaa acgacccgaa c                                                     21

<210> SEQ ID NO 262
<211> LENGTH: 21
<212> TYPE: DNA
<213> ORGANISM: Artificial
<220> FEATURE:
<223> OTHER INFORMATION: Primer

<400> SEQUENCE: 262
agagtgcgta gtaagacggg a                                                     21

<210> SEQ ID NO 263
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 263
agcgatgcgt tcgagcatcg cnacgtacaa aaacgacccg aac                             43

<210> SEQ ID NO 264
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 264
agcgatgcgt tcgagcatcg cngcgtagcg ttgtttttgt ttc                43

<210> SEQ ID NO 265
<211> LENGTH: 21
<212> TYPE: DNA
<213> ORGANISM: Artificial
<220> FEATURE:
<223> OTHER INFORMATION: Primer

<400> SEQUENCE: 265
cgacttacct ctaattccgc c                                        21

<210> SEQ ID NO 266
<211> LENGTH: 21
<212> TYPE: DNA
<213> ORGANISM: Artificial
<220> FEATURE:
<223> OTHER INFORMATION: Primer

<400> SEQUENCE: 266
gcgtagcgtt gttttgtttt c                                        21

<210> SEQ ID NO 267
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 267
agcgatgcgt tcgagcatcg cncgacttac ctctaattcc gcc                43

<210> SEQ ID NO 268
<211> LENGTH: 43
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

```
<400> SEQUENCE: 268
agcgatgcgt tcgagcatcg cngaaacgaa cgtacaaaaa cga                    43

<210> SEQ ID NO 269
<211> LENGTH: 19
<212> TYPE: DNA
<213> ORGANISM: Artificial
<220> FEATURE:
<223> OTHER INFORMATION: Primer

<400> SEQUENCE: 269
ctacgaaaca aacgcgaaa                                               19

<210> SEQ ID NO 270
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 270
agcgatgcgt tcgagcatcg cnctacgaaa caaacgcgaa a                      41

<210> SEQ ID NO 271
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 271
agcgatgcgt tcgagcatcg cncgaggatt tttcgagcgt c                      41

<210> SEQ ID NO 272
<211> LENGTH: 19
<212> TYPE: DNA
<213> ORGANISM: Artificial
<220> FEATURE:
<223> OTHER INFORMATION: Primer

<400> SEQUENCE: 272
ataccgcctc tacccaacg                                               19

<210> SEQ ID NO 273
<211> LENGTH: 19
<212> TYPE: DNA
<213> ORGANISM: Artificial
<220> FEATURE:
<223> OTHER INFORMATION: Primer

<400> SEQUENCE: 273
``` cgaggattttt tcgagcgtc                                                19

<210> SEQ ID NO 274
<211> LENGTH: 41
<212> TYPE: DNA
<213> ORGANISM: Artificial
<220> FEATURE:
<223> OTHER INFORMATION: Primer
<220> FEATURE:
<221> NAME/KEY: n
<222> LOCATION: (22)..(22)
<223> OTHER INFORMATION: Where n = Uracil
<220> FEATURE:
<221> NAME/KEY: misc_feature
<222> LOCATION: (22)..(22)
<223> OTHER INFORMATION: n is a, c, g, or t

<400> SEQUENCE: 274
agcgatgcgt tcgagcatcg cnataccgcc tctacccaac g                         41

<210> SEQ ID NO 275
<211> LENGTH: 19
<212> TYPE: DNA
<213> ORGANISM: Artificial
<220> FEATURE:
<223> OTHER INFORMATION: Primer

<400> SEQUENCE: 275
taacgtaaag ggtacgggg                                                  19

<210> SEQ ID NO 276
<211> LENGTH: 23
<212> TYPE: DNA
<213> ORGANISM: Artificial
<220> FEATURE:
<223> OTHER INFORMATION: Primer

<400> SEQUENCE: 276
gtccttctcc tactacctcc gct                                             23

<210> SEQ ID NO 277
<211> LENGTH: 38
<212> TYPE: DNA
<213> ORGANISM: Artificial
<220> FEATURE:
<223> OTHER INFORMATION: Molecular Beacon Probe

<400> SEQUENCE: 277
cgacatgccc cgactcgcct aacctcgcaa gcatgtcg                             38

<210> SEQ ID NO 278
<211> LENGTH: 23
<212> TYPE: DNA
<213> ORGANISM: Artificial
<220> FEATURE:
<223> OTHER INFORMATION: Primer

<400> SEQUENCE: 278
gtagtagttc gcggtagtcg ttt                                             23

<210> SEQ ID NO 279
<211> LENGTH: 19
<212> TYPE: DNA
<213> ORGANISM: Artificial
<220> FEATURE:
<223> OTHER INFORMATION: Primer

<400> SEQUENCE: 279

```
aacgctaaca aacaccgaa                                              19

<210> SEQ ID NO 280
<211> LENGTH: 38
<212> TYPE: DNA
<213> ORGANISM: Artificial
<220> FEATURE:
<223> OTHER INFORMATION: Molecular Beacon Probe

<400> SEQUENCE: 280
cgacatgcgc gggttgtagt tttgtcggcg gcatgtcg                         38

<210> SEQ ID NO 281
<211> LENGTH: 19
<212> TYPE: DNA
<213> ORGANISM: Artificial
<220> FEATURE:
<223> OTHER INFORMATION: Primer

<400> SEQUENCE: 281
ttcgtagtcg ttgaagcgg                                              19

<210> SEQ ID NO 282
<211> LENGTH: 21
<212> TYPE: DNA
<213> ORGANISM: Artificial
<220> FEATURE:
<223> OTHER INFORMATION: Primer

<400> SEQUENCE: 282
gcgaaactcg aaactaaacg a                                           21

<210> SEQ ID NO 283
<211> LENGTH: 36
<212> TYPE: DNA
<213> ORGANISM: Artificial
<220> FEATURE:
<223> OTHER INFORMATION: Molecular Beacon Probe

<400> SEQUENCE: 283
cgacatcggg agtggttgcg aggttaggcg atgtcg                           36

<210> SEQ ID NO 284
<211> LENGTH: 25
<212> TYPE: DNA
<213> ORGANISM: Artificial
<220> FEATURE:
<223> OTHER INFORMATION: Primer

<400> SEQUENCE: 284
gcgtcgtttt agtattttta ggttc                                       25

<210> SEQ ID NO 285
<211> LENGTH: 19
<212> TYPE: DNA
<213> ORGANISM: Artificial
<220> FEATURE:
<223> OTHER INFORMATION: Primer

<400> SEQUENCE: 285
gactactccc tcccccgac                                              19

<210> SEQ ID NO 286
<211> LENGTH: 41
<212> TYPE: DNA
```

```
<213> ORGANISM: Artificial
<220> FEATURE:
<223> OTHER INFORMATION: Molecular Beacon Probe

<400> SEQUENCE: 286
cgacatgcgt tttcgtagtc gttgaagcgg tcggcatgtc g                41

<210> SEQ ID NO 287
<211> LENGTH: 19
<212> TYPE: DNA
<213> ORGANISM: Artificial
<220> FEATURE:
<223> OTHER INFORMATION: Primer

<400> SEQUENCE: 287
gttttcgcgt cgttcgttt                                         19

<210> SEQ ID NO 288
<211> LENGTH: 41
<212> TYPE: DNA
<213> ORGANISM: Artificial
<220> FEATURE:
<223> OTHER INFORMATION: Molecular Beacon Probe

<400> SEQUENCE: 288
cgacatgcgg ttcggcggta gttttcgtag tcggcatgtc g                41

<210> SEQ ID NO 289
<211> LENGTH: 23
<212> TYPE: DNA
<213> ORGANISM: Artificial
<220> FEATURE:
<223> OTHER INFORMATION: Primer

<400> SEQUENCE: 289
gggtacgggg ttatatttat cgt                                    23

<210> SEQ ID NO 290
<211> LENGTH: 20
<212> TYPE: DNA
<213> ORGANISM: Artificial
<220> FEATURE:
<223> OTHER INFORMATION: Primer

<400> SEQUENCE: 290
ctaccgccta cttctcgtcc                                        20

<210> SEQ ID NO 291
<211> LENGTH: 27
<212> TYPE: DNA
<213> ORGANISM: Artificial
<220> FEATURE:
<223> OTHER INFORMATION: Molecular Beacon Probe

<400> SEQUENCE: 291
cgacatcggg acgaggcggc gatgtcg                                27

<210> SEQ ID NO 292
<211> LENGTH: 40
<212> TYPE: DNA
<213> ORGANISM: Artificial
<220> FEATURE:
<223> OTHER INFORMATION: Molecular Beacon Probe

<400> SEQUENCE: 292
cgacatgccc ccgcgcctaa aaaactacta cggcatgtcg                  40
```

<210> SEQ ID NO 293
<211> LENGTH: 24
<212> TYPE: DNA
<213> ORGANISM: Artificial
<220> FEATURE:
<223> OTHER INFORMATION: Primer

<400> SEQUENCE: 293
ggtacggggt tatatttatc gttg                                          24

<210> SEQ ID NO 294
<211> LENGTH: 20
<212> TYPE: DNA
<213> ORGANISM: Artificial
<220> FEATURE:
<223> OTHER INFORMATION: Primer

<400> SEQUENCE: 294
tctcctacta cctccgctcg                                               20

<210> SEQ ID NO 295
<211> LENGTH: 32
<212> TYPE: DNA
<213> ORGANISM: Artificial
<220> FEATURE:
<223> OTHER INFORMATION: Molecular Beacon Probe

<400> SEQUENCE: 295
cgacatgcct cgtcccgacc ccgcgcatgt cg                                 32

<210> SEQ ID NO 296
<211> LENGTH: 20
<212> TYPE: DNA
<213> ORGANISM: Artificial
<220> FEATURE:
<223> OTHER INFORMATION: Primer

<400> SEQUENCE: 296
gtcgagtcgg ggataagttc                                               20

<210> SEQ ID NO 297
<211> LENGTH: 21
<212> TYPE: DNA
<213> ORGANISM: Artificial
<220> FEATURE:
<223> OTHER INFORMATION: Primer

<400> SEQUENCE: 297
aaaaactact acgcccaacg a                                             21

<210> SEQ ID NO 298
<211> LENGTH: 41
<212> TYPE: DNA
<213> ORGANISM: Artificial
<220> FEATURE:
<223> OTHER INFORMATION: Molecular Beacon Probe

<400> SEQUENCE: 298
cgacatgcgc gggaaagtta acgtaaaggg tacgcatgtc g                       41

<210> SEQ ID NO 299
<211> LENGTH: 20
<212> TYPE: DNA
<213> ORGANISM: Artificial
<220> FEATURE:

<223> OTHER INFORMATION: Primer

<400> SEQUENCE: 299
aaccccgtac cctttacgtt                                              20

<210> SEQ ID NO 300
<211> LENGTH: 41
<212> TYPE: DNA
<213> ORGANISM: Artificial
<220> FEATURE:
<223> OTHER INFORMATION: Molecular Beacon Probe

<400> SEQUENCE: 300
cgacgcgcgt ttttcgtttt tttttgtagg gtttcgcgtc g                      41

<210> SEQ ID NO 301
<211> LENGTH: 19
<212> TYPE: DNA
<213> ORGANISM: Artificial
<220> FEATURE:
<223> OTHER INFORMATION: Primer

<400> SEQUENCE: 301
aaggaaaggt cgagtcggg                                               19

<210> SEQ ID NO 302
<211> LENGTH: 41
<212> TYPE: DNA
<213> ORGANISM: Artificial
<220> FEATURE:
<223> OTHER INFORMATION: Molecular Beacon Probe

<400> SEQUENCE: 302
cgacatgcgt agggtttcgc gggaaagtta acggcatgtc g                      41

<210> SEQ ID NO 303
<211> LENGTH: 23
<212> TYPE: DNA
<213> ORGANISM: Artificial
<220> FEATURE:
<223> OTHER INFORMATION: Primer

<400> SEQUENCE: 303
tataaccccg taccctttac gtt                                          23

<210> SEQ ID NO 304
<211> LENGTH: 40
<212> TYPE: DNA
<213> ORGANISM: Artificial
<220> FEATURE:
<223> OTHER INFORMATION: Molecular Beacon Probe

<400> SEQUENCE: 304
cgacatgcag ttcggagtat acggattcgc gcgcatgtcg                        40

<210> SEQ ID NO 305
<211> LENGTH: 19
<212> TYPE: DNA
<213> ORGANISM: Artificial
<220> FEATURE:
<223> OTHER INFORMATION: Primer

<400> SEQUENCE: 305
ttcgtcggtt atacggagc                                               19

```
<210> SEQ ID NO 306
<211> LENGTH: 20
<212> TYPE: DNA
<213> ORGANISM: Artificial
<220> FEATURE:
<223> OTHER INFORMATION: Primer

<400> SEQUENCE: 306
gacaaaacta caacccgcca                                               20

<210> SEQ ID NO 307
<211> LENGTH: 42
<212> TYPE: DNA
<213> ORGANISM: Artificial
<220> FEATURE:
<223> OTHER INFORMATION: Molecular Beacon Probe

<400> SEQUENCE: 307
cgacatgcgg gagttatgag ttatgaagtc gttcgcatgt cg                       42

<210> SEQ ID NO 308
<211> LENGTH: 21
<212> TYPE: DNA
<213> ORGANISM: Artificial
<220> FEATURE:
<223> OTHER INFORMATION: Primer

<400> SEQUENCE: 308
gaggttttaa gttggcggag c                                             21

<210> SEQ ID NO 309
<211> LENGTH: 21
<212> TYPE: DNA
<213> ORGANISM: Artificial
<220> FEATURE:
<223> OTHER INFORMATION: Primer

<400> SEQUENCE: 309 actcgaaaact aaacgacgcc c                                            21

<210> SEQ ID NO 310
<211> LENGTH: 26
<212> TYPE: DNA
<213> ORGANISM: Artificial
<220> FEATURE:
<223> OTHER INFORMATION: Primer

<400> SEQUENCE: 310
tttaatatgg tgtagtcgtt agcgtc                                        26

<210> SEQ ID NO 311
<211> LENGTH: 19
<212> TYPE: DNA
<213> ORGANISM: Artificial
<220> FEATURE:
<223> OTHER INFORMATION: Primer

<400> SEQUENCE: 311
cccacctacg actaccgcg                                                19

<210> SEQ ID NO 312
<211> LENGTH: 37
<212> TYPE: DNA
<213> ORGANISM: Artificial
<220> FEATURE:
<223> OTHER INFORMATION: Molecular Beacon Probe
```

```
<400> SEQUENCE: 312
cgacatgcac gaaacccgcg aacgacgacg catgtcg                              37

<210> SEQ ID NO 313
<211> LENGTH: 23
<212> TYPE: DNA
<213> ORGANISM: Artificial
<220> FEATURE:
<223> OTHER INFORMATION: Primer

<400> SEQUENCE: 313
ggggtaggtt taattttgac gac                                            23

<210> SEQ ID NO 314
<211> LENGTH: 20
<212> TYPE: DNA
<213> ORGANISM: Artificial
<220> FEATURE:
<223> OTHER INFORMATION: Primer

<400> SEQUENCE: 314
taaaaccgat acaaacgcca                                                20

<210> SEQ ID NO 315
<211> LENGTH: 37
<212> TYPE: DNA
<213> ORGANISM: Artificial
<220> FEATURE:
<223> OTHER INFORMATION: Molecluar Beacon Probe

<400> SEQUENCE: 315
cgacatgcgg ttgggaggac ggtaaggcgg catgtcg                             37

<210> SEQ ID NO 316
<211> LENGTH: 21
<212> TYPE: DNA
<213> ORGANISM: Artificial
<220> FEATURE:
<223> OTHER INFORMATION: Primer

<400> SEQUENCE: 316
tgtagtcgtt agcgtcgtcg t                                              21

<210> SEQ ID NO 317
<211> LENGTH: 21
<212> TYPE: DNA
<213> ORGANISM: Artificial
<220> FEATURE:
<223> OTHER INFORMATION: Primer

<400> SEQUENCE: 317
gaaaaacaac tcaaacccga a                                              21

<210> SEQ ID NO 318
<211> LENGTH: 35
<212> TYPE: DNA
<213> ORGANISM: Artificial
<220> FEATURE:
<223> OTHER INFORMATION: Molecular Beacon Probe

<400> SEQUENCE: 318
cgacatgcac ccgcgaacga cgacgacgca tgtcg                               35

<210> SEQ ID NO 319
<211> LENGTH: 23
```

```
<212> TYPE: DNA
<213> ORGANISM: Artificial
<220> FEATURE:
<223> OTHER INFORMATION: Primer

<400> SEQUENCE: 319
gtaggtttaa ttttgacgac gga                                           23

<210> SEQ ID NO 320
<211> LENGTH: 21
<212> TYPE: DNA
<213> ORGANISM: Artificial
<220> FEATURE:
<223> OTHER INFORMATION: Primer

<400> SEQUENCE: 320
ttaaaaccga tacaaacgcc a                                             21

<210> SEQ ID NO 321
<211> LENGTH: 36
<212> TYPE: DNA
<213> ORGANISM: Artificial
<220> FEATURE:
<223> OTHER INFORMATION: Molecular Beacon Probe

<400> SEQUENCE: 321
cgacatgccc gtacgcctta ccgtcctcgc atgtcg                             36

<210> SEQ ID NO 322
<211> LENGTH: 23
<212> TYPE: DNA
<213> ORGANISM: Artificial
<220> FEATURE:
<223> OTHER INFORMATION: Primer

<400> SEQUENCE: 322
gatatagtag agtcgcggtc gtc                                           23

<210> SEQ ID NO 323
<211> LENGTH: 24
<212> TYPE: DNA
<213> ORGANISM: Artificial
<220> FEATURE:
<223> OTHER INFORMATION: Primer

<400> SEQUENCE: 323
cgattaacta aaattcctcc gaaa                                          24

<210> SEQ ID NO 324
<211> LENGTH: 37
<212> TYPE: DNA
<213> ORGANISM: Artificial
<220> FEATURE:
<223> OTHER INFORMATION: Molecular Beacon Probe

<400> SEQUENCE: 324
cgacatgccc gaaaaacgct cgcgacccag catgtcg                            37

<210> SEQ ID NO 325
<211> LENGTH: 21
<212> TYPE: DNA
<213> ORGANISM: Artificial
<220> FEATURE:
<223> OTHER INFORMATION: Primer

<400> SEQUENCE: 325
```

-continued

```
ggggtagttt aggttcgggt c                                       21

<210> SEQ ID NO 326
<211> LENGTH: 22
<212> TYPE: DNA
<213> ORGANISM: Artificial
<220> FEATURE:
<223> OTHER INFORMATION: Primer

<400> SEQUENCE: 326
atataataca accgccaacg cc                                      22

<210> SEQ ID NO 327
<211> LENGTH: 35
<212> TYPE: DNA
<213> ORGANISM: Artificial
<220> FEATURE:
<223> OTHER INFORMATION: Molecular Beacon Probe

<400> SEQUENCE: 327
cgacatgccc gcaacgcgac aaccgcagca tgtcg                        35

<210> SEQ ID NO 328
<211> LENGTH: 20
<212> TYPE: DNA
<213> ORGANISM: Artificial
<220> FEATURE:
<223> OTHER INFORMATION: Primer

<400> SEQUENCE: 328
gtagtcgtta gcgtcgtcgt                                         20

<210> SEQ ID NO 329
<211> LENGTH: 33
<212> TYPE: DNA
<213> ORGANISM: Artificial
<220> FEATURE:
<223> OTHER INFORMATION: Molecular Beacon Probe

<400> SEQUENCE: 329
cgacatgcgc ggtagtcgta ggtgggcatg tcg                          33

<210> SEQ ID NO 330
<211> LENGTH: 20
<212> TYPE: DNA
<213> ORGANISM: Artificial
<220> FEATURE:
<223> OTHER INFORMATION: Primer

<400> SEQUENCE: 330
gaaaccgtaa ctccacgaac                                         20

<210> SEQ ID NO 331
<211> LENGTH: 36
<212> TYPE: DNA
<213> ORGANISM: Artificial
<220> FEATURE:
<223> OTHER INFORMATION: Molecular Beacon Probe

<400> SEQUENCE: 331
cgacatgcga ggacggtaag gcgtacgggc atgtcg                       36

<210> SEQ ID NO 332
<211> LENGTH: 22
<212> TYPE: DNA
<213> ORGANISM: Artificial
```

```
<220> FEATURE:
<223> OTHER INFORMATION: Primer

<400> SEQUENCE: 332
acccttaaaa ccgatacaaa cg                                              22

<210> SEQ ID NO 333
<211> LENGTH: 23
<212> TYPE: DNA
<213> ORGANISM: Artificial
<220> FEATURE:
<223> OTHER INFORMATION: Primer

<400> SEQUENCE: 333
tacggtttaa tcggaggacg tag                                             23

<210> SEQ ID NO 334
<211> LENGTH: 21
<212> TYPE: DNA
<213> ORGANISM: Artificial
<220> FEATURE:
<223> OTHER INFORMATION: Primer

<400> SEQUENCE: 334
aacgaaaata aataccgcga a                                               21

<210> SEQ ID NO 335
<211> LENGTH: 35
<212> TYPE: DNA
<213> ORGANISM: Artificial
<220> FEATURE:
<223> OTHER INFORMATION: Molecular Beacon Probe

<400> SEQUENCE: 335
cgacatgcgg gcgcgatcgg aagtacggca tgtcg                                35

<210> SEQ ID NO 336
<211> LENGTH: 20
<212> TYPE: DNA
<213> ORGANISM: Artificial
<220> FEATURE:
<223> OTHER INFORMATION: Primer

<400> SEQUENCE: 336
aataaatacc gcgaaccgaa                                                 20

<210> SEQ ID NO 337
<211> LENGTH: 19
<212> TYPE: DNA
<213> ORGANISM: Artificial
<220> FEATURE:
<223> OTHER INFORMATION: Primer

<400> SEQUENCE: 337
gaaccgaacc gaaacgaaa                                                  19

<210> SEQ ID NO 338
<211> LENGTH: 35
<212> TYPE: DNA
<213> ORGANISM: Artificial
<220> FEATURE:
<223> OTHER INFORMATION: Molecular Beacon Probe

<400> SEQUENCE: 338
cgacatgcgc ggtcgtcggc ggttttggca tgtcg                                35
```

<210> SEQ ID NO 339
<211> LENGTH: 23
<212> TYPE: DNA
<213> ORGANISM: Artificial
<220> FEATURE:
<223> OTHER INFORMATION: Primer

<400> SEQUENCE: 339
tgtaattcgg ttttagattt cgt                                              23

<210> SEQ ID NO 340
<211> LENGTH: 22
<212> TYPE: DNA
<213> ORGANISM: Artificial
<220> FEATURE:
<223> OTHER INFORMATION: Primer

<400> SEQUENCE: 340
gttcgttttt cgttttcgt tt                                                22

<210> SEQ ID NO 341
<211> LENGTH: 20
<212> TYPE: DNA
<213> ORGANISM: Artificial
<220> FEATURE:
<223> OTHER INFORMATION: Primer

<400> SEQUENCE: 341
ctaacctact aaaccgcgcc                                                  20

<210> SEQ ID NO 342
<211> LENGTH: 21
<212> TYPE: DNA
<213> ORGANISM: Artificial
<220> FEATURE:
<223> OTHER INFORMATION: Primer

<400> SEQUENCE: 342
gttttcgttc gttttcgtt t                                                 21

<210> SEQ ID NO 343
<211> LENGTH: 23
<212> TYPE: DNA
<213> ORGANISM: Artificial
<220> FEATURE:
<223> OTHER INFORMATION: Primer

<400> SEQUENCE: 343
agtagtagta gtaatgcggc ggt                                              23

<210> SEQ ID NO 344
<211> LENGTH: 20
<212> TYPE: DNA
<213> ORGANISM: Artificial
<220> FEATURE:
<223> OTHER INFORMATION: Primer

<400> SEQUENCE: 344
cgaacgaacg aaatacgaac                                                  20

<210> SEQ ID NO 345
<211> LENGTH: 35
<212> TYPE: DNA
<213> ORGANISM: Artificial
<220> FEATURE:
<223> OTHER INFORMATION: Molecular Beacon Probe

<400> SEQUENCE: 345
cgacatgcgc gtttcgggtt cggttcggca tgtcg         35

<210> SEQ ID NO 346
<211> LENGTH: 20
<212> TYPE: DNA
<213> ORGANISM: Artificial
<220> FEATURE:
<223> OTHER INFORMATION: Primer

<400> SEQUENCE: 346
gggtagttta ggttcgggtc         20

<210> SEQ ID NO 347
<211> LENGTH: 32
<212> TYPE: DNA
<213> ORGANISM: Artificial
<220> FEATURE:
<223> OTHER INFORMATION: Molecular Beacon Probe

<400> SEQUENCE: 347
cgacatgcgc gggcgttcga gggcgcatgt cg         32

<210> SEQ ID NO 348
<211> LENGTH: 21
<212> TYPE: DNA
<213> ORGANISM: Artificial
<220> FEATURE:
<223> OTHER INFORMATION: Primer

<400> SEQUENCE: 348
tacgcgtagg ttttaagtcg c         21

<210> SEQ ID NO 349
<211> LENGTH: 22
<212> TYPE: DNA
<213> ORGANISM: Artificial
<220> FEATURE:
<223> OTHER INFORMATION: Primer

<400> SEQUENCE: 349
tcccgaacta aacgaaaccc cg         22

<210> SEQ ID NO 350
<211> LENGTH: 37
<212> TYPE: DNA
<213> ORGANISM: Artificial
<220> FEATURE:
<223> OTHER INFORMATION: Molecular Beacon Probe

<400> SEQUENCE: 350
cgacatgcct acgaccgcgt cgcccattag catgtcg         37

<210> SEQ ID NO 351
<211> LENGTH: 22
<212> TYPE: DNA
<213> ORGANISM: Artificial
<220> FEATURE:
<223> OTHER INFORMATION: Primer

<400> SEQUENCE: 351
tttgttcgtt tttcgattgt tc         22

<210> SEQ ID NO 352

```
<211> LENGTH: 23
<212> TYPE: DNA
<213> ORGANISM: Artificial
<220> FEATURE:
<223> OTHER INFORMATION: Primer

<400> SEQUENCE: 352
taacgctata aaactcctac cgc                                              23

<210> SEQ ID NO 353
<211> LENGTH: 44
<212> TYPE: DNA
<213> ORGANISM: Artificial
<220> FEATURE:
<223> OTHER INFORMATION: Molecular Beacon Probe

<400> SEQUENCE: 353
cgtctcgtcg gggttcgggc gtattttttt aggtaggcga gacg                        44

<210> SEQ ID NO 354
<211> LENGTH: 20
<212> TYPE: DNA
<213> ORGANISM: Artificial
<220> FEATURE:
<223> OTHER INFORMATION: Primer

<400> SEQUENCE: 354
gggattataa gtcgcgtcgc                                                  20

<210> SEQ ID NO 355
<211> LENGTH: 20
<212> TYPE: DNA
<213> ORGANISM: Artificial
<220> FEATURE:
<223> OTHER INFORMATION: Primer

<400> SEQUENCE: 355
cgaacgcaaa accgaaatcg                                                  20

<210> SEQ ID NO 356
<211> LENGTH: 35
<212> TYPE: DNA
<213> ORGANISM: Artificial
<220> FEATURE:
<223> OTHER INFORMATION: Molecular Beacon Probe

<400> SEQUENCE: 356
cgacacgata tggcgttgag gcggttatcg tgtcg                                 35

<210> SEQ ID NO 357
<211> LENGTH: 19
<212> TYPE: DNA
<213> ORGANISM: Artificial
<220> FEATURE:
<223> OTHER INFORMATION: Primer

<400> SEQUENCE: 357
ttattttgcg agcggtttc                                                   19

<210> SEQ ID NO 358
<211> LENGTH: 23
<212> TYPE: DNA
<213> ORGANISM: Artificial
<220> FEATURE:
<223> OTHER INFORMATION: Primer

<400> SEQUENCE: 358
```
gaatactcta attccacgcg act                                        23

<210> SEQ ID NO 359
<211> LENGTH: 34
<212> TYPE: DNA
<213> ORGANISM: Artificial
<220> FEATURE:
<223> OTHER INFORMATION: Molecular Beacon Probe

<400> SEQUENCE: 359
cgacatgcgg gttcggtcgg cgcggggcat gtcg                            34

<210> SEQ ID NO 360
<211> LENGTH: 20
<212> TYPE: DNA
<213> ORGANISM: Artificial
<220> FEATURE:
<223> OTHER INFORMATION: Primer

<400> SEQUENCE: 360
gttcgttggg taaggcgttc                                            20

<210> SEQ ID NO 361
<211> LENGTH: 22
<212> TYPE: DNA
<213> ORGANISM: Artificial
<220> FEATURE:
<223> OTHER INFORMATION: Primer

<400> SEQUENCE: 361
cataaaacga acaccccgaac cg                                        22

<210> SEQ ID NO 362
<211> LENGTH: 38
<212> TYPE: DNA
<213> ORGANISM: Artificial
<220> FEATURE:
<223> OTHER INFORMATION: Molecular Beacon Probe

<400> SEQUENCE: 362
cgacatgcac cgcgcacctc ctcccgccaa gcatgtcg                        38

<210> SEQ ID NO 363
<211> LENGTH: 19
<212> TYPE: DNA
<213> ORGANISM: Artificial
<220> FEATURE:
<223> OTHER INFORMATION: Primer

<400> SEQUENCE: 363
gagatgtttc gagggttgc                                             19

<210> SEQ ID NO 364
<211> LENGTH: 20
<212> TYPE: DNA
<213> ORGANISM: Artificial
<220> FEATURE:
<223> OTHER INFORMATION: Primer

<400> SEQUENCE: 364
ccgcaatatc actaaaccga                                            20

<210> SEQ ID NO 365
<211> LENGTH: 43
<212> TYPE: DNA

```
<213> ORGANISM: Artificial
<220> FEATURE:
<223> OTHER INFORMATION: Molecular Beacon Probe

<400> SEQUENCE: 365
cgacatgcgt tcgtgttttg gtttgtcgcg gtttggcatg tcg        43

<210> SEQ ID NO 366
<211> LENGTH: 28
<212> TYPE: DNA
<213> ORGANISM: Artificial
<220> FEATURE:
<223> OTHER INFORMATION: Primer

<400> SEQUENCE: 366
gttgggtttt cgtagttttg tagatcgc                        28

<210> SEQ ID NO 367
<211> LENGTH: 18
<212> TYPE: DNA
<213> ORGANISM: Artificial
<220> FEATURE:
<223> OTHER INFORMATION: Primer

<400> SEQUENCE: 367
ctacgcccaa actcgacg                                   18

<210> SEQ ID NO 368
<211> LENGTH: 36
<212> TYPE: DNA
<213> ORGANISM: Artificial
<220> FEATURE:
<223> OTHER INFORMATION: Molecular Beacon Probe

<400> SEQUENCE: 368
cgacatgccc cgccctatcg ccgaaatcgc atgtcg                36

<210> SEQ ID NO 369
<211> LENGTH: 23
<212> TYPE: DNA
<213> ORGANISM: Artificial
<220> FEATURE:
<223> OTHER INFORMATION: Primer

<400> SEQUENCE: 369
agtgtttaga gagttcgtcg gtt                             23

<210> SEQ ID NO 370
<211> LENGTH: 22
<212> TYPE: DNA
<213> ORGANISM: Artificial
<220> FEATURE:
<223> OTHER INFORMATION: Primer

<400> SEQUENCE: 370
cgtaacgaat aaactacgcg at                              22

<210> SEQ ID NO 371
<211> LENGTH: 42
<212> TYPE: DNA
<213> ORGANISM: Artificial
<220> FEATURE:
<223> OTHER INFORMATION: Molecular Beacon Probe

<400> SEQUENCE: 371
cgacatgcgg agaattcggt ttatcgttcg tcgcgcatgt cg        42
```

<210> SEQ ID NO 372
<211> LENGTH: 23
<212> TYPE: DNA
<213> ORGANISM: Artificial
<220> FEATURE:
<223> OTHER INFORMATION: Primer

<400> SEQUENCE: 372
ttttaggtgg aattttagtt cgc                                              23

<210> SEQ ID NO 373
<211> LENGTH: 21
<212> TYPE: DNA
<213> ORGANISM: Artificial
<220> FEATURE:
<223> OTHER INFORMATION: Primer

<400> SEQUENCE: 373
ccctcctacg aacatacgaa a                                                21

<210> SEQ ID NO 374
<211> LENGTH: 40
<212> TYPE: DNA
<213> ORGANISM: Artificial
<220> FEATURE:
<223> OTHER INFORMATION: Molecular Beacon Probe

<400> SEQUENCE: 374
cgacatgccg tgcggttcga ttcgggttta aggcatgtcg                            40

<210> SEQ ID NO 375
<211> LENGTH: 21
<212> TYPE: DNA
<213> ORGANISM: Artificial
<220> FEATURE:
<223> OTHER INFORMATION: Primer

<400> SEQUENCE: 375
cggtttaatt gcgagacgta g                                                21

<210> SEQ ID NO 376
<211> LENGTH: 19
<212> TYPE: DNA
<213> ORGANISM: Artificial
<220> FEATURE:
<223> OTHER INFORMATION: Primer

<400> SEQUENCE: 376
aacgtaaaaa ccccgcgta                                                   19

<210> SEQ ID NO 377
<211> LENGTH: 33
<212> TYPE: DNA
<213> ORGANISM: Artificial
<220> FEATURE:
<223> OTHER INFORMATION: Molecular Beacon Probe

<400> SEQUENCE: 377
cgacatgccg tgcggttcga ttcgggcatg tcg                                   33

<210> SEQ ID NO 378
<211> LENGTH: 20
<212> TYPE: DNA
<213> ORGANISM: Artificial
<220> FEATURE:

<223> OTHER INFORMATION: Primer

<400> SEQUENCE: 378
gttttcgggt ttttgttcgt                                          20

<210> SEQ ID NO 379
<211> LENGTH: 21
<212> TYPE: DNA
<213> ORGANISM: Artificial
<220> FEATURE:
<223> OTHER INFORMATION: Primer

<400> SEQUENCE: 379
gactctactc gaacctccgc t                                        21

<210> SEQ ID NO 380
<211> LENGTH: 39
<212> TYPE: DNA
<213> ORGANISM: Artificial
<220> FEATURE:
<223> OTHER INFORMATION: Molecular Beacon Probe

<400> SEQUENCE: 380
cgacatgcgg gcgttcgttc gtaggaagaa ggcatgtcg                     39

<210> SEQ ID NO 381
<211> LENGTH: 19
<212> TYPE: DNA
<213> ORGANISM: Artificial
<220> FEATURE:
<223> OTHER INFORMATION: Primer

<400> SEQUENCE: 381
tgaggacgtg tagggaagc                                           19

<210> SEQ ID NO 382
<211> LENGTH: 20
<212> TYPE: DNA
<213> ORGANISM: Artificial
<220> FEATURE:
<223> OTHER INFORMATION: Primer

<400> SEQUENCE: 382
aaacgaacaa aaacccgaaa                                          20

<210> SEQ ID NO 383
<211> LENGTH: 33
<212> TYPE: DNA
<213> ORGANISM: Artificial
<220> FEATURE:
<223> OTHER INFORMATION: Molecular Beacon Probe

<400> SEQUENCE: 383
cgacatgccg agcggtgggt cggaggcatg tcg                           33

<210> SEQ ID NO 384
<211> LENGTH: 19
<212> TYPE: DNA
<213> ORGANISM: Artificial
<220> FEATURE:
<223> OTHER INFORMATION: Primer

<400> SEQUENCE: 384
gcgttagagg gtaattgcg                                           19

```
<210> SEQ ID NO 385
<211> LENGTH: 22
<212> TYPE: DNA
<213> ORGANISM: Artificial
<220> FEATURE:
<223> OTHER INFORMATION: Primer

<400> SEQUENCE: 385
ctataaattc ctccgaccga ac                                              22

<210> SEQ ID NO 386
<211> LENGTH: 31
<212> TYPE: DNA
<213> ORGANISM: Artificial
<220> FEATURE:
<223> OTHER INFORMATION: Molecular Beacon Probe

<400> SEQUENCE: 386
cgacatgccg cgtcgggttg cgggcatgtc g                                    31

<210> SEQ ID NO 387
<211> LENGTH: 19
<212> TYPE: DNA
<213> ORGANISM: Artificial
<220> FEATURE:
<223> OTHER INFORMATION: Primer

<400> SEQUENCE: 387
tttgtatttc gggcgtttc                                                  19

<210> SEQ ID NO 388
<211> LENGTH: 20
<212> TYPE: DNA
<213> ORGANISM: Artificial
<220> FEATURE:
<223> OTHER INFORMATION: Primer

<400> SEQUENCE: 388
gcaactaaaa cacatcccgc                                                 20

<210> SEQ ID NO 389
<211> LENGTH: 42
<212> TYPE: DNA
<213> ORGANISM: Artificial
<220> FEATURE:
<223> OTHER INFORMATION: Molecular Beacon Probe

<400> SEQUENCE: 389
cgacatgcgc gatatggcgt tagagggtaa ttgcgcatgt cg                        42

<210> SEQ ID NO 390
<211> LENGTH: 19
<212> TYPE: DNA
<213> ORGANISM: Artificial
<220> FEATURE:
<223> OTHER INFORMATION: Primer

<400> SEQUENCE: 390
ggtttttacg gaagtcggg                                                  19

<210> SEQ ID NO 391
<211> LENGTH: 24
<212> TYPE: DNA
<213> ORGANISM: Artificial
<220> FEATURE:
<223> OTHER INFORMATION: Primer
```

<400> SEQUENCE: 391
aatacaaacg cgatataaaa cgaa                                              24

<210> SEQ ID NO 392
<211> LENGTH: 39
<212> TYPE: DNA
<213> ORGANISM: Artificial
<220> FEATURE:
<223> OTHER INFORMATION: Molecular Beacon Probe

<400> SEQUENCE: 392
cgacatgcgc gttatttcgt ttcgtggacg ggcatgtcg                              39

<210> SEQ ID NO 393
<211> LENGTH: 19
<212> TYPE: DNA
<213> ORGANISM: Artificial
<220> FEATURE:
<223> OTHER INFORMATION: Primer

<400> SEQUENCE: 393
gatttcgcgt attgttcgg                                                    19

<210> SEQ ID NO 394
<211> LENGTH: 19
<212> TYPE: DNA
<213> ORGANISM: Artificial
<220> FEATURE:
<223> OTHER INFORMATION: Primer

<400> SEQUENCE: 394
gatccaacta cgaaacgca                                                    19

<210> SEQ ID NO 395
<211> LENGTH: 38
<212> TYPE: DNA
<213> ORGANISM: Artificial
<220> FEATURE:
<223> OTHER INFORMATION: Molecular Beacon Probe

<400> SEQUENCE: 395
cgacatgcgg tttggattcg ggtcggatcg gcatgtcg                               38

<210> SEQ ID NO 396
<211> LENGTH: 22
<212> TYPE: DNA
<213> ORGANISM: Artificial
<220> FEATURE:
<223> OTHER INFORMATION: Primer

<400> SEQUENCE: 396
ttcgtttcga gaagtattac gc                                                22

<210> SEQ ID NO 397
<211> LENGTH: 20
<212> TYPE: DNA
<213> ORGANISM: Artificial
<220> FEATURE:
<223> OTHER INFORMATION: Primer

<400> SEQUENCE: 397
gcgctaaaaa ctcaacgtcc                                                   20

<210> SEQ ID NO 398
<211> LENGTH: 43

```
<212> TYPE: DNA
<213> ORGANISM: Artificial
<220> FEATURE:
<223> OTHER INFORMATION: Molecular Beacon Probe

<400> SEQUENCE: 398
cgacatgcga gtcgtcggtt agcgggttat tttcggcatg tcg        43

<210> SEQ ID NO 399
<211> LENGTH: 21
<212> TYPE: DNA
<213> ORGANISM: Artificial
<220> FEATURE:
<223> OTHER INFORMATION: Primer

<400> SEQUENCE: 399
ttcgttttcg gtagttatgg c                               21

<210> SEQ ID NO 400
<211> LENGTH: 19
<212> TYPE: DNA
<213> ORGANISM: Artificial
<220> FEATURE:
<223> OTHER INFORMATION: Primer

<400> SEQUENCE: 400
gatcccctaa actctccgc                                  19

<210> SEQ ID NO 401
<211> LENGTH: 42
<212> TYPE: DNA
<213> ORGANISM: Artificial
<220> FEATURE:
<223> OTHER INFORMATION: Molecular Beacon Probe

<400> SEQUENCE: 401
cgacatgccg ggttttggat tttcgcggtt gtcggcatgt cg         42

<210> SEQ ID NO 402
<211> LENGTH: 20
<212> TYPE: DNA
<213> ORGANISM: Artificial
<220> FEATURE:
<223> OTHER INFORMATION: Primer

<400> SEQUENCE: 402
cggagagttt aggggatcgt                                 20

<210> SEQ ID NO 403
<211> LENGTH: 19
<212> TYPE: DNA
<213> ORGANISM: Artificial
<220> FEATURE:
<223> OTHER INFORMATION: Primer

<400> SEQUENCE: 403
ctctatctac accgcgcca                                  19

<210> SEQ ID NO 404
<211> LENGTH: 40
<212> TYPE: DNA
<213> ORGANISM: Artificial
<220> FEATURE:
<223> OTHER INFORMATION: Molecular Beacon Probe

<400> SEQUENCE: 404
```

```
cgacatgcgt ttaggttggt acgcgttgga gggcatgtcg                            40
```

<210> SEQ ID NO 405
<211> LENGTH: 21
<212> TYPE: DNA
<213> ORGANISM: Artificial
<220> FEATURE:
<223> OTHER INFORMATION: Primer

<400> SEQUENCE: 405

```
atcggtgtcg ttttacgttt c                                               21
```

<210> SEQ ID NO 406
<211> LENGTH: 22
<212> TYPE: DNA
<213> ORGANISM: Artificial
<220> FEATURE:
<223> OTHER INFORMATION: Primer

<400> SEQUENCE: 406

```
gtaaatctcc aaccctacga ac                                              22
```

<210> SEQ ID NO 407
<211> LENGTH: 33
<212> TYPE: DNA
<213> ORGANISM: Artificial
<220> FEATURE:
<223> OTHER INFORMATION: Molecular Beacon Probe

<400> SEQUENCE: 407

```
cgacatgcgc ggagggagga gtcgggcatg tcg                                  33
```

<210> SEQ ID NO 408
<211> LENGTH: 22
<212> TYPE: DNA
<213> ORGANISM: Artificial
<220> FEATURE:
<223> OTHER INFORMATION: Primer

<400> SEQUENCE: 408

```
tagggaatcg gtgtcgtttt ac                                              22
```

<210> SEQ ID NO 409
<211> LENGTH: 23
<212> TYPE: DNA
<213> ORGANISM: Artificial
<220> FEATURE:
<223> OTHER INFORMATION: Primer

<400> SEQUENCE: 409

```
cgtaaatctc caaccctacg aac                                             23
```

<210> SEQ ID NO 410
<211> LENGTH: 37
<212> TYPE: DNA
<213> ORGANISM: Artificial
<220> FEATURE:
<223> OTHER INFORMATION: Moleclular Beacon Probe

<400> SEQUENCE: 410

```
cgacatgccg gagggaggag tcggttcggg catgtcg                              37
```

<210> SEQ ID NO 411
<211> LENGTH: 20
<212> TYPE: DNA
<213> ORGANISM: Artificial

```
<220> FEATURE:
<223> OTHER INFORMATION: primer

<400> SEQUENCE: 411
tgaggttttt cgagtcggtt                                           20

<210> SEQ ID NO 412
<211> LENGTH: 19
<212> TYPE: DNA
<213> ORGANISM: Artificial
<220> FEATURE:
<223> OTHER INFORMATION: Primer

<400> SEQUENCE: 412
ccacaacgtc aaaacgaaa                                            19

<210> SEQ ID NO 413
<211> LENGTH: 35
<212> TYPE: DNA
<213> ORGANISM: Artificial
<220> FEATURE:
<223> OTHER INFORMATION: Molecular Beacon Probe

<400> SEQUENCE: 413
cgacatgccg ggttttagtc gatcggggca tgtcg                          35

<210> SEQ ID NO 414
<211> LENGTH: 20
<212> TYPE: DNA
<213> ORGANISM: Artificial
<220> FEATURE:
<223> OTHER INFORMATION: primer

<400> SEQUENCE: 414
acgttcgcgt tatgattgtc                                           20

<210> SEQ ID NO 415
<211> LENGTH: 19
<212> TYPE: DNA
<213> ORGANISM: Artificial
<220> FEATURE:
<223> OTHER INFORMATION: Primer

<400> SEQUENCE: 415 ccgacccta ctaccgtct                                             19

<210> SEQ ID NO 416
<211> LENGTH: 40
<212> TYPE: DNA
<213> ORGANISM: Artificial
<220> FEATURE:
<223> OTHER INFORMATION: Molecular Beacon Probe

<400> SEQUENCE: 416
cgacatgccg tagtcggagg tgttggttat cggcatgtcg                     40

<210> SEQ ID NO 417
<211> LENGTH: 21
<212> TYPE: DNA
<213> ORGANISM: Artificial
<220> FEATURE:
<223> OTHER INFORMATION: Primer

<400> SEQUENCE: 417
gaggttatcg tcgttgttcg t                                         21
```

<210> SEQ ID NO 418
<211> LENGTH: 34
<212> TYPE: DNA
<213> ORGANISM: Artificial
<220> FEATURE:
<223> OTHER INFORMATION: Molecular Beacon Probe

<400> SEQUENCE: 418
cgacatgccg cgggttgagt cgtcgggcat gtcg        34

<210> SEQ ID NO 419
<211> LENGTH: 24
<212> TYPE: DNA
<213> ORGANISM: Artificial
<220> FEATURE:
<223> OTHER INFORMATION: primer

<400> SEQUENCE: 419
ttagggatta ttttcggatt tttc        24

<210> SEQ ID NO 420
<211> LENGTH: 20
<212> TYPE: DNA
<213> ORGANISM: Artificial
<220> FEATURE:
<223> OTHER INFORMATION: Primer

<400> SEQUENCE: 420
ttctcgaaac gaacaacgac        20

<210> SEQ ID NO 421
<211> LENGTH: 39
<212> TYPE: DNA
<213> ORGANISM: Artificial
<220> FEATURE:
<223> OTHER INFORMATION: Molecular Beacon Probe

<400> SEQUENCE: 421
cgacatgccg ttcggtatta gcgcgtaagg ggcatgtcg        39

<210> SEQ ID NO 422
<211> LENGTH: 19
<212> TYPE: DNA
<213> ORGANISM: Artificial
<220> FEATURE:
<223> OTHER INFORMATION: Primer

<400> SEQUENCE: 422
cggtagaagg ggaagcgtt        19

<210> SEQ ID NO 423
<211> LENGTH: 19
<212> TYPE: DNA
<213> ORGANISM: Artificial
<220> FEATURE:
<223> OTHER INFORMATION: Primer

<400> SEQUENCE: 423
ctcatcgcca taaccatcg        19

<210> SEQ ID NO 424
<211> LENGTH: 33
<212> TYPE: DNA
<213> ORGANISM: Artificial
<220> FEATURE:
<223> OTHER INFORMATION: Molecular Beacon Probe

```
<400> SEQUENCE: 424
cgacatgcgc gtgaggcggc gttcggcatg tcg                                33

<210> SEQ ID NO 425
<211> LENGTH: 21
<212> TYPE: DNA
<213> ORGANISM: Artificial
<220> FEATURE:
<223> OTHER INFORMATION: Primer

<400> SEQUENCE: 425
ctataaaact cctaccgcgc c                                            21

<210> SEQ ID NO 426
<211> LENGTH: 41
<212> TYPE: DNA
<213> ORGANISM: Artificial
<220> FEATURE:
<223> OTHER INFORMATION: Molecular Beacon Probe

<400> SEQUENCE: 426
cgacatgccg gggttcgggc gtatttttt agggcatgtc g                       41

<210> SEQ ID NO 427
<211> LENGTH: 21
<212> TYPE: DNA
<213> ORGANISM: Artificial
<220> FEATURE:
<223> OTHER INFORMATION: Primer

<400> SEQUENCE: 427
tgtgcgcgta gaagaggttt c                                            21

<210> SEQ ID NO 428
<211> LENGTH: 22
<212> TYPE: DNA
<213> ORGANISM: Artificial
<220> FEATURE:
<223> OTHER INFORMATION: Primer

<400> SEQUENCE: 428
cgaaaacaaa acataaacga cc                                           22

<210> SEQ ID NO 429
<211> LENGTH: 43
<212> TYPE: DNA
<213> ORGANISM: Artificial
<220> FEATURE:
<223> OTHER INFORMATION: Molecular Beacon Probe

<400> SEQUENCE: 429
cgacatgcgg ttagagcgag ggtagttagt attgggcatg tcg                    43

<210> SEQ ID NO 430
<211> LENGTH: 20
<212> TYPE: DNA
<213> ORGANISM: Artificial
<220> FEATURE:
<223> OTHER INFORMATION: Primer

<400> SEQUENCE: 430
gtgcgcgtag aagaggtttc                                              20

<210> SEQ ID NO 431
```

```
<211> LENGTH: 19
<212> TYPE: DNA
<213> ORGANISM: Artificial
<220> FEATURE:
<223> OTHER INFORMATION: Primer

<400> SEQUENCE: 431
aaaacataaa cgaccccg                                                 19

<210> SEQ ID NO 432
<211> LENGTH: 40
<212> TYPE: DNA
<213> ORGANISM: Artificial
<220> FEATURE:
<223> OTHER INFORMATION: Molecular Beacon Probe

<400> SEQUENCE: 432
cgacatgcga gcgagggtag ttagtattgg cggcatgtcg                         40

<210> SEQ ID NO 433
<211> LENGTH: 23
<212> TYPE: DNA
<213> ORGANISM: Artificial
<220> FEATURE:
<223> OTHER INFORMATION: Primer

<400> SEQUENCE: 433
tgtgtcggtt tagagtatcg ttg                                           23

<210> SEQ ID NO 434
<211> LENGTH: 20
<212> TYPE: DNA
<213> ORGANISM: Artificial
<220> FEATURE:
<223> OTHER INFORMATION: Primer

<400> SEQUENCE: 434
caattaccat aacgaccgcc                                               20

<210> SEQ ID NO 435
<211> LENGTH: 41
<212> TYPE: DNA
<213> ORGANISM: Artificial
<220> FEATURE:
<223> OTHER INFORMATION: Molecular Beacon Probe

<400> SEQUENCE: 435
cgacatgcgt tattatggtg tcggttcggt tgggcatgtc g                       41

<210> SEQ ID NO 436
<211> LENGTH: 21
<212> TYPE: DNA
<213> ORGANISM: Artificial
<220> FEATURE:
<223> OTHER INFORMATION: Primer

<400> SEQUENCE: 436
gccccaatta ccataacgac c                                             21

<210> SEQ ID NO 437
<211> LENGTH: 25
<212> TYPE: DNA
<213> ORGANISM: Artificial
<220> FEATURE:
<223> OTHER INFORMATION: Primer

<400> SEQUENCE: 437
```

```
atttatgtgt cggtttagag tatcg                                           25

<210> SEQ ID NO 438
<211> LENGTH: 21
<212> TYPE: DNA
<213> ORGANISM: Artificial
<220> FEATURE:
<223> OTHER INFORMATION: Primer

<400> SEQUENCE: 438
tcgagtttta gttttggttg c                                               21

<210> SEQ ID NO 439
<211> LENGTH: 23
<212> TYPE: DNA
<213> ORGANISM: Artificial
<220> FEATURE:
<223> OTHER INFORMATION: Primer

<400> SEQUENCE: 439
aaataacgat cctaactccg aaa                                             23

<210> SEQ ID NO 440
<211> LENGTH: 35
<212> TYPE: DNA
<213> ORGANISM: Artificial
<220> FEATURE:
<223> OTHER INFORMATION: Molecular Beacon Probe

<400> SEQUENCE: 440
cgacatgccg gttcgggatt tcgggaggca tgtcg                                35

<210> SEQ ID NO 441
<211> LENGTH: 25
<212> TYPE: DNA
<213> ORGANISM: Artificial
<220> FEATURE:
<223> OTHER INFORMATION: Primer

<400> SEQUENCE: 441
tttagtaagt tttagcgttt acgtc                                           25

<210> SEQ ID NO 442
<211> LENGTH: 22
<212> TYPE: DNA
<213> ORGANISM: Artificial
<220> FEATURE:
<223> OTHER INFORMATION: Primer

<400> SEQUENCE: 442
gaataaactc ctcccaaacg aa                                              22

<210> SEQ ID NO 443
<211> LENGTH: 38
<212> TYPE: DNA
<213> ORGANISM: Artificial
<220> FEATURE:
<223> OTHER INFORMATION: Molecular Beacon Probe

<400> SEQUENCE: 443
cgacatgcga gggtcgtgtt tatcgttcgg gcatgtcg                             38

<210> SEQ ID NO 444
<211> LENGTH: 20
<212> TYPE: DNA
```

```
<213> ORGANISM: Artificial
<220> FEATURE:
<223> OTHER INFORMATION: Primer

<400> SEQUENCE: 444
atttaggtaa cgggttgggc                                                20

<210> SEQ ID NO 445
<211> LENGTH: 20
<212> TYPE: DNA
<213> ORGANISM: Artificial
<220> FEATURE:
<223> OTHER INFORMATION: Primer

<400> SEQUENCE: 445
actccccgaa tacaaacgaa                                                20

<210> SEQ ID NO 446
<211> LENGTH: 37
<212> TYPE: DNA
<213> ORGANISM: Artificial
<220> FEATURE:
<223> OTHER INFORMATION: Molecular Beacon Probe

<400> SEQUENCE: 446
cgacatgcgg ttcgaggtag gtggcgttgg catgtcg                             37

<210> SEQ ID NO 447
<211> LENGTH: 23
<212> TYPE: DNA
<213> ORGANISM: Artificial
<220> FEATURE:
<223> OTHER INFORMATION: Primer

<400> SEQUENCE: 447
ttcgtagagt gattttagcg ttt                                            23

<210> SEQ ID NO 448
<211> LENGTH: 19
<212> TYPE: DNA
<213> ORGANISM: Artificial
<220> FEATURE:
<223> OTHER INFORMATION: Primer

<400> SEQUENCE: 448
aacgccacct acctcgaac                                                 19

<210> SEQ ID NO 449
<211> LENGTH: 39
<212> TYPE: DNA
<213> ORGANISM: Artificial
<220> FEATURE:
<223> OTHER INFORMATION: Molecular Beacon Probe

<400> SEQUENCE: 449
cgacatgcgc ggacgtcggg gagaatttag ggcatgtcg                           39

<210> SEQ ID NO 450
<211> LENGTH: 19
<212> TYPE: DNA
<213> ORGANISM: Artificial
<220> FEATURE:
<223> OTHER INFORMATION: Primer

<400> SEQUENCE: 450
taatttgttt tcgcgtcgg                                                 19
```

<210> SEQ ID NO 451
<211> LENGTH: 23
<212> TYPE: DNA
<213> ORGANISM: Artificial
<220> FEATURE:
<223> OTHER INFORMATION: Primer

<400> SEQUENCE: 451
ctaaaatcac tctacgaacg acc                                           23

<210> SEQ ID NO 452
<211> LENGTH: 36
<212> TYPE: DNA
<213> ORGANISM: Artificial
<220> FEATURE:
<223> OTHER INFORMATION: Molecular Beacon Probe

<400> SEQUENCE: 452
cgacatgcgg acgggagcgg ttgtttcggc atgtcg                             36

<210> SEQ ID NO 453
<211> LENGTH: 23
<212> TYPE: DNA
<213> ORGANISM: Artificial
<220> FEATURE:
<223> OTHER INFORMATION: Primer

<400> SEQUENCE: 453
cgtttcggat gttttgattt tac                                           23

<210> SEQ ID NO 454
<211> LENGTH: 19
<212> TYPE: DNA
<213> ORGANISM: Artificial
<220> FEATURE:
<223> OTHER INFORMATION: Primer

<400> SEQUENCE: 454
actctacgaa cgaccccgc                                                19

<210> SEQ ID NO 455
<211> LENGTH: 32
<212> TYPE: DNA
<213> ORGANISM: Artificial
<220> FEATURE:
<223> OTHER INFORMATION: Molecular Beacon Probe

<400> SEQUENCE: 455
cgacatgccg gaggacggga gcgggcatgt cg                                 32

<210> SEQ ID NO 456
<211> LENGTH: 19
<212> TYPE: DNA
<213> ORGANISM: Artificial
<220> FEATURE:
<223> OTHER INFORMATION: Primer

<400> SEQUENCE: 456
ttcgtcggtg attttggtc                                                19

<210> SEQ ID NO 457
<211> LENGTH: 36
<212> TYPE: DNA
<213> ORGANISM: Artificial
<220> FEATURE:

```
<223> OTHER INFORMATION: Molecular Beacon Probe

<400> SEQUENCE: 457
cgacatgccg tcggtcgggt ttatggtcgc atgtcg                          36

<210> SEQ ID NO 458
<211> LENGTH: 19
<212> TYPE: DNA
<213> ORGANISM: Artificial
<220> FEATURE:
<223> OTHER INFORMATION: Primer

<400> SEQUENCE: 458
acgttgttac gaaatcggg                                             19

<210> SEQ ID NO 459
<211> LENGTH: 21
<212> TYPE: DNA
<213> ORGANISM: Artificial
<220> FEATURE:
<223> OTHER INFORMATION: Primer

<400> SEQUENCE: 459
aaacgcctaa ctccaacgaa a                                          21

<210> SEQ ID NO 460
<211> LENGTH: 45
<212> TYPE: DNA
<213> ORGANISM: Artificial
<220> FEATURE:
<223> OTHER INFORMATION: Molecular Beacon Probe

<400> SEQUENCE: 460
cgacatgcgg cgtacgtttt tcgttttttt gtcggcggca tgtcg                45

<210> SEQ ID NO 461
<211> LENGTH: 20
<212> TYPE: DNA
<213> ORGANISM: Artificial
<220> FEATURE:
<223> OTHER INFORMATION: Primer

<400> SEQUENCE: 461
ctccaacgaa acctaacgca                                            20

<210> SEQ ID NO 462
<211> LENGTH: 19
<212> TYPE: DNA
<213> ORGANISM: Artificial
<220> FEATURE:
<223> OTHER INFORMATION: Primer

<400> SEQUENCE: 462
cgttgttacg aaatcgggt                                             19

<210> SEQ ID NO 463
<211> LENGTH: 21
<212> TYPE: DNA
<213> ORGANISM: Artificial
<220> FEATURE:
<223> OTHER INFORMATION: Primer

<400> SEQUENCE: 463
gaaacctaac gcacctaaac g                                          21
```

```
<210> SEQ ID NO 464
<211> LENGTH: 19
<212> TYPE: DNA
<213> ORGANISM: Artificial
<220> FEATURE:
<223> OTHER INFORMATION: Primer

<400> SEQUENCE: 464
aacgcaccta aacgcgcta                                                  19

<210> SEQ ID NO 465
<211> LENGTH: 23
<212> TYPE: DNA
<213> ORGANISM: Artificial
<220> FEATURE:
<223> OTHER INFORMATION: Primer

<400> SEQUENCE: 465
gatacgaggt agtcgttttc gtt                                             23

<210> SEQ ID NO 466
<211> LENGTH: 36
<212> TYPE: DNA
<213> ORGANISM: Artificial
<220> FEATURE:
<223> OTHER INFORMATION: Molecular Beacon Probe

<400> SEQUENCE: 466
cgacatgcgc ggttatgggt tcggtcgggc atgtcg                               36

<210> SEQ ID NO 467
<211> LENGTH: 19
<212> TYPE: DNA
<213> ORGANISM: Artificial
<220> FEATURE:
<223> OTHER INFORMATION: Primer

<400> SEQUENCE: 467
gacgttgggg ttattttgc                                                  19

<210> SEQ ID NO 468
<211> LENGTH: 46
<212> TYPE: DNA
<213> ORGANISM: Artificial
<220> FEATURE:
<223> OTHER INFORMATION: Molecular Beacon Probe

<400> SEQUENCE: 468
cgacatgcgc gatacgaggt agtcgttttc gttttcggc atgtcg                     46

<210> SEQ ID NO 469
<211> LENGTH: 21
<212> TYPE: DNA
<213> ORGANISM: Artificial
<220> FEATURE:
<223> OTHER INFORMATION: Primer

<400> SEQUENCE: 469
cgtcgttttc gtttagttcg t                                               21

<210> SEQ ID NO 470
<211> LENGTH: 20
<212> TYPE: DNA
<213> ORGANISM: Artificial
<220> FEATURE:
<223> OTHER INFORMATION: Primer
```

<400> SEQUENCE: 470
gcaaaataac cccaacgtcc                                              20

<210> SEQ ID NO 471
<211> LENGTH: 34
<212> TYPE: DNA
<213> ORGANISM: Artificial
<220> FEATURE:
<223> OTHER INFORMATION: Molecular Beacon Probe

<400> SEQUENCE: 471
cgacatgcgc ggaggaggtg gtcgaggcat gtcg                              34

<210> SEQ ID NO 472
<211> LENGTH: 19
<212> TYPE: DNA
<213> ORGANISM: Artificial
<220> FEATURE:
<223> OTHER INFORMATION: Primer

<400> SEQUENCE: 472
gattggggat aggaatcgc                                               19

<210> SEQ ID NO 473
<211> LENGTH: 19
<212> TYPE: DNA
<213> ORGANISM: Artificial
<220> FEATURE:
<223> OTHER INFORMATION: Primer

<400> SEQUENCE: 473
aacgacgaac gaatcgaaa                                               19

<210> SEQ ID NO 474
<211> LENGTH: 20
<212> TYPE: DNA
<213> ORGANISM: Artificial
<220> FEATURE:
<223> OTHER INFORMATION: Primer

<400> SEQUENCE: 474
aacccgaaac aaataacgct                                              20

<210> SEQ ID NO 475
<211> LENGTH: 38
<212> TYPE: DNA
<213> ORGANISM: Artificial
<220> FEATURE:
<223> OTHER INFORMATION: Molecular Beacon Probe

<400> SEQUENCE: 475
cgacatgcgc ggttttcga atgtaggcgg gcatgtcg                           38

<210> SEQ ID NO 476
<211> LENGTH: 23
<212> TYPE: DNA
<213> ORGANISM: Artificial
<220> FEATURE:
<223> OTHER INFORMATION: Primer

<400> SEQUENCE: 476
ataacgctaa aaacaaaacc ccg                                          23

<210> SEQ ID NO 477
<211> LENGTH: 19

```
<212> TYPE: DNA
<213> ORGANISM: Artificial
<220> FEATURE:
<223> OTHER INFORMATION: Primer

<400> SEQUENCE: 477
aaaacaaaac cccgcgaaa                                              19

<210> SEQ ID NO 478
<211> LENGTH: 19
<212> TYPE: DNA
<213> ORGANISM: Artificial
<220> FEATURE:
<223> OTHER INFORMATION: Primer

<400> SEQUENCE: 478
cggggtgata gttttcgtg                                              19

<210> SEQ ID NO 479
<211> LENGTH: 22
<212> TYPE: DNA
<213> ORGANISM: Artificial
<220> FEATURE:
<223> OTHER INFORMATION: Primer

<400> SEQUENCE: 479
cgactttcta ctccaaacga cc                                          22

<210> SEQ ID NO 480
<211> LENGTH: 34
<212> TYPE: DNA
<213> ORGANISM: Artificial
<220> FEATURE:
<223> OTHER INFORMATION: Molecular Beacon Probe

<400> SEQUENCE: 480
cgacatgcgg gtcggtcgga cgttcggcat gtcg                             34

<210> SEQ ID NO 481
<211> LENGTH: 23
<212> TYPE: DNA
<213> ORGANISM: Artificial
<220> FEATURE:
<223> OTHER INFORMATION: Primer

<400> SEQUENCE: 481
tagaaattgt tggcgttgtt ttc                                         23

<210> SEQ ID NO 482
<211> LENGTH: 21
<212> TYPE: DNA
<213> ORGANISM: Artificial
<220> FEATURE:
<223> OTHER INFORMATION: Primer

<400> SEQUENCE: 482
taccgaaccc tacttctccg t                                           21

<210> SEQ ID NO 483
<211> LENGTH: 45
<212> TYPE: DNA
<213> ORGANISM: Artificial
<220> FEATURE:
<223> OTHER INFORMATION: Molecular Beacon Probe

<400> SEQUENCE: 483
```

```
cgacatgccg tataggaatt ggcggtagtt ttgcgtggca tgtcg              45

<210> SEQ ID NO 484
<211> LENGTH: 20
<212> TYPE: DNA
<213> ORGANISM: Artificial
<220> FEATURE:
<223> OTHER INFORMATION: Primer

<400> SEQUENCE: 484
tagtcgtcgg cgtaaggagc                                          20

<210> SEQ ID NO 485
<211> LENGTH: 21
<212> TYPE: DNA
<213> ORGANISM: Artificial
<220> FEATURE:
<223> OTHER INFORMATION: Primer

<400> SEQUENCE: 485
aaaactacga aaacaacgcc a                                        21

<210> SEQ ID NO 486
<211> LENGTH: 33
<212> TYPE: DNA
<213> ORGANISM: Artificial
<220> FEATURE:
<223> OTHER INFORMATION: Molecular Beacon Probe

<400> SEQUENCE: 486
cgacatgctg ggtgcgcgta gggtagcatg tcg                           33

<210> SEQ ID NO 487
<211> LENGTH: 19
<212> TYPE: DNA
<213> ORGANISM: Artificial
<220> FEATURE:
<223> OTHER INFORMATION: Primer

<400> SEQUENCE: 487
gtgttcgttt tatgcgggg                                           19

<210> SEQ ID NO 488
<211> LENGTH: 23
<212> TYPE: DNA
<213> ORGANISM: Artificial
<220> FEATURE:
<223> OTHER INFORMATION: Primer

<400> SEQUENCE: 488
tcttacacaa tttacaacgc gaa                                      23

<210> SEQ ID NO 489
<211> LENGTH: 37
<212> TYPE: DNA
<213> ORGANISM: Artificial
<220> FEATURE:
<223> OTHER INFORMATION: Molecular Beacon Probe

<400> SEQUENCE: 489
cgacatgccg ttcggtcgat tttcgtcggg catgtcg                       37

<210> SEQ ID NO 490
<211> LENGTH: 19
<212> TYPE: DNA
<213> ORGANISM: Artificial
```

-continued

```
<220> FEATURE:
<223> OTHER INFORMATION: Primer

<400> SEQUENCE: 490
tttttgtttt aggcggttc                                                 19

<210> SEQ ID NO 491
<211> LENGTH: 20
<212> TYPE: DNA
<213> ORGANISM: Artificial
<220> FEATURE:
<223> OTHER INFORMATION: Primer

<400> SEQUENCE: 491
gacgaaataa caatccccgt                                                20

<210> SEQ ID NO 492
<211> LENGTH: 25
<212> TYPE: DNA
<213> ORGANISM: Artificial
<220> FEATURE:
<223> OTHER INFORMATION: Primer

<400> SEQUENCE: 492
ttcgttagga aaagtagtag aatcg                                          25

<210> SEQ ID NO 493
<211> LENGTH: 19
<212> TYPE: DNA
<213> ORGANISM: Artificial
<220> FEATURE:
<223> OTHER INFORMATION: Primer

<400> SEQUENCE: 493
gccaaacgct ttctcgaac                                                 19

<210> SEQ ID NO 494
<211> LENGTH: 38
<212> TYPE: DNA
<213> ORGANISM: Artificial
<220> FEATURE:
<223> OTHER INFORMATION: Molecular Beacon Probe

<400> SEQUENCE: 494
cgacatgcgg gtaaggcgtt cgagaaagcg gcatgtcg                            38

<210> SEQ ID NO 495
<211> LENGTH: 37
<212> TYPE: DNA
<213> ORGANISM: Artificial
<220> FEATURE:
<223> OTHER INFORMATION: Molecular Beacon Probe

<400> SEQUENCE: 495
cgacatgcgt cggtcggacg ttcgtttcgg catgtcg                             37

<210> SEQ ID NO 496
<211> LENGTH: 21
<212> TYPE: DNA
<213> ORGANISM: Artificial
<220> FEATURE:
<223> OTHER INFORMATION: Primer

<400> SEQUENCE: 496
gtcgttagtt tttgtacggg g                                              21
```

```
<210> SEQ ID NO 497
<211> LENGTH: 21
<212> TYPE: DNA
<213> ORGANISM: Artificial
<220> FEATURE:
<223> OTHER INFORMATION: Primer

<400> SEQUENCE: 497
gaaaatccta aatacgcgca a                                              21

<210> SEQ ID NO 498
<211> LENGTH: 42
<212> TYPE: DNA
<213> ORGANISM: Artificial
<220> FEATURE:
<223> OTHER INFORMATION: Molecular Beacon Probe

<400> SEQUENCE: 498
cgacatgcgg gaggtttgcg acgatgtttg ttgggcatgt cg                       42

<210> SEQ ID NO 499
<211> LENGTH: 22
<212> TYPE: DNA
<213> ORGANISM: Artificial
<220> FEATURE:
<223> OTHER INFORMATION: Primer

<400> SEQUENCE: 499
ggcgttagag tttagtttcg gt                                             22

<210> SEQ ID NO 500
<211> LENGTH: 19
<212> TYPE: DNA
<213> ORGANISM: Artificial
<220> FEATURE:
<223> OTHER INFORMATION: Primer

<400> SEQUENCE: 500
taatccgaat cccacgtcc                                                 19

<210> SEQ ID NO 501
<211> LENGTH: 35
<212> TYPE: DNA
<213> ORGANISM: Artificial
<220> FEATURE:
<223> OTHER INFORMATION: Molecular Beacon Probe

<400> SEQUENCE: 501
cgacatgcgg tgtagttttg ggcgcgggca tgtcg                               35

<210> SEQ ID NO 502
<211> LENGTH: 20
<212> TYPE: DNA
<213> ORGANISM: Artificial
<220> FEATURE:
<223> OTHER INFORMATION: Primer

<400> SEQUENCE: 502
cggtttagtg atattgcggg                                                20

<210> SEQ ID NO 503
<211> LENGTH: 21
<212> TYPE: DNA
<213> ORGANISM: Artificial
<220> FEATURE:
<223> OTHER INFORMATION: Molecular Beacon Probe
```

-continued

<400> SEQUENCE: 503
acgtaaaact cgaaccacga c                                            21

<210> SEQ ID NO 504
<211> LENGTH: 40
<212> TYPE: DNA
<213> ORGANISM: Artificial
<220> FEATURE:
<223> OTHER INFORMATION: Molecular Beacon Probe

<400> SEQUENCE: 504
cgacatgcga tgtggttaat ggagcggcga gggcatgtcg                        40

<210> SEQ ID NO 505
<211> LENGTH: 19
<212> TYPE: DNA
<213> ORGANISM: Artificial
<220> FEATURE:
<223> OTHER INFORMATION: Primer

<400> SEQUENCE: 505
ttagtgatat tgcgggcgt                                               19

<210> SEQ ID NO 506
<211> LENGTH: 23
<212> TYPE: DNA
<213> ORGANISM: Artificial
<220> FEATURE:
<223> OTHER INFORMATION: Primer

<400> SEQUENCE: 506
cgacctaaac gtaaacctaa cga                                          23

<210> SEQ ID NO 507
<211> LENGTH: 31
<212> TYPE: DNA
<213> ORGANISM: Artificial
<220> FEATURE:
<223> OTHER INFORMATION: Molecular BEacon Probe

<400> SEQUENCE: 507
cgacatgcgg agcggcgagg gcggcatgtc g                                 31

<210> SEQ ID NO 508
<211> LENGTH: 23
<212> TYPE: DNA
<213> ORGANISM: Artificial
<220> FEATURE:
<223> OTHER INFORMATION: Primer

<400> SEQUENCE: 508
tattgagatg tttcgagggt tgc                                          23

<210> SEQ ID NO 509
<211> LENGTH: 24
<212> TYPE: DNA
<213> ORGANISM: Artificial
<220> FEATURE:
<223> OTHER INFORMATION: Primer

<400> SEQUENCE: 509
ctaaatacgc tataaaccaa accg                                         24

<210> SEQ ID NO 510

```
<211> LENGTH: 38
<212> TYPE: DNA
<213> ORGANISM: Artificial
<220> FEATURE:
<223> OTHER INFORMATION: Molecular Beacon Probe

<400> SEQUENCE: 510
cgacatgccg gttcgaagtc gtcgttcgtg gcatgtcg                                  38

<210> SEQ ID NO 511
<211> LENGTH: 20
<212> TYPE: DNA
<213> ORGANISM: Artificial
<220> FEATURE:
<223> OTHER INFORMATION: Primer

<400> SEQUENCE: 511
tcgagttaag ggcgagtttc                                                      20

<210> SEQ ID NO 512
<211> LENGTH: 23
<212> TYPE: DNA
<213> ORGANISM: Artificial
<220> FEATURE:
<223> OTHER INFORMATION: Primer

<400> SEQUENCE: 512
tctaaattct actacgccaa ccg                                                  23

<210> SEQ ID NO 513
<211> LENGTH: 41
<212> TYPE: DNA
<213> ORGANISM: Artificial
<220> FEATURE:
<223> OTHER INFORMATION: MOlecular BEacon Probe

<400> SEQUENCE: 513
cgacatgcgg tgtgggttaa ggacgagcgt aaggcatgtc g                              41

<210> SEQ ID NO 514
<211> LENGTH: 20
<212> TYPE: DNA
<213> ORGANISM: Artificial
<220> FEATURE:
<223> OTHER INFORMATION: Primer

<400> SEQUENCE: 514
attctactac gccaaccgct                                                      20

<210> SEQ ID NO 515
<211> LENGTH: 41
<212> TYPE: DNA
<213> ORGANISM: Artificial
<220> FEATURE:
<223> OTHER INFORMATION: Molecular Beacon Probe

<400> SEQUENCE: 515
cgacatgccg gcggtcgatg aacgttttta tgggcatgtc g                              41

<210> SEQ ID NO 516
<211> LENGTH: 20
<212> TYPE: DNA
<213> ORGANISM: Artificial
<220> FEATURE:
<223> OTHER INFORMATION: Primer

<400> SEQUENCE: 516
```

```
cgaatagcgg agtatcggtc                                              20

<210> SEQ ID NO 517
<211> LENGTH: 19
<212> TYPE: DNA
<213> ORGANISM: Artificial
<220> FEATURE:
<223> OTHER INFORMATION: Primer

<400> SEQUENCE: 517
actacgccaa ccgcttacg                                               19

<210> SEQ ID NO 518
<211> LENGTH: 32
<212> TYPE: DNA
<213> ORGANISM: Artificial
<220> FEATURE:
<223> OTHER INFORMATION: Molecular Beacon Probe

<400> SEQUENCE: 518
cgacatcgcg ggtcgagtta agggcgatgt cg                                32

<210> SEQ ID NO 519
<211> LENGTH: 25
<212> TYPE: DNA
<213> ORGANISM: Artificial
<220> FEATURE:
<223> OTHER INFORMATION: Primer

<400> SEQUENCE: 519
tttagtattt tgtttaattc ggcgt                                        25

<210> SEQ ID NO 520
<211> LENGTH: 19
<212> TYPE: DNA
<213> ORGANISM: Artificial
<220> FEATURE:
<223> OTHER INFORMATION: Primer

<400> SEQUENCE: 520
aacgaatccc gtatccgac                                               19

<210> SEQ ID NO 521
<211> LENGTH: 45
<212> TYPE: DNA
<213> ORGANISM: Artificial
<220> FEATURE:
<223> OTHER INFORMATION: Molecular Beacon Probe

<400> SEQUENCE: 521
cgacatgcgg attttgttgc gttagtcgtt tgcgttcgca tgtcg                  45

<210> SEQ ID NO 522
<211> LENGTH: 27
<212> TYPE: DNA
<213> ORGANISM: Artificial
<220> FEATURE:
<223> OTHER INFORMATION: Primer

<400> SEQUENCE: 522
tttgttggtt attttttttt tattttt                                      27

<210> SEQ ID NO 523
<211> LENGTH: 23
<212> TYPE: DNA
```

```
<213> ORGANISM: Artificial
<220> FEATURE:
<223> OTHER INFORMATION: Primer

<400> SEQUENCE: 523
cccccaaact caataataaa aac                                              23

<210> SEQ ID NO 524
<211> LENGTH: 2001
<212> TYPE: DNA
<213> ORGANISM: Artificial
<220> FEATURE:
<223> OTHER INFORMATION: Methylated NDRG4 Sequence

<400> SEQUENCE: 524
gtttaataga gttttgtatg gaaaagattg gaatttaggg aggagtagag tttcgtttaa      60
ggttatcggt cgagtttgaa tagaattcgg ttttttagga gttttgtttt tagttgtttt     120
gtttaaataa aattttttag gttattagat tttcgtattt tttggagtgg gattttattt     180
gggattaaag gagggttggt gagggagtg gtaggaggga ggagtgtttc ggggtttcga      240
gtaggatgag tttgaggaag agacgggttt ttatgttttt tttttcgttt agataatgga     300
ggtgaattga ggggagtaga gattttttta ttttttaggg tgggattttga gggattagga    360 tattttgtt aggggatgtt ttttttatt tttgtataag tttttaagg atattttcgg        420 gtttcgaaaa cggggggagg gggacgacgt ttagaggtt tttgagtttt tggttttttt      480
cgattttaag ggttttttttt tttcggtttt taggcggcga cggcgggtag cgcgaagtag    540
taggcgtagg ggcgttggga tggggatgtt tttgtaggtt taaggttttt tttgggagtt     600
taaataaaga ttacggtagc gtcgtttttt tttcgggaa ttcgacgtcg cgcggttata     660 gggggttgg aggggcgggt agggtttcgt agcgtattta gtatagttcg cgcggcggag    720
cgggtgagaa gtcggcgggg gcgcggatcg atcgggtgt tttttaggtt tcgcgtcgcg     780
gttttcgttc gttttttcgt tcgtttatcg ggtattttag tcgcgtagaa ggcggaagtt    840
acgcgcgagg gatcgcggtt cgttcgggat tagttttagg ttcggtatcg tttcgcgggt    900
cgagcgttta tattcgttaa atttacgcgg gtacgttttc gcggcgtatc gttttttagtt  960 cggttttcgt ttttgtagtc gcgggtacgc ggaggggttt ttggttgttc gtatttgtat    1020
tcgcgcgtcg gcgcgtcga agttctgttt ttcgtttgcg cgtttgtttc gttcgtatttt    1080 tcgcggtgag tcggcggcgt tttcgttttt gagtttaggg ttagtttttt tcgtcgtcgc    1140
ggttgttgcg cgcgttttcg tttagtttag tttagtttcg agtacgattt tagttttacg    1200
tacgatttta gtttcgcgag tttcgtatcg attcgttttc gttttatttc gttttcgcgg    1260
gggcggcgtt tttttttttt cgcggttttc gttttttttt ttcgtttttt cggtcgcgtt    1320
ggggattttt agtcgtcgtt cgcgattttt tatcgcgacg ttcggaggcg gcggggtttt    1380
tttgttcggg cggcgggtac gggggattat ttttacggt gttatcgtat ttatttcgcg     1440 ttttttttttc gttttttgga gtttatcggg attaggtggc ggcgggtgtt tttttggggg   1500
tgcgcggtta tgtaattggt ggatttttttt aaatcgtttt ggaggggga gcgcggcgtt    1560 ggggcggga gagcgttttt ggttgtgagt tgttttttgtc gtttcgtttc gcgttttttt    1620
gtcgtttcgt ttcgggtttt tcgcgttttt tttttcggtt cggtcgagcg cgttgtttcg    1680
acgtcgttat ttagagtcgg gtcgcgtcgg gcgtcgagat gaaggtgttg ggatatcggt    1740
tggagttgtt tataggtatc gttcgtttgt ttcgtagtcg gtcgttattt ttcgagttgg    1800
agcggatttc gggcgcggcg gtcggggatt ggggcggttc gggtttgagt aggaagggt    1860
```

```
gcggatttta attaagtttt agttttgtgt tatttgtttg tgtgcggagt ttagtttcgg    1920
gagaggattt gaggttgtgg cgagtttttg gcgttggcgt tcgggttgcg ggagtatcgg    1980 ttaggggtg gttttatggg g                                               2001
```

<210> SEQ ID NO 525
<211> LENGTH: 4001
<212> TYPE: DNA
<213> ORGANISM: Artificial
<220> FEATURE:
<223> OTHER INFORMATION: Methylated NDRG2 Sequence

<400> SEQUENCE: 525

```
gtttgttttg cgttttgcg taggttttt attaggtttt ttttgagtta ttttgattta     60
gagacgaatt tagatgttgg aattttagg tttttttttt tttattttta agtaagacga    120
tttttgataa agaaaagttt gtaggtaaaa gttttattc gaggttttt ttttttttag    180 gtttttttgg tgttgatgag atttttttg ttttgcgtat ttttggttgt gatttttatt   240
ttagtaggtt tttttttgtt taggagagtg ttaaattggt atttagaggg aagaggggat   300
taggagagga gttagggtgt ttagttttg tgttagtttt tggggaaaaa gttataaagg    360
gagtgggaga aggaataga agaaaagttg ggtgtttaa attggggat gtaggggag     420 ttttttagat ttggggttgt tgaaggtgg gttttagttc gattagtttt tttattgtgg    480 gttattttt tttttttggt tttttttttt tttagtaga ttttgttaag tgggatgaa    540 agggtattg atgttttttg gatgggaggg gtattgcggg tggtgagggt ggtggtggga    600
gggtggtttt taggtaggag ggggtaggga aatttggggg ttttggggg gtagtcggtg    660 ttggtgttgt agttggtagt ttaagtttta ttggttattg ttttttgattg gtttggcgtt    720 tagttttcga aatggtaatt taggaattag tttgaagggg gttggggtgg atatgatttt   780
gggattgggg gagttataag gggggtaggt ggggagaaat ttagttaggt ttttttttgt   840
ttaaataatt tcgaattttt ttaagttata ttttaatta attaatttat tttagggagt    900 ttttttcga ggggtataag gagagtttat tttagggtgt gtgtgtgtgt gtgcgtgtgc    960
gtgtgtgtgt aaagtttata gtggtaaatt tattcgggta tcgagaggga cgcggtagat   1020
tttgagatta tttttcgggt attgcgattt agcgggtttg agttggtttt ttattttggg   1080
tcggattggg aggggttagc ggcgaagtta tagggttttt tgggttttag tttaggatat   1140 tgcgttttt ttaagttttt attttatttt cgtagggtta atttcgtttt tgcgtttgtt    1200
tatttaggag ttagagtttt tgggggtttt cggtttttt ttcgcgtttt ttgaggtatt    1260
gattttagag ttttgttgg ttattttttt tttattttc gtttgttcgc gatcgttttt    1320
tatttatagc ggttttcgt attttcgtt tttatttttt cgttttgttg tttaattttt     1380
ttcggagtag tcggagagta ggcgtcggga cgtagtaaag agaggagagg tattaggatt   1440
ttgggtacga gggagtcgga attttgcgt tttcgacgtt ttttcgtgtt tttttcggc    1500 gttagtatat ttgttttgt tagtcggcga gattttcgtt ttttagcgg cggtttcgtt     1560 tattttttt tttttaatt tagttttttg tgttcgggcg ggggagtcg aattcgtggg    1620 gtgttagtat ttcgggttcg tttttttatt atcggttttt attattgagt ttggggcga     1680 aggaaggagt tagagtgtaa ttgtagattt aggtcgtgga tggggcggtg ttgagggtag   1740
tcgagggatt tttttaggg ttgagggatt ttcgtatttt ttatatcgtt ttaatgcggg    1800
gagggggtgg tggaatgttt tggtgagtcg agtagagttt ggaagcgttt agtcgttcgt   1860
```

```
ttttcgtttt tcggttttag tataattttt ttttgagcgg tagtttgggc ggggtgaaag    1920
gggggcgtg tttattgggg gtttgggcg ggtttgcggg gagtttagcg ttcgtgggcg      1980
ggttggggcg ggtcggggc gggtttgcgg gaagttcgag tcgggcggg ttcgagttaa     2040
aggtaagtga aggtggaagc ggtcgcggcg gtagtaggta gggggagggg taggcgaggg   2100
gtcgtagggt ttggaaggcg ttagtcgggt cggcgggcgg tgtgattgat tcgcgttttt    2160
tggagttgga ggttcggggg aaagggttag tacggagcgg gcgttcggtt gttgcgtata    2220
aaggttgagg tttaagagt tgtagggcgt gtttgggggt cgcgcgaggt tgtgtgtaag     2280
gttcggggcg tttggtatcg gttacgtaag ggtgttagtt tttacgcgga cgggttgcgt    2340
agggattcgt agggacgggt ttcgggtgtt gggttcggtc ggttttttt gttttattta    2400
tttttttcg atggcgtttg ttttcgcggg tcgtcggggg agaacgggag aagattgtgg    2460
gatcgttttt tttttttt tttattcgt gggatttata cggagattga gtagaggaga     2520
gaagcgacgg tattaattt tgtgtttgtt tttaaattgt ggaggaaat agttatgttt     2580
tgttattttt tttattgg agagttgtta aaaattttgg ggatttttta ttttttcgcg    2640
tttagttttt ttgtagatag aaaattgagg ttaaatgtag taattaattg gggtaaggtt    2700
atattgggag tggtagagtc gggattcgaa ttcggaggtt ttgatagggt tatttttta    2760
tttttatatt agtatttttt tttttttttc gcgtagtttg aattgatgtt tttgtagttt    2820
atattgattt cggttcgagt ttagagagga cgtgtttttt ggatttaggg gtagatagat    2880
attgggagg gttagtgatt cgaggaggtt gatgattttg ggagtttggg ttttggttga    2940
ggttttcgt ttttgaaaga tttaggttt gttttttatg ttatttattt cgttgttgtg     3000
ttttttaga ttttagagtt agaaggagtg agaattttga ttttaattt tattgtattt     3060
agttaatagg agtttagtaa gtgatttat ttcgtaggtt gtaggttttt ttttgtgtag     3120
gtttgtttag gtgttttgtt ttttattat taatgttgaa tttgcggagt ttatttagag    3180
ttgggaggaa gggttttggg aggaagggag tattgggtt ggttggatag atgtttttt     3240
tatgttgttt tttttatttt ttttattggt tatgttgttt tggttatttt agtttttt     3300
tgagttgtcg attttgggt tttaattgaa ggttatggtt aattgtgaat ttttatagtt    3360
tcgttttttg gtattttgtt tttagaata tttagttatt gagttataag ttttattttt    3420
tatttgagag tgtggggtgg ttttaaata tagttcgaga aatttgagtt atattttgt    3480
ttttatttgg tattttggtt tagggtagag gagggagggg tttggaggtg tggtgttgag    3540
ggtggtagtg gggatggtga gtattaagag aagggttgtt ttgattttt ttttaaagtt    3600
tttatcgatt agtttggaaa cggagttggg ggtaggaaag gttttttgtg tgtttagag    3660
tagttttaa ttttttggtt tttttgtttt ttgtatttttt ttgtgttgag agaggaagtt   3720
tggtgtttga ggcgatgtgg ggatgtagag ataattttt agttttattt tttatttttg    3780
ttaggttatt atggcggagt tgtaggaggt gtagattata gaggagaagt tattgttgtt    3840
aggatagacg tttgaggcgg ttaaggttat tagagatcgt ttgattttta tgtttaaatt    3900
ttagatttt aagtatttt tttgtttttt aattttttaa gcgtattgat tttatttta     3960
tttatattat tgttttatta ttatttagt ttttttttt a                         4001
```

<210> SEQ ID NO 526
<211> LENGTH: 16
<212> TYPE: DNA
<213> ORGANISM: Artificial
<220> FEATURE:
<223> OTHER INFORMATION: Primer

```
<400> SEQUENCE: 526
agccctgcct gatgaa                                                       16

<210> SEQ ID NO 527
<211> LENGTH: 17
<212> TYPE: DNA
<213> ORGANISM: Artificial
<220> FEATURE:
<223> OTHER INFORMATION: Primer

<400> SEQUENCE: 527
tgtgtgggta gcaccaa                                                      17

<210> SEQ ID NO 528
<211> LENGTH: 19
<212> TYPE: DNA
<213> ORGANISM: Artificial
<220> FEATURE:
<223> OTHER INFORMATION: Primer

<400> SEQUENCE: 528
agctctctga tgggcagtg                                                    19

<210> SEQ ID NO 529
<211> LENGTH: 19
<212> TYPE: DNA
<213> ORGANISM: Artificial
<220> FEATURE:
<223> OTHER INFORMATION: Primer

<400> SEQUENCE: 529
tggaagatag cccccaaat                                                    19

<210> SEQ ID NO 530
<211> LENGTH: 16
<212> TYPE: DNA
<213> ORGANISM: Artificial
<220> FEATURE:
<223> OTHER INFORMATION: Primer

<400> SEQUENCE: 530
cccagccccg acttgc                                                       16

<210> SEQ ID NO 531
<211> LENGTH: 19
<212> TYPE: DNA
<213> ORGANISM: Artificial
<220> FEATURE:
<223> OTHER INFORMATION: Primer

<400> SEQUENCE: 531
ctaagacctc aaaggcgcg                                                    19

<210> SEQ ID NO 532
<211> LENGTH: 17
<212> TYPE: DNA
<213> ORGANISM: Artificial
<220> FEATURE:
<223> OTHER INFORMATION: Primer

<400> SEQUENCE: 532
tgtccttctc cgcccgg                                                      17

<210> SEQ ID NO 533
```

```
<211> LENGTH: 18
<212> TYPE: DNA
<213> ORGANISM: Artificial
<220> FEATURE:
<223> OTHER INFORMATION: Primer

<400> SEQUENCE: 533
cccctctgtt tgccttcc                                               18

<210> SEQ ID NO 534
<211> LENGTH: 16
<212> TYPE: DNA
<213> ORGANISM: Artificial
<220> FEATURE:
<223> OTHER INFORMATION: Primer

<400> SEQUENCE: 534
ctggccaggt ggggtg                                                 16

<210> SEQ ID NO 535
<211> LENGTH: 17
<212> TYPE: DNA
<213> ORGANISM: Artificial
<220> FEATURE:
<223> OTHER INFORMATION: Primer

<400> SEQUENCE: 535
gccaggtggg gtgaggg                                                17

<210> SEQ ID NO 536
<211> LENGTH: 18
<212> TYPE: DNA
<213> ORGANISM: Artificial
<220> FEATURE:
<223> OTHER INFORMATION: Primer

<400> SEQUENCE: 536
ctgcgtcacc tcattccc                                               18

<210> SEQ ID NO 537
<211> LENGTH: 18
<212> TYPE: DNA
<213> ORGANISM: Artificial
<220> FEATURE:
<223> OTHER INFORMATION: Primer

<400> SEQUENCE: 537
tcaccgctct ggctgatg                                               18

<210> SEQ ID NO 538
<211> LENGTH: 19
<212> TYPE: DNA
<213> ORGANISM: Artificial
<220> FEATURE:
<223> OTHER INFORMATION: Primer

<400> SEQUENCE: 538
gaggagccaa gagcggagg                                              19

<210> SEQ ID NO 539
<211> LENGTH: 19
<212> TYPE: DNA
<213> ORGANISM: Artificial
<220> FEATURE:
<223> OTHER INFORMATION: Primer

<400> SEQUENCE: 539
``` ccccctctgct cagccatag                                                19

<210> SEQ ID NO 540
<211> LENGTH: 19
<212> TYPE: DNA
<213> ORGANISM: Artificial
<220> FEATURE:
<223> OTHER INFORMATION: Primer

<400> SEQUENCE: 540
gctggagaca ggcagaggg                                                 19

<210> SEQ ID NO 541
<211> LENGTH: 18
<212> TYPE: DNA
<213> ORGANISM: Artificial
<220> FEATURE:
<223> OTHER INFORMATION: Primer

<400> SEQUENCE: 541
ggagacaggc agaggggg                                                  18

<210> SEQ ID NO 542
<211> LENGTH: 19
<212> TYPE: DNA
<213> ORGANISM: Artificial
<220> FEATURE:
<223> OTHER INFORMATION: Primer

<400> SEQUENCE: 542
gtaggtaccc tgagccccc                                                 19

<210> SEQ ID NO 543
<211> LENGTH: 16
<212> TYPE: DNA
<213> ORGANISM: Artificial
<220> FEATURE:
<223> OTHER INFORMATION: Primer

<400> SEQUENCE: 543
acccctgggc cctagc                                                    16

<210> SEQ ID NO 544
<211> LENGTH: 19
<212> TYPE: DNA
<213> ORGANISM: Artificial
<220> FEATURE:
<223> OTHER INFORMATION: Primer

<400> SEQUENCE: 544
ccctctgcct gtctccagc                                                 19

<210> SEQ ID NO 545
<211> LENGTH: 18
<212> TYPE: DNA
<213> ORGANISM: Artificial
<220> FEATURE:
<223> OTHER INFORMATION: Primer

<400> SEQUENCE: 545
ggaaatggca ccccctagc                                                 18

<210> SEQ ID NO 546
<211> LENGTH: 16
<212> TYPE: DNA

-continued

<210> SEQ ID NO 546
<211> LENGTH: 16
<212> TYPE: DNA
<213> ORGANISM: Artificial
<220> FEATURE:
<223> OTHER INFORMATION: Primer

<400> SEQUENCE: 546
gggggcatgg ggagac                                               16

<210> SEQ ID NO 547
<211> LENGTH: 19
<212> TYPE: DNA
<213> ORGANISM: Artificial
<220> FEATURE:
<223> OTHER INFORMATION: Primer

<400> SEQUENCE: 547
gcacccctag ccctagagt                                            19

<210> SEQ ID NO 548
<211> LENGTH: 25
<212> TYPE: DNA
<213> ORGANISM: Artificial
<220> FEATURE:
<223> OTHER INFORMATION: Primer

<400> SEQUENCE: 548
ccttgaagac tttacagagt gtttc                                     25

<210> SEQ ID NO 549
<211> LENGTH: 18
<212> TYPE: DNA
<213> ORGANISM: Artificial
<220> FEATURE:
<223> OTHER INFORMATION: Primer

<400> SEQUENCE: 549
gtatacccac cccacccc                                             18

<210> SEQ ID NO 550
<211> LENGTH: 17
<212> TYPE: DNA
<213> ORGANISM: Artificial
<220> FEATURE:
<223> OTHER INFORMATION: Primer

<400> SEQUENCE: 550
ctgcacccat cctggcc                                              17

<210> SEQ ID NO 551
<211> LENGTH: 18
<212> TYPE: DNA
<213> ORGANISM: Artificial
<220> FEATURE:
<223> OTHER INFORMATION: Primer

<400> SEQUENCE: 551
ggggtggggt gggtatac                                             18

<210> SEQ ID NO 552
<211> LENGTH: 17
<212> TYPE: DNA
<213> ORGANISM: Artificial
<220> FEATURE:
<223> OTHER INFORMATION: Primer

<400> SEQUENCE: 552
gctgggaggg gcaaatc                                              17

<210> SEQ ID NO 553
<211> LENGTH: 19
<212> TYPE: DNA
<213> ORGANISM: Artificial
<220> FEATURE:
<223> OTHER INFORMATION: Primer

<400> SEQUENCE: 553
ggcaaatccc agatcaccc                                               19

<210> SEQ ID NO 554
<211> LENGTH: 19
<212> TYPE: DNA
<213> ORGANISM: Artificial
<220> FEATURE:
<223> OTHER INFORMATION: Primer

<400> SEQUENCE: 554
gcctccatcc atctccctg                                               19

<210> SEQ ID NO 555
<211> LENGTH: 17
<212> TYPE: DNA
<213> ORGANISM: Artificial
<220> FEATURE:
<223> OTHER INFORMATION: Primer

<400> SEQUENCE: 555
ggctgctgat cccaccc                                                 17

<210> SEQ ID NO 556
<211> LENGTH: 19
<212> TYPE: DNA
<213> ORGANISM: Artificial
<220> FEATURE:
<223> OTHER INFORMATION: Primer

<400> SEQUENCE: 556
catgcctcca tccatctcc                                               19

<210> SEQ ID NO 557
<211> LENGTH: 18
<212> TYPE: DNA
<213> ORGANISM: Artificial
<220> FEATURE:
<223> OTHER INFORMATION: Primer

<400> SEQUENCE: 557
cacctctgcc tctgcccc                                                18

<210> SEQ ID NO 558
<211> LENGTH: 18
<212> TYPE: DNA
<213> ORGANISM: Artificial
<220> FEATURE:
<223> OTHER INFORMATION: Primer

<400> SEQUENCE: 558
ccccagtgag cccacagc                                                18

<210> SEQ ID NO 559
<211> LENGTH: 16
<212> TYPE: DNA
<213> ORGANISM: Artificial
<220> FEATURE:

<223> OTHER INFORMATION: Primer

<400> SEQUENCE: 559
cctctgcccc tccccc                                                          16

<210> SEQ ID NO 560
<211> LENGTH: 16
<212> TYPE: DNA
<213> ORGANISM: Artificial
<220> FEATURE:
<223> OTHER INFORMATION: Primer

<400> SEQUENCE: 560
tgccttggca atgggg                                                          16

<210> SEQ ID NO 561
<211> LENGTH: 18
<212> TYPE: DNA
<213> ORGANISM: Artificial
<220> FEATURE:
<223> OTHER INFORMATION: Primer

<400> SEQUENCE: 561
cagggctggg gaagaaag                                                        18

<210> SEQ ID NO 562
<211> LENGTH: 17
<212> TYPE: DNA
<213> ORGANISM: Artificial
<220> FEATURE:
<223> OTHER INFORMATION: Primer

<400> SEQUENCE: 562
cttggcaatg ggggtgg                                                         17

<210> SEQ ID NO 563
<211> LENGTH: 20
<212> TYPE: DNA
<213> ORGANISM: Artificial
<220> FEATURE:
<223> OTHER INFORMATION: Primer

<400> SEQUENCE: 563
ggagcttgtc ctggagtgag                                                      20

<210> SEQ ID NO 564
<211> LENGTH: 21
<212> TYPE: DNA
<213> ORGANISM: Artificial
<220> FEATURE:
<223> OTHER INFORMATION: Primer

<400> SEQUENCE: 564
gtggggtgga aatgtactca c                                                    21

<210> SEQ ID NO 565
<211> LENGTH: 17
<212> TYPE: DNA
<213> ORGANISM: Artificial
<220> FEATURE:
<223> OTHER INFORMATION: Primer

<400> SEQUENCE: 565
tggagtgagg gccctgc                                                         17

```
<210> SEQ ID NO 566
<211> LENGTH: 17
<212> TYPE: DNA
<213> ORGANISM: Artificial
<220> FEATURE:
<223> OTHER INFORMATION: Primer

<400> SEQUENCE: 566
tgcccgccag tcctcag                                                     17

<210> SEQ ID NO 567
<211> LENGTH: 19
<212> TYPE: DNA
<213> ORGANISM: Artificial
<220> FEATURE:
<223> OTHER INFORMATION: Primer

<400> SEQUENCE: 567
taaagggaac atgagccgg                                                   19

<210> SEQ ID NO 568
<211> LENGTH: 18
<212> TYPE: DNA
<213> ORGANISM: Artificial
<220> FEATURE:
<223> OTHER INFORMATION: Primer

<400> SEQUENCE: 568
cagtcctcag gcccatcc                                                    18

<210> SEQ ID NO 569
<211> LENGTH: 22
<212> TYPE: DNA
<213> ORGANISM: Artificial
<220> FEATURE:
<223> OTHER INFORMATION: Primer

<400> SEQUENCE: 569 gatygggtg tttttaggt tt                                                 22
```

The invention claimed is:

1. A method, comprising:
   (a) hybridizing DNA from a sample to an oligonucleotide capture probe and isolating DNA hybridized to the oligonucleotide capture probe;
   (b) treating DNA obtained from step (a) with a reagent that modifies unmethylated DNA;
   (c) amplifying the treated DNA with primers that hybridize to CpG dinucleotides in a target sequence that is within a promoter region of a human NDRG4 gene that corresponds to positions 1-1000 of the methylated and bisulfite-treated sequence of SEQ ID NO: 524, to produce amplified DNA that comprises CpG dinucleotides; and
   (d) detecting production of the amplified DNA.

2. The method of claim 1, wherein the reagent that modifies unmethylated DNA is selected from a methylation-sensitive restriction enzyme and a reagent that converts non-methylated cytosines to uracil.

3. The method of claim 2, wherein the reagent that modifies unmethylated DNA is a reagent that converts non-methylated cytosines to uracil.

4. The method of claim 1, wherein detecting production of the amplified DNA comprises detecting hybridization of a probe that hybridizes to the amplified DNA.

5. The method of claim 4, wherein the probe hybridizes to CpG dinucleotides in the target sequence.

6. The method of claim 4, wherein the probe is a hydrolytic probe and hybridization of the probe to the amplified DNA is detected by detecting hydrolysis of the probe.

7. The method of claim 1, wherein the sample comprises one or more of a tissue sample, a fecal sample and/or a bodily fluid sample.

8. The method of claim 7, wherein the bodily fluid sample comprises a blood sample and/or a plasma sample.

* * * * *